(12) United States Patent
Rajgarhia et al.

(10) Patent No.: US 9,758,799 B2
(45) Date of Patent: *Sep. 12, 2017

(54) GENETICALLY MODIFIED YEAST SPECIES, AND FERMENTATION PROCESSES USING GENETICALLY MODIFIED YEAST

(71) Applicant: Cargill Incorporated, Wayzata, MN (US)

(72) Inventors: Vineet Rajgarhia, Kingsport, TN (US); Kari Koivuranta, Helsinki (FI); Merja Penttila, Helsinki (FI); Marja Ilmen, Helsinki (FI); Pirkko Suominen, Maple Grove, MN (US); Aristos Aristidou, Maple Grove, MN (US); Christopher Kenneth Miller, Cottage Gove, MN (US); Stacey Olson, St. Bonifacius, MN (US); Laura Ruohonen, Helsinki (FI)

(73) Assignee: Cargill Incorporated, Wayzata, MN (US)

( * ) Notice: Subject to any disclaimer, the term of this patent is extended or adjusted under 35 U.S.C. 154(b) by 9 days.

This patent is subject to a terminal disclaimer.

(21) Appl. No.: 15/201,913

(22) Filed: Jul. 5, 2016

(65) Prior Publication Data

US 2016/0340697 A1    Nov. 24, 2016

Related U.S. Application Data

(60) Continuation of application No. 14/038,238, filed on Sep. 26, 2013, which is a continuation of application No. 13/107,882, filed on May 14, 2011, now Pat. No. 8,623,633, which is a division of application No. 10/554,887, filed as application No. PCT/US2004/013592 on May 3, 2004, now Pat. No. 7,943,366.

(60) Provisional application No. 60/467,727, filed on May 2, 2003.

(51) Int. Cl.

| | | |
|---|---|---|
| *C12P 7/22* | (2006.01) | |
| *C12P 7/14* | (2006.01) | |
| *C12N 9/92* | (2006.01) | |
| *C12N 15/81* | (2006.01) | |
| *C12P 7/06* | (2006.01) | |
| *C12P 7/56* | (2006.01) | |
| *C12N 1/16* | (2006.01) | |
| *C12N 9/04* | (2006.01) | |
| *C12N 9/12* | (2006.01) | |
| *C12N 9/24* | (2006.01) | |
| *C12N 9/88* | (2006.01) | |

(52) U.S. Cl.
CPC .......... *C12P 7/14* (2013.01); *C12N 1/16* (2013.01); *C12N 9/0006* (2013.01); *C12N 9/1205* (2013.01); *C12N 9/1217* (2013.01); *C12N 9/248* (2013.01); *C12N 9/88* (2013.01); *C12N 9/92* (2013.01); *C12N 15/81* (2013.01); *C12N 15/815* (2013.01); *C12P 7/06* (2013.01); *C12P 7/56* (2013.01); *C12Y 101/01009* (2013.01); *C12Y 207/01017* (2013.01); *C12Y 207/02003* (2013.01); *C12Y 302/01037* (2013.01); *C12Y 401/01001* (2013.01); *C12Y 501/03002* (2013.01); *C12Y 503/01005* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,866,382 A | 2/1999 | Halborn | |
| 6,410,302 B1 | 6/2002 | Traff | |
| 6,475,768 B1 | 11/2002 | Otero | |
| 6,582,944 B1 | 6/2003 | Halborn | |
| 8,097,448 B2 * | 1/2012 | Suominen | C12N 9/0006 435/137 |
| 8,137,953 B2 * | 3/2012 | Miller | C12N 9/0006 435/254.2 |
| 8,232,089 B2 * | 7/2012 | Urano | C12P 7/16 435/160 |

FOREIGN PATENT DOCUMENTS

| | | |
|---|---|---|
| WO | 95/13360 A | 5/1995 |
| WO | 97/42307 A | 11/1997 |
| WO | 99/14335 A | 3/1999 |
| WO | 99/54477 A | 10/1999 |
| WO | 00/71789 A | 11/2000 |
| WO | 02/42471 A | 5/2002 |
| WO | 03/049525 A | 6/2003 |
| WO | 03/062430 A | 7/2003 |
| WO | 03/102152 A | 12/2003 |

(Continued)

OTHER PUBLICATIONS

Harhangi et al.. Arch Microbiol (2003) vol. 180, pp. 134-141.*
Xylose isomerase [*Piromyces* sp. E2], retrieved on Oct. 11, 2016, GenBank: CAB76571.1.*
Shehalata et al., Microbiological Reviews, Jun. 1996, vol. 60, No. 2, pp. 280-300.
Traff et al., Appl. and Envir. Microbiol. Dec. 2001, vol. 67, pp. 5668-5674.
Voth et al., Nucleic Acids Research, Jun. 2001, vol. 29, No. 12, pp. e59.
Kuyper et al., FEMS Yeast Research 1574 (2003) pp. 1-10.
Richard et al., FEBS Letters 57 (1999) 135-138.

(Continued)

*Primary Examiner* — Jim Ketter
(74) *Attorney, Agent, or Firm* — Gary C Cohn PLLC

(57) ABSTRACT

Yeast cells are transformed with an exogenous xylose isomerase gene. Additional genetic modifications enhance the ability of the transformed cells to ferment xylose to ethanol or other desired fermentation products. Those modifications include deletion of non-specific or specific aldose reductase gene(s), deletion of xylitol dehydrogenase gene(s) and/or overexpression of xylulokinase.

7 Claims, 49 Drawing Sheets

(56) References Cited

FOREIGN PATENT DOCUMENTS

Figure 1:
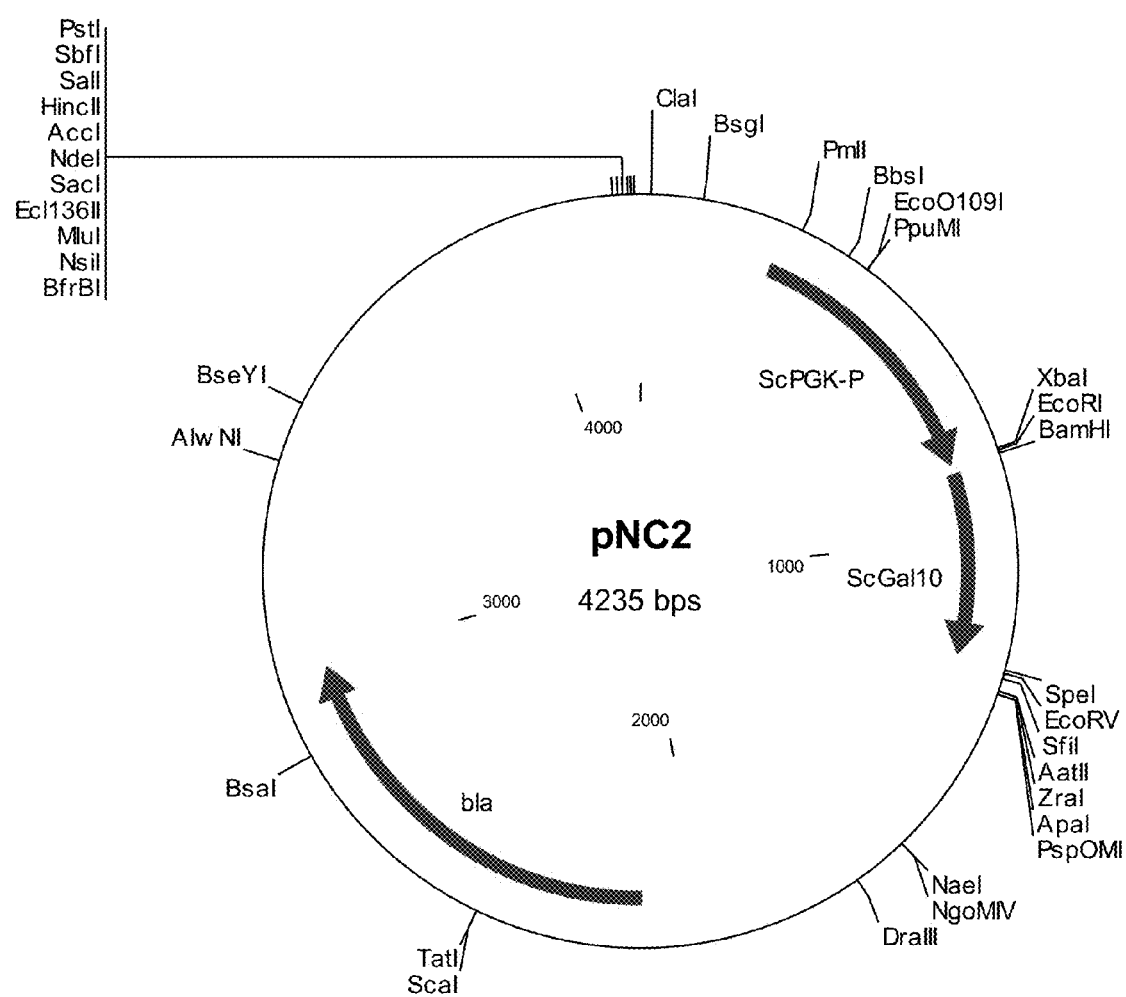

WO       03/102201 A     12/2003
WO     2005/023998 A     3/2005

OTHER PUBLICATIONS

Zyl et al., Appl. and Environmental Microbiology vol. 59, No. 5 (1993) pp. 1487-1494.
Kuyper et al., FEMS Yeast Research 4 (2003) pp. 69-78.
Kuyper et al. FEMS Yeast Research 4 (2004) pp. 665-664.
Linden et al., Appl. and Environmental Microbiology, vol. 58, No. 5 (1992) pp. 1661-1669.
Lonn et al., Enzyme and Microbial Technology 32 (2003), pp. 567-573.
Fincham et al., Microbiological Reviews vol. 51, No. 1 (1989) pp. 148-170.
Johannson et al., Appl. and Environmental Microbiology, vol. 67. No. 9 (2001) pp. 4249-4255.
Metzger et al., Eur. J. Biochem. 228 (1995), pp. 50-54.
Harhangi et al., Arch. Microbiol. 180 (2003), pp. 134-141.

\* cited by examiner

SEQUENCE LISTING

```
<160> NUMBER OF SEQ ID NOS: 167

<210> SEQ ID NO 1
<211> LENGTH: 816
<212> TYPE: DNA
<213> ORGANISM: Saccharomyces cerevisiae

<400> SEQUENCE: 1
atcgattaat ttttttttct ttcctctttt tattaacctt aatttttatt ttagattcct      60
gacttcaact caagacgcac agatattata acatctgcac aataggcatt tgcaagaatt     120
actcgtgagt aaggaaagag tgaggaacta tcgcatacct gcatttaaag atgccgattt     180
gggcgcgaat cctttatttt ggcttcaccc tcatactatt atcagggcca gaaaaaggaa     240
gtgtttccct ccttcttgaa ttgatgttac cctcataaag cacgtggcct cttatcgaga     300
aagaaattac cgtcgctcgt gatttgtttg caaaaagaac aaaactgaaa aaacccagac     360
acgctcgact tcctgtcttc ctattgattg cagcttccaa tttcgtcaca caacaaggtc     420
ctagcgacgg ctcacaggtt ttgtaacaag caatcgaagg ttctggaatg gcgggaaagg     480
gtttagtacc acatgctatg atgcccactg tgatctccag agcaaagttc gttcgatcgt     540
actgttactc tctctctttc aaacagaatt gtccgaatcg tgtgacaaca acagcctgtt     600
ctcacacact cttttcttct aaccaagggg gtggtttagt ttagtagaac ctcgtgaaac     660
ttacatttac atatatataa acttgcataa attggtcaat gcaagaaata catatttggt     720
cttttctaat tcgtagtttt tcaagttctt agatgctttc ttttttctctt ttttacagat     780 catcaaggaa gtaattatct acttttaca acaaag                                816

<210> SEQ ID NO 2
<211> LENGTH: 376
<212> TYPE: DNA
<213> ORGANISM: Saccharomyces cerevisiae

<400> SEQUENCE: 2
gtagatacat tgatgctatc aatccagaga actggaaaga ttgtgtagcc ttgaaaaacg      60
gtgaaactta cgggtccaag attgtctaca gattttcctg atttgccagc ttactatcct     120
tcttgaaaat atgcactcta tatcttttag ttcttaattg caacacatag atttgctgta     180
taacgaattt tatgctatttt tttaaatttg gagttcagtg ataaaagtgt cacagcgaat     240
ttcctcacat gtagggaccg aattgtttac aagttctctg taccaccatg gagacatcaa     300
aaattgaaaa tctatggaaa gatatggacg gtagcaacaa gaatatagca cgagccgcgg     360
atttatttcg ttacgc                                                     376

<210> SEQ ID NO 3
<211> LENGTH: 27
<212> TYPE: DNA
<213> ORGANISM: Artificial
<220> FEATURE:
<223> OTHER INFORMATION: PDC gene amplification primer
```

<400> SEQUENCE: 3

```
ccatcgataa caagctcatg caaagag                                        27
```

<210> SEQ ID NO 4
<211> LENGTH: 28
<212> TYPE: DNA
<213> ORGANISM: Artificial
<220> FEATURE:
<223> OTHER INFORMATION: PDC gene amplication primer

<400> SEQUENCE: 4

```
gctctagatt tgactgtgtt attttgcg                                       28
```

<210> SEQ ID NO 5
<211> LENGTH: 1774
<212> TYPE: DNA
<213> ORGANISM: Saccharomyces cerevisiae

<400> SEQUENCE: 5

```
aacaagctca tgcaaagagg tggtacccgc acgccgaaat gcatgcaagt aacctattca    60
aagtaatatc tcatacatgt ttcatgaggg taacaacatg cgactgggtg agcatatgtt   120
ccgctgatgt gatgtgcaag ataaacaagc aaggcagaaa ctaacttctt cttcatgtaa   180
taaacacacc ccgcgtttat ttacctatct ctaaacttca acaccttata tcataactaa   240
tatttcttga gataagcaca ctgcacccat accttcctta aaaacgtagc ttccagtttt   300
tggtggttcc ggcttccttc ccgattccgc ccgctaaacg catattttg ttgcctggtg   360
gcatttgcaa aatgcataac ctatgcattt aaaagattat gtatgctctt ctgacttttc   420
gtgtgatgag gctcgtggaa aaaatgaata atttatgaat ttgagaacaa ttttgtgttg   480
ttacggtatt ttactatgga ataatcaatc aattgaggat tttatgcaaa tatcgtttga   540
atatttttcc gacccttga gtacttttct tcataattgc ataatattgt ccgctgcccc   600
ttttctgtt agacggtgtc ttgatctact tgctatcgtt caacaccacc ttattttcta   660
actattttt ttttagctca tttgaatcag cttatggtga tggcacattt ttgcataaac   720
ctagctgtcc tcgttgaaca taggaaaaaa aaatatataa acaaggctct ttcactctcc   780
ttgcaatcag atttgggttt gttccctta ttttcatatt tcttgtcata ttcctttctc   840
aattattatt ttctactcat aacctcacgc aaaataacac agtcaaaaac aagctcatgc   900
aaagaggtgg tacccgcacg ccgaaatgca tgcaagtaac ctattcaaag taatatctca   960
tacatgtttc atgagggtaa caacatgcga ctgggtgagc atatgttccg ctgatgtgat  1020
gtgcaagata aacaagcaag gcagaaacta acttcttctt catgtaataa acacacccg  1080
cgtttattta cctatctcta aacttcaaca cctatatca taactaatat tcttgagat   1140
aagcacactg cacccatacc ttccttaaaa acgtagcttc agttttgg tggttccggc   1200
ttccttcccg attccgcccg ctaaacgcat atttttgttg cctggtggca tttgcaaaat  1260
gcataaccta tgcatttaaa agattatgta tgctcttctg acttttcgtg tgatgaggct  1320
cgtggaaaaa atgaataatt tatgaatttg agaacaattt tgtgttgtta cggtatttta  1380
ctatggaata atcaatcaat tgaggatttt atgcaaatat cgtttgaata ttttccgac   1440
cctttgagta cttttcttca taattgcata atattgtccg ctgccctt tctgttaga   1500
cggtgtcttg atctacttgc tatcgttcaa caccaccta tttctaact atttttttt    1560
tagctcattt gaatcagctt atggtgatgg cacatttttg cataacctag ctgtcctcg   1620
ttgaacatag gaaaaaaaaa tatataaaca aggctctttc actctccttg caatcagatt  1680
```

-continued

```
tgggtttgtt ccctttattt tcatatttct tgtcatattc ctttctcaat tattattttc    1740
tactcataac ctcacgcaaa ataacacagt caaa                                1774
```

<210> SEQ ID NO 6
<211> LENGTH: 1235
<212> TYPE: DNA
<213> ORGANISM: Artificial
<220> FEATURE:
<223> OTHER INFORMATION: Restriction fragment with PKG1 promoter and
      GAL10 terminator

<400> SEQUENCE: 6

```
ggccgcggat cgctcttccg ctatcgatta attttttttt ctttcctctt tttattaacc     60 ttaatttta ttttagattc ctgacttcaa ctcaagacgc acagatatta taacatctgc    120
acaataggca tttgcaagaa ttactcgtga gtaaggaaag agtgaggaac tatcgcatac    180
ctgcatttaa agatgccgat ttgggcgcga atcctttatt ttggcttcac cctcatacta    240
ttatcagggc cagaaaaagg aagtgttttcc ctccttcttg aattgatgtt accctcataa    300
agcacgtggc ctcttatcga gaaagaaatt accgtcgctc gtgatttgtt tgcaaaaaga    360
acaaaactga aaaaacccag acacgctcga cttcctgtct tcctattgat tgcagcttcc    420
aatttcgtca cacaacaagg tcctagcgac ggctcacagg ttttgtaaca agcaatcgaa    480
ggttctggaa tggcgggaaa gggtttagta ccacatgcta tgatgcccac tgtgatctcc    540
agagcaaagt tcgttcgatc gtactgttac tctctctctt tcaaacagaa ttgtccgaat    600
cgtgtgacaa caacagcctg ttctcacaca ctcttttctt ctaaccaagg gggtggttta    660
gtttagtaga acctcgtgaa acttacattt acatatatat aaacttgcat aaattggtca    720
atgcaagaaa tacatatttg gtcttttcta attcgtagtt tttcaagttc ttagatgctt    780 tcttttctc tttttacag atcatcaagg aagtaattat ctactttta caacaaatct       840 agaattcgga tccggtagat acattgatgc tatcaatcaa gagaactgga agattgtgt    900 aaccttgaaa aacggtgaaa cttacgggtc caagaccctc tacagatttt cctgatttgc    960
cagcttacta tccttcttga aaatatgcac tctatatctt ttagttctta attgcaacac   1020
atagatttgc tgtataacga attttatgct atttttttaaa tttggagttc agtgataaaa   1080
gtgtcacagc gaatttcctc acatgtagga ccgaattgtt tacaagttct ctgtaccacc   1140
atggagacat caaagattga aaatctatgg aaagatatgg acggtagcaa caagaatata   1200
gcacgagccg cggatttatt tcgttacgca tgcgc                              1235
```

<210> SEQ ID NO 7
<211> LENGTH: 1314
<212> TYPE: DNA
<213> ORGANISM: Artificial
<220> FEATURE:
<223> OTHER INFORMATION: Restriction fragment containing PDC1 promoter
      and GAL10 terminator

<400> SEQUENCE: 7

```
ggccgcggat cgctcttccg ctatcgataa caagctcatg caaagaggtg gtacccgcac     60
gccgaaatgc atgcaagtaa cctattcaaa gtaatatctc atacatgttt catgagggta    120
acaacatgcg actgggtgag catatgttcc gctgatgtga tgtgcaagat aaacaagcaa    180
ggcagaaact aacttcttct tcatgtaata aacacacccc gcgttatttt acctatctct    240
aaacttcaac accttatatc ataactaata tttcttgaga taagcacact gcacccatac    300
```

```
cttccttaaa aacgtagctt ccagttttg gtggttccgg cttccttccc gattccgccc      360
gctaaacgca tattttgtt gcctggtggc atttgcaaaa tgcataacct atgcatttaa      420
aagattatgt atgctcttct gacttttcgt gtgatgaggc tcgtggaaaa atgaataat     480 ttatgaattt gagaacaatt ttgtgttgtt acggtatttt actatggaat aatcaatcaa     540
ttgaggattt tatgcaaata tcgtttgaat attttccga cccttgagt actttcttc      600 ataattgcat aatattgtcc gctgccctt tttctgttag acggtgtctt gatctacttg      660
ctatcgttca acaccacctt attttctaac tattttttt ttagctcatt tgaatcagct      720
tatggtgatg gcacatttt gcataaacct agctgtcctc gttgaacata ggaaaaaaaa      780
atatataaac aaggctcttt cactctcctt gcaatcagat ttgggtttgt tccctttatt     840
ttcatatttc ttgtcatatt cctttctcaa ttattatttt ctactcataa cctcacgcaa     900
aataacacag tcaaatctag aattcggatc cggtagatac attgatgcta tcaatccaga    960
gaactggaaa gattgtgtag ccttgaaaaa cggtgaaact tacgggtcca agattgtcta   1020
cagattttcc tgatttgcca gcttactatc cttcttgaaa atatgcactc tatatctttt   1080
agttcttaat tgcaacacat agatttgctg tataacgaat tttatgctat ttttaaatt    1140 tggagttcag tgataaaagt gtcacagcga atttcctcac atgtagggac cgaattgttt   1200 acaagtctc tgtaccacca tggagacatc aaaaattgaa aatctatgga aagatatgga    1260
cggtagcaac aagaatatag cacgagccgc ggatttattt cgttacgcat gcgc         1314
```

<210> SEQ ID NO 8
<211> LENGTH: 30
<212> TYPE: DNA
<213> ORGANISM: Artificial
<220> FEATURE:
<223> OTHER INFORMATION: G418 amplification primer

<400> SEQUENCE: 8
gctctagatg agccatattc aacgggaaac                                       30

<210> SEQ ID NO 9
<211> LENGTH: 30
<212> TYPE: DNA
<213> ORGANISM: Artificial
<220> FEATURE:
<223> OTHER INFORMATION: G418 amplification primer

<400> SEQUENCE: 9
atggatcctt agaaaaactc atcgagcatc                                       30

<210> SEQ ID NO 10
<211> LENGTH: 30
<212> TYPE: DNA
<213> ORGANISM: Artificial
<220> FEATURE:
<223> OTHER INFORMATION: K. marxianus PDC 5' flank amplification primer

<400> SEQUENCE: 10
caagaaggta cccctctcta aacttgaaca                                       30

<210> SEQ ID NO 11
<211> LENGTH: 32
<212> TYPE: DNA
<213> ORGANISM: Artificial
<220> FEATURE:
<223> OTHER INFORMATION: K. marxianus PDC1 5' flank amplification primer

<400> SEQUENCE: 11
gtaattcctg caggtgcaat tatttggttt gg                                32

<210> SEQ ID NO 12
<211> LENGTH: 32
<212> TYPE: DNA
<213> ORGANISM: Artificial
<220> FEATURE:
<223> OTHER INFORMATION: K. marxianus PDC 3' flank amplification primer

<400> SEQUENCE: 12
ccaagccctg caggagaggg agaggataaa ga                                32

<210> SEQ ID NO 13
<211> LENGTH: 30
<212> TYPE: DNA
<213> ORGANISM: Artificial
<220> FEATURE:
<223> OTHER INFORMATION: K. marxianus PDC 3' flank amplification primer

<400> SEQUENCE: 13
ctcgtaacgc gtgtacaagt tgtggaacaa                                   30

<210> SEQ ID NO 14
<211> LENGTH: 30
<212> TYPE: DNA
<213> ORGANISM: Artificial
<220> FEATURE:
<223> OTHER INFORMATION: S. cerevisiae CYC1 terminator, multiple cloning
      site amplification primer

<400> SEQUENCE: 14
atcctgcagg taatacgact cactataggg                                   30

<210> SEQ ID NO 15
<211> LENGTH: 30
<212> TYPE: DNA
<213> ORGANISM: Artificial
<220> FEATURE:
<223> OTHER INFORMATION: S. cerevisiae CYC1 terminator, multiple cloning
      site amplification primer

<400> SEQUENCE: 15
tagagacgag cttgcaaatt aaagccttcg                                   30

<210> SEQ ID NO 16
<211> LENGTH: 40
<212> TYPE: DNA
<213> ORGANISM: Artificial
<220> FEATURE:
<223> OTHER INFORMATION: poly hig-Tag, ScCYC1 terminator amplification
      primer

<400> SEQUENCE: 16
atattaacct gcaggacatc atcaccatca ccattgagtt                        40

<210> SEQ ID NO 17
<211> LENGTH: 24
<212> TYPE: DNA
<213> ORGANISM: Artificial
<220> FEATURE:
<223> OTHER INFORMATION: poly his-tag, ScCYC1 terminator amplification
      primer

<400> SEQUENCE: 17
gaggaagcgg aagagcgccc aata                                         24

<210> SEQ ID NO 18
<211> LENGTH: 29
<212> TYPE: DNA
<213> ORGANISM: Artificial
<220> FEATURE:
<223> OTHER INFORMATION: hygromycin resistance gene amplification primer

<400> SEQUENCE: 18
aagctctaga tgaaaaagcc tgaactcac                               29

<210> SEQ ID NO 19
<211> LENGTH: 29
<212> TYPE: DNA
<213> ORGANISM: Artificial
<220> FEATURE:
<223> OTHER INFORMATION: hygromycin resistance gene amplification primer

<400> SEQUENCE: 19
cgcggatccc tattcctttg ccctcggac                               29

<210> SEQ ID NO 20
<211> LENGTH: 60
<212> TYPE: DNA
<213> ORGANISM: Artificial
<220> FEATURE:
<223> OTHER INFORMATION: Piromyces xylose isomerase gene reconstruction
      primer

<400> SEQUENCE: 20
agcgtgaaaa ggaacacatg ccactatgc ttaccatggc tcgtgactac gctcgttcca     60

<210> SEQ ID NO 21
<211> LENGTH: 62
<212> TYPE: DNA
<213> ORGANISM: Artificial
<220> FEATURE:
<223> OTHER INFORMATION: Piromyces xylose isomerase gene reconstruction
      primer

<400> SEQUENCE: 21
ggttccattg ctttggttc aatgaggaaa gtacccttga atcccttgga acgagcgtag     60
tc                                                                  62

<210> SEQ ID NO 22
<211> LENGTH: 55
<212> TYPE: DNA
<213> ORGANISM: Artificial
<220> FEATURE:
<223> OTHER INFORMATION: Piromyces xylose isomerase gene reconstruction
      primer

<400> SEQUENCE: 22
ggtcgtgaag gttacatgag tctccttaac actgaccaaa agcgtgaaaa ggaac         55

<210> SEQ ID NO 23
<211> LENGTH: 52
<212> TYPE: DNA
<213> ORGANISM: Artificial
<220> FEATURE:
<223> OTHER INFORMATION: Piromyces xylose isomerase gene reconstruction
      primer

<400> SEQUENCE: 23
gcggtttcag tgtcaacatc gtattggtgc ttggttggtt ccattggctt tg            52

-continued

<210> SEQ ID NO 24
<211> LENGTH: 60
<212> TYPE: DNA
<213> ORGANISM: Artificial
<220> FEATURE:
<223> OTHER INFORMATION: Piromyces xylose isomerase gene reconstruction
      primer

<400> SEQUENCE: 24
gacgccggta ttgaacttgg tgctgaaaac tacgtcttct ggggtggtcg tgaaggttac    60

<210> SEQ ID NO 25
<211> LENGTH: 60
<212> TYPE: DNA
<213> ORGANISM: Artificial
<220> FEATURE:
<223> OTHER INFORMATION: Piromyces xylose isomerase gene reconstruction
      primer

<400> SEQUENCE: 25
ccttgaagtc cttgtctaag ttgtgggcct taaggaaacc aatagcggtt tcagtgtcaa    60

<210> SEQ ID NO 26
<211> LENGTH: 63
<212> TYPE: DNA
<213> ORGANISM: Artificial
<220> FEATURE:
<223> OTHER INFORMATION: Piromyces xylose isomerase gene reconstruction
      primer

<400> SEQUENCE: 26
gactttgatg ttgtcgcccg tgctattgtt caaattaaga acgccataga cgccggtatt    60
gaa                                                                  63

<210> SEQ ID NO 27
<211> LENGTH: 63
<212> TYPE: DNA
<213> ORGANISM: Artificial
<220> FEATURE:
<223> OTHER INFORMATION: Piromyces xylose isomerase gene reconstruction
      primer

<400> SEQUENCE: 27
gttcgaaagt gtgaccagca agagtagcgt ggttaacttc aatgttgacc ttgaagtcct    60
tgt                                                                  63

<210> SEQ ID NO 28
<211> LENGTH: 63
<212> TYPE: DNA
<213> ORGANISM: Artificial
<220> FEATURE:
<223> OTHER INFORMATION: Piromyces xylose isomerase gene reconstruction
      primer

<400> SEQUENCE: 28
acgtcttcgg tcacaagcgt tacatgaacg gtgcctccac taacccagac tttgatgttg    60
tcg                                                                  63

<210> SEQ ID NO 29
<211> LENGTH: 65
<212> TYPE: DNA
<213> ORGANISM: Artificial
<220> FEATURE:
<223> OTHER INFORMATION: Piromyces xylose isomerase gene reconstruction
      primer

<400> SEQUENCE: 29
agcatcaatg gaaccgagca taccagcatc aacagcacag gcaagttcgt gttcgaaagt    60
gtgac    65

<210> SEQ ID NO 30
<211> LENGTH: 65
<212> TYPE: DNA
<213> ORGANISM: Artificial
<220> FEATURE:
<223> OTHER INFORMATION: Piromyces xylose isomerase gene reconstruction
      primer

<400> SEQUENCE: 30
caaggaaaag caaaaggaaa ccggtattaa gcttctctgg agtactgcta acgtcttcgg    60
tcaca    65

<210> SEQ ID NO 31
<211> LENGTH: 66
<212> TYPE: DNA
<213> ORGANISM: Artificial
<220> FEATURE:
<223> OTHER INFORMATION: Piromyces xylose isomerase gene reconstruction
      primer

<400> SEQUENCE: 31
tcaattggga attgatcagt atcccaaccg ttttggtagt caccacggtt agcatcaatg    60
gaaccg    66

<210> SEQ ID NO 32
<211> LENGTH: 64
<212> TYPE: DNA
<213> ORGANISM: Artificial
<220> FEATURE:
<223> OTHER INFORMATION: Piromyces xylose isomerase gene reconstruction
      primer

<400> SEQUENCE: 32
ctctattgaa gaatacgaat ccaaccttaa ggctgtcgtt gcttacctca aggaaaagca    60
aaag    64

<210> SEQ ID NO 33
<211> LENGTH: 64
<212> TYPE: DNA
<213> ORGANISM: Artificial
<220> FEATURE:
<223> OTHER INFORMATION: Piromyces xylose isomerase gene reconstruction
      primer

<400> SEQUENCE: 33
ccaccaccac ggatgatttc catccaagct tggacgagtt cgtattgatc aattgggaat    60
tgat    64

<210> SEQ ID NO 34
<211> LENGTH: 60
<212> TYPE: DNA
<213> ORGANISM: Artificial
<220> FEATURE:
<223> OTHER INFORMATION: Piromyces xylose isomerase gene reconstruction
      primer

<400> SEQUENCE: 34
atactactgt tccacgatg ttgatcttgt ttccgaaggt aactctattg aagaatacga    60

```
<210> SEQ ID NO 35
<211> LENGTH: 66
<212> TYPE: DNA
<213> ORGANISM: Artificial
<220> FEATURE:
<223> OTHER INFORMATION: Piromyces xylose isomerase gene reconstruction
      primer

<400> SEQUENCE: 35
agtagagtta cgacgagtct tggcatcgaa gttggtacca ccagtaacga aaccaccacc     60
acggat                                                               66

<210> SEQ ID NO 36
<211> LENGTH: 45
<212> TYPE: DNA
<213> ORGANISM: Artificial
<220> FEATURE:
<223> OTHER INFORMATION: Piromyces xylose isomerase gene reconstruction
      primer

<400> SEQUENCE: 36
gaaatcatgc aaaagcttgg tattccatac tactgtttcc acgat                    45

<210> SEQ ID NO 37
<211> LENGTH: 56
<212> TYPE: DNA
<213> ORGANISM: Artificial
<220> FEATURE:
<223> OTHER INFORMATION: Piromyces xylose isomerase gene reconstruction
      primer

<400> SEQUENCE: 37
gtgggcaatg atgatgtctt cgaggtcagt agagttacga cgagtcttgg catcga        56

<210> SEQ ID NO 38
<211> LENGTH: 56
<212> TYPE: DNA
<213> ORGANISM: Artificial
<220> FEATURE:
<223> OTHER INFORMATION: Piromyces xylose isomerase gene reconstruction
      primer

<400> SEQUENCE: 38
tgaaattgcc aagcaaaagg ttgatgctgg tttcgaaatc atgcaaaagc ttggta        56

<210> SEQ ID NO 39
<211> LENGTH: 51
<212> TYPE: DNA
<213> ORGANISM: Artificial
<220> FEATURE:
<223> OTHER INFORMATION: Piromyces xylose isomerase gene reconstruction
      primer

<400> SEQUENCE: 39
gagccatagc atccatacca gaaacgtggg caatgatgat gtcttcgagg t             51

<210> SEQ ID NO 40
<211> LENGTH: 63
<212> TYPE: DNA
<213> ORGANISM: Artificial
<220> FEATURE:
<223> OTHER INFORMATION: Piromyces xylose isomerase gene reconstruction
      primer

<400> SEQUENCE: 40
caaaaggttg atgctggttt cgaaatcatg caaaagcttg gtattccata ctactgtttc    60
```

-continued

```
cac                                                              63

<210> SEQ ID NO 41
<211> LENGTH: 67
<212> TYPE: DNA
<213> ORGANISM: Artificial
<220> FEATURE:
<223> OTHER INFORMATION: Piromyces xylose isomerase gene reconstruction
      primer

<400> SEQUENCE: 41
gccatagcat ccataccaga aacgtgggca atgatgatgt cttcgaggtc agtagagtta      60
cgacgag                                                              67

<210> SEQ ID NO 42
<211> LENGTH: 68
<212> TYPE: DNA
<213> ORGANISM: Artificial
<220> FEATURE:
<223> OTHER INFORMATION: Piromyces xylose isomerase gene reconstruction
      primer

<400> SEQUENCE: 42
gtacaaagtc tttcccatgg aacgaaggta ctgatgctat tgaaattgcc aagcaaaagg      60
ttgatgct                                                             68

<210> SEQ ID NO 43
<211> LENGTH: 61
<212> TYPE: DNA
<213> ORGANISM: Artificial
<220> FEATURE:
<223> OTHER INFORMATION: Piromyces xylose isomerase gene reconstruction
      primer

<400> SEQUENCE: 43
gtatggagat tcttggagga gcttggcagc gttttcaaga gcacgagcca tagcatccat      60
a                                                                    61

<210> SEQ ID NO 44
<211> LENGTH: 61
<212> TYPE: DNA
<213> ORGANISM: Artificial
<220> FEATURE:
<223> OTHER INFORMATION: Piromyces xylose isomerase gene reconstruction
      primer

<400> SEQUENCE: 44
ggtggcacac tctttgcgcc gaaggtgctg accaattcgg tggaggtaca aagtctttcc      60
c                                                                    61

<210> SEQ ID NO 45
<211> LENGTH: 60
<212> TYPE: DNA
<213> ORGANISM: Artificial
<220> FEATURE:
<223> OTHER INFORMATION: Piromyces xylose isomerase gene reconstruction
      primer

<400> SEQUENCE: 45
ataccactgt cgaaggaagc gtaacgttcc ttcttcatct tggtgtatgg agattcttgg      60

<210> SEQ ID NO 46
<211> LENGTH: 55
```

```
<212> TYPE: DNA
<213> ORGANISM: Artificial
<220> FEATURE:
<223> OTHER INFORMATION: Piromyces xylose isomerase gene reconstruction
      primer

<400> SEQUENCE: 46
gtaagaaaat gaaggattgg ttacgtttcg ccatggcctg gtggcacact ctttg         55

<210> SEQ ID NO 47
<211> LENGTH: 55
<212> TYPE: DNA
<213> ORGANISM: Artificial
<220> FEATURE:
<223> OTHER INFORMATION: Piromyces xylose isomerase gene reconstruction
      primer

<400> SEQUENCE: 47
gtgagcttac catcttcaaa gtccttacca ataccactgt cgaaggaagc gtaac         55

<210> SEQ ID NO 48
<211> LENGTH: 50
<212> TYPE: DNA
<213> ORGANISM: Artificial
<220> FEATURE:
<223> OTHER INFORMATION: Piromyces xylose isomerase gene reconstruction
      primer

<400> SEQUENCE: 48
ctacgatgct gaaaaggaag tcatgggtaa gaaaatgaag gattggttac               50

<210> SEQ ID NO 49
<211> LENGTH: 55
<212> TYPE: DNA
<213> ORGANISM: Artificial
<220> FEATURE:
<223> OTHER INFORMATION: Piromyces xylose isomerase gene reconstruction
      primer

<400> SEQUENCE: 49
ttaccgtatt cgtaaacttg ttcgagggtg agcttaccat cttcaaagtc cttac         55

<210> SEQ ID NO 50
<211> LENGTH: 60
<212> TYPE: DNA
<213> ORGANISM: Artificial
<220> FEATURE:
<223> OTHER INFORMATION: Piromyces xylose isomerase gene reconstruction
      primer

<400> SEQUENCE: 50
ggattctaag aatccattag ccttccacta ctacgatgct gaaaaggaag tcatgggtaa    60

<210> SEQ ID NO 51
<211> LENGTH: 62
<212> TYPE: DNA
<213> ORGANISM: Artificial
<220> FEATURE:
<223> OTHER INFORMATION: Piromyces xylose isomerase gene reconstruction
      primer

<400> SEQUENCE: 51
gcttaccaga agtttgcttt ggttcaccgt tcttcttacc gtattcgtaa acttgttcga    60
gg                                                                   62

<210> SEQ ID NO 52
```

<211> LENGTH: 65
<212> TYPE: DNA
<213> ORGANISM: Artificial
<220> FEATURE:
<223> OTHER INFORMATION: Piromyces xylose isomerase gene reconstruction primer

<400> SEQUENCE: 52
atggctaagg aatatttccc acaaattcaa aagattaagt tcgaaggtaa ggattctaag    60
aatcc    65

<210> SEQ ID NO 53
<211> LENGTH: 55
<212> TYPE: DNA
<213> ORGANISM: Artificial
<220> FEATURE:
<223> OTHER INFORMATION: Piromyces xylose isomerase gene reconstruction primer

<400> SEQUENCE: 53
ttattggtac atggcaacaa tagcttcgta gagttcttgc ttaccagaag tttgc    55

<210> SEQ ID NO 54
<211> LENGTH: 35
<212> TYPE: DNA
<213> ORGANISM: Artificial
<220> FEATURE:
<223> OTHER INFORMATION: Piromyces xylose isomerase mutagenic primer

<400> SEQUENCE: 54
ggattggtta cgtttcgcca tggcctggtg gcaca    35

<210> SEQ ID NO 55
<211> LENGTH: 35
<212> TYPE: DNA
<213> ORGANISM: Artificial
<220> FEATURE:
<223> OTHER INFORMATION: Piromyces xylose isomerase mutagenic primer

<400> SEQUENCE: 55
ctatgcttac catggctcgt gactacgctc gttcc    35

<210> SEQ ID NO 56
<211> LENGTH: 39
<212> TYPE: DNA
<213> ORGANISM: Artificial
<220> FEATURE:
<223> OTHER INFORMATION: Piromyces xylose isomerase mutagenic primer

<400> SEQUENCE: 56
gctggtatgc tcggttccat tgatgctaac cgtggtgac    39

<210> SEQ ID NO 57
<211> LENGTH: 35
<212> TYPE: DNA
<213> ORGANISM: Artificial
<220> FEATURE:
<223> OTHER INFORMATION: Piromyces xylose isomerase mutagenic primer

<400> SEQUENCE: 57
gttgcttacc tcaaggaaaa gcaaaaggaa accgg    35

<210> SEQ ID NO 58
<211> LENGTH: 1314
<212> TYPE: DNA
<213> ORGANISM: Artificial
<220> FEATURE:
<223> OTHER INFORMATION: Reconstructed Pirmoyces sp. E2 xylose isomerase gene

<400> SEQUENCE: 58

```
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt gcgccgaagg tgctgaccaa     180
ttcggtggag gtacaaagtc tttcccatgg aacgaaggta ctgatgctat tgaaattgcc     240
aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccggtattaa gcttctctgg     420
agtactgcta acgtcttcgg tcacaagcgt tacatgaacg gtgcctccac taacccagac     480
tttgatgttg tcgcccgtgc tattgttcaa attaagaacg ccatagacgc cggtattgaa     540
cttggtgctg aaaactacgt cttctggggt ggtcgtgaag gttacatgag tctccttaac     600
actgaccaaa agcgtgaaaa ggaacacatg ccactatgc ttaccatggc tcgtgactac     660
gctcgttcca agggattcaa gggtactttc ctcattgaac aaagccaat ggaaccaacc     720
aagcaccaat acgatgttga cactgaaacc gctattggtt tccttaaggc ccacaactta     780
gacaaggact tcaaggtcaa cattgaagtt aaccacgcta ctcttgctgg tcacactttc     840
gaacacgaac ttgcctgtgc tgttgatgct ggtatgctcg gttccattga tgctaaccgt     900
ggtgactacc aaaacggttg ggatactgat caattcccaa ttgatcaata cgaactcgtc     960
caagcttgga tggaaatcat ccgtggtggt ggtttcgtta ctggtggtac caacttcgat    1020
gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga agaaggaacg ttacgcttcc ttcgacagtg gtattggtaa ggactttgaa    1200
gatggtaagc tcaccctcga acaagtttac gaatacggta agaagaacgg tgaaccaaag    1260
caaacttctg gtaagcaaga actctacgaa gctattgttg ccatgtacca ataa           1314
```

<210> SEQ ID NO 59
<211> LENGTH: 437
<212> TYPE: PRT
<213> ORGANISM: Artificial
<220> FEATURE:
<223> OTHER INFORMATION: Deduced amino acid sequence encoded by reconstructed Piromyces sp. E2 xylose isomerase gene

<400> SEQUENCE: 59

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
            85                  90                  95
```

```
Pro Tyr Tyr Cys Phe His Asp Val Asp Leu Val Ser Glu Gly Asn Ser
             100                 105                 110

Ile Glu Glu Tyr Glu Ser Asn Leu Lys Ala Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 60
<211> LENGTH: 42
<212> TYPE: DNA
<213> ORGANISM: Artificial
<220> FEATURE:
<223> OTHER INFORMATION: Piromyces xylose isomerase gene amplification
      primer

<400> SEQUENCE: 60
atcgtattcc tgcaggatgg ctaaggaata tttcccacaa at                        42
```

```
<210> SEQ ID NO 61
<211> LENGTH: 44
<212> TYPE: DNA
<213> ORGANISM: Artificial
<220> FEATURE:
<223> OTHER INFORMATION: Piromyces xylose isomerase amplification primer

<400> SEQUENCE: 61
atatcgaacc tgcaggttat tggtacatgg caacaatagc ttcg                44

<210> SEQ ID NO 62
<211> LENGTH: 43
<212> TYPE: DNA
<213> ORGANISM: Artificial
<220> FEATURE:
<223> OTHER INFORMATION: Piromyces xylose isomerase gene mutagenic
      primer

<400> SEQUENCE: 62
gctattgttg ccatgtacca acctgcagga catcatcacc atc                 43

<210> SEQ ID NO 63
<211> LENGTH: 26
<212> TYPE: DNA
<213> ORGANISM: Artificial
<220> FEATURE:
<223> OTHER INFORMATION: Amplification primer for upstream flank of K.
      marxianus xylose reductase gene

<400> SEQUENCE: 63
aggtaatata ggtaaacaaa gatcac                                    26

<210> SEQ ID NO 64
<211> LENGTH: 27
<212> TYPE: DNA
<213> ORGANISM: Artificial
<220> FEATURE:
<223> OTHER INFORMATION: Amplification primer for upstream flank of K.
      marxianus xylose reductase gene

<400> SEQUENCE: 64
tatgtatgtg tgtgctactt accacag                                   27

<210> SEQ ID NO 65
<211> LENGTH: 28
<212> TYPE: DNA
<213> ORGANISM: Artificial
<220> FEATURE:
<223> OTHER INFORMATION: Amplification primer for downstream flank of K.
      marxianus xylose reductase gene

<400> SEQUENCE: 65
cctggaattt tcatgaaact gatataag                                  28

<210> SEQ ID NO 66
<211> LENGTH: 27
<212> TYPE: DNA
<213> ORGANISM: Artificial
<220> FEATURE:
<223> OTHER INFORMATION: Amplification primer for downstream flank of K.
      marxianus xylose reductase gene

<400> SEQUENCE: 66
actaaactcg ctttgttctg gctcatc                                   27

<210> SEQ ID NO 67
```

-continued

```
<211> LENGTH: 25
<212> TYPE: DNA
<213> ORGANISM: Artificial
<220> FEATURE:
<223> OTHER INFORMATION: Amplification primer for K. marxianus xylose
      reductase region

<400> SEQUENCE: 67
gccagaggta gagagcacaa agtaa                                            25

<210> SEQ ID NO 68
<211> LENGTH: 25
<212> TYPE: DNA
<213> ORGANISM: Artificial
<220> FEATURE:
<223> OTHER INFORMATION: Amplification primer for K. marxianus xylose
      reductase region

<400> SEQUENCE: 68
cgaagccaac tcgcttctat ctggt                                            25

<210> SEQ ID NO 69
<211> LENGTH: 31
<212> TYPE: DNA
<213> ORGANISM: Artificial
<220> FEATURE:
<223> OTHER INFORMATION: Amplification primer for K. marxianus promoter
      region.

<400> SEQUENCE: 69
tattactgca gtgcacccga aaagtttgag a                                     31

<210> SEQ ID NO 70
<211> LENGTH: 31
<212> TYPE: DNA
<213> ORGANISM: Artificial
<220> FEATURE:
<223> OTHER INFORMATION: Amplification primer for K. marxianus promoter
      region.

<400> SEQUENCE: 70
atcgtctgca gactacacca gggcgtagta t                                     31

<210> SEQ ID NO 71
<211> LENGTH: 41
<212> TYPE: DNA
<213> ORGANISM: Artificial
<220> FEATURE:
<223> OTHER INFORMATION: Amplification primer for K. marxianus
      terminator region.

<400> SEQUENCE: 71
cgtagtatct gggccctatc tggtattatc taagaacgat t                          41

<210> SEQ ID NO 72
<211> LENGTH: 43
<212> TYPE: DNA
<213> ORGANISM: Artificial
<220> FEATURE:
<223> OTHER INFORMATION: Amplification primer for K. marxianus
      terminator region.

<400> SEQUENCE: 72
tatacgtact tagggcccgc tatgcccctc actttactaa tat                        43

<210> SEQ ID NO 73
<211> LENGTH: 16
```

```
<212> TYPE: DNA
<213> ORGANISM: Artificial
<220> FEATURE:
<223> OTHER INFORMATION: Amplification primer for K. marxianus promoter
      region.

<400> SEQUENCE: 73
cgtagtatct gggccc                                                      16

<210> SEQ ID NO 74
<211> LENGTH: 18
<212> TYPE: DNA
<213> ORGANISM: Artificial
<220> FEATURE:
<223> OTHER INFORMATION: Amplification primer for K. marxianus promoter
      region.

<400> SEQUENCE: 74
tatacgtact tagggccc                                                    18

<210> SEQ ID NO 75
<211> LENGTH: 20
<212> TYPE: DNA
<213> ORGANISM: Artificial
<220> FEATURE:
<223> OTHER INFORMATION: Amplification primer for K. marxianus promoter
      region.

<400> SEQUENCE: 75
caggacttgt tgcgtggcgc                                                  20

<210> SEQ ID NO 76
<211> LENGTH: 20
<212> TYPE: DNA
<213> ORGANISM: Artificial
<220> FEATURE:
<223> OTHER INFORMATION: Amplification primer for K. marxianus promoter
      region.

<400> SEQUENCE: 76
gtatagatta acagtgtgtt                                                  20

<210> SEQ ID NO 77
<211> LENGTH: 25
<212> TYPE: DNA
<213> ORGANISM: Artificial
<220> FEATURE:
<223> OTHER INFORMATION: Amplification primer for K. marxianus promoter
      region.

<400> SEQUENCE: 77
ccacgagcct catcacacga aaagt                                            25

<210> SEQ ID NO 78
<211> LENGTH: 27
<212> TYPE: DNA
<213> ORGANISM: Artificial
<220> FEATURE:
<223> OTHER INFORMATION: G418 gene amplification primer

<400> SEQUENCE: 78
gtcttcgatt tgacctactt ctaccag                                          27

<210> SEQ ID NO 79
<211> LENGTH: 24
<212> TYPE: DNA
<213> ORGANISM: Artificial
```

```
<220> FEATURE:
<223> OTHER INFORMATION: Amplification primer for G418 gene

<400> SEQUENCE: 79
cgtaatagcg aagaggcccg cacc                                           24

<210> SEQ ID NO 80
<211> LENGTH: 28
<212> TYPE: DNA
<213> ORGANISM: Artificial
<220> FEATURE:
<223> OTHER INFORMATION: Amplification primer for G418 gene

<400> SEQUENCE: 80
atccgttctc aatcactaca gtagctta                                       28

<210> SEQ ID NO 81
<211> LENGTH: 30
<212> TYPE: DNA
<213> ORGANISM: Artificial
<220> FEATURE:
<223> OTHER INFORMATION: Amplification primer for S. cerevisiae
      xylulokinase gene

<400> SEQUENCE: 81
taggatccat gttgtgttca gtaattcaga                                     30

<210> SEQ ID NO 82
<211> LENGTH: 30
<212> TYPE: DNA
<213> ORGANISM: Artificial
<220> FEATURE:
<223> OTHER INFORMATION: Amplification primer for S. cerevisiae
      xylulokinase gene

<400> SEQUENCE: 82
taggatcctt agatgagagt cttttccagt                                     30

<210> SEQ ID NO 83
<211> LENGTH: 1803
<212> TYPE: DNA
<213> ORGANISM: Saccharomyces cerevisiae

<400> SEQUENCE: 83
atgttgtgtt cagtaattca gagacagaca agagaggttt ccaacacaat gtctttagac    60
tcatactatc ttgggtttga tctttcgacc caacaactga atgtctcgc cattaaccag    120 gacctaaaaa ttgtccattc agaaacagtg gaatttgaaa aggatcttcc gcattatcac    180
acaaagaagg gtgtctatat acacggcgac actatcgaat gtcccgtagc catgtggtta    240
gaggctctag atctggttct ctcgaaatat cgcgaggcta aatttccatt gaacaaagtt    300
atggccgtct cagggtcctg ccagcagcac gggtctgtct actggtcctc ccaagccgaa    360
tctctgttag agcaattgaa taagaaaccg gaaaagatt tattgcacta cgtgagctct    420
gtagcatttg caaggcaaac cgcccccaat tggcaagacc acagtactgc aaagcaatgt    480
caagagtttg aagagtgcat aggtgggcct gaaaaaatgg ctcaattaac agggtccaga    540
gcccatttta gatttactgg tcctcaaatt ctgaaaattg cacaattaga accagaagct    600
tacgaaaaaa caaagaccat ttctttagtg tctaatttt tgacttctat cttagtgggc    660
catcttgttg aattagagga ggcagatgcc tgtggtatga accttttatga tatacgtgaa    720 agaaaattca gtgatgagct actacatcta attgatagtt cttctaagga taaaactatc    780
```

```
agacaaaaat taatgagagc acccatgaaa aatttgatag cgggtaccat ctgtaaatat    840
tttattgaga agtacggttt caatacaaac tgcaaggtct ctcccatgac tggggataat    900
ttagccacta tatgttcttt accccctgcgg aagaatgacg ttctcgtttc cctaggaaca   960
agtactacag ttcttctggt caccgataag tatcacccct ctccgaacta tcatcttttc  1020
attcatccaa ctctgccaaa ccattatatg ggtatgattt gttattgtaa tggttctttg  1080
gcaagggaga ggataagaga cgagttaaac aaagaacggg aaaataatta tgagaagact  1140
aacgattgga ctctttttaa tcaagctgtg ctagatgact cagaaagtag tgaaaatgaa  1200
ttaggtgtat attttcctct gggggagatc gttcctagcg taaaagccat aaacaaaagg  1260
gttatcttca atccaaaaac gggtatgatt gaaagagagg tggccaagtt caaagacaag  1320
aggcacgatg ccaaaaatat tgtagaatca caggctttaa gttgcagggt aagaatatct  1380
cccctgcttt cggattcaaa cgcaagctca acagagac tgaacgaaga tacaatcgtg  1440
aagtttgatt acgatgaatc tccgctgcgg gactacctaa ataaaaggcc agaaaggact  1500
ttttttgtag gtggggcttc taaaaacgat gctattgtga agaagtttgc tcaagtcatt  1560
ggtgctacaa agggtaattt taggctagaa acaccaaact catgtgccct tggtggttgt  1620
tataaggcca tgtggtcatt gttatatgac tctaataaaa ttgcagttcc ttttgataaa  1680
tttctgaatg acaatttttcc atggcatgta atggaaagca tatccgatgt ggataatgaa  1740
aattgggatc gctataattc caagattgtc cccttaagcg aactggaaaa gactctcatc  1800
taa                                                                1803
```

<210> SEQ ID NO 84
<211> LENGTH: 600
<212> TYPE: PRT
<213> ORGANISM: Saccharomyces cerevisiae

<400> SEQUENCE: 84

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190
```

```
Ile Ala Gln Leu Glu Pro Glu Ala Tyr Glu Lys Thr Lys Thr Ile Ser
            195                 200                 205

Leu Val Ser Asn Phe Leu Thr Ser Ile Leu Val Gly His Leu Val Glu
            210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
            245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
            275                 280                 285

Thr Asn Cys Lys Val Ser Pro Met Thr Gly Asp Asn Leu Ala Thr Ile
            290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
            325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
            355                 360                 365

Leu Asn Lys Glu Arg Glu Asn Asn Tyr Glu Lys Thr Asn Asp Trp Thr
            370                 375                 380

Leu Phe Asn Gln Ala Val Leu Asp Ser Glu Ser Ser Glu Asn Glu
385                 390                 395                 400

Leu Gly Val Tyr Phe Pro Leu Gly Glu Ile Val Pro Ser Val Lys Ala
            405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
            435                 440                 445

Glu Ser Gln Ala Leu Ser Cys Arg Val Arg Ile Ser Pro Leu Leu Ser
            450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
            485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
            515                 520                 525

Leu Glu Thr Pro Asn Ser Cys Ala Leu Gly Gly Cys Tyr Lys Ala Met
            530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
            565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
            595                 600
```

```
<210> SEQ ID NO 85
<211> LENGTH: 23
<212> TYPE: DNA
<213> ORGANISM: Artificial
<220> FEATURE:
<223> OTHER INFORMATION: Amplification primer for S. cerevisiae TEF1
      promoter

<400> SEQUENCE: 85
gacactatag aatactcaag cta                                              23

<210> SEQ ID NO 86
<211> LENGTH: 29
<212> TYPE: DNA
<213> ORGANISM: Artificial
<220> FEATURE:
<223> OTHER INFORMATION: Amplification primer for S. cerevisiae TEF1
      promoter

<400> SEQUENCE: 86
cgtctagatt cctcaccttg tcgtattat                                        29

<210> SEQ ID NO 87
<211> LENGTH: 42
<212> TYPE: DNA
<213> ORGANISM: Artificial
<220> FEATURE:
<223> OTHER INFORMATION: Amplification primer for S. cerevisiae TEF1
      promoter

<400> SEQUENCE: 87
tattacgtat atgcgaattc cccacacacc atagcttcaa aa                         42

<210> SEQ ID NO 88
<211> LENGTH: 45
<212> TYPE: DNA
<213> ORGANISM: Artificial
<220> FEATURE:
<223> OTHER INFORMATION: Amplification primer for S. cerevisiae TEF1
      promoter

<400> SEQUENCE: 88
acgtattacg tagaattctg tcgtattata ctatgccgat atact                      45

<210> SEQ ID NO 89
<211> LENGTH: 20
<212> TYPE: DNA
<213> ORGANISM: Artificial
<220> FEATURE:
<223> OTHER INFORMATION: Amplification primer for S. cerevisiae TEF1
      promoter

<400> SEQUENCE: 89
tattacgtat atgcgaattc                                                  20

<210> SEQ ID NO 90
<211> LENGTH: 18
<212> TYPE: DNA
<213> ORGANISM: Artificial
<220> FEATURE:
<223> OTHER INFORMATION: Amplification primer for S. cerevisiae TEF1
      promoter

<400> SEQUENCE: 90
acgtattacg tagaattc                                                    18
```

```
<210> SEQ ID NO 91
<211> LENGTH: 27
<212> TYPE: DNA
<213> ORGANISM: Artificial
<220> FEATURE:
<223> OTHER INFORMATION: S. cerevisiae/HisG gene amplification primer

<400> SEQUENCE: 91
ggactccgcg catcgccgta ccacttc                                   27

<210> SEQ ID NO 92
<211> LENGTH: 20
<212> TYPE: DNA
<213> ORGANISM: Artificial
<220> FEATURE:
<223> OTHER INFORMATION: S. cerevisiae/HisG gene amplification primer

<400> SEQUENCE: 92
tacgggacat tcgatagtgt                                           20

<210> SEQ ID NO 93
<211> LENGTH: 18
<212> TYPE: DNA
<213> ORGANISM: Artificial
<220> FEATURE:
<223> OTHER INFORMATION: S. cerevisiae/HisG gene amplification primer

<400> SEQUENCE: 93
caggaaacag ctatgacc                                             18

<210> SEQ ID NO 94
<211> LENGTH: 24
<212> TYPE: DNA
<213> ORGANISM: Artificial
<220> FEATURE:
<223> OTHER INFORMATION: S. cerevisiae/HisG gene amplification primer

<400> SEQUENCE: 94
gtagtgaaaa tgaattaggt gtat                                      24

<210> SEQ ID NO 95
<211> LENGTH: 18
<212> TYPE: DNA
<213> ORGANISM: Artificial
<220> FEATURE:
<223> OTHER INFORMATION: S. cerevisiae xylulokkinase gene amplification
      primer

<400> SEQUENCE: 95
gttttcccag tcacgacg                                             18

<210> SEQ ID NO 96
<211> LENGTH: 40
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 96
accaaaaaca ctgcatagac taatattatt aatactatat                     40

<210> SEQ ID NO 97
<211> LENGTH: 40
<212> TYPE: DNA
<213> ORGANISM: Artificial
<220> FEATURE:
```

```
<223> OTHER INFORMATION: K. marxianus xylitol dehydrogenase gene
      amplification primer

<400> SEQUENCE: 97
ggttgataat ttgtattttt gttattggta gcgctcgctc                              40

<210> SEQ ID NO 98
<211> LENGTH: 40
<212> TYPE: DNA
<213> ORGANISM: Artificial
<220> FEATURE:
<223> OTHER INFORMATION: K. marxianus xylitol dehydrogenase terminator
      amplification primer

<400> SEQUENCE: 98
catgtttcaa aactgtgatt gaacgttatt tatgaatatg                              40

<210> SEQ ID NO 99
<211> LENGTH: 40
<212> TYPE: DNA
<213> ORGANISM: Artificial
<220> FEATURE:
<223> OTHER INFORMATION: K. marxianus xylitol dehydrogenase terminator
      amplification primer

<400> SEQUENCE: 99
cctagggata ggttccgctc ctgttgggtt ataacgactc                              40

<210> SEQ ID NO 100
<211> LENGTH: 40
<212> TYPE: DNA
<213> ORGANISM: Artificial
<220> FEATURE:
<223> OTHER INFORMATION: K. marxianus xylitol dehydrogenase terminator
      amplification primer

<400> SEQUENCE: 100
atctatgcat gccatgtttc aaaactgtga ttgaacgtta                              40

<210> SEQ ID NO 101
<211> LENGTH: 40
<212> TYPE: DNA
<213> ORGANISM: Artificial
<220> FEATURE:
<223> OTHER INFORMATION: K. marxianus xylitol dehydrogenase terminator
      amplification primer

<400> SEQUENCE: 101
agttaagcat gccctaggga taggttccgc tcctgttggg                              40

<210> SEQ ID NO 102
<211> LENGTH: 20
<212> TYPE: DNA
<213> ORGANISM: Artificial
<220> FEATURE:
<223> OTHER INFORMATION: K. marxianus xylitol dehydrogenase terminator
      amplification primer

<400> SEQUENCE: 102
atctatgcat gccatgtttc                                                    20

<210> SEQ ID NO 103
<211> LENGTH: 20
<212> TYPE: DNA
<213> ORGANISM: Artificial
<220> FEATURE:
<223> OTHER INFORMATION: K. marxianus xylitol dehydrogenase terminator
``` amplification primer

<400> SEQUENCE: 103
agttaagcat gccctaggga                                          20

<210> SEQ ID NO 104
<211> LENGTH: 25
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 104
atgaccaaca ctcaaaaagc cgttg                                    25

<210> SEQ ID NO 105
<211> LENGTH: 25
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 105
tcattctgga ccatcaatga tagtc                                    25

<210> SEQ ID NO 106
<211> LENGTH: 25
<212> TYPE: DNA
<213> ORGANISM: Artificial
<220> FEATURE:
<223> OTHER INFORMATION: Hygromycin gene amplification primer

<400> SEQUENCE: 106
atgttcacaa gatgaaatat taccc                                    25

<210> SEQ ID NO 107
<211> LENGTH: 25
<212> TYPE: DNA
<213> ORGANISM: Artificial
<220> FEATURE:
<223> OTHER INFORMATION: Hygromycin gene amplification primer

<400> SEQUENCE: 107
tgagcttgtt atcgatagcg gaaga                                    25

<210> SEQ ID NO 108
<211> LENGTH: 25
<212> TYPE: DNA
<213> ORGANISM: Artificial
<220> FEATURE:
<223> OTHER INFORMATION: Hygromycin gene amplification primer

<400> SEQUENCE: 108
gtaggaacct ttggtgccac gtaag                                    25

<210> SEQ ID NO 109
<211> LENGTH: 21
<212> TYPE: DNA
<213> ORGANISM: Artificial
<220> FEATURE:
<223> OTHER INFORMATION: Hygromycin gene amplification primer

<400> SEQUENCE: 109
ggccgcacta gagtcgacct g                                        21

<210> SEQ ID NO 110
<211> LENGTH: 20
<212> TYPE: DNA
<213> ORGANISM: Artificial
<220> FEATURE:
<223> OTHER INFORMATION: Piromyces xylose isomerase gene amplification
      primer

<400> SEQUENCE: 110
tgaacggtgc ctccactaac                                                   20

<210> SEQ ID NO 111
<211> LENGTH: 20
<212> TYPE: DNA
<213> ORGANISM: Artificial
<220> FEATURE:
<223> OTHER INFORMATION: Piromyces xylose isomerase gene amplification
      primer

<400> SEQUENCE: 111
gccctctagg atcagcgggt                                                   20

<210> SEQ ID NO 112
<211> LENGTH: 42
<212> TYPE: DNA
<213> ORGANISM: Artificial
<220> FEATURE:
<223> OTHER INFORMATION: Piromyces xylose isomerase gene amplification
      primer

<400> SEQUENCE: 112
atcgtattcc tgcaggatgg ctaaggaata tttcccacaa at                          42

<210> SEQ ID NO 113
<211> LENGTH: 44
<212> TYPE: DNA
<213> ORGANISM: Artificial
<220> FEATURE:
<223> OTHER INFORMATION: Piromyces xylose isomerase gene amplification
      primer

<400> SEQUENCE: 113
atatcgaacc tgcaggttat tggtacatgg caacaatagc ttcg                        44

<210> SEQ ID NO 114
<211> LENGTH: 33
<212> TYPE: DNA
<213> ORGANISM: Artificial
<220> FEATURE:
<223> OTHER INFORMATION: L. helveticus lactate dehydrogenase gene
      amplification primer

<400> SEQUENCE: 114
tattagcatg cgacgtcggt aatctccgaa cag                                    33

<210> SEQ ID NO 115
<211> LENGTH: 23
<212> TYPE: DNA
<213> ORGANISM: Artificial
<220> FEATURE:
<223> OTHER INFORMATION: L. helveticus lactate dehydrogenase gene
      amplification primer

<400> SEQUENCE: 115
gaaatgcatg cccacaggac ggg                                               23

<210> SEQ ID NO 116
<211> LENGTH: 37
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 116
attaatccgc gggggaaata cggacgggat tgaacgc                              37

<210> SEQ ID NO 117
<211> LENGTH: 37
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 117
tattaaccgc ggcttattgt ggatcgaatt gtaatgt                              37

<210> SEQ ID NO 118
<211> LENGTH: 20
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 118
tagcagcacg ttccttatat                                                 20

<210> SEQ ID NO 119
<211> LENGTH: 20
<212> TYPE: DNA
<213> ORGANISM: Artificial
<220> FEATURE:
<223> OTHER INFORMATION: K. marxianus xylitol dehydrogenase gene
      amplification primer

<400> SEQUENCE: 119
ctatggtata gcgctgccta                                                 20

<210> SEQ ID NO 120
<211> LENGTH: 28
<212> TYPE: DNA
<213> ORGANISM: Artificial
<220> FEATURE:
<223> OTHER INFORMATION: Ura3 gene amplification primer

<400> SEQUENCE: 120
cttcaacaac aacaccactt gattcatg                                        28

<210> SEQ ID NO 121
<211> LENGTH: 20
<212> TYPE: DNA
<213> ORGANISM: Artificial
<220> FEATURE:
<223> OTHER INFORMATION: Ura3 gene amplification primer

<400> SEQUENCE: 121
gtgcagttgg gttaagaata                                                 20

<210> SEQ ID NO 122
<211> LENGTH: 26

```
<212> TYPE: DNA
<213> ORGANISM: Artificial
<220> FEATURE:
<223> OTHER INFORMATION: S. cerevisiae xylulokinase gene amplification
      primer

<400> SEQUENCE: 122
gaggcagatg cctgtggtat gaacct                                         26

<210> SEQ ID NO 123
<211> LENGTH: 24
<212> TYPE: DNA
<213> ORGANISM: Artificial
<220> FEATURE:
<223> OTHER INFORMATION: S. cerevisiae xylulokinase gene amplification
      primer

<400> SEQUENCE: 123
cgaaataaat ccgcggctcg tgct                                           24

<210> SEQ ID NO 124
<211> LENGTH: 36
<212> TYPE: DNA
<213> ORGANISM: Artificial
<220> FEATURE:
<223> OTHER INFORMATION: K. marxianus xylose reductase gene
      amplification primer

<400> SEQUENCE: 124
attataccgc gggtagagag cacaaagtaa cgcaac                              36

<210> SEQ ID NO 125
<211> LENGTH: 36
<212> TYPE: DNA
<213> ORGANISM: Artificial
<220> FEATURE:
<223> OTHER INFORMATION: K. marxianus xylose reductase gene
      amplification primer

<400> SEQUENCE: 125
taatatccgc ggggctgtct tttgacaatt aggtcg                              36

<210> SEQ ID NO 126
<211> LENGTH: 20
<212> TYPE: DNA
<213> ORGANISM: Artificial
<220> FEATURE:
<223> OTHER INFORMATION: K. marxianus xylose reductase gene
      amplification primer

<400> SEQUENCE: 126
tcccctatat agatgatggc                                                20

<210> SEQ ID NO 127
<211> LENGTH: 26
<212> TYPE: DNA
<213> ORGANISM: Artificial
<220> FEATURE:
<223> OTHER INFORMATION: K. marxianus xylose reductase gene
      amplification primer

<400> SEQUENCE: 127
ggtatctcaa acttttcggg tgcatt                                         26

<210> SEQ ID NO 128
<211> LENGTH: 26
<212> TYPE: DNA
```

<213> ORGANISM: Artificial
<220> FEATURE:
<223> OTHER INFORMATION: K. marxianus xylose reductase gene
      amplification primer

<400> SEQUENCE: 128
tcccatgggt cgttaaatct caatcc                                           26

<210> SEQ ID NO 129
<211> LENGTH: 20
<212> TYPE: DNA
<213> ORGANISM: Artificial
<220> FEATURE:
<223> OTHER INFORMATION: Ura3 gene amplification primer

<400> SEQUENCE: 129
gcccactatc ctttgtcgag                                                  20

<210> SEQ ID NO 130
<211> LENGTH: 37
<212> TYPE: DNA
<213> ORGANISM: Artificial
<220> FEATURE:
<223> OTHER INFORMATION: K. marxianus xylose reductase gene
      amplification primer

<400> SEQUENCE: 130
attatagagc tcggtagaga gcacaaagta acgcaac                               37

<210> SEQ ID NO 131
<211> LENGTH: 38
<212> TYPE: DNA
<213> ORGANISM: Artificial
<220> FEATURE:
<223> OTHER INFORMATION: K. marxianus xylose reductase gene
      amplification primer

<400> SEQUENCE: 131
tattaagcgg ccgcggctgt cttttgacaa ttaggtcg                              38

<210> SEQ ID NO 132
<211> LENGTH: 20
<212> TYPE: DNA
<213> ORGANISM: Artificial
<220> FEATURE:
<223> OTHER INFORMATION: K. marxianus xylose reductase gene
      amplification primer

<400> SEQUENCE: 132
aggacgtgcg cacccacctg                                                  20

<210> SEQ ID NO 133
<211> LENGTH: 20
<212> TYPE: DNA
<213> ORGANISM: Artificial
<220> FEATURE:
<223> OTHER INFORMATION: K. marxianus xylose reductase gene
      amplification primer

<400> SEQUENCE: 133
gtttccacca cccagacaac                                                  20

<210> SEQ ID NO 134
<211> LENGTH: 23
<212> TYPE: DNA
<213> ORGANISM: Artificial
<220> FEATURE:

<223> OTHER INFORMATION: K. marxianus xylitol dehydrogenase gene
      amplification primer

<400> SEQUENCE: 134
caatgcaaag gtggtttatg taa                                            23

<210> SEQ ID NO 135
<211> LENGTH: 45
<212> TYPE: DNA
<213> ORGANISM: Artificial
<220> FEATURE:
<223> OTHER INFORMATION: C. sonorensis xylitol dehydrogenase gene 5'
      flank amplification primer

<400> SEQUENCE: 135
actgtcgagc tcgtttaaac acctattcgg gagtcaatca accat                    45

<210> SEQ ID NO 136
<211> LENGTH: 40
<212> TYPE: DNA
<213> ORGANISM: Artificial
<220> FEATURE:
<223> OTHER INFORMATION: C. sonorensis xylitol dehydrogenase gene 5'
      flank amplification primer

<400> SEQUENCE: 136
actgacgcgt cgacgtatgt ataataaggt atgattctgg                          40

<210> SEQ ID NO 137
<211> LENGTH: 39
<212> TYPE: DNA
<213> ORGANISM: Artificial
<220> FEATURE:
<223> OTHER INFORMATION: C. sonorensis xylitol dehydrogenase gene 3'
      flank amplification primer

<400> SEQUENCE: 137
ggcccgcggc cgctaggcta gttttctaaa attttggtg                           39

<210> SEQ ID NO 138
<211> LENGTH: 37
<212> TYPE: DNA
<213> ORGANISM: Artificial
<220> FEATURE:
<223> OTHER INFORMATION: C. sonorensis xylitol dehydrogenase gene 3'
      flank amplification primer

<400> SEQUENCE: 138
gggacgggcc caagtatgag aaatattgat gatatag                             37

<210> SEQ ID NO 139
<211> LENGTH: 26
<212> TYPE: DNA
<213> ORGANISM: Artificial
<220> FEATURE:
<223> OTHER INFORMATION: C. sonorensis xylose reductase amplification
      primer
<220> FEATURE:
<221> NAME/KEY: misc_feature
<223> OTHER INFORMATION: D = A/G/T; R = A/G; Y = C/T; W = A/T

<400> SEQUENCE: 139
gadgaraart ayccwccagg wttcta                                         26

<210> SEQ ID NO 140
<211> LENGTH: 24
<212> TYPE: DNA

```
<213> ORGANISM: Artificial
<220> FEATURE:
<223> OTHER INFORMATION: C. sonorensis xylose reductase amplification
      primer
<220> FEATURE:
<221> NAME/KEY: misc_feature
<223> OTHER INFORMATION: D = A/G/T; K = G/T; Y = C/T; W = A/T; R = A/G

<400> SEQUENCE: 140
ccadkyccaw ggrtyrttra atct                                            24

<210> SEQ ID NO 141
<211> LENGTH: 45
<212> TYPE: DNA
<213> ORGANISM: Artificial
<220> FEATURE:
<223> OTHER INFORMATION: C. sonorensis xylose reductase 5' flank
      amplification primer

<400> SEQUENCE: 141
actgtcgagc tcgtttaaac cttcaccttaa aattccccaa ttgag                    45

<210> SEQ ID NO 142
<211> LENGTH: 41
<212> TYPE: DNA
<213> ORGANISM: Artificial
<220> FEATURE:
<223> OTHER INFORMATION: C. sonorensis xylose reductase 5' flank
      amplification primer

<400> SEQUENCE: 142
actgacgcgt cgactcttgt ttgattgtgt gttgattgat c                         41

<210> SEQ ID NO 143
<211> LENGTH: 40
<212> TYPE: DNA
<213> ORGANISM: Artificial
<220> FEATURE:
<223> OTHER INFORMATION: C. sonorensis xylose reductase 3' flank
      amplification primer

<400> SEQUENCE: 143
ggcccgcggc cgctaagcag ctagtatagg caagatgtag                           40

<210> SEQ ID NO 144
<211> LENGTH: 36
<212> TYPE: DNA
<213> ORGANISM: Artificial
<220> FEATURE:
<223> OTHER INFORMATION: C. sonorensis xylose reductase 3' flank
      amplification primer

<400> SEQUENCE: 144
gggacgggcc caactgtaat aatccgactt tcaacg                               36

<210> SEQ ID NO 145
<211> LENGTH: 76
<212> TYPE: DNA
<213> ORGANISM: Artificial
<220> FEATURE:
<223> OTHER INFORMATION: Piromyces xylose isomerase gene amplification
      primer

<400> SEQUENCE: 145
ggacatgcat gcatttgggg tacccaaggc cttccgctct agaaaacaat ggctaaggaa     60
tatttcccac aaattc                                                    76
```

<210> SEQ ID NO 146
<211> LENGTH: 53
<212> TYPE: DNA
<213> ORGANISM: Artificial
<220> FEATURE:
<223> OTHER INFORMATION: Piromyces xylose isomerase gene amplification
      primer

<400> SEQUENCE: 146
ccaatgcatt ggttcctgca gggaattcga caacatcaaa gtctgggtta gtg         53

<210> SEQ ID NO 147
<211> LENGTH: 53
<212> TYPE: DNA
<213> ORGANISM: Artificial
<220> FEATURE:
<223> OTHER INFORMATION: S. cerevisiae xylulokinase gene amplification
      primer

<400> SEQUENCE: 147
aaggccttgc ggccgcctct agaaaacaat gttgtgttca gtaattcaga gac         53

<210> SEQ ID NO 148
<211> LENGTH: 35
<212> TYPE: DNA
<213> ORGANISM: Artificial
<220> FEATURE:
<223> OTHER INFORMATION: S. cerevisiae xylulokinase gene amplification
      primer

<400> SEQUENCE: 148
gaaaaggcct tgttcaatgg aaatttagcc tcgcg                             35

<210> SEQ ID NO 149
<211> LENGTH: 49
<212> TYPE: DNA
<213> ORGANISM: Artificial
<220> FEATURE:
<223> OTHER INFORMATION: C aberensis xylose isomerase gene amplification
      primer
<220> FEATURE:
<221> NAME/KEY: misc_feature
<223> OTHER INFORMATION: Y = C/T; M = A/C; R = A/G; S = G/C

<400> SEQUENCE: 149
aattaattcc tgcaggatgg ttaaggaata yttcycmrmc attsraaag              49

<210> SEQ ID NO 150
<211> LENGTH: 47
<212> TYPE: DNA
<213> ORGANISM: Artificial
<220> FEATURE:
<223> OTHER INFORMATION: C aberensis xylose isomerase gene amplification
      primer

<400> SEQUENCE: 150
aattaattcc tgcaggttac atgtacatag caacaatagc ttcgtaa                47

<210> SEQ ID NO 151
<211> LENGTH: 1314
<212> TYPE: DNA
<213> ORGANISM: Cyllamyces aberensis

<400> SEQUENCE: 151
atggttaagg aatacttccc cgccattcaa aagattaagt tcgaaggtaa ggattccaag   60
aatccaatgg ccttccacta ttacgatgct gaaaagaaa ttatgggtaa gagatgaag   120

```
gattggttac gtttcgctat ggcctggtgg cacactcttt gtgccgaagg ttctgaccaa    180
ttcggtccag gtactaagac tttcccatgg aacgaaggta ccgacccaat tgaaaaggct    240
aaacaaaagg tcgatgctgg tttcgaaatc atgaccaagc ttggtattga acactactgt    300
ttccacgatg ttgatcttgt tgatgaaggt aagaatgttg aagaatacga aaagaacctt    360
aagactatcg ttgcttacct taaggaaaag caaaaggaaa ctggtattaa acttctctgg    420
agtactgcta acgtcttcgg tcacaaacgt tacatgaacg gtgcttccac taacccagac    480
tttgatgttg ttgcccgtgc tattgttcaa attaagaacg ctatggatgc cggtattgaa    540
ctcggtgccg aaaactacgt cttctgggt ggtcgtgaag ttacatgag tctccttaac    600 actgaccaaa agcgtgaaaa ggaacacatg gctatgatgc tcggtttagc cagagattac    660
gctcgttcca agggtttcaa gggtactttc ctcattgaac aaagccaat ggaaccaacc    720 aagcaccaat acgatgttga cactgaaact gtcattggtt cctcagagc tcatggttta    780 gacaaggact tcaagattaa cattgaagtt aaccacgcta ctcttgctgg tcacactttc    840
gaacacgaac ttgcctgtgc tgttgatgcc ggtatgctcg gttctattga tgctaaccgt    900
ggtgattacc aaaacggttg ggatactgat caattcccaa ttgaccaata cgagcttgtt    960
caagcttgga tggaaattat ccgtggtggt ggtttcacta ctggtggtac taacttcgat   1020
gccaagactc gtcgtaactc taccgatctt gaagacatca ttattgccca catttctggt   1080
atggatgcta tggctcgtgc cctcgaaaac gctgccaagc tccttaccga atctccatac   1140
aagaagatga aggctgaccg ttacgcttcc ttcgactctg gtatgggtaa ggacttcgaa   1200
gatggtaagc ttaccttcga acaagtttac gaatacggta agaaggttaa cgaaccaaaa   1260
caaacctctg gtaaacaaga actttacgaa gctattgttg ctatgtacat gtaa          1314
```

<210> SEQ ID NO 152
<211> LENGTH: 437
<212> TYPE: PRT
<213> ORGANISM: Cyllamyces aberensis

<400> SEQUENCE: 152

```
Met Val Lys Glu Tyr Phe Pro Ala Ile Gln Lys Ile Lys Phe Glu Gly
1               5                   10                  15

Lys Asp Ser Lys Asn Pro Met Ala Phe His Tyr Tyr Asp Ala Glu Lys
            20                  25                  30

Glu Ile Met Gly Lys Lys Met Lys Asp Trp Leu Arg Phe Ala Met Ala
        35                  40                  45

Trp Trp His Thr Leu Cys Ala Glu Gly Ser Asp Gln Phe Gly Pro Gly
    50                  55                  60

Thr Lys Thr Phe Pro Trp Asn Glu Gly Thr Asp Pro Ile Glu Lys Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Asp Glu Gly Lys Asn
            100                 105                 110

Val Glu Glu Tyr Glu Lys Asn Leu Lys Thr Ile Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160
```

```
Phe Asp Val Val Ala Arg Ala Ile Val Gln Ile Lys Asn Ala Met Asp
                165                 170                 175
Ala Gly Ile Glu Leu Gly Ala Glu Asn Tyr Val Phe Trp Gly Gly Arg
            180                 185                 190
Glu Gly Tyr Met Ser Leu Leu Asn Thr Asp Gln Lys Arg Glu Lys Glu
        195                 200                 205
His Met Ala Met Met Leu Gly Leu Ala Arg Asp Tyr Ala Arg Ser Lys
    210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Val Ile Gly Phe Leu Arg
                245                 250                 255
Ala His Gly Leu Asp Lys Asp Phe Lys Ile Asn Ile Glu Val Asn His
            260                 265                 270
Ala Thr Leu Ala Gly His Thr Phe Glu His Glu Leu Ala Cys Ala Val
        275                 280                 285
Asp Ala Gly Met Leu Gly Ser Ile Asp Ala Asn Arg Gly Asp Tyr Gln
    290                 295                 300
Asn Gly Trp Asp Thr Asp Gln Phe Pro Ile Asp Gln Tyr Glu Leu Val
305                 310                 315                 320
Gln Ala Trp Met Glu Ile Ile Arg Gly Gly Phe Thr Thr Gly Gly
                325                 330                 335
Thr Asn Phe Asp Ala Lys Thr Arg Arg Asn Ser Thr Asp Leu Glu Asp
            340                 345                 350
Ile Ile Ile Ala His Ile Ser Gly Met Asp Ala Met Ala Arg Ala Leu
        355                 360                 365
Glu Asn Ala Ala Lys Leu Leu Thr Glu Ser Pro Tyr Lys Lys Met Lys
    370                 375                 380
Ala Asp Arg Tyr Ala Ser Phe Asp Ser Gly Met Gly Lys Asp Phe Glu
385                 390                 395                 400
Asp Gly Lys Leu Thr Phe Glu Gln Val Tyr Tyr Gly Lys Lys Val
                405                 410                 415
Asn Glu Pro Lys Gln Thr Ser Gly Lys Gln Glu Leu Tyr Glu Ala Ile
            420                 425                 430
Val Ala Met Tyr Met
        435

<210> SEQ ID NO 153
<211> LENGTH: 39
<212> TYPE: DNA
<213> ORGANISM: Artificial
<220> FEATURE:
<223> OTHER INFORMATION: K. marxianus Ura3 isolation primer

<400> SEQUENCE: 153
atatatgcat gccgtacctt agaatcctta tttgtatca                              39

<210> SEQ ID NO 154
<211> LENGTH: 39
<212> TYPE: DNA
<213> ORGANISM: Artificial
<220> FEATURE:
<223> OTHER INFORMATION: K. marxianus Ura3 isolation primer

<400> SEQUENCE: 154
atatatgcat gctaaactct ttttctttgg ttgtgaaat                              39
```

<210> SEQ ID NO 155
<211> LENGTH: 1805
<212> TYPE: DNA
<213> ORGANISM: Kluyveromyces marxianus

<400> SEQUENCE: 155

| | | | | | |
|---|---|---|---|---|---|
| ccgtacctta | gaatccttat | ttgtatcatc | actcccagtc | aacagtactc | taatataatg | 60 |
| cgtatagtca | aatctggccg | gtcgaaacag | ttttaatgga | gttctcatat | agaatgaagt | 120 |
| catctgataa | accatagatc | ttccaccagc | agttaaagca | ccaacaagtg | acgaattctg | 180 |
| attggaaaga | ccattctgct | ttacttttag | agcatcttgg | tcttctgagc | tcattatacc | 240 |
| tcaatcaaaa | ctgaaattag | gtgcctgtca | cggctctttt | tttactgtac | ctgtgacttc | 300 |
| ctttcttatt | tccaaggatg | ctcatcacaa | tacgcttcta | gatctattat | gcattataat | 360 |
| taatagttgt | agctacaaaa | ggtaaaagaa | agtccggggc | aggcaacaat | agaaatcggc | 420 |
| aaaaaaaact | acagaaatac | taagagcttc | ttccccattc | agtcatcgca | tttcgaaaca | 480 |
| agaggggaat | ggctctggct | agggaactaa | ccaccatcgc | ctgactctat | gcactaacca | 540 |
| cgtgactaca | tatatgtgat | cgttttaac | atttttcaaa | ggctgtgtgt | ctggctgttt | 600 |
| ccattaattt | tcactgatta | agcagtcata | ttgaatctga | gctcatcacc | aacaagaaat | 660 |
| actaccgtaa | aagtgtaaaa | gttcgtttaa | atcatttgta | aactggaaca | gcaagaggaa | 720 |
| gtatcatcag | ctagcccata | aactaatcaa | aggaggatgt | cgactaagag | ttactcggaa | 780 |
| agagcagctg | ctcatagaag | tccagttgct | gccaagcttt | taaacttgat | ggaagagaag | 840 |
| aagtcaaact | tatgtgcttc | tcttgatgtt | cgtaaaacaa | cagagttgtt | aagattagtt | 900 |
| gaggttttgg | gtccatatat | ctgtctattg | aagcacacatg | tagatatctt | ggaggatttc | 960 |
| agctttgaga | ataccattgt | gccgttgaag | caattagcag | agaaacacaa | gtttttgata | 1020 |
| tttgaagaca | ggaagtttgc | cgacattggg | aacactgtta | aattacaata | cacgtctggt | 1080 |
| gtataccgta | tcgccgaatg | gtctgatatc | accaatgcac | acggtgtgac | tggtgcgggc | 1140 |
| attgttgctg | gtttgaagca | aggtgccgag | gaagttacga | aagaacctag | agggttgtta | 1200 |
| atgcttgccg | agttatcgtc | caaggggtct | ctagcgcacg | gtaatacac | tcgtgggacc | 1260 |
| gtggaaattg | ccaagagtga | taaggacttt | gttattggat | ttattgctca | aaacgatatg | 1320 |
| ggtggaagag | aagagggcta | cgattggttg | atcatgacgc | caggtgttgg | tcttgatgac | 1380 |
| aaaggtgatg | ctttgggaca | acaatacaga | actgtggatg | aagttgttgc | cggtggatca | 1440 |
| gacatcatta | ttgttggtag | aggtctttc | gcaaagggaa | gagatcctgt | agtggaaggt | 1500 |
| gagagataca | gaaaggcggg | atgggacgct | tacttgaaga | gagtaggcag | atccgcttaa | 1560 |
| gagttctccg | agaacaagca | gaggttcgag | tgtactcgga | tcagaagtta | caagttgatc | 1620 |
| gtttatatat | aaactataca | gagatgttag | agtgtaatgg | cattgcgcac | attgtatacg | 1680 |
| ctacaagttt | agtcacgtgc | tagaagctgt | tttttttgcac | cgaaaatttt | tttttttttt | 1740 |
| ttttttgttt | tttggtgaag | tacattatgt | gaaatttcac | aaccaaagaa | aaagagttta | 1800 |
| gcatg | | | | | 1805 |

<210> SEQ ID NO 156
<211> LENGTH: 22
<212> TYPE: DNA
<213> ORGANISM: Artificial
<220> FEATURE:
<223> OTHER INFORMATION: K. marxianus Ura3 gene screening primer

<400> SEQUENCE: 156

```
agtgtattca ccgtgcgcta ga                                              22
```

<210> SEQ ID NO 157
<211> LENGTH: 22
<212> TYPE: DNA
<213> ORGANISM: Artificial
<220> FEATURE:
<223> OTHER INFORMATION: K. marxianus Ura3 gene screening primer

<400> SEQUENCE: 157

```
cccattcagt catcgcattt cg                                              22
```

<210> SEQ ID NO 158
<211> LENGTH: 22
<212> TYPE: DNA
<213> ORGANISM: Artificial
<220> FEATURE:
<223> OTHER INFORMATION: C. aberensis xylose isomerase gene internal
      screening primer

<400> SEQUENCE: 158

```
cgatgttgac actgaaactg tc                                              22
```

<210> SEQ ID NO 159
<211> LENGTH: 22
<212> TYPE: DNA
<213> ORGANISM: Artificial
<220> FEATURE:
<223> OTHER INFORMATION: C. aberensis xylose isomerase gene internal
      screening primer

<400> SEQUENCE: 159

```
gaagtcctta cccataccag ag                                              22
```

<210> SEQ ID NO 160
<211> LENGTH: 42
<212> TYPE: DNA
<213> ORGANISM: Artificial
<220> FEATURE:
<223> OTHER INFORMATION: B. thetaiotamicron xylose isomerase gene
      isolation primer

<400> SEQUENCE: 160

```
aattaattcc tgcaggatgg caacaaaaga attttttccg gg                        42
```

<210> SEQ ID NO 161
<211> LENGTH: 43
<212> TYPE: DNA
<213> ORGANISM: Artificial
<220> FEATURE:
<223> OTHER INFORMATION: B. thetaiotamicron xylose isomerase gene
      isolation primer

<400> SEQUENCE: 161

```
aattaattcc tgcaggttag caatacatat tcagaattgc ctc                       43
```

<210> SEQ ID NO 162
<211> LENGTH: 1317
<212> TYPE: DNA
<213> ORGANISM: Bacteroides thetaiotaomicron

<400> SEQUENCE: 162

```
atggcaacaa agaattttt tccgggaatt gaaagatta aatttgaagg taaagatagt       60
aagaacccga tggcattccg ttattacgat gcagagaagg tgattaatgg taaaaagatg    120
aaggattggc tgagattcgc tatggcatgg tggcacacat tgtgcgctga aggtggtgat    180
```

```
cagttcggtg gcggaacaaa gcaattccca tggaatggta atgcagatgc tatacaggca      240 gcaaagata agatggatgc aggatttgaa ttcatgcaga agatgggtat cgaatactat       300
tgcttccatg acgtagactt ggtttcggaa ggtgccagtg tagaagaata cgaagctaac      360
ctgaaagaaa tcgtagctta tgcaaaacag aaacaggcag aaaccggtat caaactactg      420
tggggtactg ctaatgtatt cggtcacgcc cgctatatga acggtgcagc taccaatcct      480
gacttcgatg tagtagctcg tgctgctgtt cagatcaaaa atgcgattga tgcaacgatt      540
gaacttggcg gagagaatta tgtgttttgg ggtggtcgtg aaggctatat gtctcttctg      600
aacacagatc agaaacgtga aaagaacac cttgcacaga tgttgacgat gctcgtgac       660 tatgcccgtg cccgtggttt caaaggtact ttcctgatcg aaccgaaacc gatggaaccg      720
actaaacatc aatatgacgt agatacggaa actgtaatcg gcttcctgaa agctcatggt      780
ctggataagg atttcaaagt aaatatcgag gtgaatcacg caactttggc aggtcacact      840
ttcgagcatg aattggctgt agctgtagac aatggtatgt tgggctcaat tgacgccaat      900
cgtggtgact atcagaatgg ctgggataca gaccaattcc cgatcgacaa ttatgaactg      960
actcaggcta tgatgcagat tatccgtaat ggtggtctcg gtaccggtgg tacgaacttt     1020
gatgctaaaa cccgtcgtaa ttctactgat ctggaagata tctttattgc tcacatcgca     1080
ggtatggacg ctatggcccg tgcactcgaa agtgcagcgg ctctgctcga cgaatctccc     1140
tataagaaga tgctggctga ccgttatgct tcatttgatg ggggcaaagg taagaatttt     1200
gaagacggca agctgactct ggaggatgtg gttgcttatg caaaaacaaa aggcgaaccg     1260
aaacagacta gcggcaagca agaactttat gaggcaattc tgaatatgta ttgctaa        1317
```

<210> SEQ ID NO 163
<211> LENGTH: 438
<212> TYPE: PRT
<213> ORGANISM: Bacteroides thetaiotaomicron

<400> SEQUENCE: 163

```
Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
            20                  25                  30

Lys Val Ile Asn Gly Lys Lys Met Lys Asp Trp Leu Arg Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175
```

Asp Ala Thr Ile Glu Leu Gly Gly Glu Asn Tyr Val Phe Trp Gly Gly
            180                 185                 190

Arg Glu Gly Tyr Met Ser Leu Leu Asn Thr Asp Gln Lys Arg Glu Lys
            195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
            245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
            325                 330                 335

Gly Thr Asn Phe Asp Ala Lys Thr Arg Arg Asn Ser Thr Asp Leu Glu
        340                 345                 350

Asp Ile Phe Ile Ala His Ile Ala Gly Met Asp Ala Met Ala Arg Ala
    355                 360                 365

Leu Glu Ser Ala Ala Ala Leu Leu Asp Glu Ser Pro Tyr Lys Lys Met
    370                 375                 380

Leu Ala Asp Arg Tyr Ala Ser Phe Asp Gly Lys Gly Lys Glu Phe
385                 390                 395                 400

Glu Asp Gly Lys Leu Thr Leu Glu Asp Val Val Ala Tyr Ala Lys Thr
            405                 410                 415

Lys Gly Glu Pro Lys Gln Thr Ser Gly Lys Gln Glu Leu Tyr Glu Ala
            420                 425                 430

Ile Leu Asn Met Tyr Cys
        435

<210> SEQ ID NO 164
<211> LENGTH: 19
<212> TYPE: DNA
<213> ORGANISM: Artificial
<220> FEATURE:
<223> OTHER INFORMATION: B. thetaiotamicron xylose isomerase gene
      screening primer

<400> SEQUENCE: 164
ggcgtgaatg taagcgtga                                                    19

<210> SEQ ID NO 165
<211> LENGTH: 21
<212> TYPE: DNA
<213> ORGANISM: Artificial
<220> FEATURE:
<223> OTHER INFORMATION: B. thetaiotamicron xylose isomerase gene
      screening primer

<400> SEQUENCE: 165
ctgtagacaa tggtatgttg g                                                 21

```
<210> SEQ ID NO 166
<211> LENGTH: 32
<212> TYPE: DNA
<213> ORGANISM: Artificial
<220> FEATURE:
<223> OTHER INFORMATION: K. marxianus PDC promoter, Piromyces xylose
      isomerase and S. cerevisiae CYC1 terminator amplification primer

<400> SEQUENCE: 166
attgttaatt aactctctaa acttgaacag cc                                    32

<210> SEQ ID NO 167
<211> LENGTH: 34
<212> TYPE: DNA
<213> ORGANISM: Artificial
<220> FEATURE:
<223> OTHER INFORMATION: K. marxianus PDC promoter, Piromyces xylose
      isomerase and S. cerevisiae CYC1 terminator amplification primer

<400> SEQUENCE: 167
attaatacgc gtagcttgca aattaaagcc ttcg                                  34
```

GENETICALLY MODIFIED YEAST SPECIES, AND FERMENTATION PROCESSES USING GENETICALLY MODIFIED YEAST

CROSS-REFERENCE TO RELATED APPLICATION

This application is a continuation of copending application Ser. No. 14/035,238, filed 24 Sep. 2013, which is a continuation of copending application Ser. No. 13/107,882, filed 14 May 2011, which is a divisional of application Ser. No. 10/554,887, filed 28 Oct. 2005, now U.S. Pat. No. 7,943,366, which is a ¶371 application corresponding to PCT/US04/013592, filed 3 May 2004, which claims benefit of U.S. provisional application 60/467,727, filed 2 May 2003.

This application claims benefit of U.S. Provisional Application No. 60/467,727, filed May 2, 2003.

This invention was made under contract no. DE-FC07-021D14349 with the United States Department of Energy. The United States Government has certain rights to this invention.

This invention relates to certain genetically modified yeast species.

Because of the gradual depletion of world-wide petroleum and natural gas feedstocks, a desire on the part of oil-importing nations to decrease their dependence on foreign sources of oil, and a desire to establish a more sustainable basis to the economy, much effort is being devoted to the production of fuels and organic chemicals and plastics from alternative feedstocks. Fermentation processes offer the possibility of producing a variety of fuels and chemicals from naturally-occurring sugar sources. For example, ethanol is produced in significant quantity by fermenting glucose, most typically glucose obtained by hydrolysing corn starch. A yeast species, *Saccharomyces cerevisiae*, is a common biocatalyst for fermenting glucose to ethanol.

These sugars represent a relatively expensive carbon source. Biomass, i.e. plant matter hydrolysate, offers the possibility of being a particularly inexpensive source of carbon. Biomass consists mainly of cellulose and hemicellulose. Cellulose can be broken down into hexose sugars, typically glucose. Most yeasts, including *S. cerevisiae*, metabolise hexose sugars quite efficiently. Hemicellulose, on the other hand, is rich in pentose sugars such as xylose, so efficient carbon utilization requires that these pentose sugars be metabolised as well. Very few yeast efficiently metabolize xylose to ethanol or other desirable fermentation products. So, in order to exploit the full economic potential offered by using biomass carbon sources, it is necessary to provide a biocatalyst that can efficiently convert xylose to desirable fermentation products.

Various bacteria are capable of metabolising xylose into fermentation products, but these generally produce a mixture of products, rather than a single predominant product as is usually desired. The common by-products are sometimes toxic to the bacteria. Even though certain bacteria have been metabolically engineered to perform homoethanolic fermentions, bacteria tend to perform poorly in the harsh environment of lignocellulosic hydrolysates, which are a common source of xylose-rich substrates.

Some yeast species such as *S. cerevisiae* are known to ferment hexose sugars predominantly into ethanol, rather than the mixtures of products typically produced by bacteria. Some yeasts have other characteristics that make them good candidates for various types of fermentation process, such as resistance to low pH environments, resistance to certain fermentation co-products such as acetic acid and furfural, and resistance to ethanol itself.

Most yeast species metabolise xylose (if at all) via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via an XK enzyme. This pathway operates inefficiently in yeast species because it introduces a redox imbalance in the cell. The xylose-to-xylitol step uses NADH as a cofactor, whereas the xylitol-to-xylulose step uses NADPH as a cofactor. Other processes must operate to restore the redox imbalance within the cell. This often means that the organism cannot grow anaerobically on xylose or other pentose sugar.

Nonetheless, attempts have been made to introduce exogenous XR and XDH genes into yeast species such as *S. cerevisiae* in order to achieve conversion of xylose to ethanol. See, for example, U.S. Pat. No. 5,866,382, WO 95/13362 and WO 97/42307. The engineered yeast did not produce ethanol efficiently.

Other organisms can isomerise xylose into xylulose and then phosphorylate the xylulose to xylulose 5-phosphate, which then is further metabolised through the cell's central carbon pathway. The isomerization is promoted by a catalytic enzyme, xylose isomerase (XI) and the phosphorylation is catalysed by a xylulokinase (XK) enzyme. This pathway is common in bacteria, but relatively rare in eukaryotic species such as yeast. It does not create the redox imbalance created in the xylose-to-xylitol-to-xylulose pathway, and thus is in principle a more efficient anaerobic mechanism. An anaerobic fungus, *Piromyces* sp. E2 (ATCC 76762), is known to possess a gene that expresses an active XI enzyme.

However, no wild type or recombinant yeast species has had the capacity to efficiently produce desirable fermentation products from xylose or other pentose sugar feedstocks. An attempt to introduce the *Piromyces* sp. E2 XI gene into *S. cerevisiae* resulted in very slow growth on xylose and did not result in reported ethanol production. See Kuyper et al., "High-Level Functional Expression of a Fungal Xylose Isomerase: The Key to Efficient Ethanolic Fermentation of Xylose by *Saccharomyces Cerevisiae*?", FEMS Yeast Research 1574 (2003) 1-10, and WO 03/062430A1.

A yeast species that can efficiently ferment xylose and other pentose sugars into a desired fermentation product is therefore very desirable.

In one aspect, this invention is a genetically modified yeast cell having a functional, exogenous xylose isomerase gene, wherein the exogenous xylose isomerase gene is operatively linked to promoter and terminator sequences that are functional in the yeast cell, and the modified yeast cell further has a deletion or disruption of a native gene that encodes for an enzyme that catalyzes the conversion of xylose to xylitol.

In a second aspect, this invention is a genetically modified yeast cell of the genera *Kluyveromyces* or *Candida*, having integrated into its genome a functional, exogenous xylose isomerase gene, wherein the exogenous xylose isomerase gene is operatively linked to promoter and terminator sequences that are functional in the yeast cell.

In another aspect, this invention is a genetically modified yeast cell having a functional, exogenous xylose isomerase gene, wherein the exogenous xylose isomerase gene is operatively linked to promoter and terminator sequences that are functional in the yeast cell, and which further contains a functional, exogenous xylulokinase gene operatively linked to promoter and terminator sequences that are functional in the yeast cell.

In still another aspect, this invention is a genetically modified yeast cell having a deletion or disruption of a functional, native gene that produces an enzyme that catalyzes the reaction of xylitol to xylulose or of xylulose to xylitol.

In another aspect, this invention a genetically modified yeast cell having a deletion or disruption of a native gene that produces an enzyme that catalyzes the conversion of xylose to xylitol.

In a still further aspect, this invention is fermentation process in which a cell of any of the preceding aspects is cultured under fermentation conditions in a fermentation broth that includes a pentose sugar.

Figure 2:
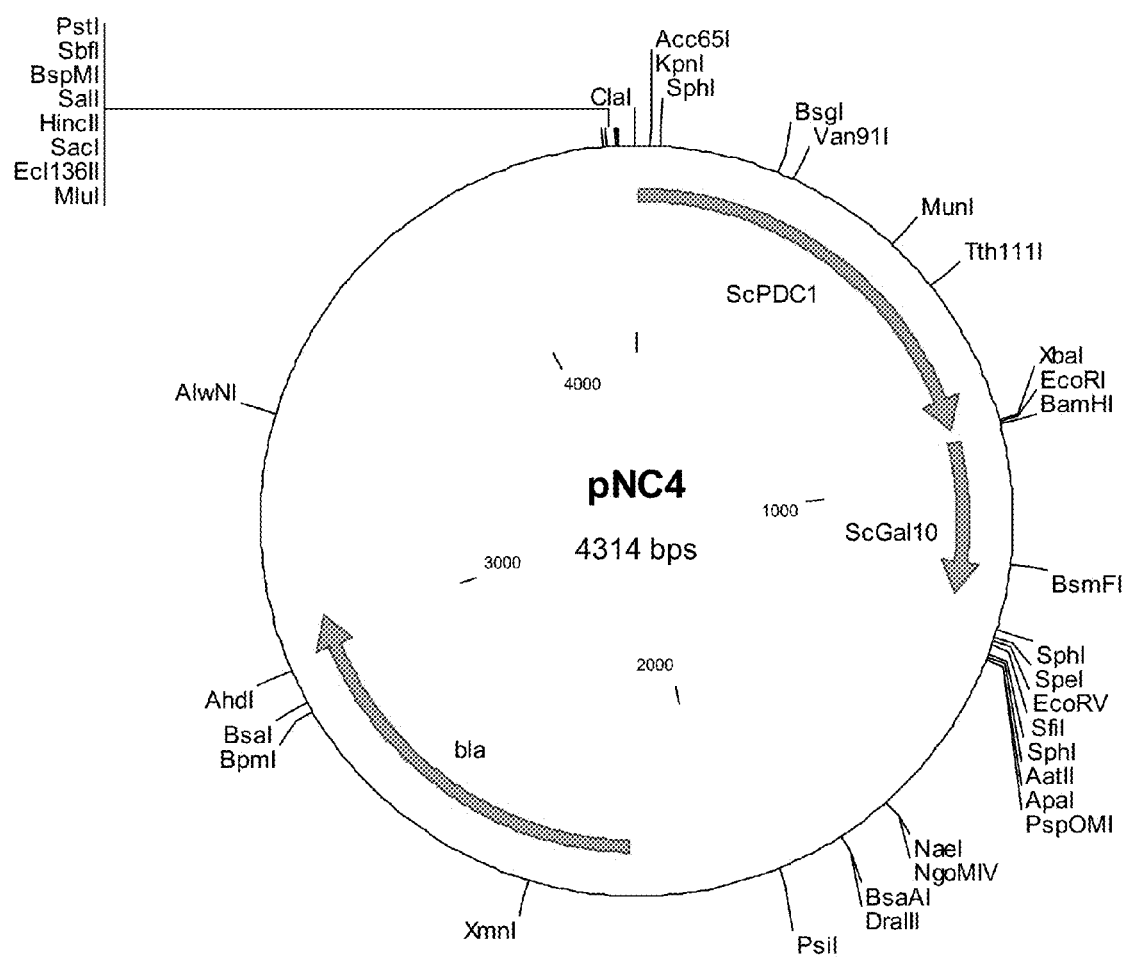
Figure 3:
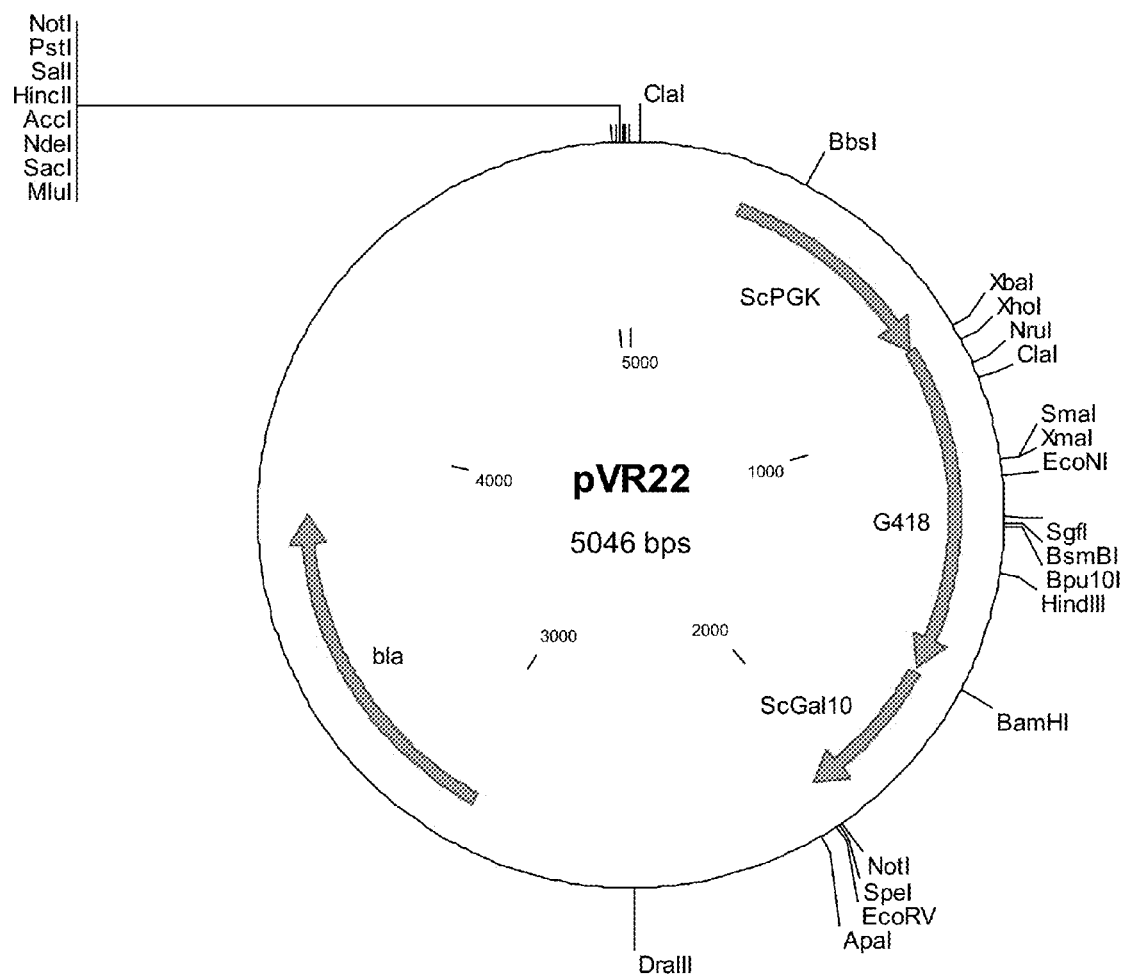
Figure 4:
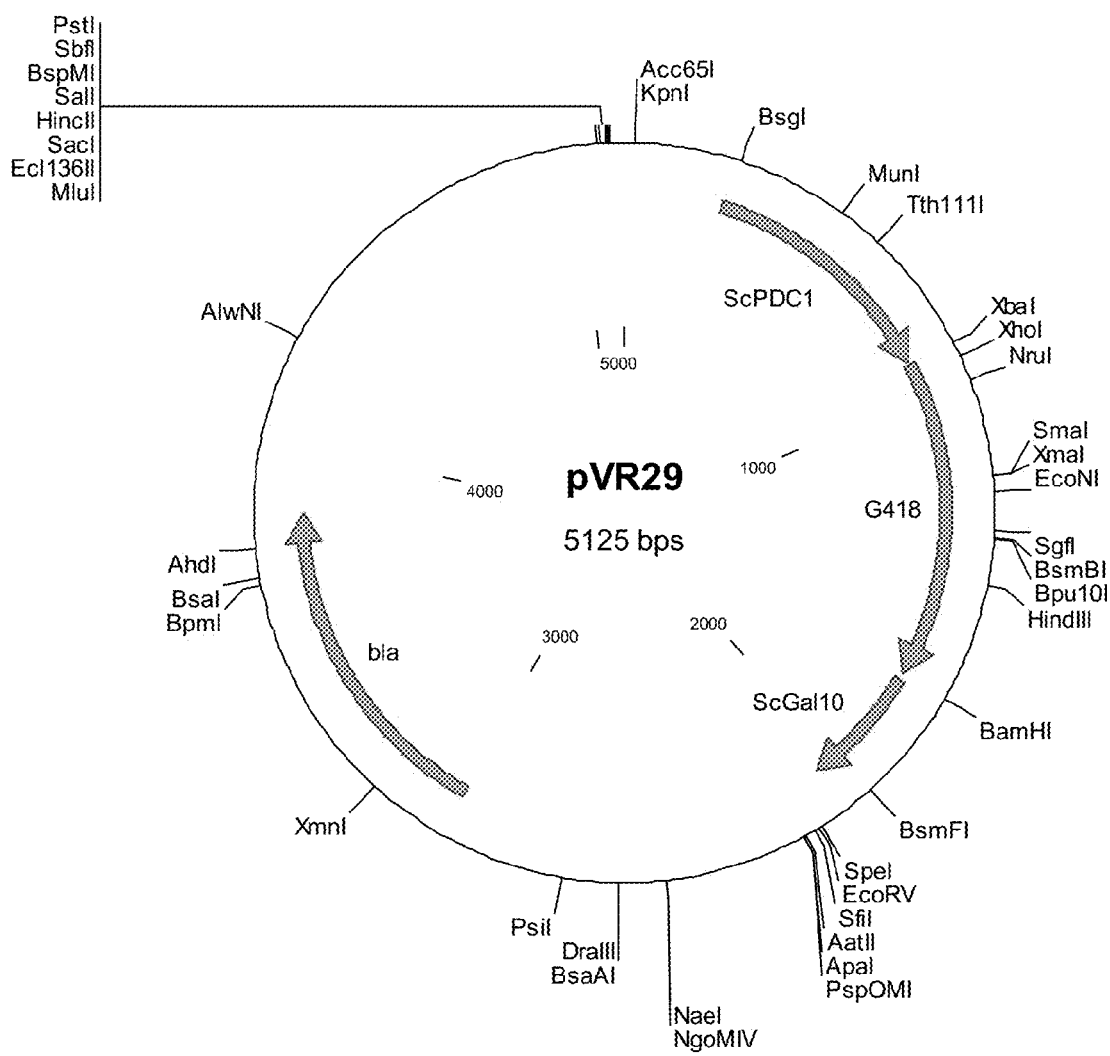
Figure 5:
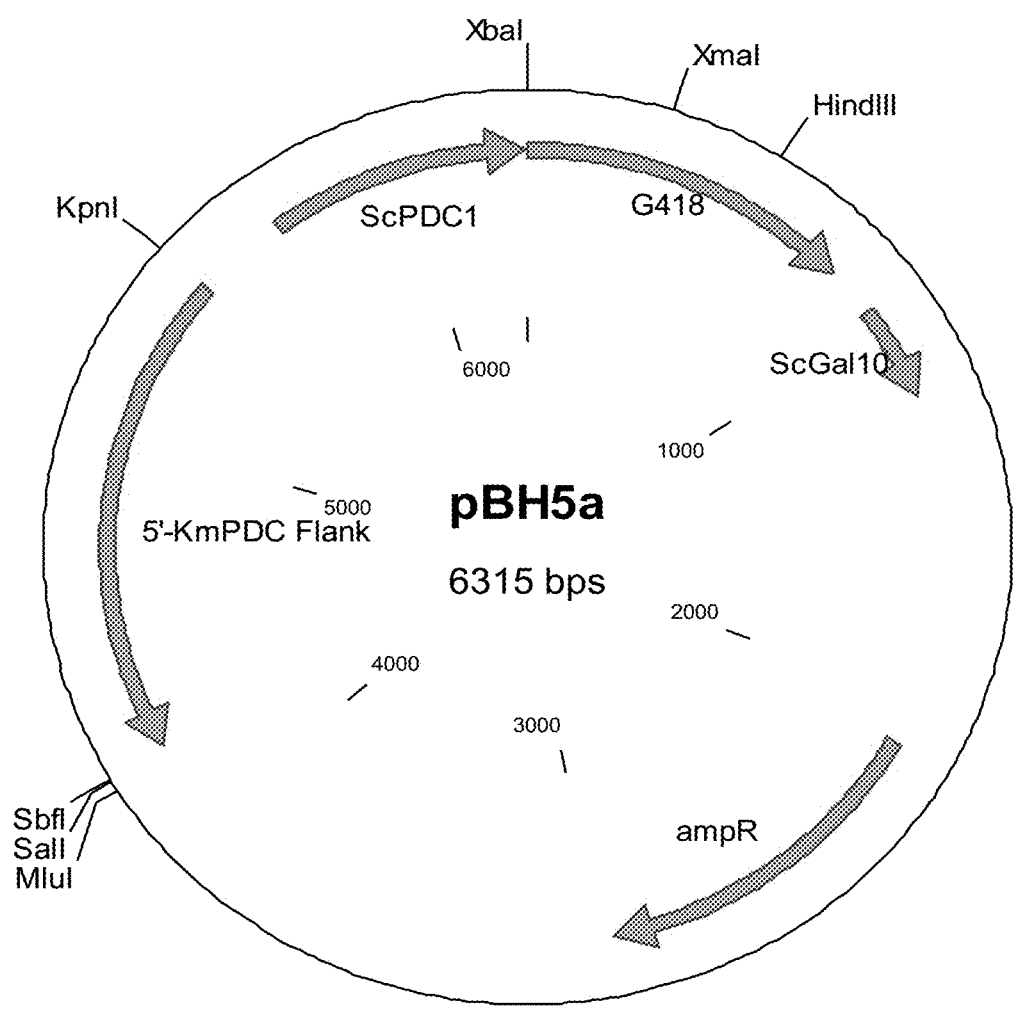
Figure 6:
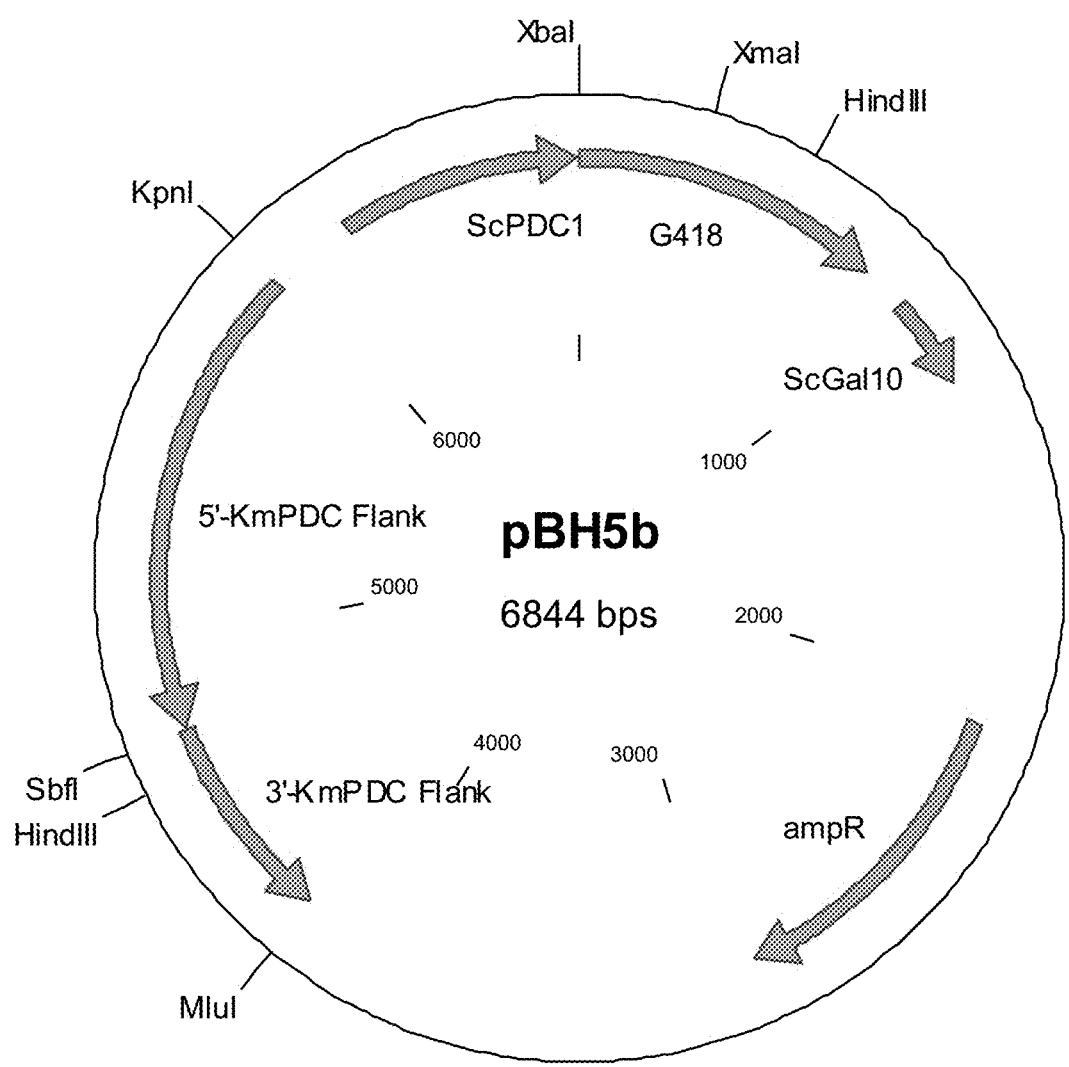
Figure 7:
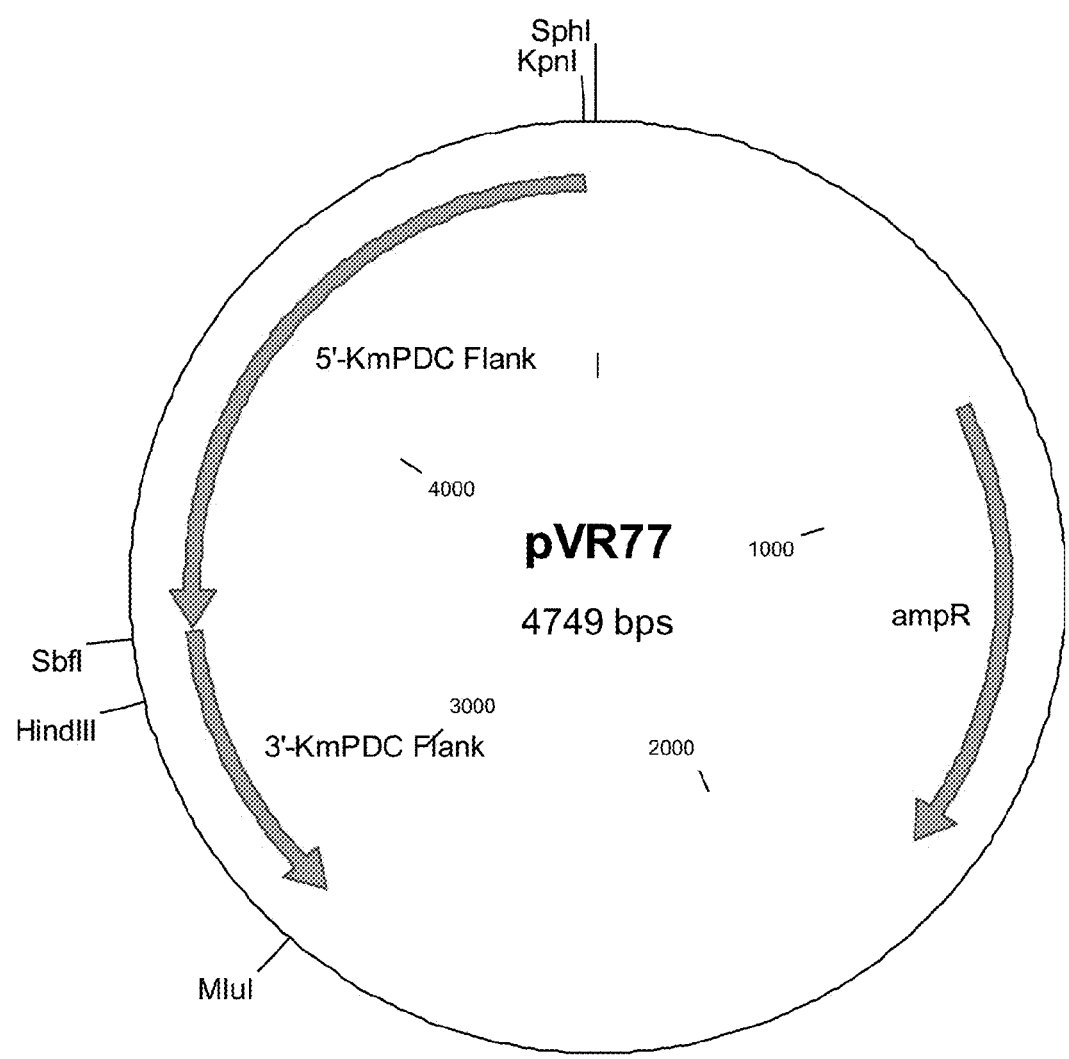
Figure 8:
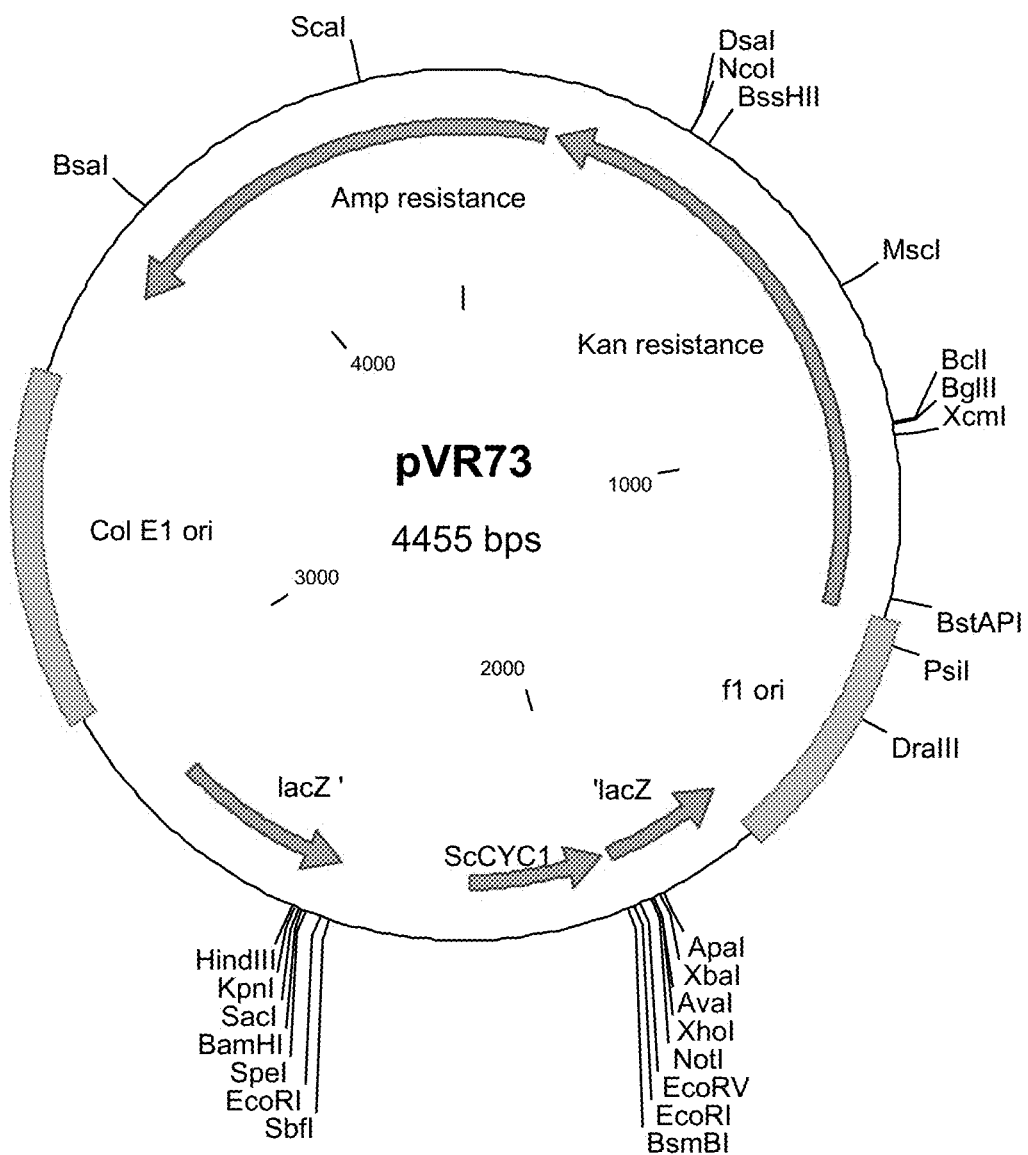
Figure 9:
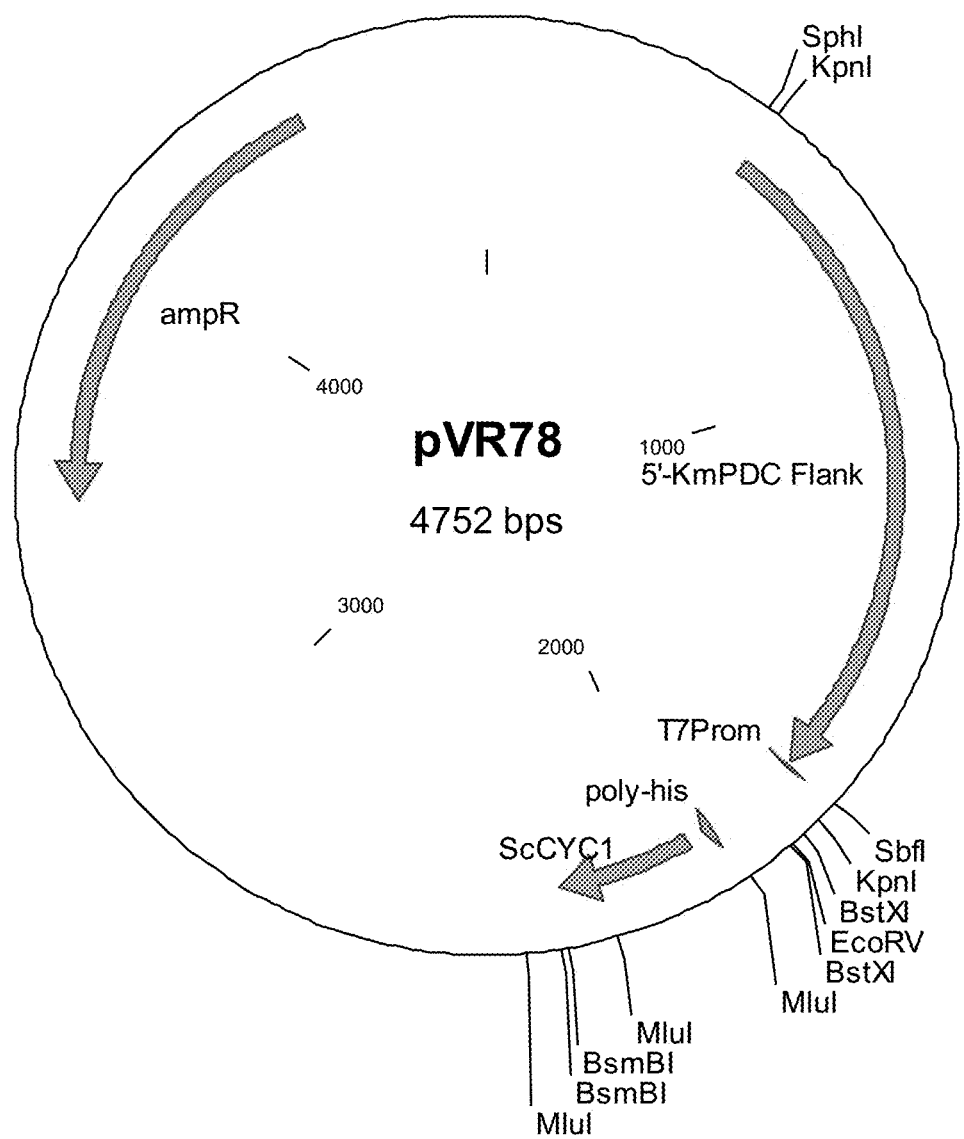
Figure 10:
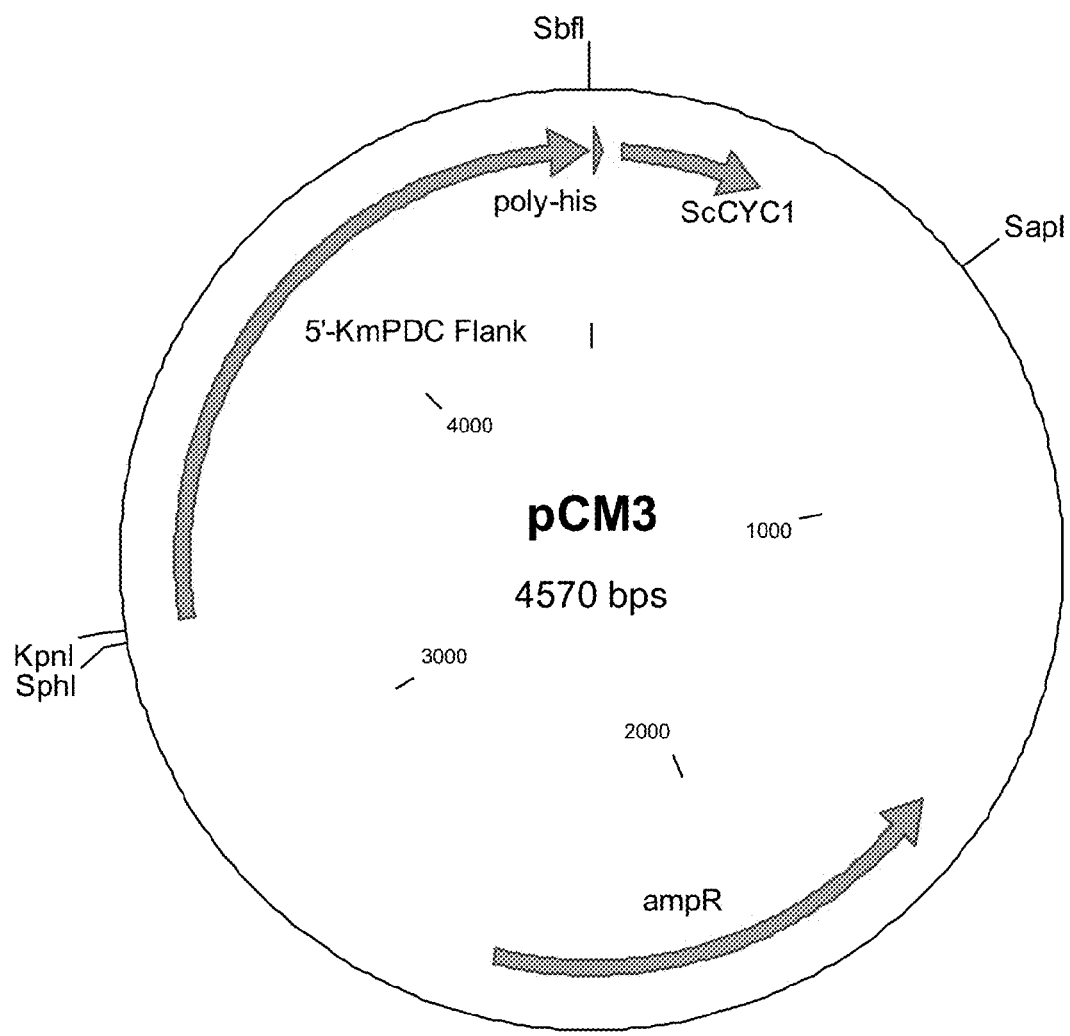
Figure 11:
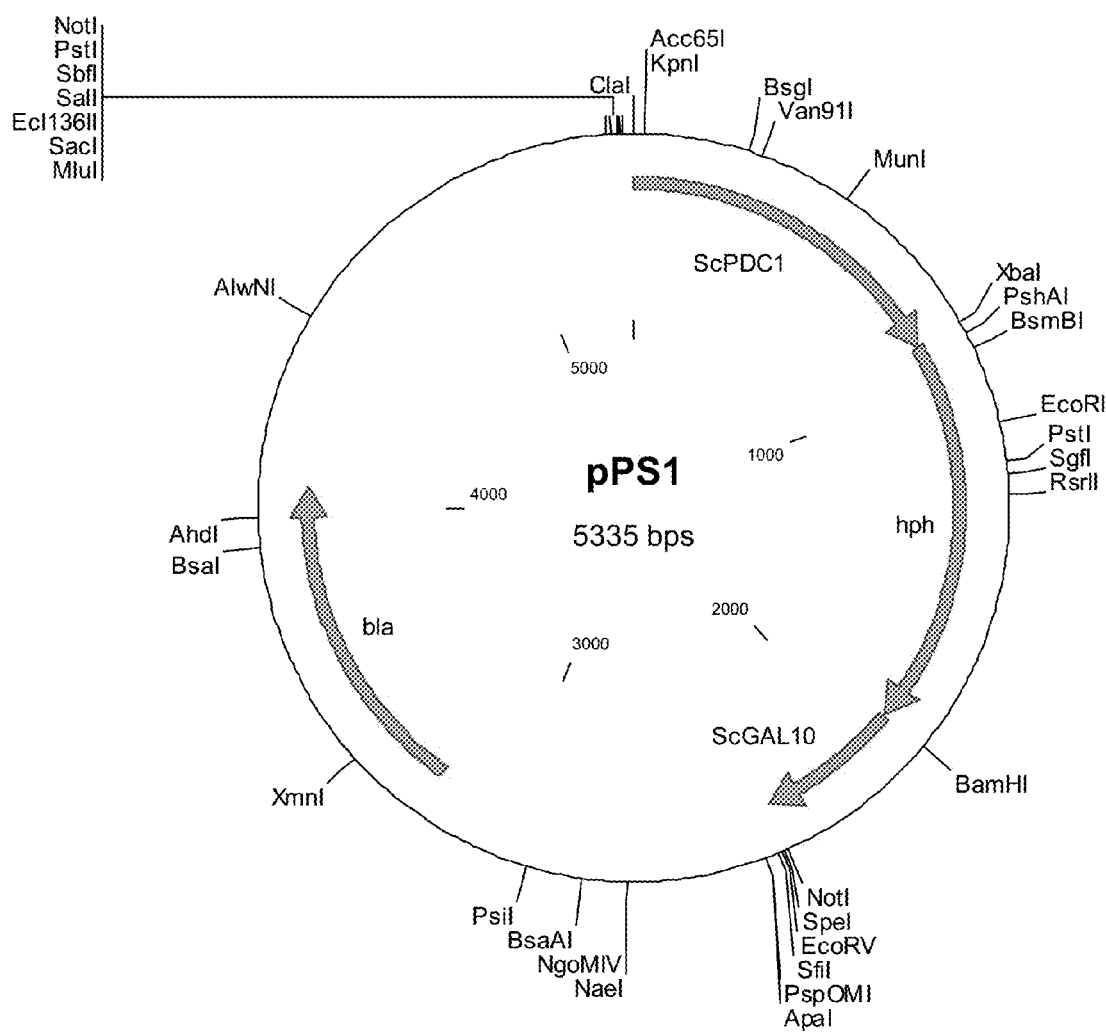
Figure 12:
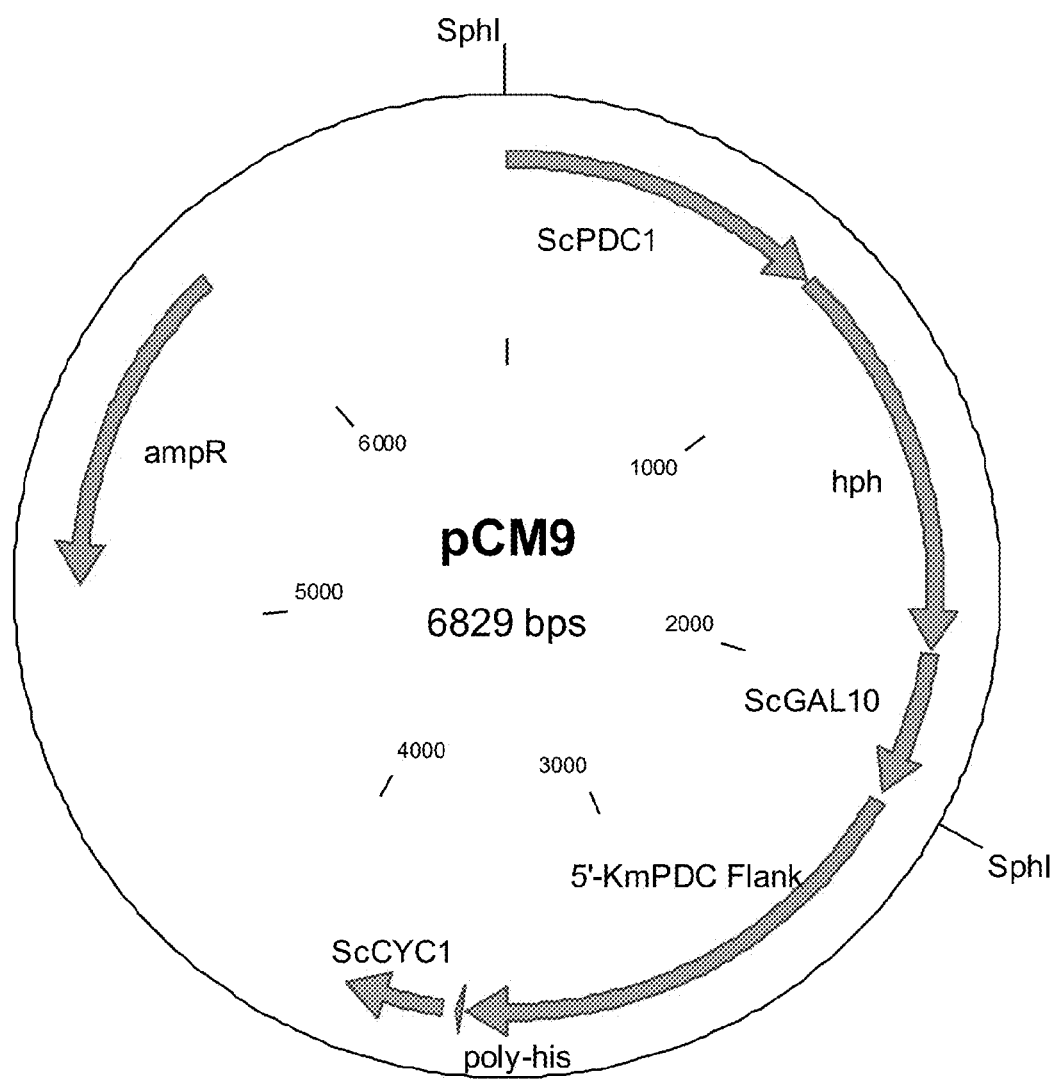
Figure 13:
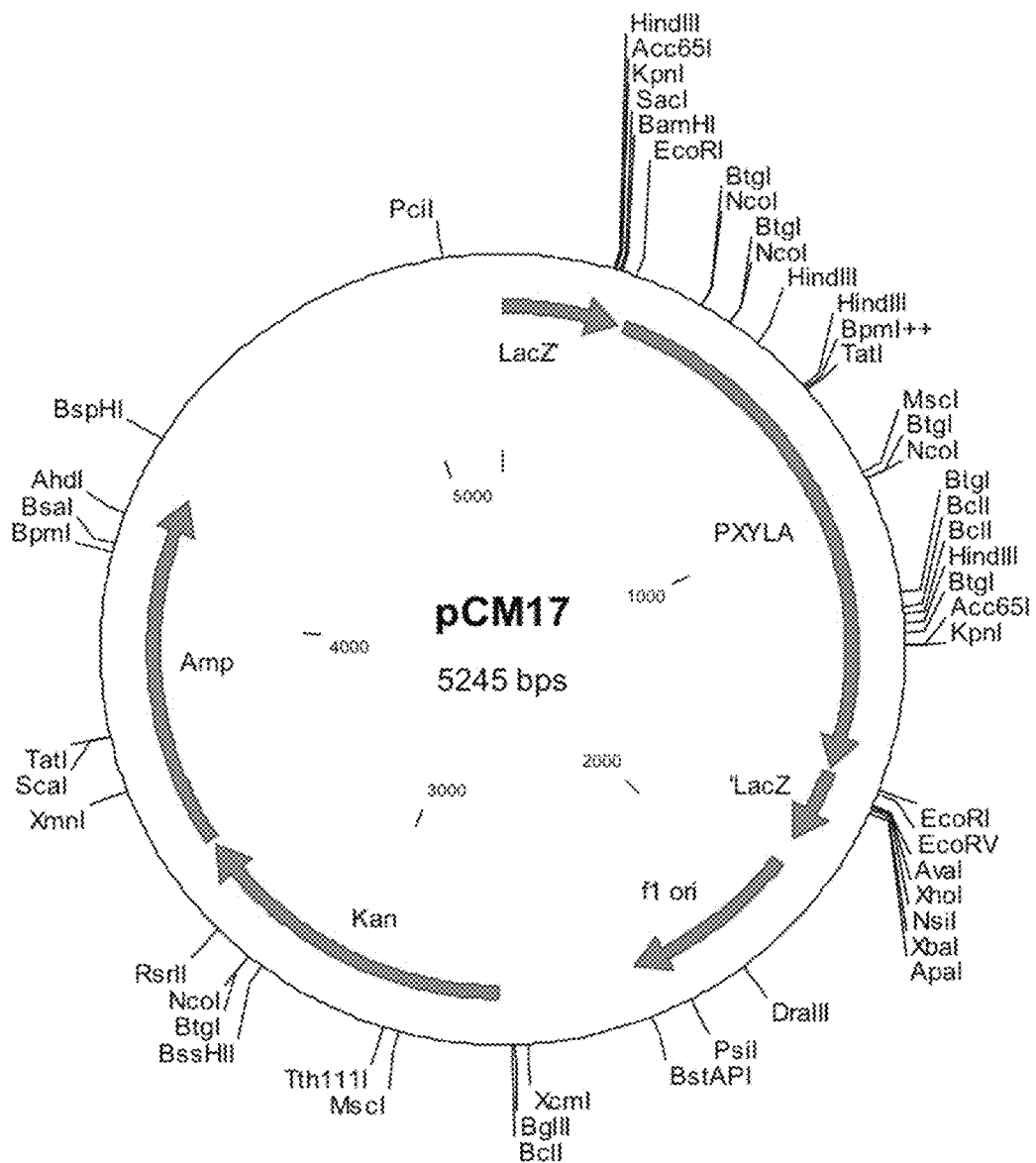
Figure 14:
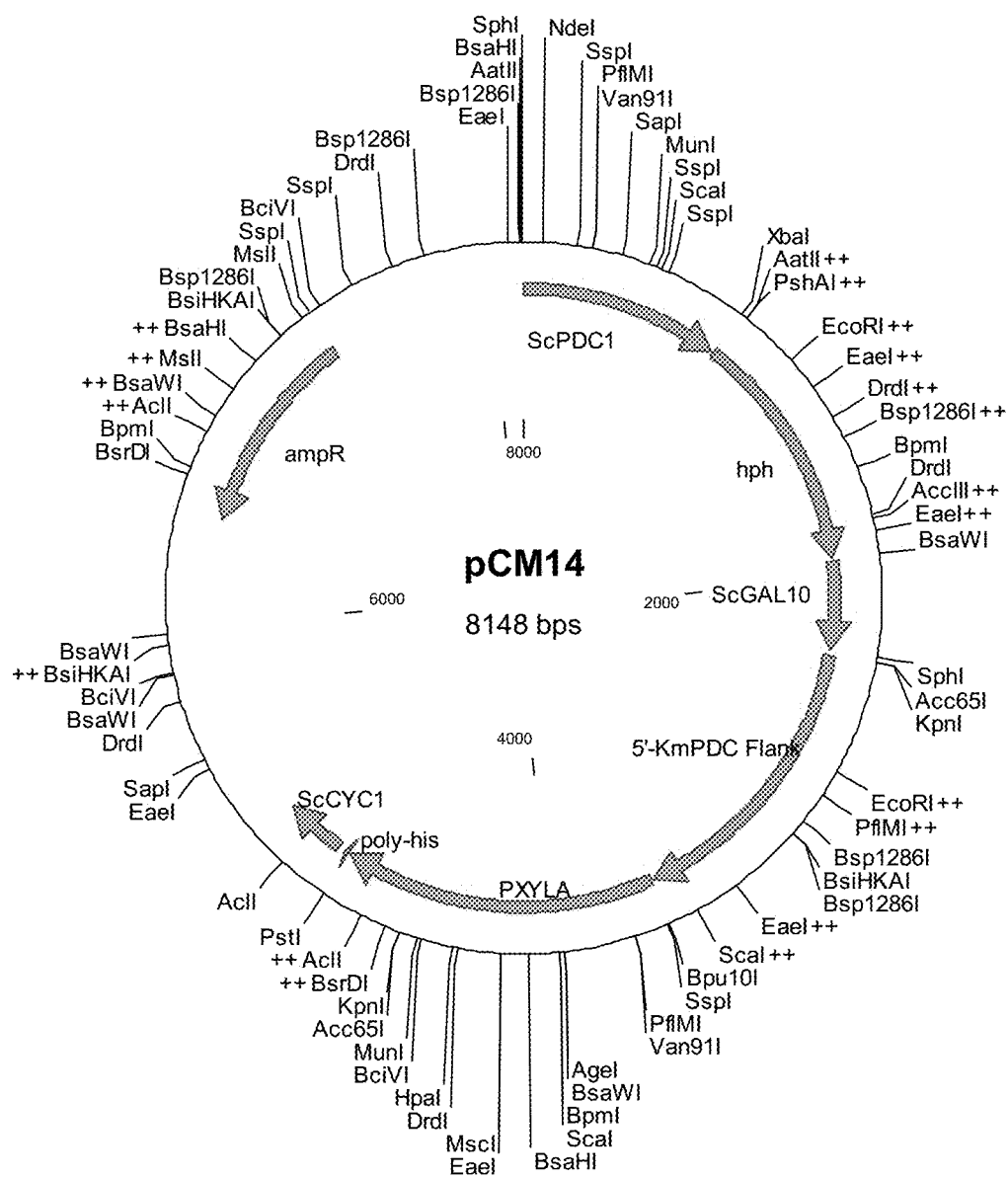
Figure 15:
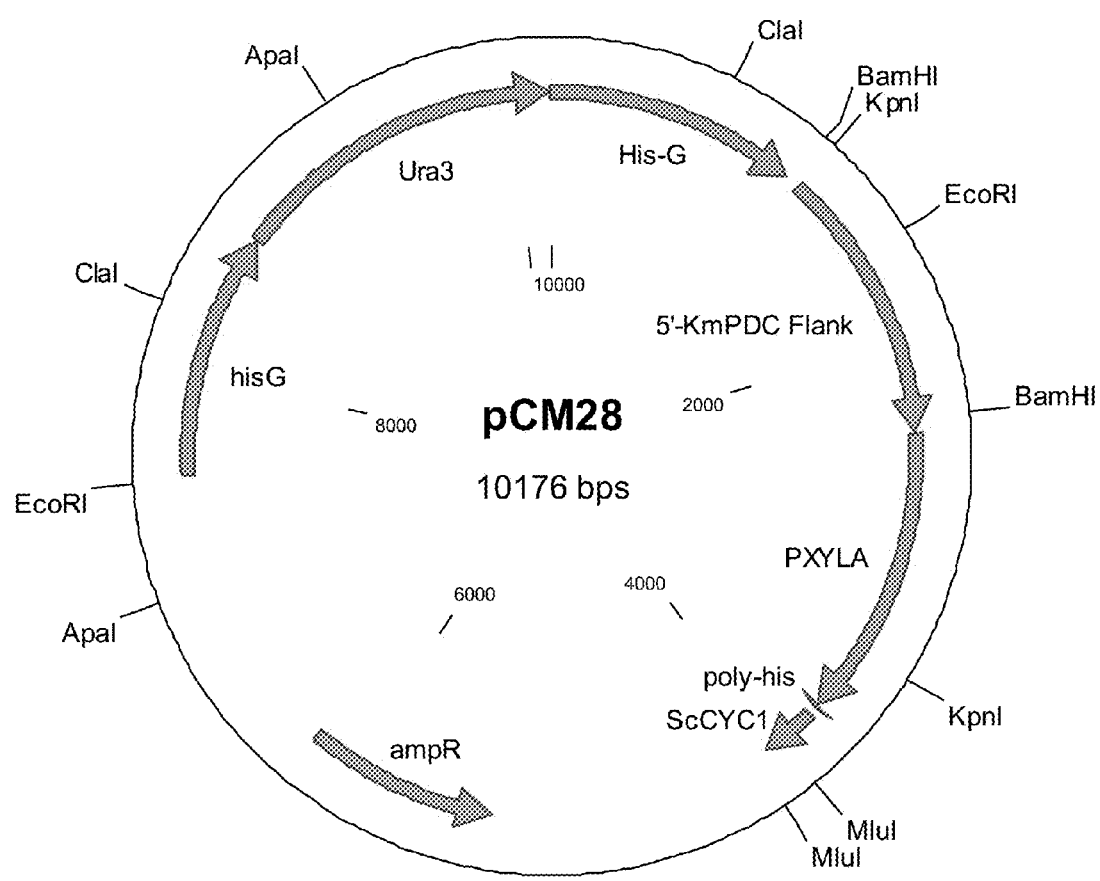
Figure 16:
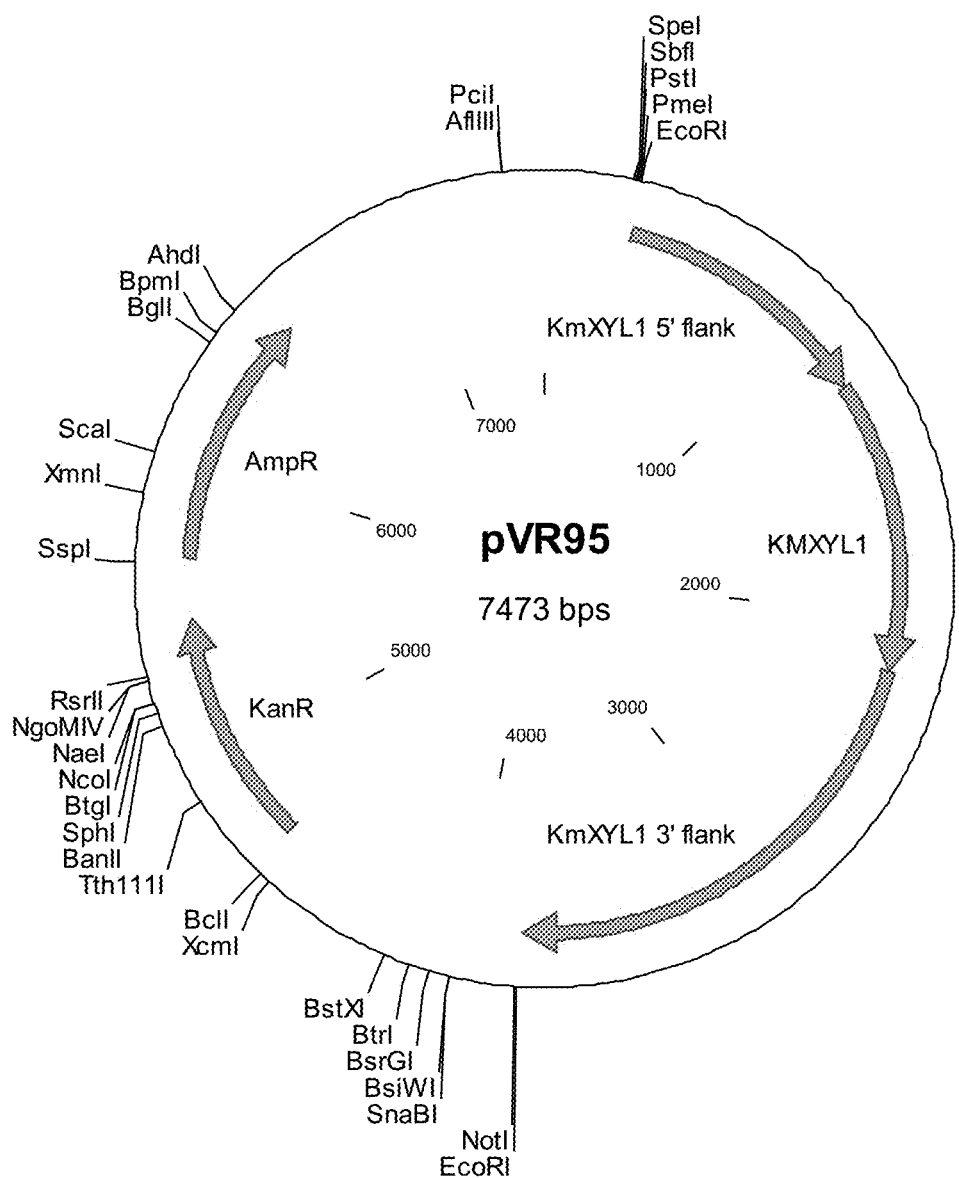
Figure 17:
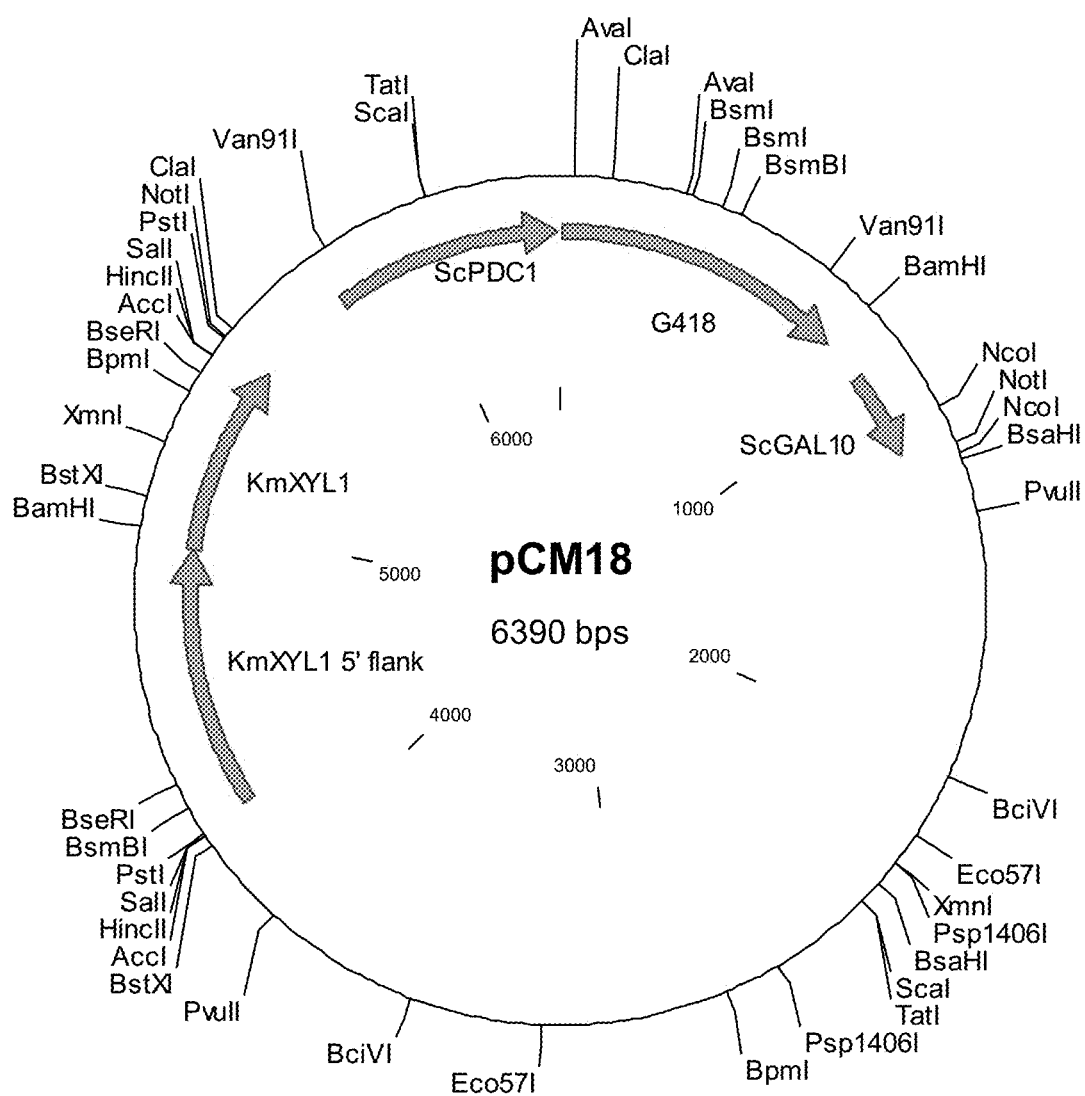
Figure 18:
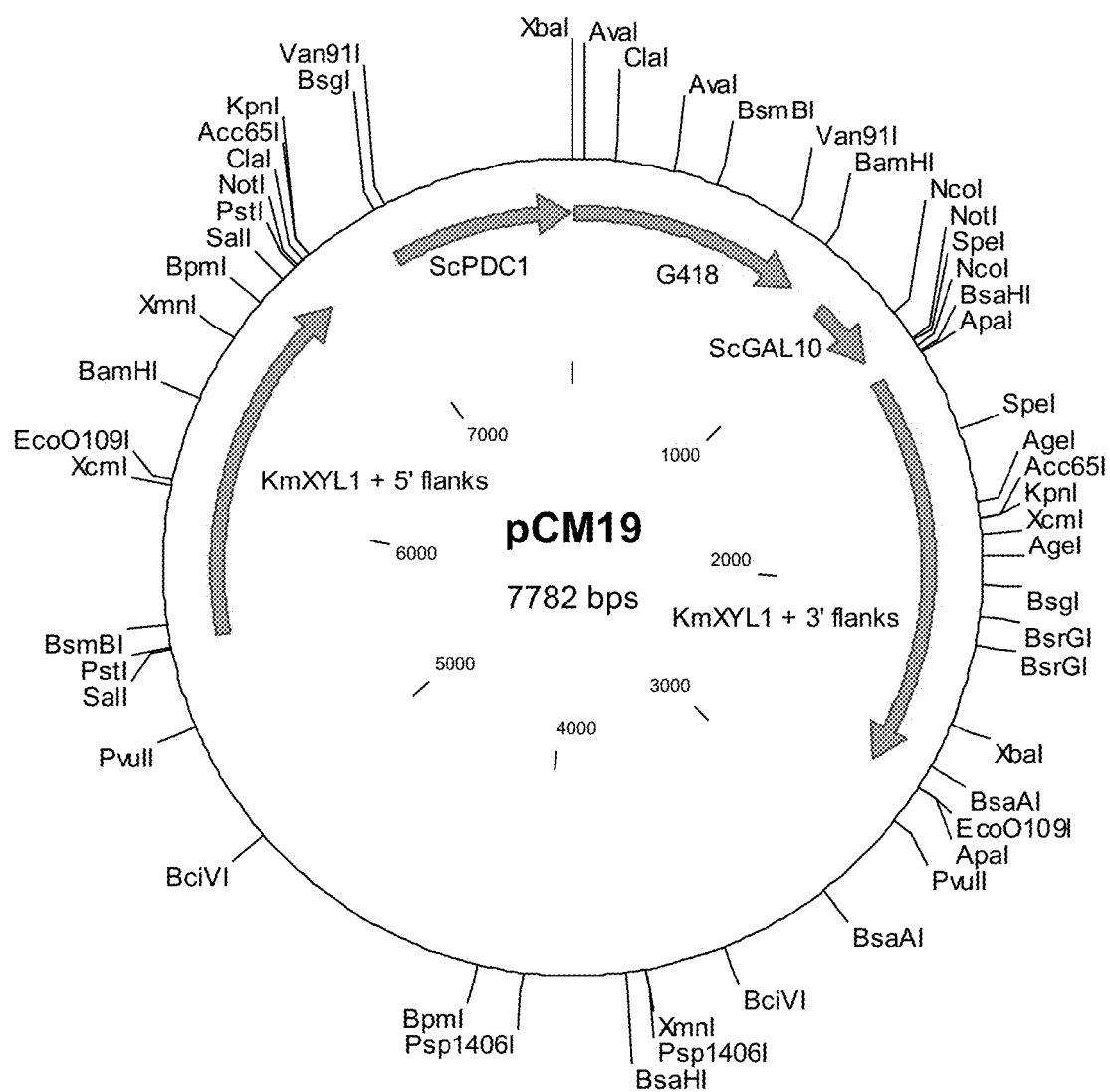
Figure 19:
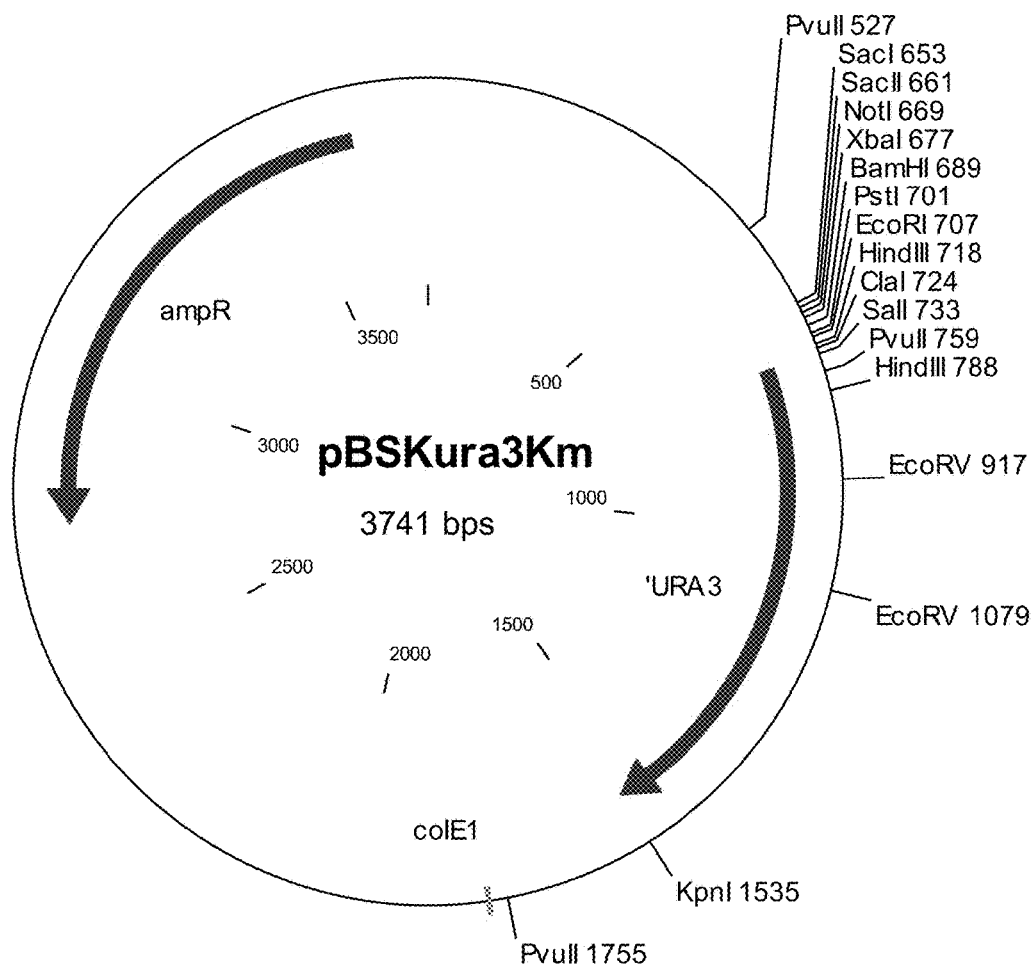
Figure 20:
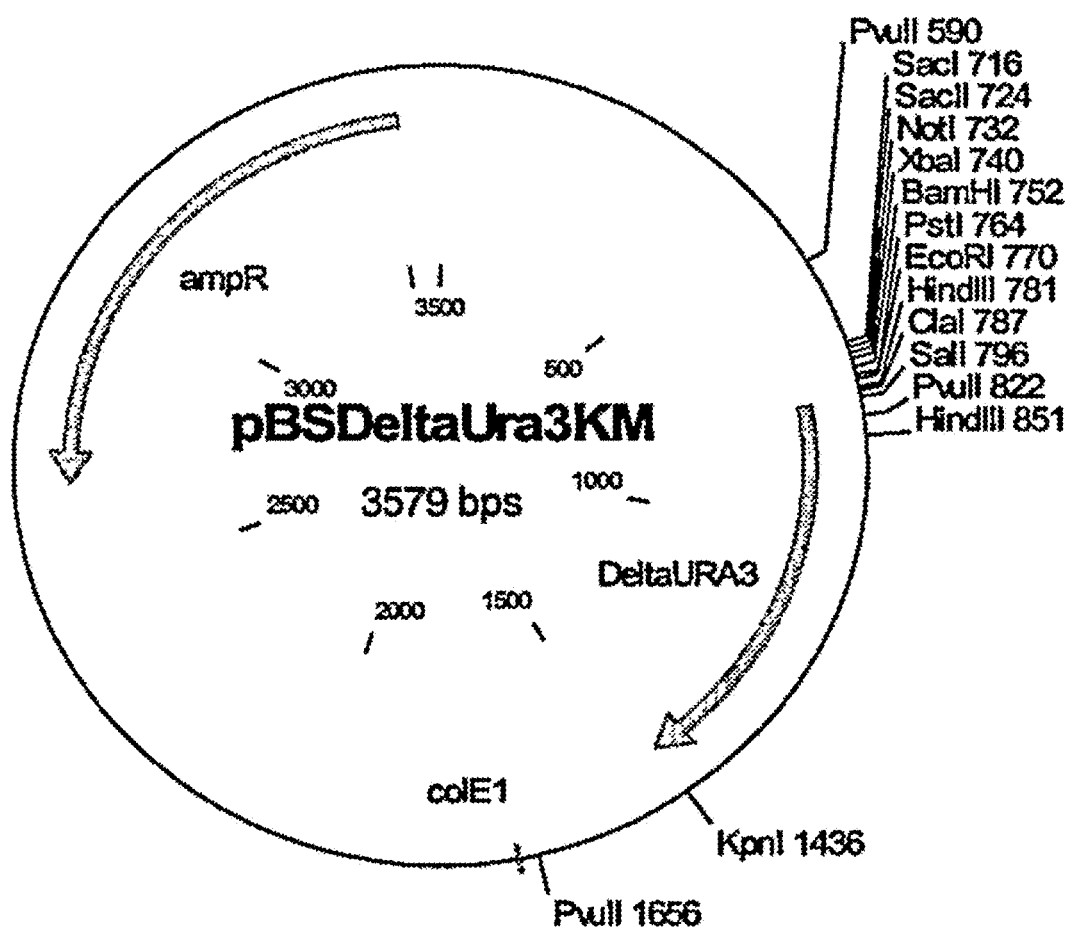
Figure 21:
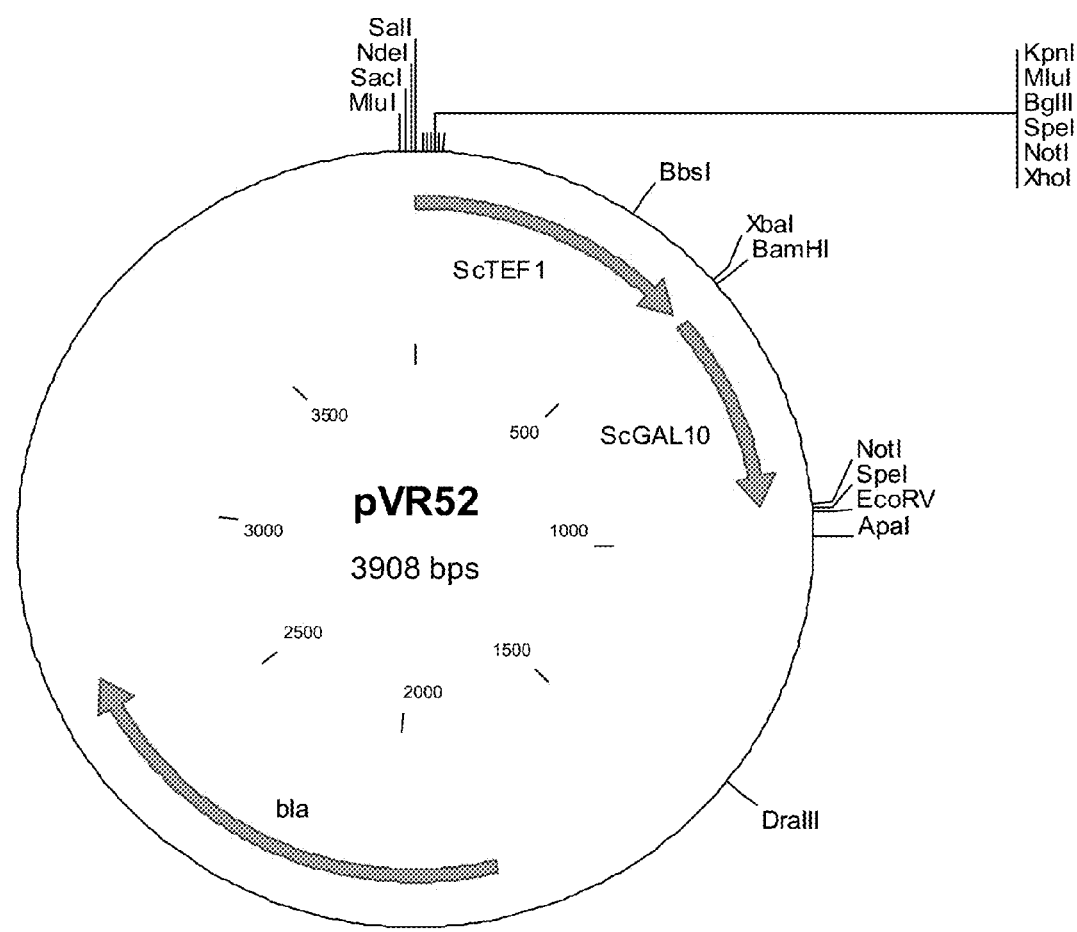
Figure 22:
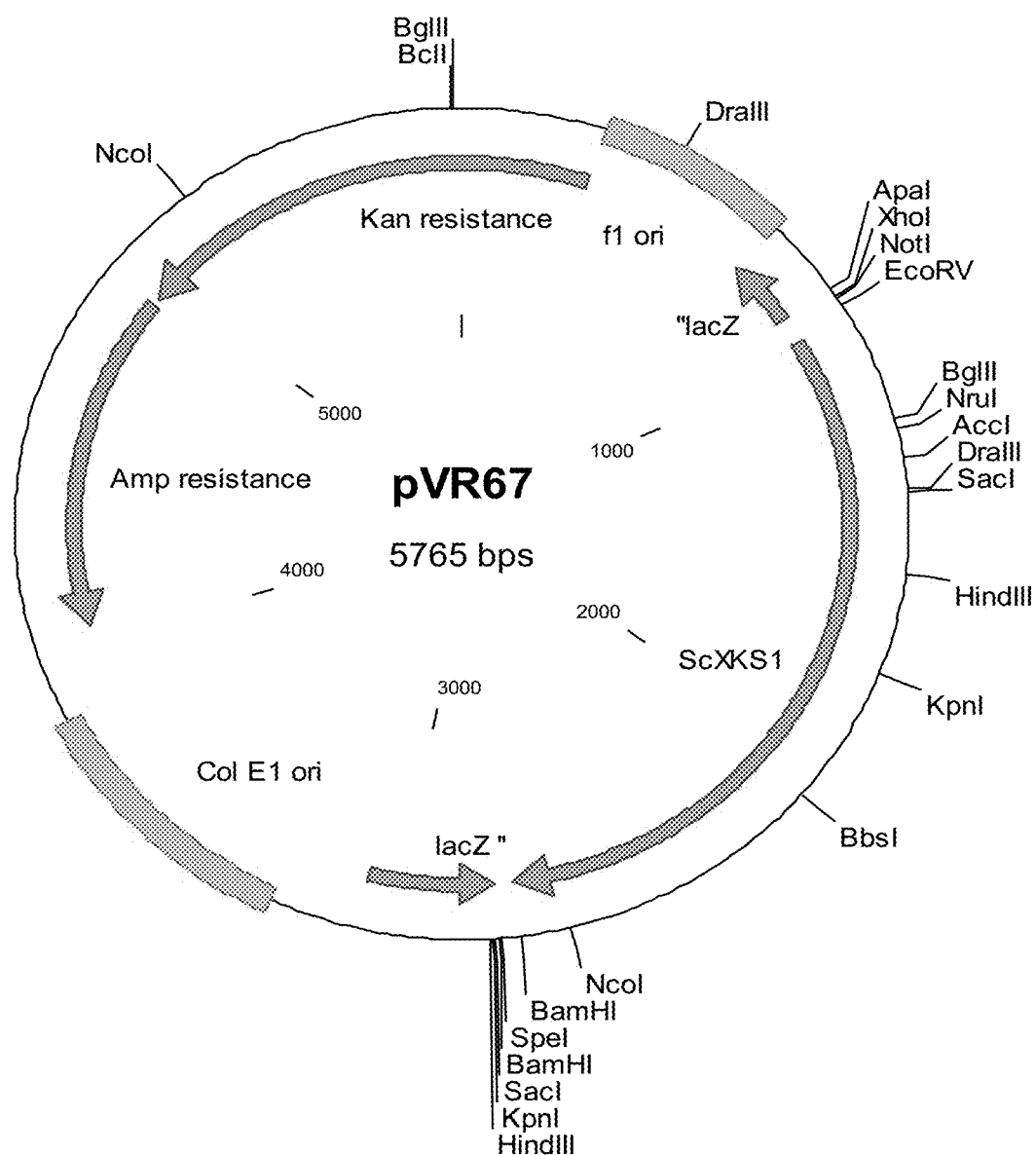
Figure 23:
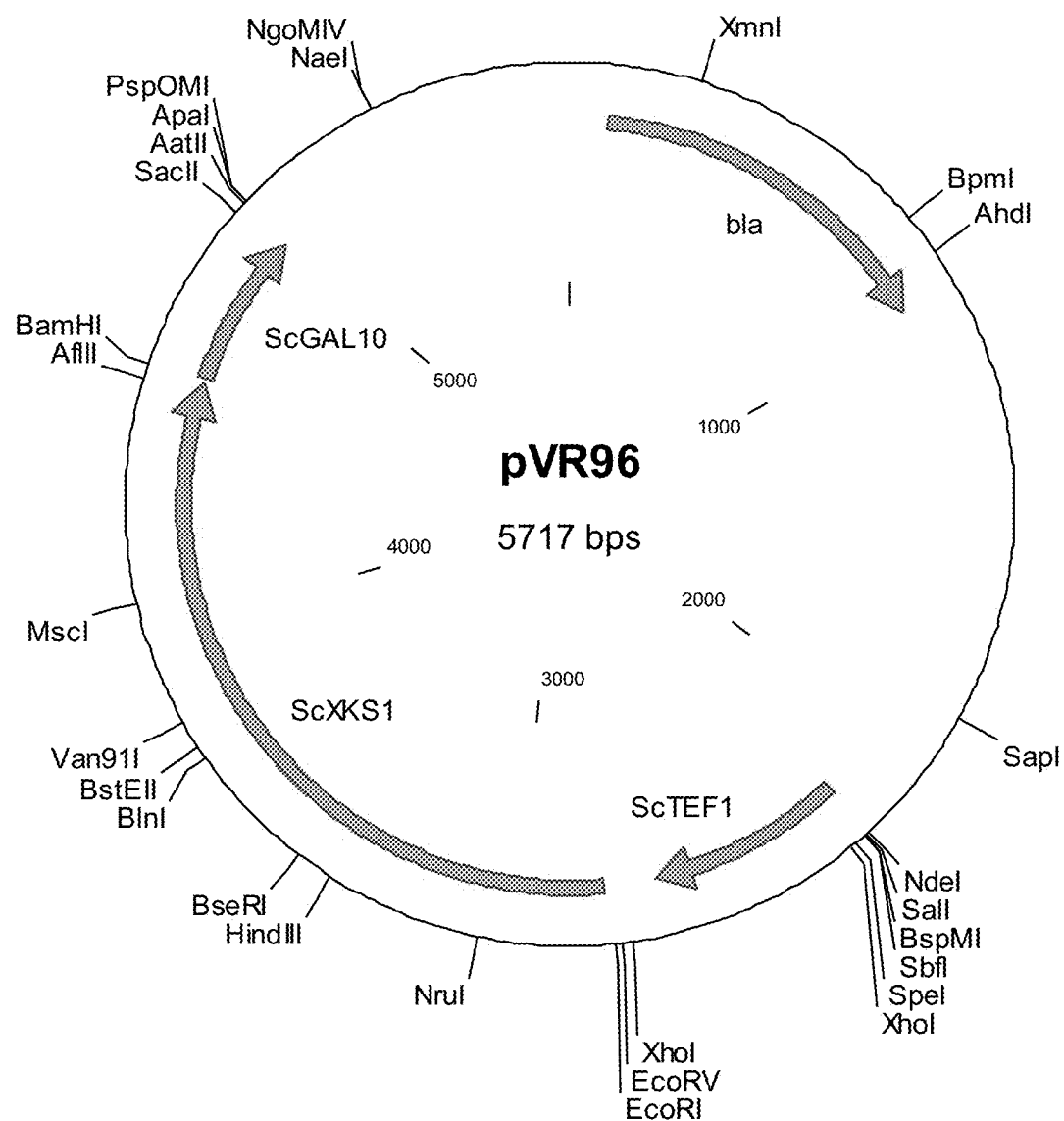
Figure 24:
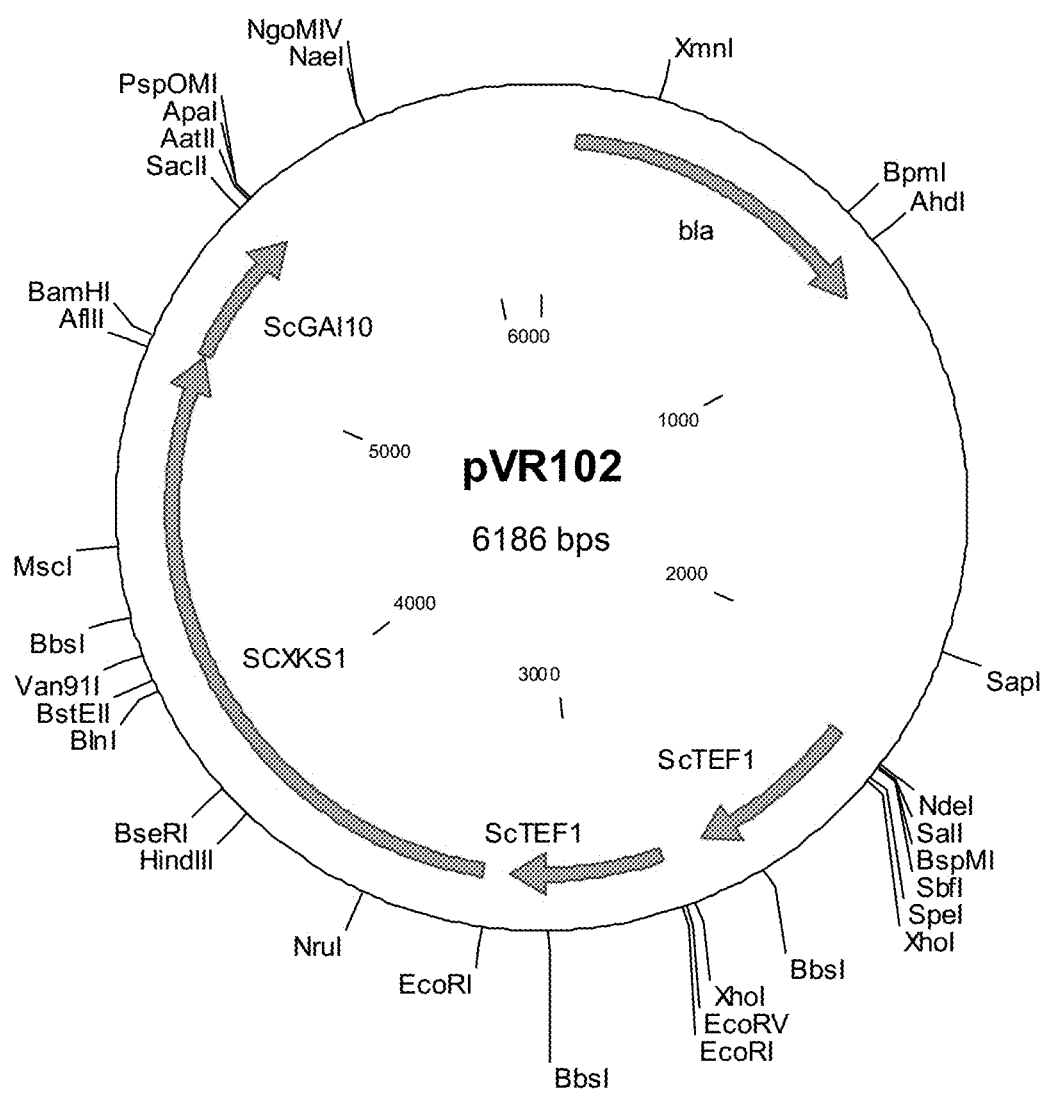
Figure 25:
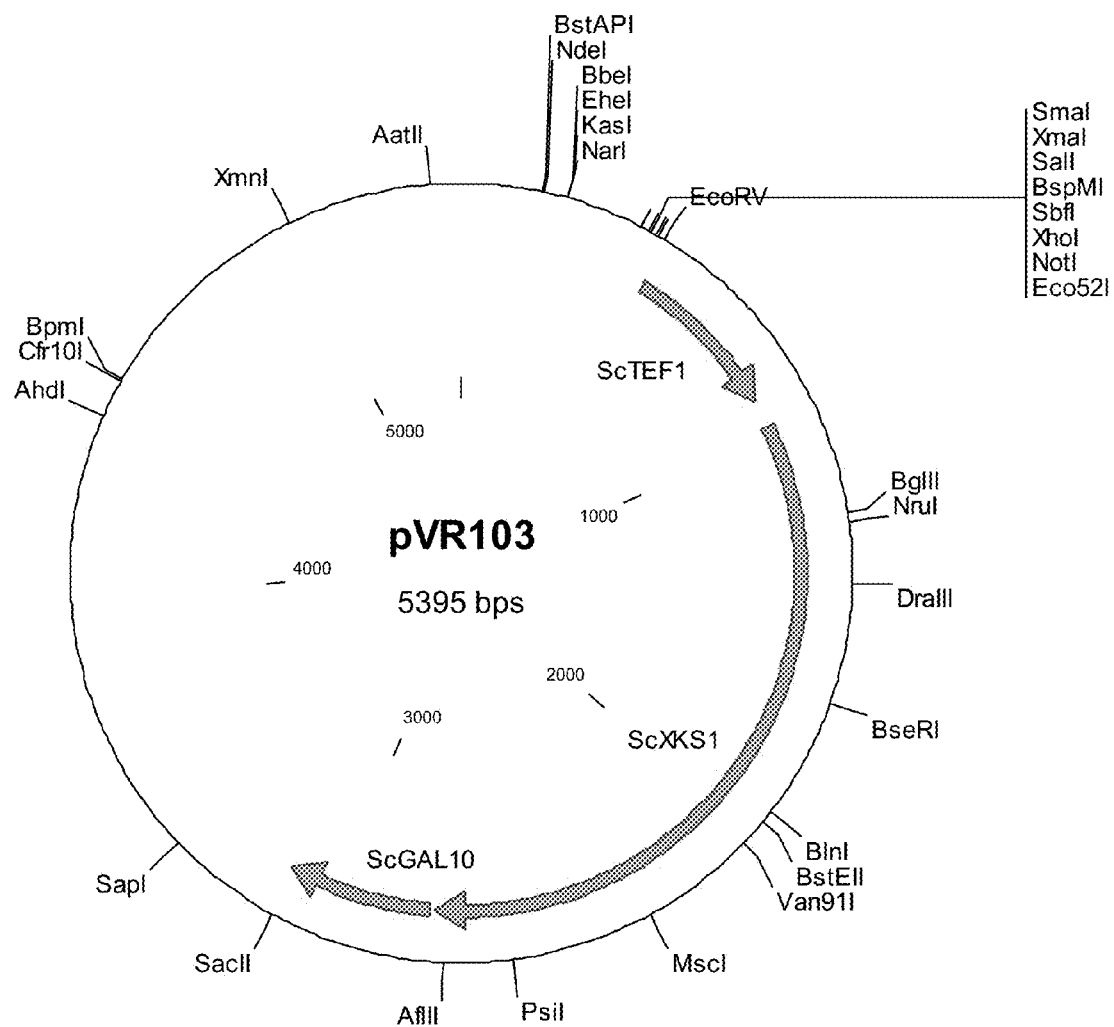
Figure 26:
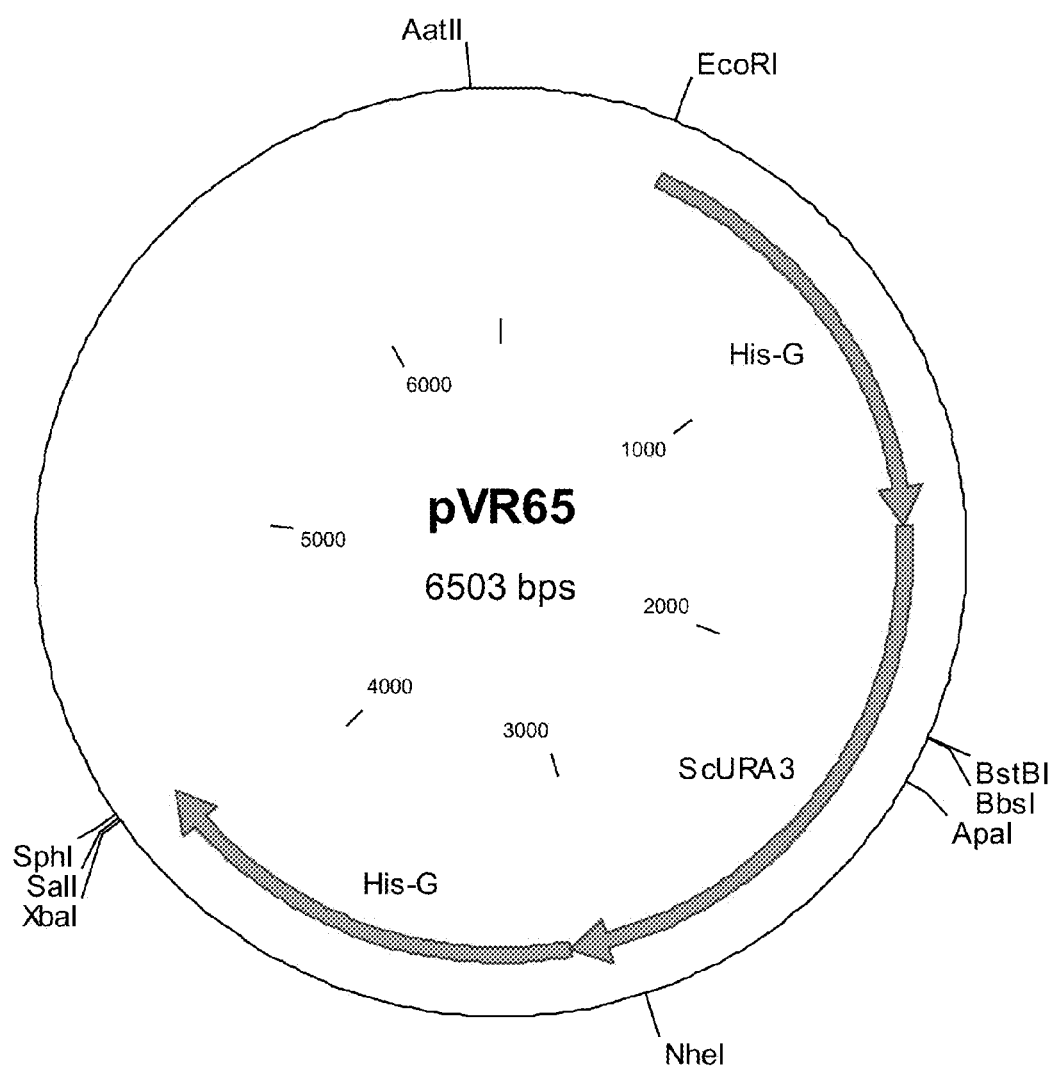
Figure 27:
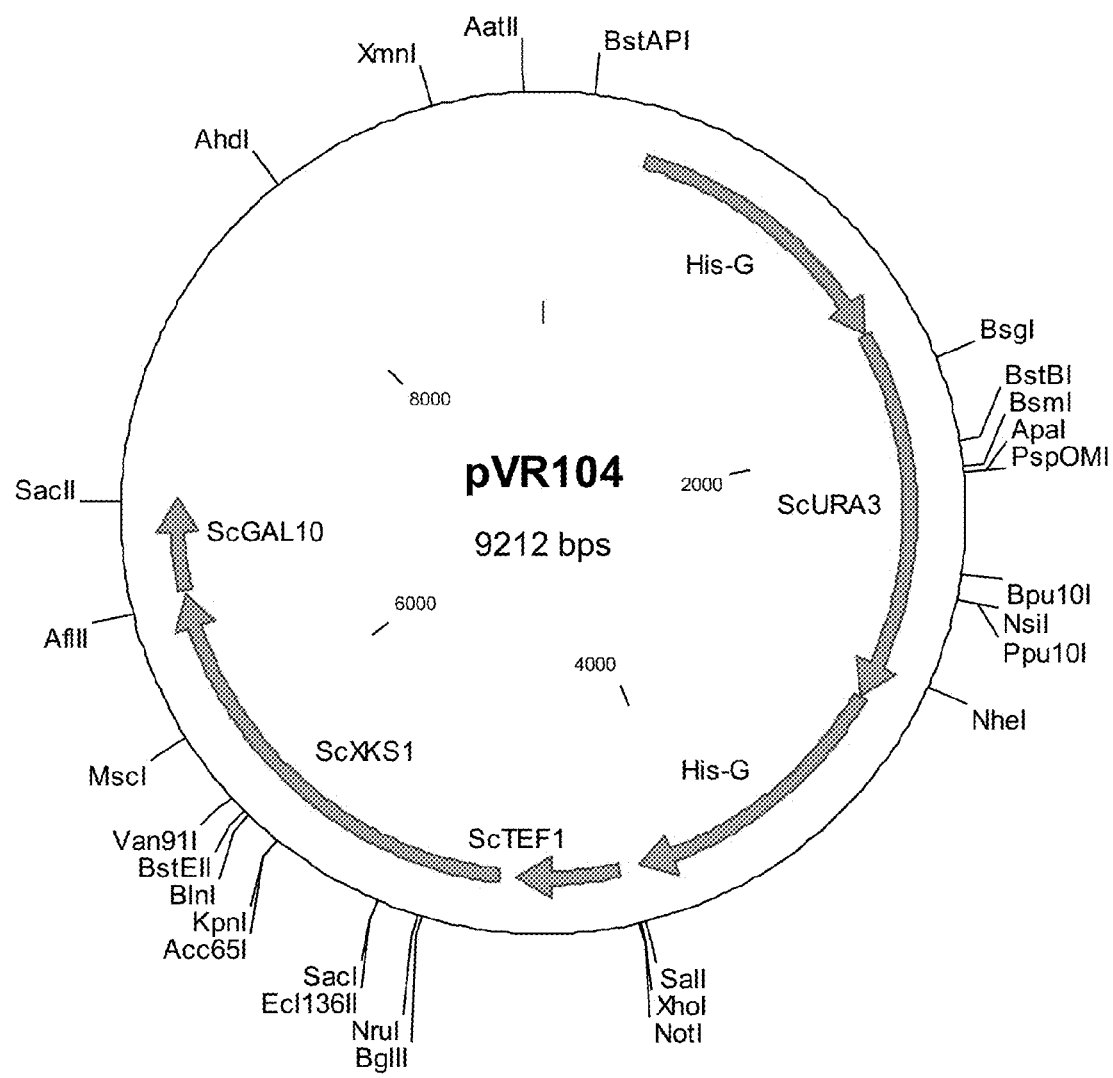
Figure 28:
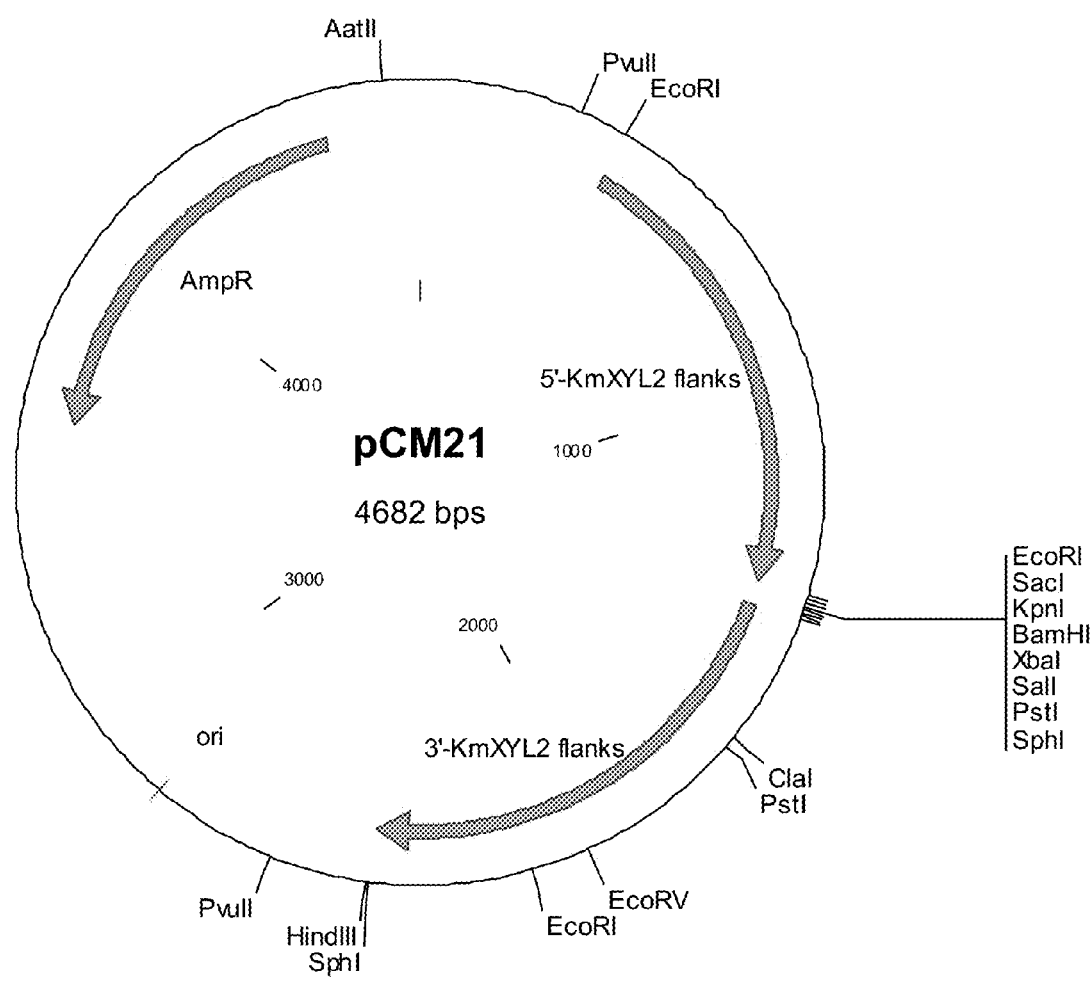
Figure 29:
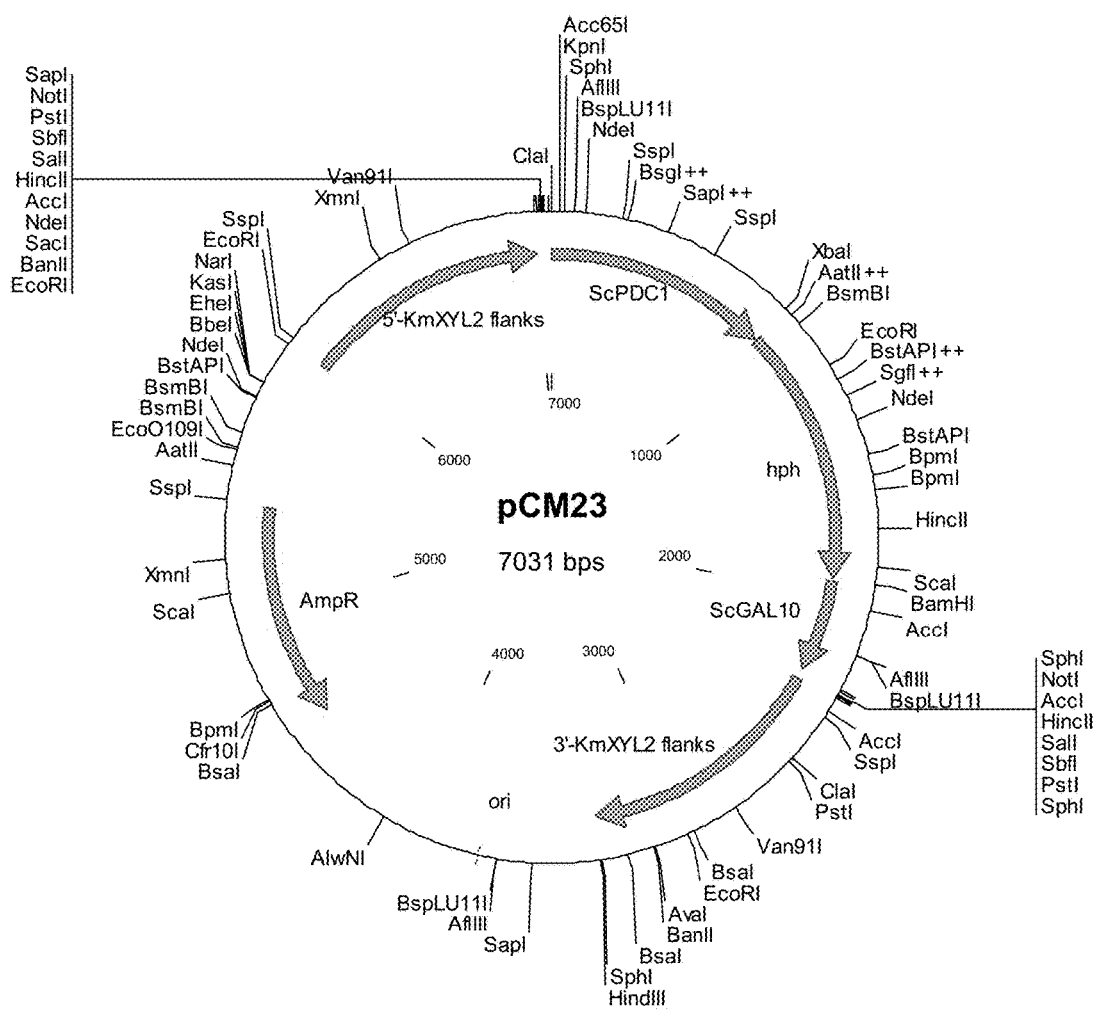
Figure 30:
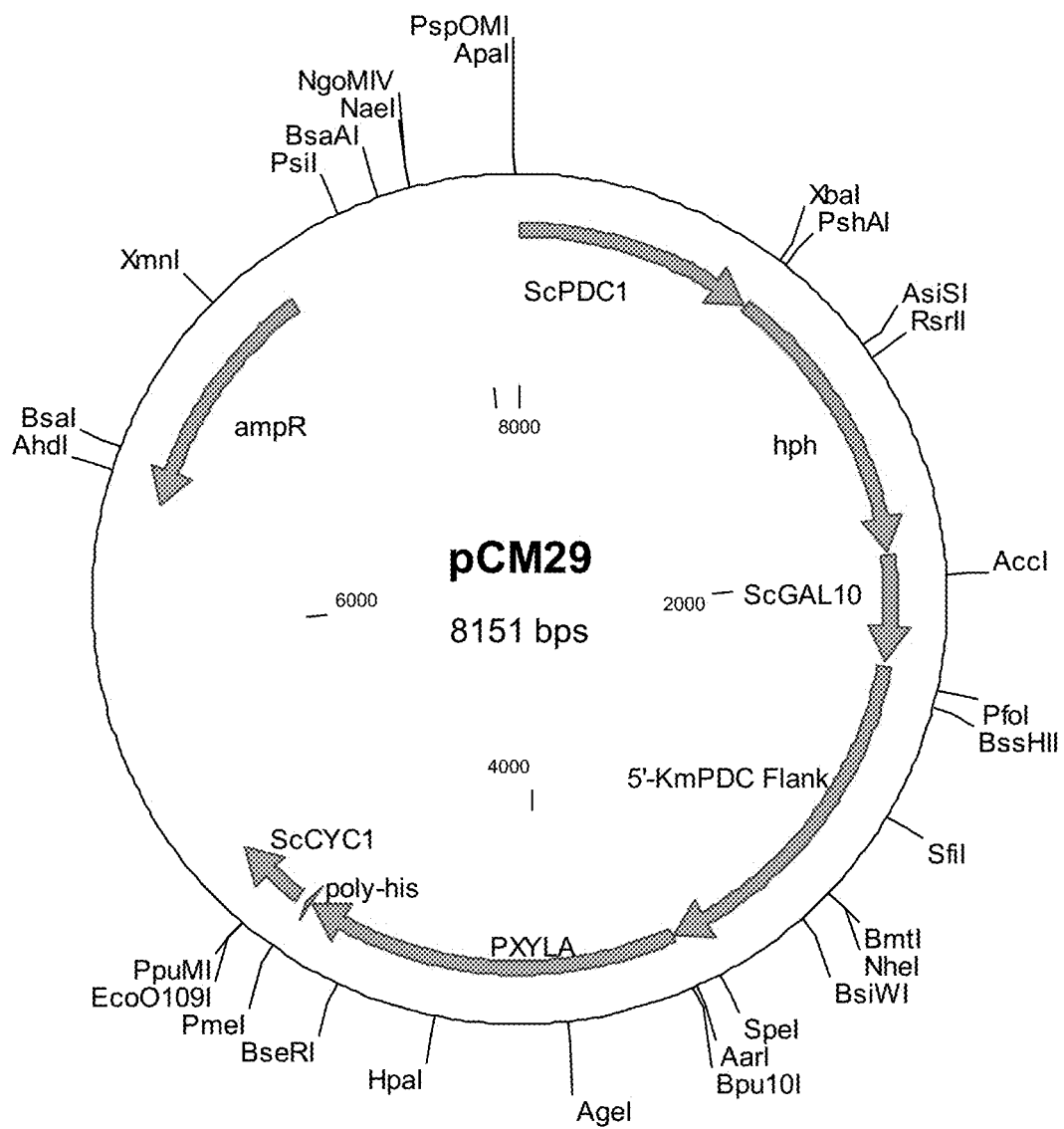
Figure 31:
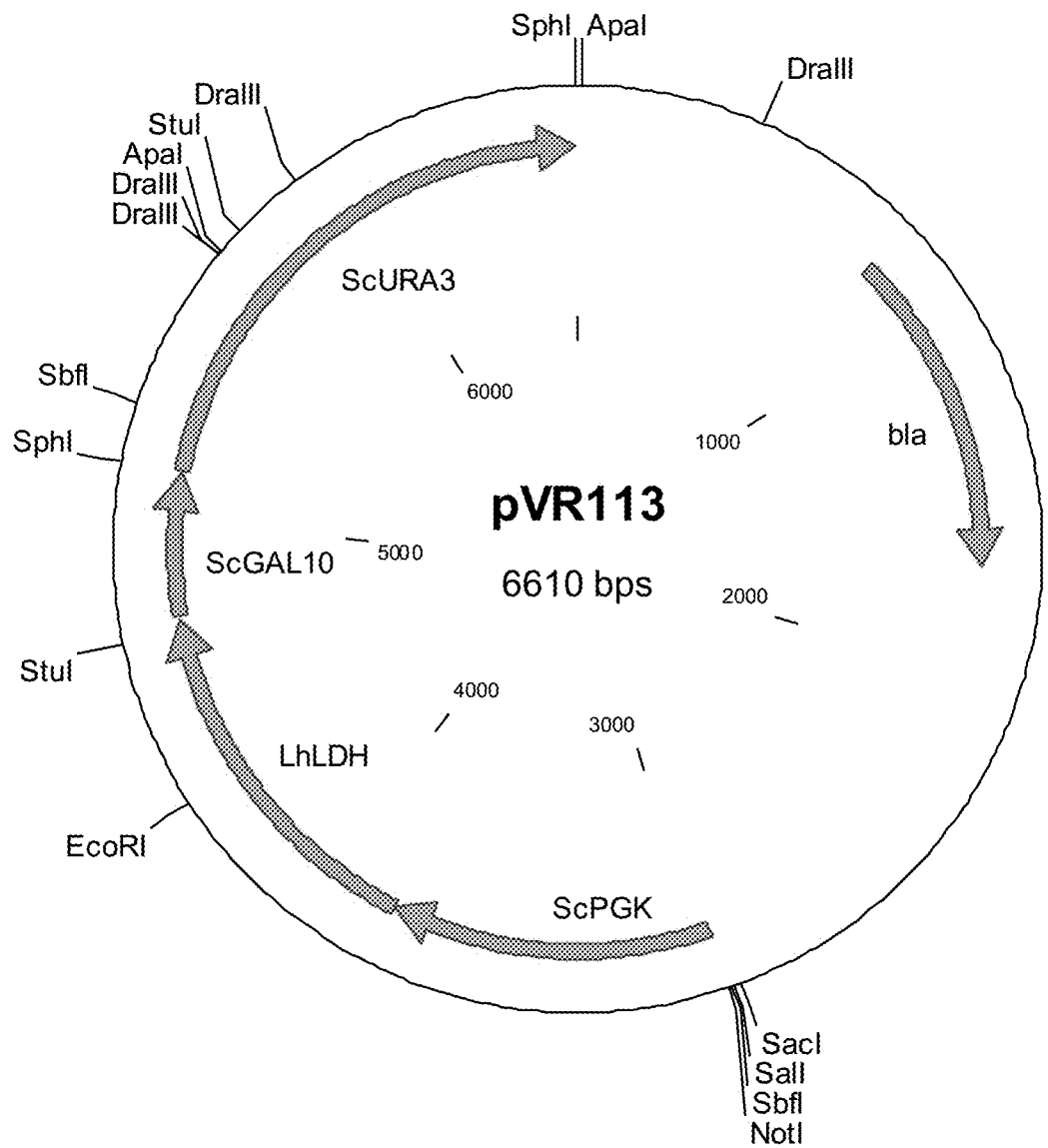
Figure 32:
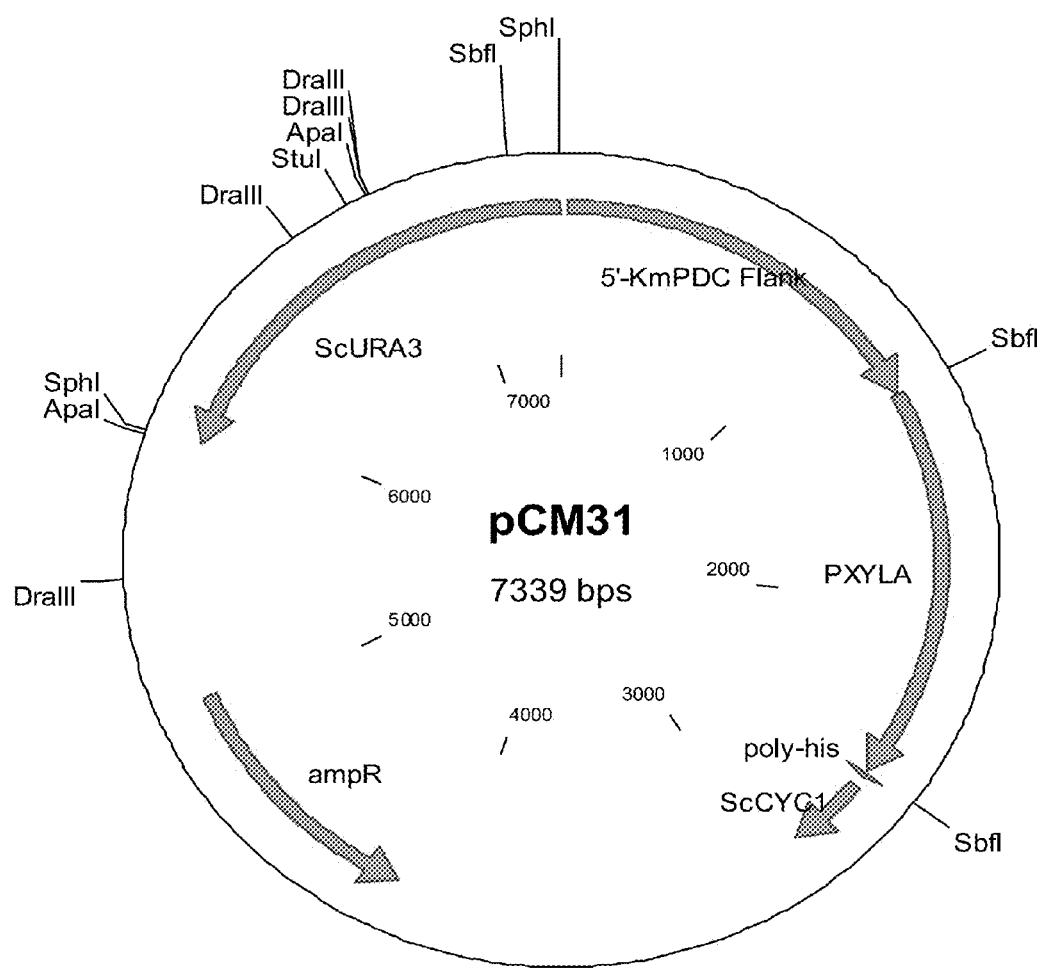
Figure 33:
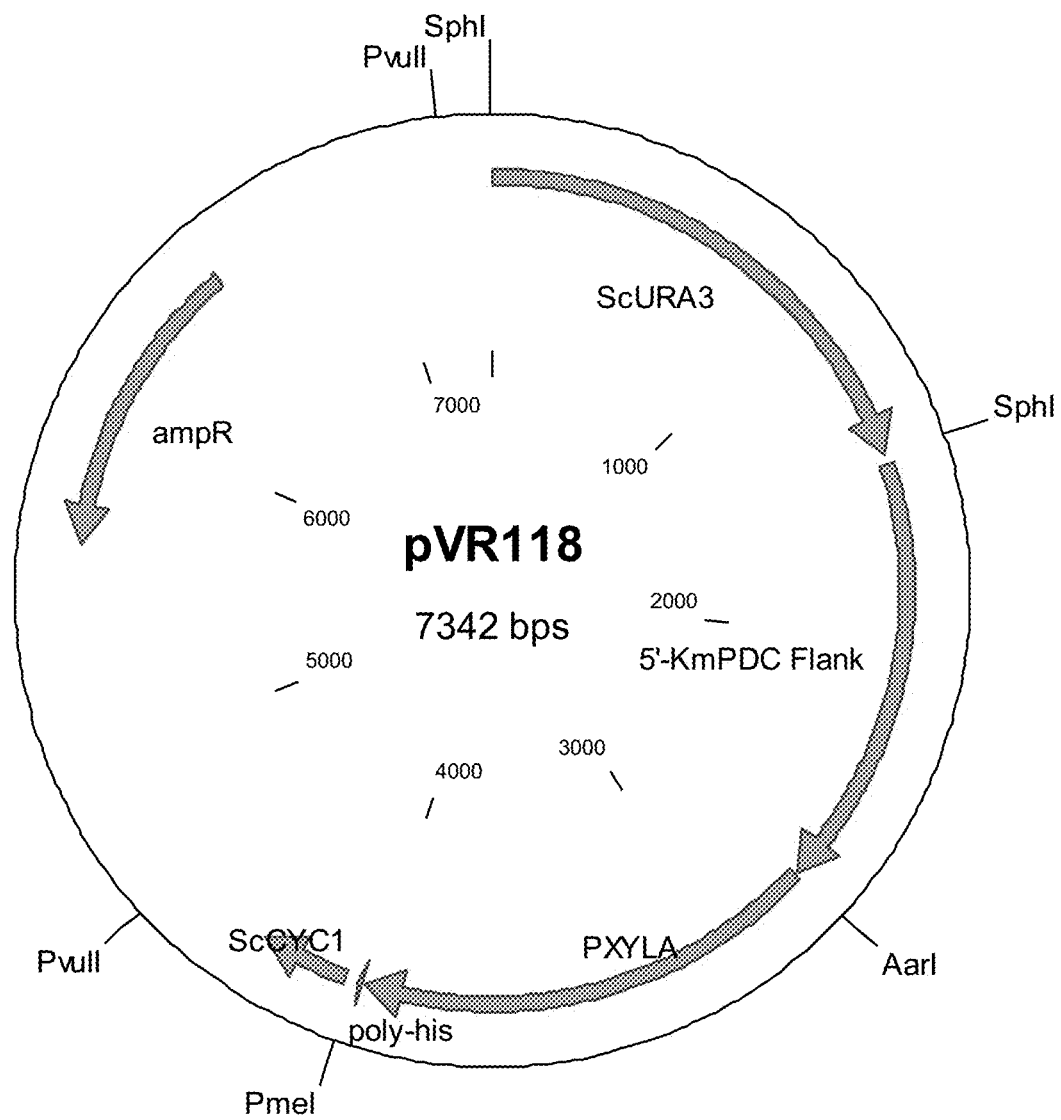
Figure 34:
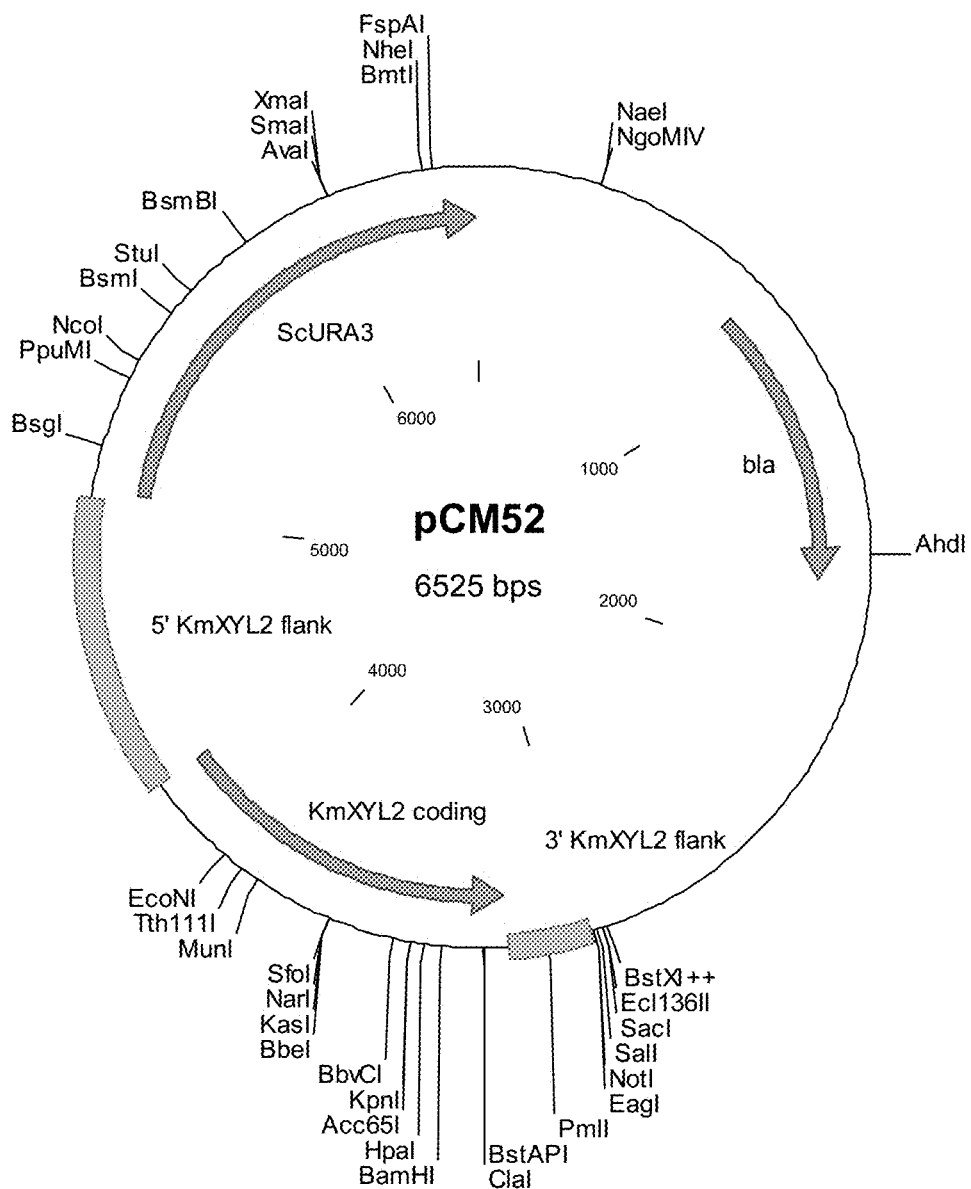
Figure 35:
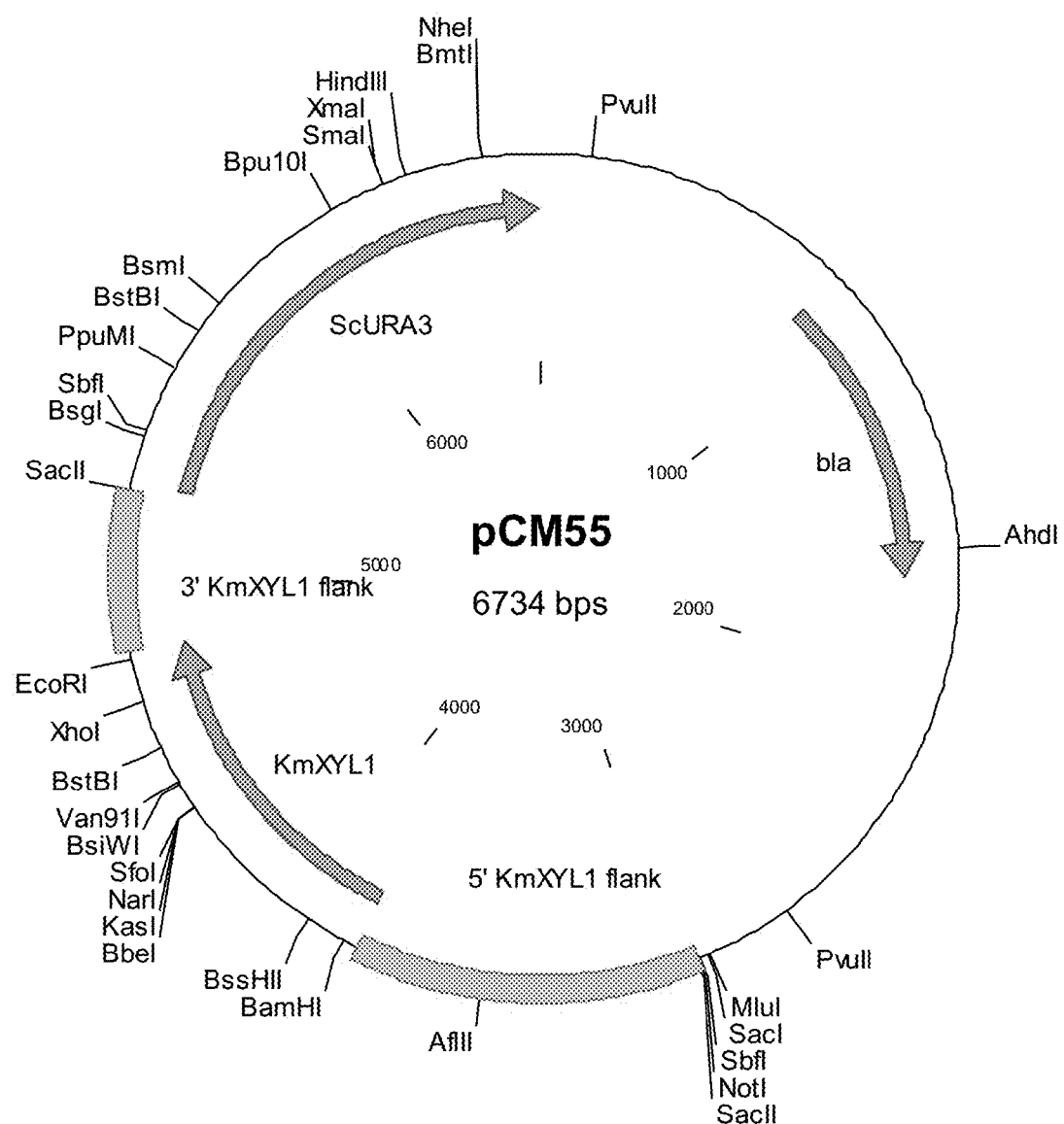
Figure 36:
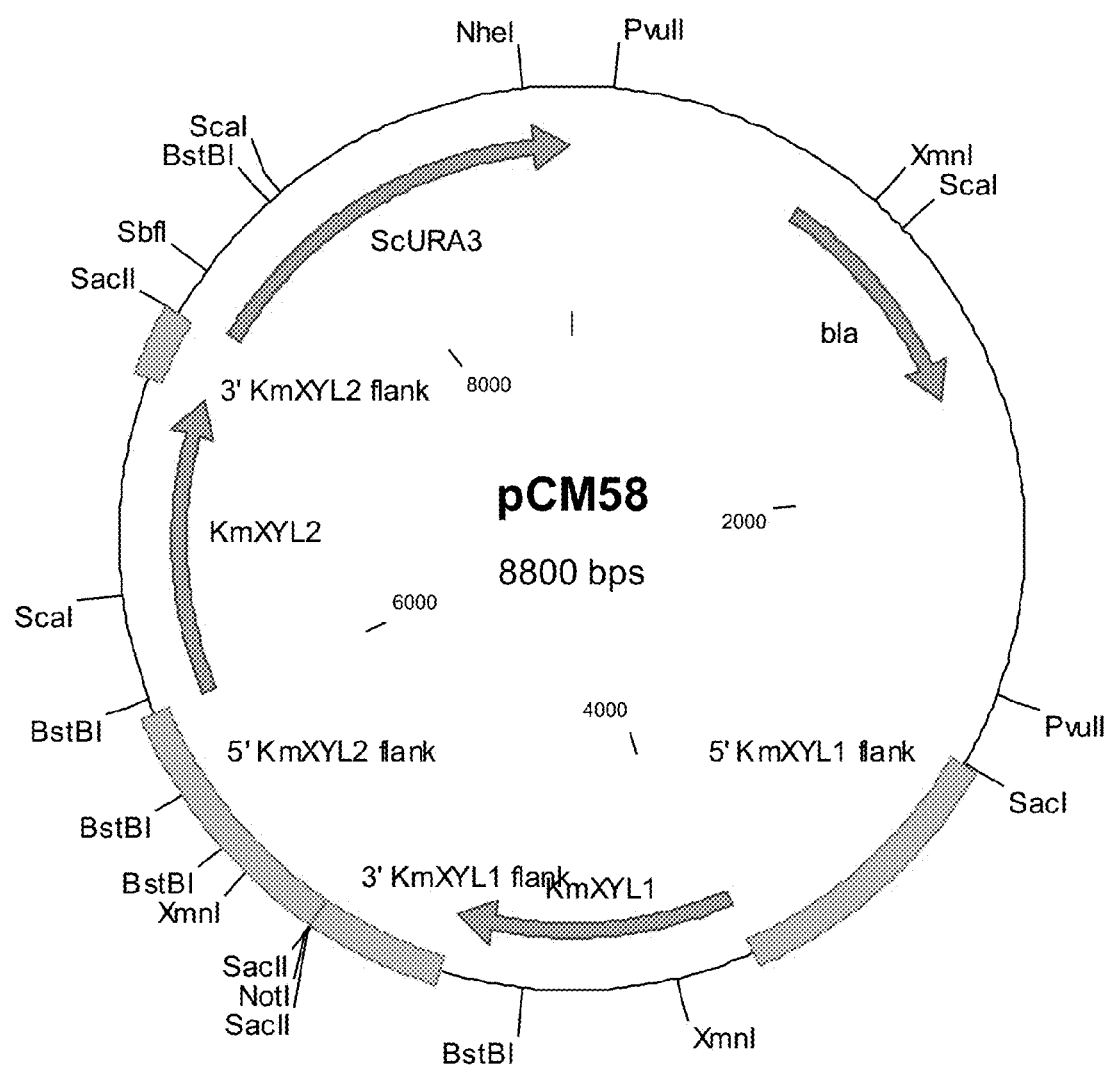
Figure 37:
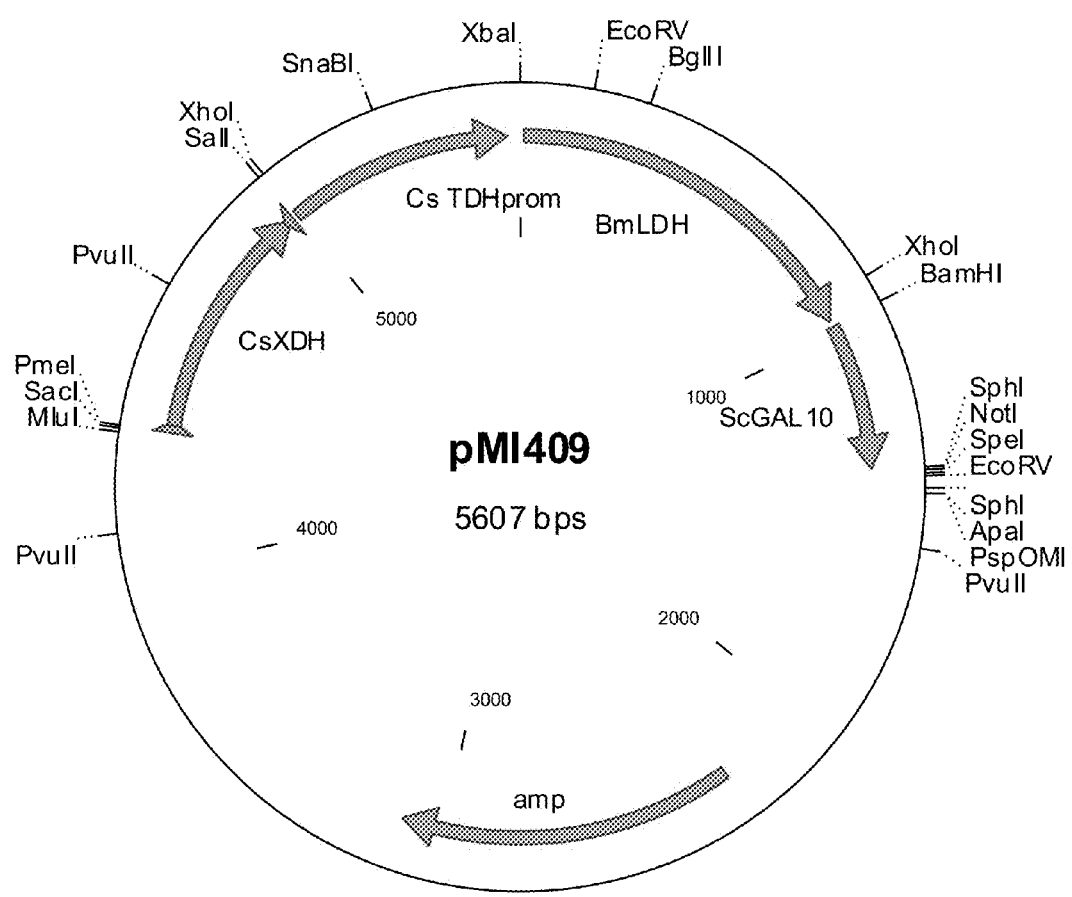
Figure 38:
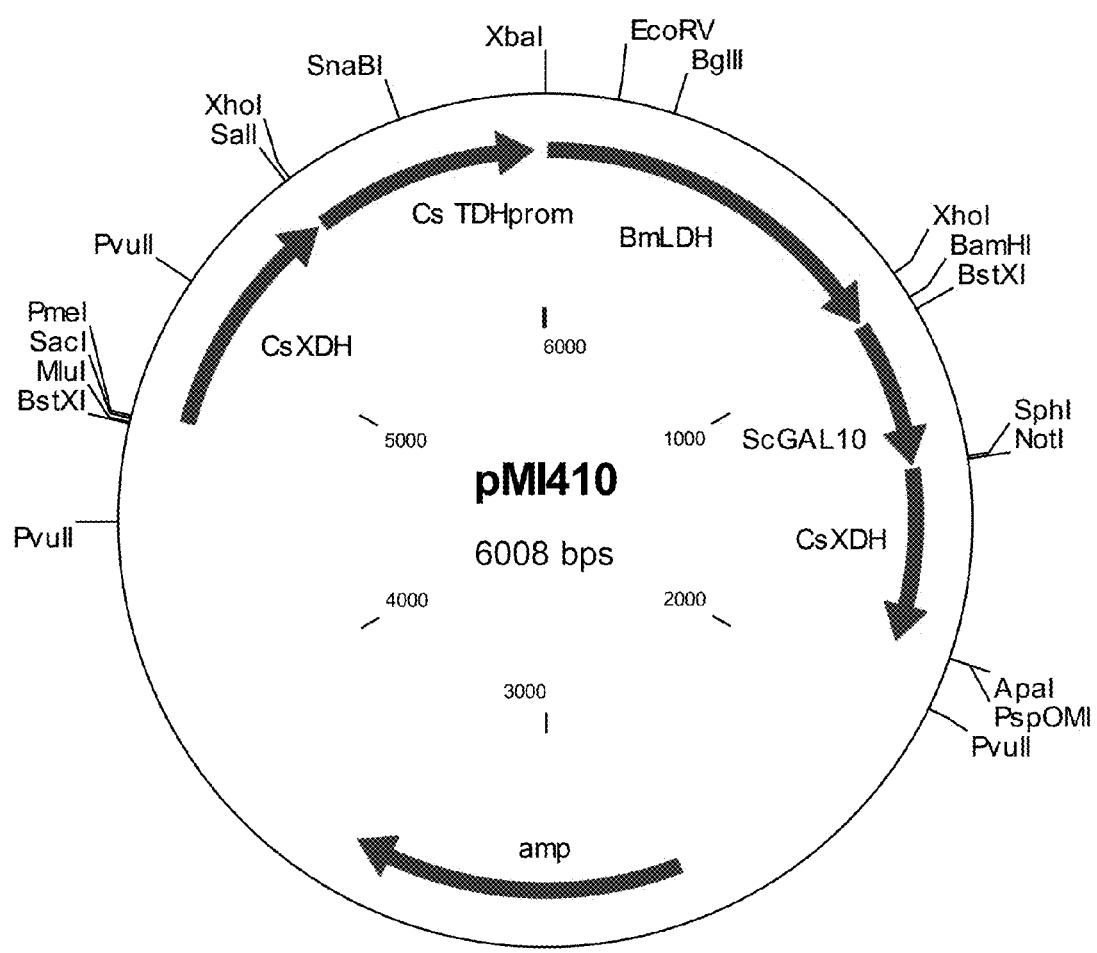
Figure 39:
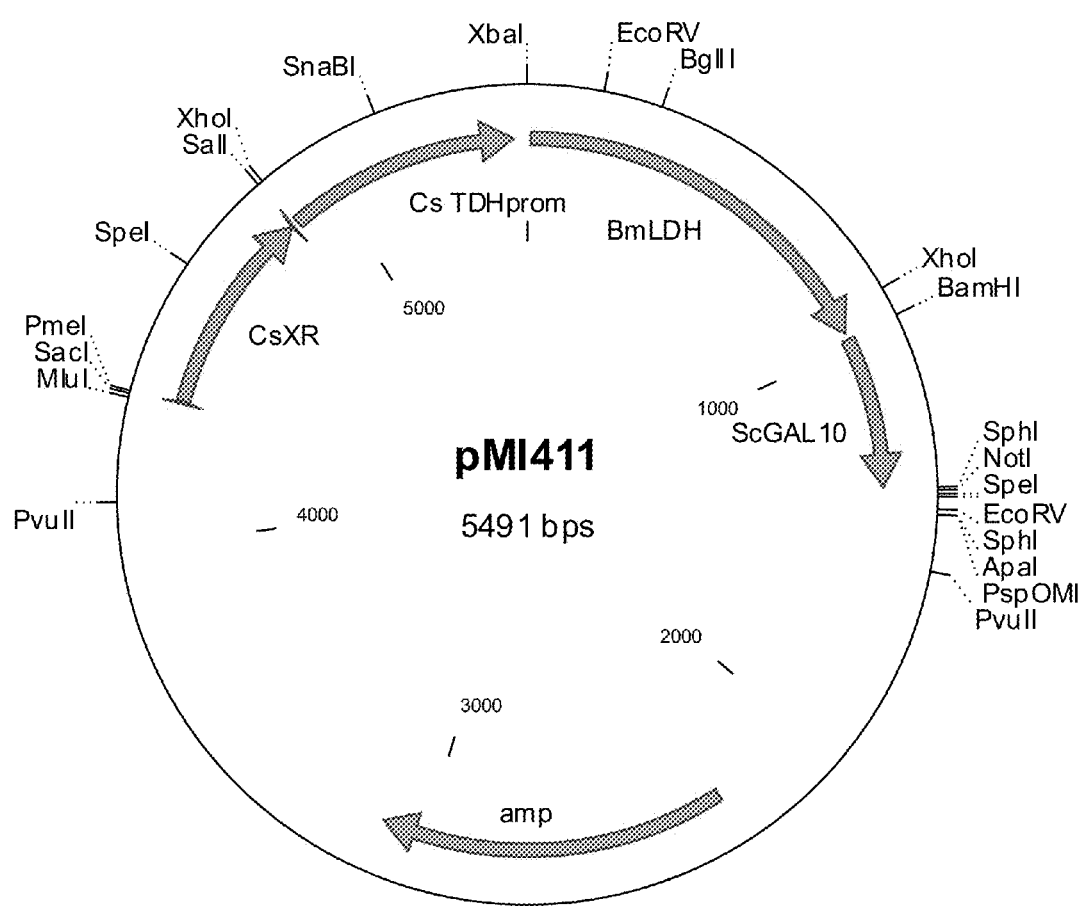
Figure 40:
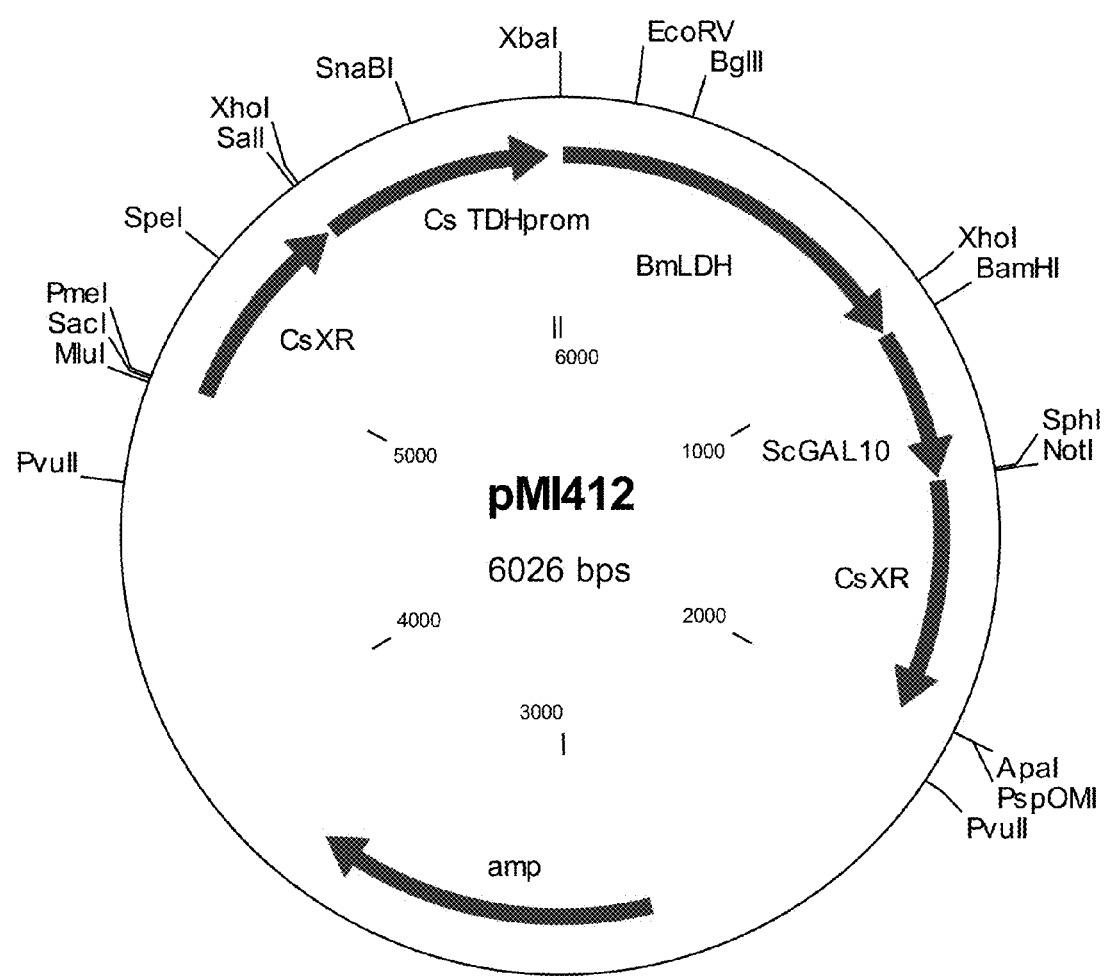
Figure 41:
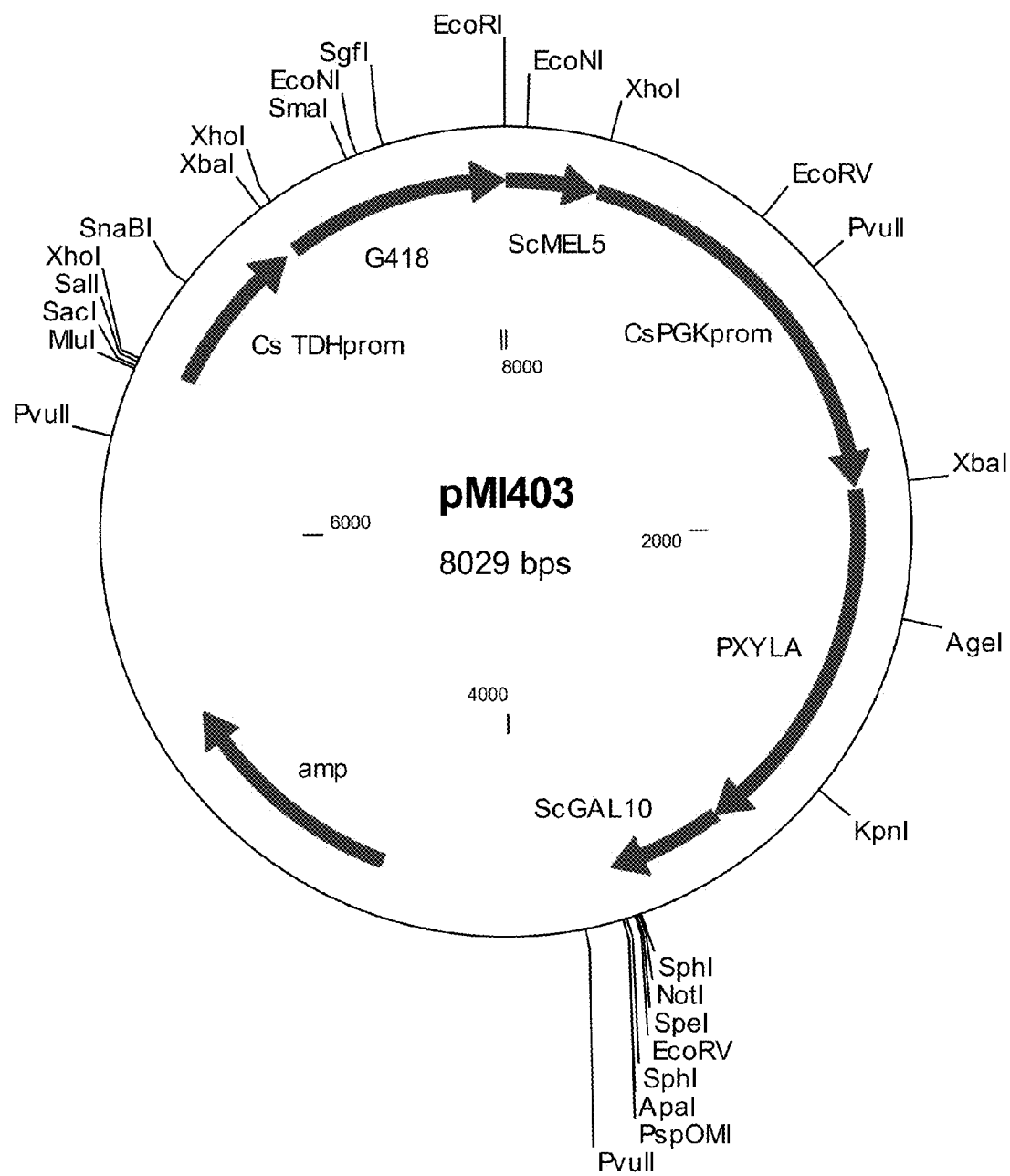
Figure 42:
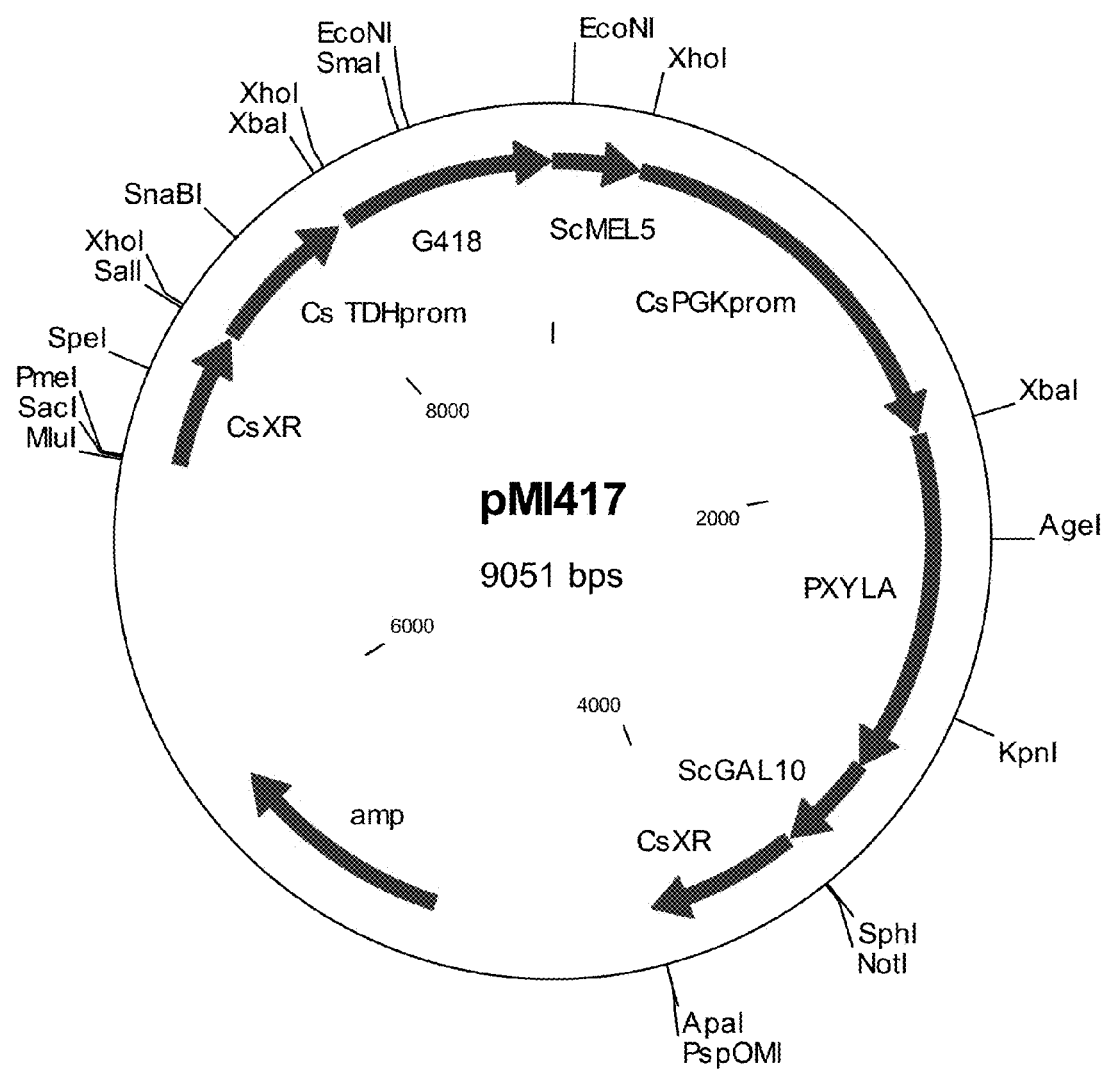
Figure 43:
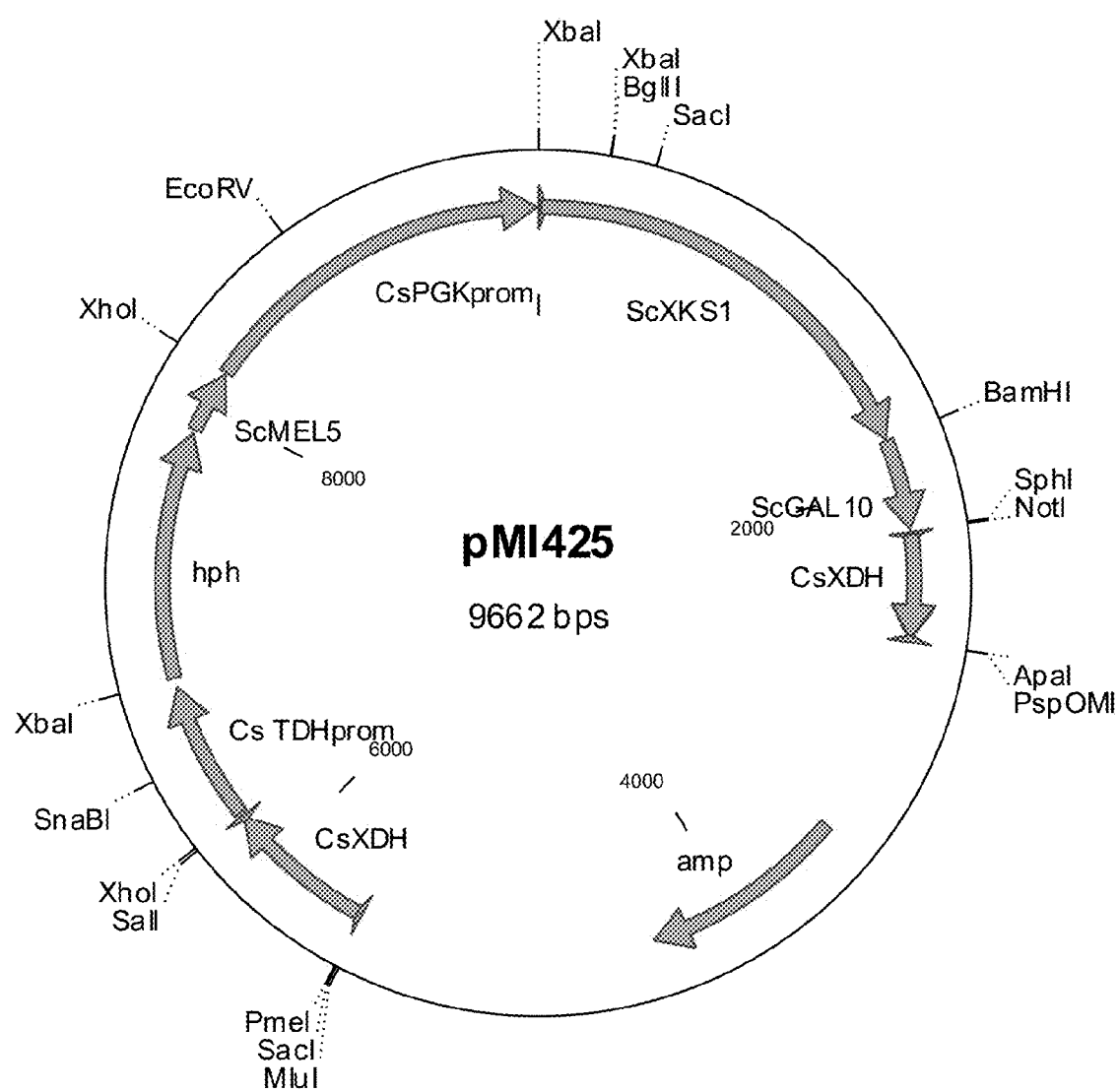
Figure 44:
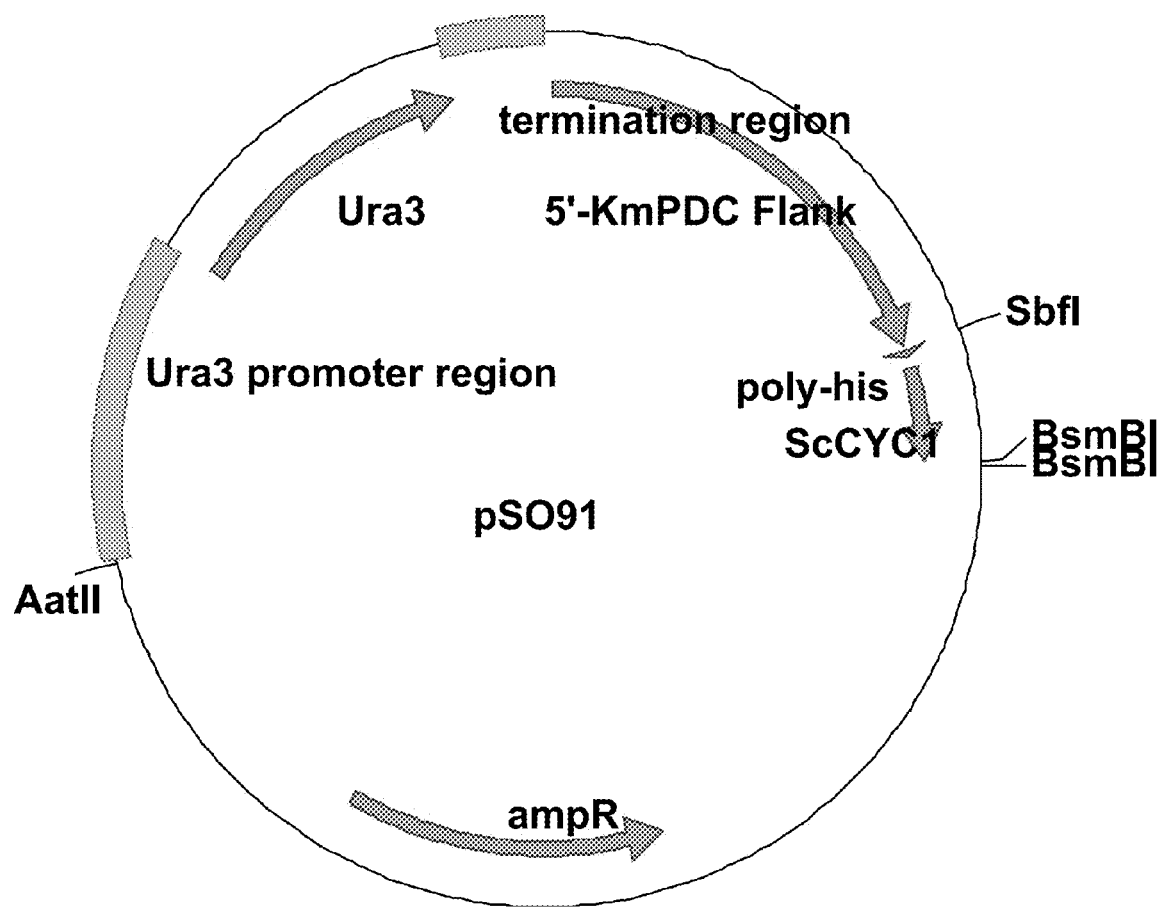
Figure 45:
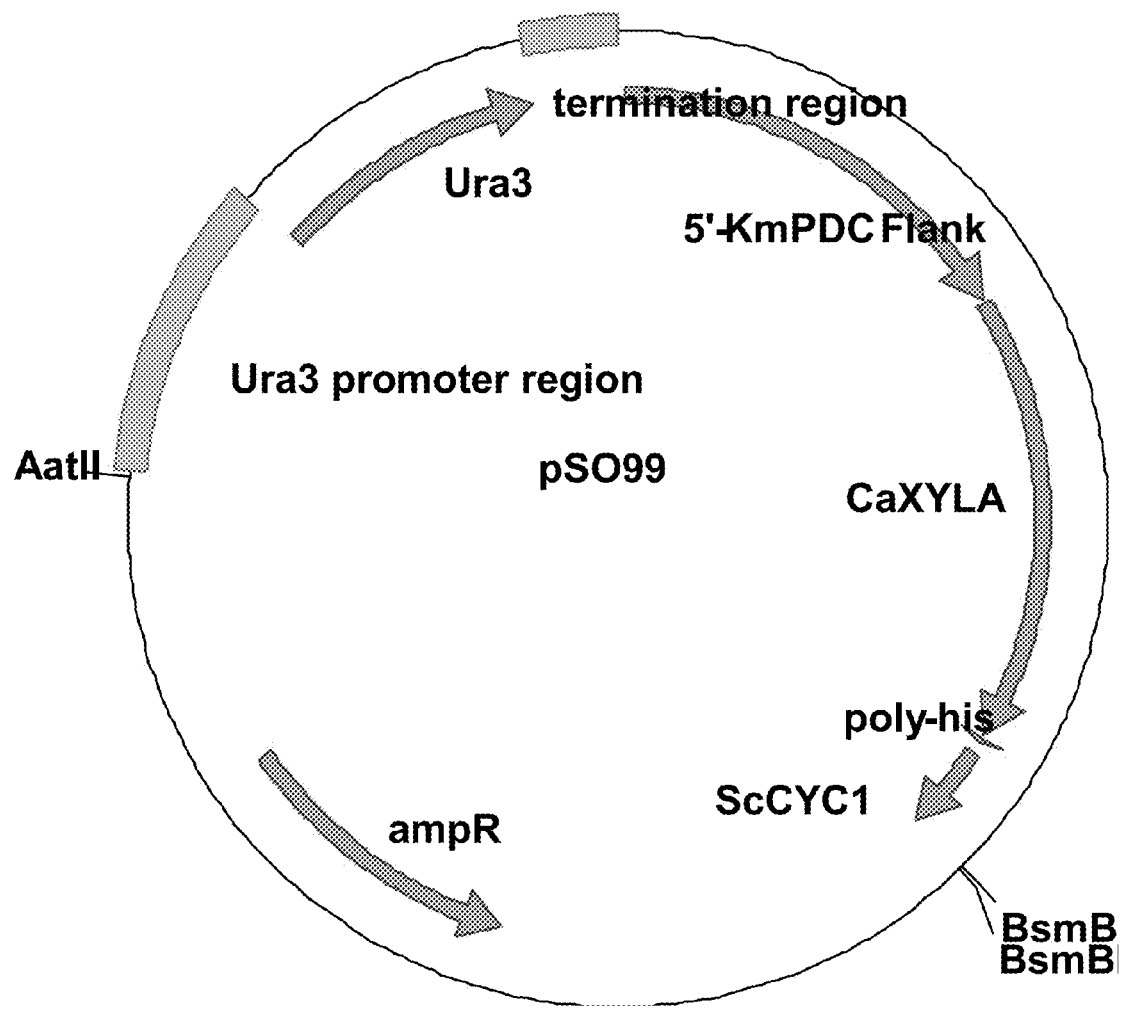
Figure 46:
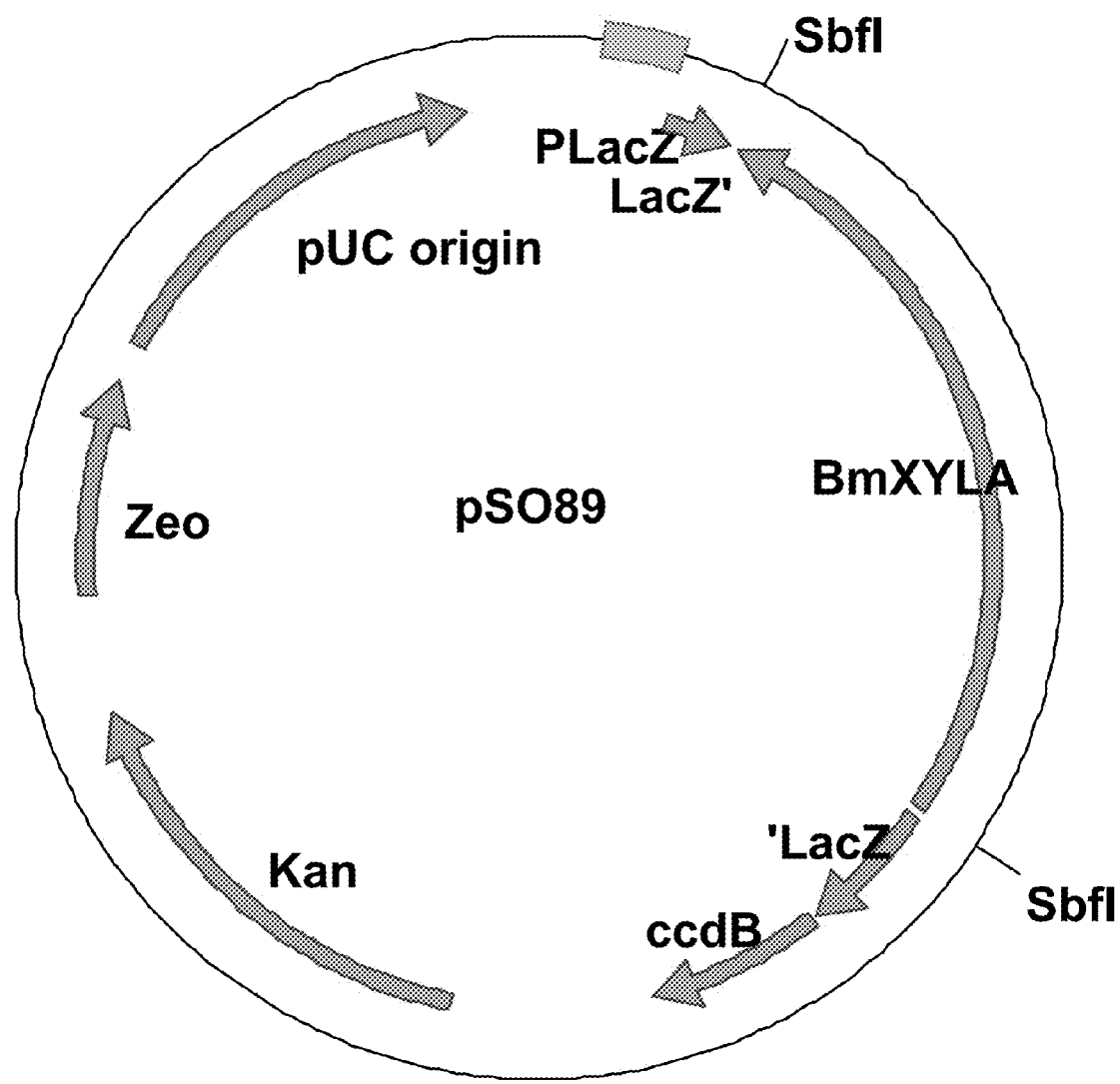
Figure 47:
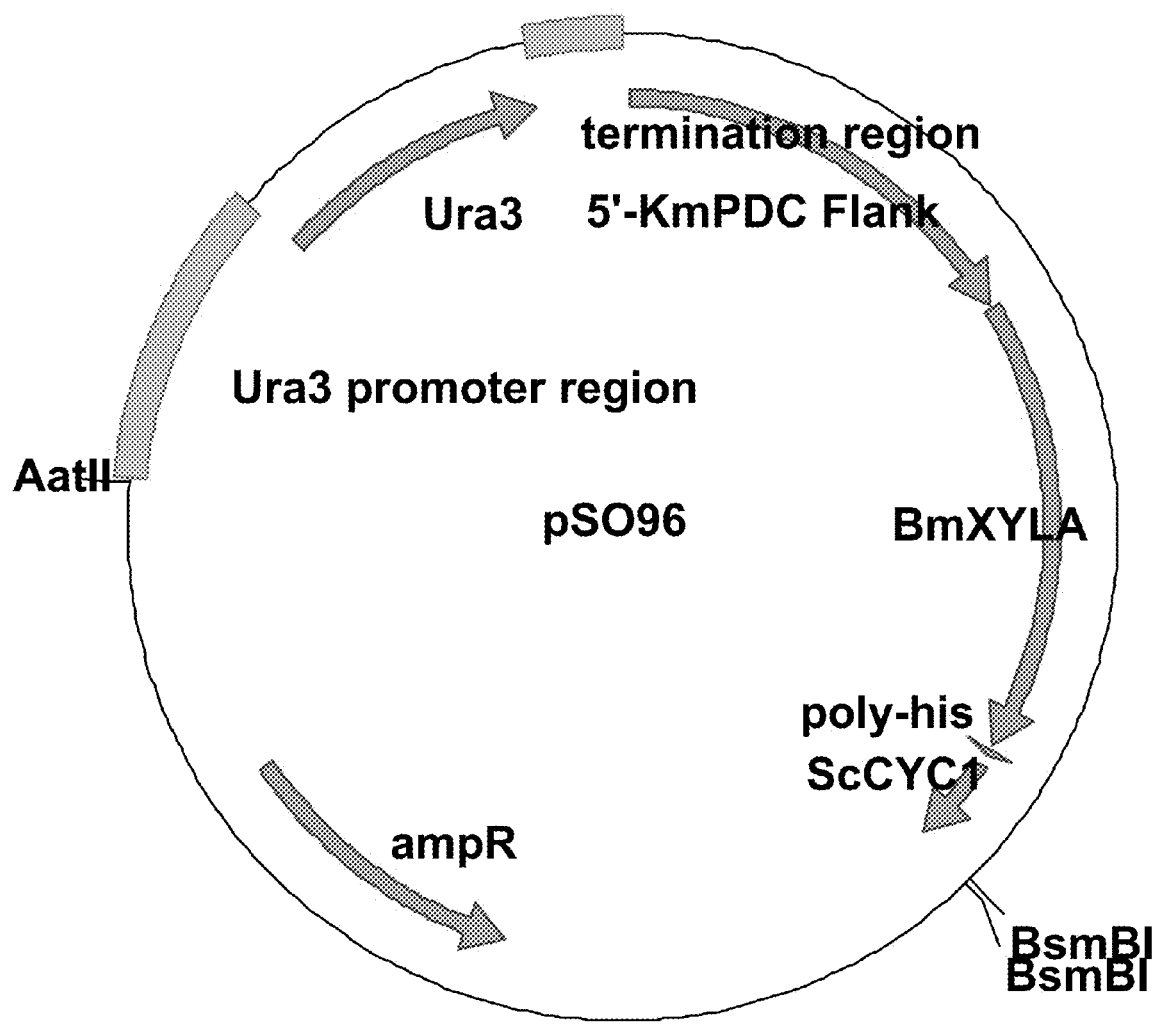
Figure 48:
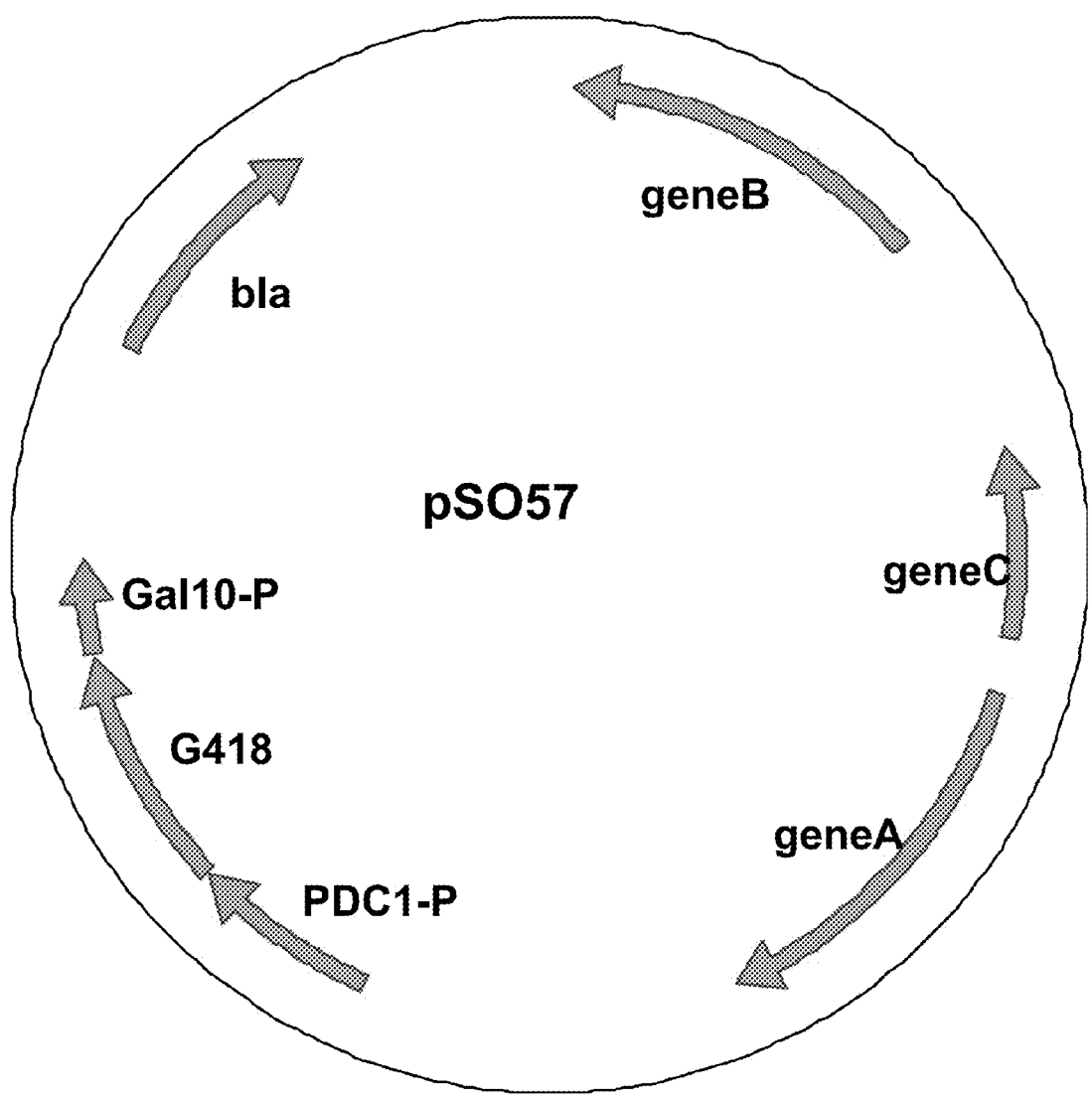
Figure 49:
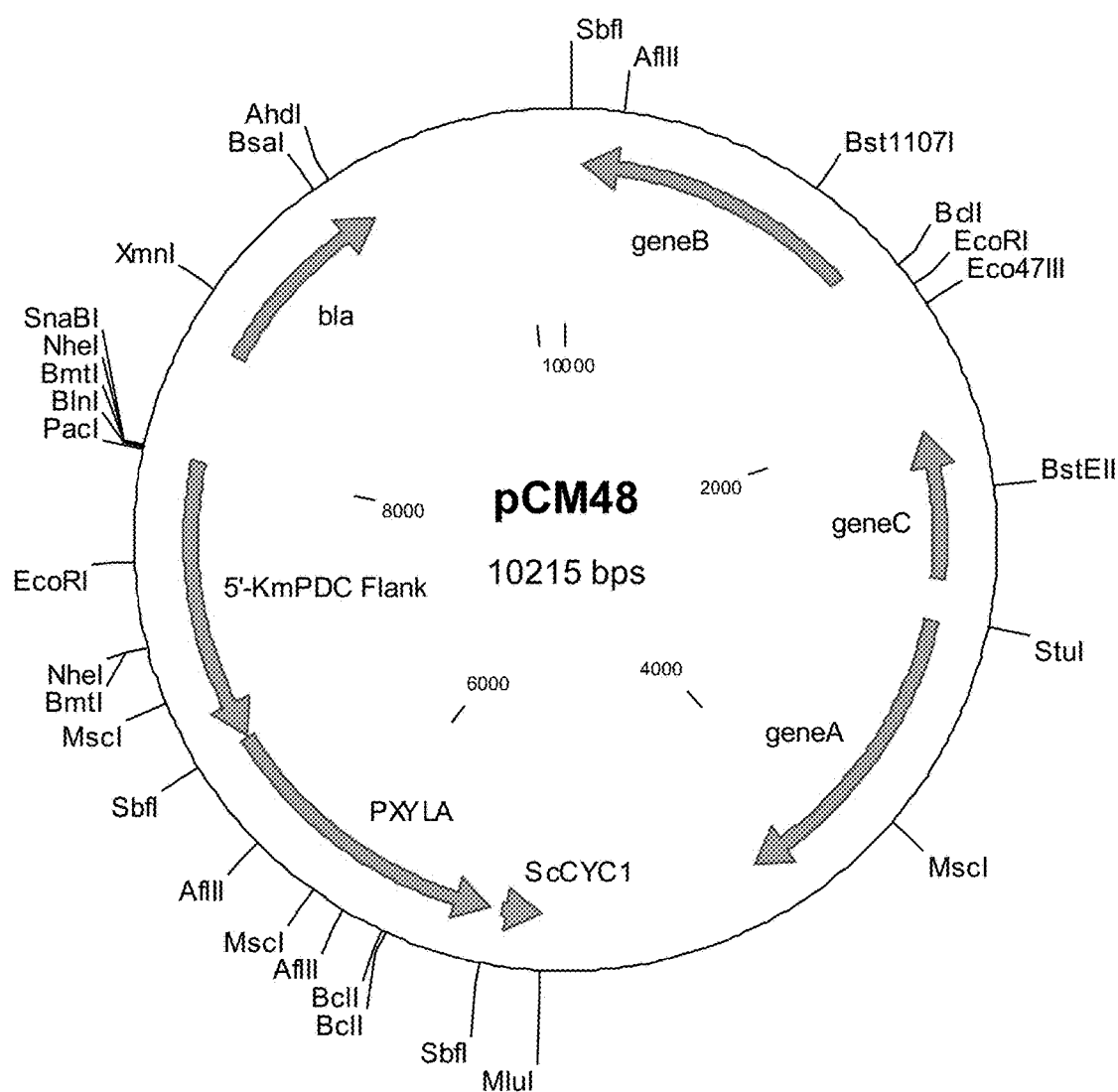

FIG. 1 is a diagram depicting the pNC2 plasmid.
FIG. 2 is a diagram depicting the pNC4 plasmid.
FIG. 3 is a diagram depicting the pVR22 plasmid.
FIG. 4 is a diagram depicting the pVR29 plasmid.
FIG. 5 is a diagram depicting the pBH5a
FIG. 6 is a diagram depicting the pBH5b plasmid.
FIG. 7 is a diagram depicting the pVR77 plasmid.
FIG. 8 is a diagram depicting the pVR73 plasmid.
FIG. 9 is a diagram depicting the pVR78 plasmid.
FIG. 10 is a diagram depicting the pCM3 plasmid.
FIG. 11 is a diagram depicting the pPS1 plasmid.
FIG. 12 is a diagram depicting the pCM9 plasmid.
FIG. 13 is a diagram depicting the pCM17 plasmid.
FIG. 14 is a diagram depicting the pCM14 plasmid.
FIG. 15 is a diagram depicting the pCM28 plasmid.
FIG. 16 is a diagram depicting the pVR 95 plasmid.
FIG. 17 is a diagram depicting the pCM18 plasmid.
FIG. 18 is a diagram depicting the pCM19 plasmid.
FIG. 19 is a diagram depicting the pBSKura3Km plasmid.
FIG. 20 is a diagram depicting the pBSDeltaUra3KM plasmid.
FIG. 21 is a diagram depicting the pVR52 plasmid.
FIG. 22 is a diagram depicting the pVR67 plasmid.
FIG. 23 is a diagram depicting the VR96 plasmid.
FIG. 24 is a diagram depicting the pVR102 plasmid.
FIG. 25 is a diagram depicting the pVR103 plasmid.
FIG. 26 is a diagram depicting the pVR65 plasmid.
FIG. 27 is a diagram depicting the pVR104 plasmid.
FIG. 28 is a diagram depicting the pCM21 plasmid.
FIG. 29 is a diagram depicting the pCM23 plasmid.
FIG. 30 is a diagram depicting the pCM29 plasmid.
FIG. 31 is a diagram depicting the pVR113 plasmid.
FIG. 32 is a diagram depicting the pCM31 plasmid.
FIG. 33 is a diagram depicting the pVR118 plasmid.
FIG. 34 is a diagram depicting the pCM52 plasmid.
FIG. 35 is a diagram depicting the pCM55 plasmid.
FIG. 36 is a diagram depicting the pCM58 plasmid.
FIG. 37 is a diagram depicting the pMI409 plasmid.
FIG. 38 is a diagram depicting the pMI410 plasmid.
FIG. 39 is a diagram depicting the pMI411 plasmid.
FIG. 40 is a diagram depicting the pMI412 plasmid.
FIG. 41 is a diagram depicting the pMI403 plasmid.
FIG. 42 is a diagram depicting the pMI417 plasmid.
FIG. 43 is a diagram depicting the pMI425 plasmid.
FIG. 44 is a diagram depicting the pSO91 plasmid.
FIG. 45 is a diagram depicting the pSO99 plasmid.
FIG. 46 is a diagram depicting the pSO89 plasmid.
FIG. 47 is a diagram depicting the pSO96 plasmid.
FIG. 48 is a diagram depicting the pSO57 plasmid.
FIG. 49 is a diagram depicting the pCM48 plasmid.

The genetically modified yeast of the invention is made by performing certain genetic modifications to a host yeast cell.

A suitable host yeast cell contains at least one native gene that produces an active enzyme that is capable of catalyzing the conversion of D-xylose to xylitol. These may be specific to the xylose xylitol reduction, or may be non-specific (i.e., operate on a range of pentose sugars). Enzymes produced by such genes are variously referred to by EC number 1.1.1.21, and formally as alditol:NAD(P) 1-oxidoreductase). The enzyme encoded by such genes generally has the following activity: D-xylose+NAD(P)H=xylitol+NAD+ (i.e. it can use either NADPH or NADH as redox cofactors, or both). A gene expressing a xylose reductase enzyme is referred to herein as a "xylose reductase gene", or an "XR gene". In some instances, specific XR genes are designated "XYL1" genes herein.

The term "native" is used herein with respect to genetic materials (e.g., a gene, promoter or terminator) that are found (apart from individual-to-individual mutations which do not affect its function) within the genome of the unmodified cells of that species of yeast.

A host yeast cell capable of converting D-xylose to xylitol will generally have the native ability to further convert xylitol to D-xylulose. This is generally accomplished by expressing a xylitol dehydrogenase (XDH) enzyme that is encoded by a gene referred to herein as a "xylitol dehydrogenase gene" or an "XDH gene". Enzymes encoded by such genes are variously referred to by EC number 1.1.1.9, commonly as xylitol dehydrogenase and systematically a xylitol:NAD+2-oxidoreductase (D-xylulose-forming). These genes generally have the following activity: xylitol+ NAD(P)+=D-xylulose+NAD(P)H (although NAD+ is by far the preferred substrate, some do use NADP+). Specific XDH genes are designated "XYL2" genes herein. A suitable host cell has one or more native genes that produce a functional aldose reductase or xylose reductase enzyme and a functional XDH enzyme. An enzyme is "functional" within the context of this invention if it is capable of performing its usual or intended role. A gene is "functional" within the context of this invention if it expresses a functional enzyme.

Another suitable host yeast cell has the ability to transport xylose across its cell wall or membrane.

Another suitable host yeast cell is one that naturally grows on xylose, such as one having an active natural pathway from xylulose-5-phosphate to glyceraldehyde-3-phosphate. In this invention, the pathway from xylulose-5-phosphate to glyceraldehyde-3-phosphate is considered to be active if at least 10% of glucose-based sugars are metabolized by the wild type cell through the hexose monophosphate pathway. Preferably, at least 20, more preferably at least 30%, especially at least 40% of ribulose-5-phosphate is metabolised through this pathway.

Suitable host cells include, for example, yeast cells of the genera *Kluyveromyces*, *Candida*, *Pichia*, *Hansenula*, *Trichosporon*, *Brettanomyces*, *Pachysolen* and *Yamadazyma*. Yeast species of particular interest include *K. marxianus*, *K. lactis*, *K. thermotolerans*, *C. sonorensis*, *C. methanosorbosa*, *C. diddensiae*, *C. parapsilosis*, *C. naeodendra*, *C. balnkii*, *C. entomophila*, *C. scehatae*, *P. tannophilus* and *P. stipitis*. *K. marxianus*, *C. sonorensis*, *C. scehatae*, *Pachysolen tannophilus* and *Pichia stipitis* are examples of yeast cells that grow on xylose. They have a natural xylulose-5-phosphate to glyceraldehyde-3-phosphate pathway, natural functional aldose and/or xylose reductase genes, active xylitol dehydrogenase genes, and natural ability to transport xylose through the cell wall or membrane. Preferred host cells include those of the species *K. marxianus*, *K. lactis*, *K. thermotolerans*, *C. sonorensis* and *C. methanosorbosa*.

The host cell may contain genetic modifications other than those specifically described herein. For example, the host cell may be genetically modified to produce (or not produce) a particular type of fermentation product by further metabolizing xylulose-5-phosphate and/or glyceraldehyde-3-phosphate. Specific examples of such modifications include the deletion or disruption of a native pyruvate decarboxylase (PDC) gene, and the insertion of exogenous genes such as an L-lactate dehydrogenase (L-LDH) or D-lactate dehydrogenase (D-LDH) gene. Methods for making modifications of these types are described, for example, in WO 99/14335, WO 00/71738, WO 02/42471, WO 03/102201, WO 03/102152 and WO 03/049525. These modifications may be present in the host cell prior to further modifying the host cell as described herein, or may be done simultaneously with or after such further modifications as described herein.

Genetically modified yeast cells of certain aspects of the invention include a functional, exogenous xylose isomerase (XI) gene that is preferably integrated into the genome of the host cell. In this context, "exogenous" means (1) the XI gene is not native to the host cell, (2) the XI gene is native to the host cell, but the genome of the host cell has been modified to provide additional functional copies of the native XI gene, or (3) both (1) and (2). Examples of suitable XI genes include XI genes native to *Piromyces* species E2 (such as the *Piromyces* sp. E2 xylA encoding gene sequence in Genbank (Accession # AJ249909)) and *Cyllamyces aberensis* as well as those obtained from other anaerobic fungi. Nucleotide sequences for the *Piromyces* species E2 and *Cyllamyces Aberensis* XI genes are identified as SEQ. ID. NOs. 58 and 151, respectively. Deduced amino acid sequences for proteins produced by these XI genes are identified as SEQ. ID. No. 59 and 152, respectively. A suitable bacterial XI gene is native to *Bacteroides thetaiotaomicron*. The nucleotide sequence for this *B. thetaiotamicron* XI gene is identified as SEQ. ID. NO. 162. The deduced amino acid sequence for the enzyme produced by this gene is identified as SEQ. ID. NO. 163. Suitable XI genes include those that are at least 60%, 80%, 90%, 95%, 98% or 99% homologous to SEQ. ID. NOs. 58 or 151. Suitable XI genes include those that encode for enzymes that are at least 60%, 80%, 90%, 95%, 98% or 99% homologous to SEQ. ID. NOs. 59 or 152. Some suitable xylose isomerase genes are no greater than 95% or no greater than 90% homologous to SEQ. ID. NO. 58 or encode an enzyme that is no greater than 95% or no greater than 90% homologous to SEQ. ID. NO. 59. Other suitable xylose isomerase genes are bacterial xylose isomerase genes that are at least 60, 80, 90, 95, 98 or 99% homologous to SEQ. ID. NO. 162 and/or produce an enzyme that is at least 60, 80, 90, 95, 98 or 99% homologous to SEQ. ID. NO. 163.

Percent homology of amino acid sequences can conveniently computed using BLAST version 2.2.1 software with default parameters. Sequences having an identities score and a positives score of at least XX %, using the BLAST version 2.2.1 algorithm with default parameters are considered at least XX % homologous. Particularly suitable xylose isomerase genes include those that encode for an enzyme that has an identities score of at least 60%, compared with SEQ. ID. NO. 163, an identities score of less than 95%, compared with SEQ. ID. NO. 59, and a positives score of less than 97%, compared with SEQ. ID. NO. 59.

The exogenous XI gene is under the control of a promoter and a terminator, both of which are functional in the modified yeast cell. As used herein, the term "promoter" refers to an untranscribed sequence located upstream (i.e., 5') to the translation start codon of a structural gene (generally within about 1 to 1000 bp, preferably 1-500 bp, especially 1-100 bp) and which controls the start of transcription of the structural gene. Similarly, the term "terminator" refers to an untranscribed sequence located downstream (i.e., 3') to the translation finish codon of a structural gene (generally within about 1 to 1000 bp, more typically 1-500 base pairs and especially 1-100 base pairs) and which controls the end of transcription of the structural gene. A promoter or terminator is "operatively linked" to a structural gene if its position in the genome relative to that of the structural gene such that the promoter or terminator, as the case may be, performs its transcriptional control function.

Promoters and terminator sequences may be native to the yeast cell or exogenous. Promoter and terminator sequences that are highly homologous (i.e., 90% or more, especially 95% or more, most preferably 99% or more homologous) in their functional portions to functional portions of promoter and terminator sequences, respectively, that are native to the cell are useful as well, particularly when the insertion of the exogenous gene is targeted at a specific site in the cell's genome.

A suitable promoter is at least 90%, 95% or 99% homologous to a promoter that is native to a yeast gene. A more suitable promoter is at least 90%, 95% or 99% homologous to a promoter for a gene that is native of the host cell. Particularly useful promoters include promoters for yeast pyruvate decarboxylase (PDC), phosphoglycerate kinase (PGK), xylose reductase, (XR), xylitol dehydrogenase (XDH) and transcription enhancer factor-1 (TEF-1) genes, especially from such genes as are native to the host cell.

A suitable terminator is at least 90%, 95% or 99% homologous to a terminator that is native to a yeast gene. The terminator may be at least 90%, 95% or 99% homologous to a terminator for a gene that is native of the host cell. Particularly useful terminators include terminators for yeast pyruvate decarboxylase (PDC), xylose reductase, (XR), xylitol dehydrogenase (XDH) or iso-2-cytochrome c (CYC) genes, or a terminator from the galactose family of genes in yeast, particularly the so-called GAL10 terminator. A *S. cerevisiae* GAL10 terminator and a *S. cerevisiae* CYC1 terminator have been shown to be effective terminators for exogenous XI genes in yeast.

The use of native (to the host cell) promoters and terminators, together with respective upstream and downstream flanking regions, can permit the targeted integration of the XI gene into specific loci of the host cell's genome, and for simultaneous integration the XI gene and deletion of another native gene, such as, for example, an XR, XDH or PDC gene.

A poly-his(tidine) tail may be present at the 3' end of the XI gene. A method for accomplishing this is described in Example 3 below. The presence of the poly-his tail may diminish the performance of the XI gene, however. The poly-his tail is not critical to the invention and may be omitted if desired.

The exogenous XI gene may be integrated randomly into the host cell's genome or inserted at one or more targeted locations. Examples of targeted locations include the loci of a gene that is desirably deleted or disrupted, such as an XR, XDH or PDC gene. In some embodiments, integration of the XI gene adjacent to the site of a native PDC gene appears to be related to improved performance of the modified yeast cell in producing fermentation products. Integration at the PDC locus may be accomplished with or without deletion or disruption of the native PDC gene, but it is preferred to maintain the native PDC gene intact and functional, particularly when a desired fermentation product is ethanol or other product that is a pyruvate metabolite.

Targeted integration can be accomplished by designing a vector having regions that are homologous to the upstream (5'-) and downstream (3'-) flanks of the target gene. Either of both of these regions may include a portion of the coding region of the target gene. The XI cassette (including associated promoters and terminators if different from those of the target gene) and selection markers (with associated promoters and terminators as may be needed) will reside on the vector between the regions that are homologous to the upstream and downstream flanks of the target gene.

The genetically modified yeast cell may contain a single copy or multiple copies of the exogenous XI gene. If multiple copies of the exogenous XI gene are present, from 2 to 10 or more copies may be present, such as from about 2-8 or from about 2-5 copies. Multiple copies of the exogenous XI gene may be integrated at a single locus (so they are adjacent each other), or at several loci within the host cell's genome. In an embodiment of particular interest, multiple copies of the exogenous XI gene are incorporated at or adjacent to the locus of a native PDC gene, with or without deletion or disruption of the native PDC gene. It is possible for different exogenous XI genes to be under the control of different types of promoters and/or terminators.

Performance of the modified yeast, especially under anaerobic conditions, is improved by making one or more additional modifications to its genome, and/or selecting host cells having certain characteristics. These include one or more of (1) low XR (or other aldose reductase) activity, (2) low XDH activity and (3) XK overexpression.

The host cell may naturally have or be modified to have low aldose reductase activity. Such a low aldose reductase activity, measured in the manner described in Example 4E below, is suitably less than 10 mU/mg or less than 5 mU/mg. If the host cell contains one or more aldose reductase genes that produce enzymes that catalyze the conversion of xylose to xylitol, one or more of these genes is suitably disrupted or deleted. In general, the gene(s) selected for disruption or deletion are those which individually or collectively (1) account for at least 40%, preferably at least 50% of the host cell's xylose→xylitol reduction activity, and/or (2) are XR genes, i.e., genes that encode an enzyme specific to the xylose→xylitol reduction. It is generally preferred to delete or disrupt at least one XR gene. Deletion or disruption preferably achieves at least a 50% reduction in enzyme activity, and more preferably reduced xylose reductase activity to below 10 mU/mg or 5 mU/mg.

By "delete or disrupt", it is meant that the entire coding region of the gene is eliminated (deletion), or the gene or its promoter and/or terminator region is modified (such as by deletion, insertion, or mutation) so that the gene no longer produces an active enzyme, or produces an enzyme with severely reduced activity. The deletion or disruption can be accomplished by genetic engineering methods, forced evolution or mutagenesis and/or selection or screening. In the case of the XR or non-specific aldose reductase gene, a suitable method for accomplishing this is to clone the upstream and downstream flanking regions for the gene (which may include a portion of the coding region for the gene), produce a vector containing the cloned upstream and downstream flanks, and transform the host cell with the vector. The vector may contain other genetic material such as a marker gene or other gene that is desirably inserted into the genome of the host cell at the locus of the native XR or non-specific aldose gene (such as an XI gene, XK gene or a gene that enables the cell to produce a desired fermentation product, as an L- or D-LDH gene).

One method of deleting the XR or non-specific aldose reductase gene is to transform the host cell with a vector containing regions that are homologous to the upstream (5'-) and downstream (3'-) flanks of the target gene. Such flanking sequences can be obtained, for example, by amplifying the appropriate regions by PCR using suitably designed primers and genomic DNA as the template. Either of both of these regions may include a portion of the coding region of the target gene, although the vector should not contain the entire functional portion of the gene. Such flanking sequences are generally sequences of at least 50 base pairs, or at least 100 or at least 500 base pairs. Although there is in theory no upper limit to the length of the flanking sequence, it is preferably up to about 4000 base pairs, more preferably up to about 1200 base pairs in length. The flanking sequences are each at least 90%, preferably at least 95%, more preferably at least 98% and even more preferably at least 99% homologous to the corresponding sequences in the cell's genome. These flanking sequences may include the promoter and terminator sequences, respectively, of the target gene. The vector may in addition contain one or more selection marker cassettes (with associated promoters and terminators as may be needed) that advantageously reside between the regions that are homologous to the upstream and downstream flanks of the target gene. Such a vector can delete the target gene in a homologous recombination, inserting the selection marker gene at the locus of the deleted target gene. The vector may instead of or in addition to the selection marker cassette include another expression cassette, such as an XI expression cassette, and L- or D-LDH cassette or a xylulokinase expression cassette, all of which may include associated promoters and terminators. Vectors can also be designed to take advantage of spontaneous loopout events, such as are described in WO 03/102152.

The host cell may naturally have or be modified to have low xylitol dehydrogenase activity. Such a low xylitol dehydrogenase enzyme activity, measured in the manner described in Example 6B below, is suitably less than 2 mU/mg or less than 1 mU/mg. If the host cell contains one or more xylitol dehydrogenase genes resulting in higher xylitol dehydrogenase enzyme activities, one or more of these genes is suitably disrupted or deleted. XDH gene deletion or disruption can be performed in a way analogous to described before with respect to aldose reductase deletion or disruption. Deletion can be performed by incorporating upstream and downstream flanks of the XDH gene into a transformation vector, instead of the flanks of the XR or non-specific aldose reductase gene. As before, the vector may include one or more selection marker cassettes and/or one or more other expression cassettes. Deletion or disruption preferably achieves at least a 50% reduction in enzyme activity, and more preferably reduced xylitol dehydrogenase activity to below 2 mU/mg or 1 mU/mg.

The modified cell preferably expresses a xylulokinase enzyme having an activity of at least 100 mU/mg, such as at least 300 mU/mg or at least 500 mU/mg, measured as described in Example 5E below. The xylulokinase enzyme is referred to variously as EC 2.7.1.17 and systematically as ATP:D-xylulose 5-phosphotransferase. Its activity is generally ATP+D-xylulose=ADP+D-xylulose 5-phosphateXylulokinase (XK). Overexpression can be achieved, for example, by forced evolution (under conditions that favor selection of mutants that overexpress the enzyme), mutagenesis or by integrating one or more functional exogenous xylulokinase genes into the genome of the host cell. In this context, "exogenous" means (1) the XK gene is not native to the host cell, (2) the XK gene is native to the host cell, but the genome of the host cell has been modified to provide additional functional copies of the native XK gene, or (3) both (1) and (2). Suitable xylulokinase genes include yeast xylulokinase genes. A preferred example of a suitable XK gene is the *S. cerevisiae* XK gene (ScXKS1). A nucleotide sequence for the ScXKS1 gene is identified as SEQ. ID. NO. 83. The deduced amino acid sequence for the enzymes produced by the ScXKS1 gene is identified as SEQ. ID. NO. 84. Suitable XK genes include those that are at least 70%, 80%, 90%, 95%, 98% or 99% homologous to SEQ. ID. NO. 83. Suitable XK genes include those that encode for enzymes that are at least 70%, 80%, 90%, 95%, 98% or 99% homologous to SEQ. ID. NO. 84. Other suitable XK genes are native to *K. marxianus* or *C. sonorensis*, or are at least 70%, 80%, 80%, 95%, 98% or 99% homologous to either of these.

The exogenous XK gene is under the control of a promoter and a terminator, both of which are functional in the modified yeast cell. Suitable promoters and terminator sequences may be native to the host cell or exhibit a high homology (i.e., 90% or greater, especially 95% or greater, most preferably 99% or greater homology) to a native promoters or terminator. Such promoters and terminators are particularly useful when the exogenous XK gene is targeted at a specific site in the host cell's genome. Other suitable promoters and terminators are native to the organism from which the XK gene was obtained or exhibit a similarly high homology to such native promoter and/or terminators. For example, suitable promoters and terminators for the ScXKS1 gene identified above include promoters and terminators for *S. cerevisiae* genes. The promoter and/or terminators may be those native to the particular XK gene or exhibit a similarly high homology to such promoter and/and terminator.

Particularly useful promoters for the ScXKS1 gene include *S. cerevisiae* pyruvate decarboxylase (PDC), phosphoglycerate kinase (PGK), xylose reductase, (XR), xylitol dehydrogenase (XDH) and transcription enhancer factor-1 (TEF-1) promoters. Particularly useful terminators for the ScXKS1 gene include *S. cerevisiae* pyruvate decarboxylase (PDC), xylose reductase, (XR), xylitol dehydrogenase (XDH) or iso-2-cytochrome c (CYC) terminators, or a terminator from the galactose family of genes in yeast, particularly the so-called GAL10 terminator. A *S. cerevisiae* GAL10 terminator and a *S. cerevisiae* CYC1 terminator have been shown to be effective terminators for exogenous XI genes in yeast.

The exogenous XK gene may be integrated randomly into the host cell's genome, or inserted at one or more targeted locations, using methods analogous to those for inserting the XR gene, as discussed above. Examples of targeted locations include the loci of a gene that is desirably deleted or disrupted, such as an XR, XDH or PDC gene. As before, targeted integration can be accomplished by designing a vector having regions that are homologous to the upstream (5'-) and downstream (3'-) flanks of the target gene. Either of both of these regions may include a portion of the coding region of the target gene. The XK cassette (including associated promoters and terminators if different from those of the target gene) and selection markers (with associated promoters and terminators as may be needed) will reside on the vector between the regions that are homologous to the upstream and downstream flanks of the target gene.

The genetically modified yeast cell may contain a single copy or multiple copies (such as from 2 to 10 or more copies, from 2 to 8 or from 2 to 5 copies) of the exogenous XK gene. Multiple copies of the exogenous XK gene may be integrated at a single locus (so they are adjacent each other), or at several loci within the host cell's genome. It is possible for different exogenous XK genes to be under the control of different types of promoters and/or terminators.

Cells according to the invention that have low xylose reductase activity, low xylitol dehydrogenase activity and overexpressed xylulokinase activity are excellent hosts for screening exogenous xylose isomerase genes for activity in the host cell. These genetic modifications create a cellular environment that tends to favor xylose isomerase expression, so if a certain gene is in fact active, its activity is less likely to be suppressed by the cellular environment and therefore be measurable in the cell.

Genetic modification of the host cell is accomplished in one or more steps via the design and construction of appropriate vectors and transformation of the host cell with those vectors. Electroporation and/or chemical (such as calcium chloride- or lithium acetate-based) transformation methods can be used. Methods for transforming yeast strains are described in WO 99/14335, WO 00/71738, WO 02/42471, WO 03/102201, WO 03/102152 and WO 03/049525; these methods are generally applicable for transforming host cells in accordance with this invention. The DNA used in the transformations can either be cut with particular restriction enzymes or used as circular DNA.

General approaches to transformation vector design have been discussed above in a general sense. Some specific transformation vector designs are as follows, with components listed in order of reading/transcription. All can be circularized or linearized. All may contain restriction sites of various types for linearization or fragmentation. Vectors may further contain a backbone portion (such as for propagation in *E. coli*, which are conveniently obtained from commercially available yeast or bacterial vectors.

1. Upstream (5'-) region of host cell XR gene; marker expression cassette, host downstream (3'-) region of host XR gene. The marker expression cassette may be a hygromycin, Ura3 or G418 resistance expression cassette with promoters and terminators as needed. A Ura3 cassette may be a HisG-Ura3-HisG cassette. A G418 cassette may include the ScPDC1 promoter and ScGAl10 terminator.

2. Same as (1), with XI cassette (including promoter and terminator operatively linked to the gene) located between the 5'- and 3'-regions of the host cell XR gene. The XI cassette may include a promoter that is native to the host cell. The XI cassette may include a ScCYC1 or ScGAL10 terminator.

3. Same as (1) or (2), with XK cassette (including promoter and terminator operatively linked to the gene) located between the 5'- and 3'-regions of the host cell XR gene. The XK cassette may include a promoter that is native to the host cell, or a ScTEF1 promoter. The XI cassette may include a ScCYC1 or ScGAL10 terminator.

4. Upstream (5'-) region of host cell XDH gene; marker expression cassette, host downstream (3'-) region of host XDH gene. The marker expression cassette may be a hygromycin, Ura3 or G418 resistance expression cassette with promoters and terminators as needed. A Ura3 cassette may be a HisG-Ura3-HisG cassette. A G418 cassette may include the ScPDC1 promoter and ScGAl10 terminator.

5. Same as (4), with XI cassette (including promoter and terminator operatively linked to the gene) located between the 5'- and 3'-regions of the host cell XR gene. The XI cassette may include a promoter that is native to the host cell. The XI cassette may include a ScCYC1 or ScGAL10 terminator.

6. Same as (4) or (5), with XK cassette (including promoter and terminator operatively linked to the gene) located between the 5'- and 3'-regions of the host cell XR gene. The XK cassette may include a promoter that is native to the host cell, or a ScTEF1 promoter. The XI cassette may include a ScCYC1 or ScGAL10 terminator.

7. HisG-Ura3-HisG cassette preceded or followed by an XI cassette or XK cassette.

8. An XI cassette including a *K. marxianus* promoter or a *C. sonorensis* promoter, the XI cassette being preceded or followed by a marker expression cassette. The *K. marxianus* or *C. sonorensis* promoter may be a PDC or PGK promoter. The terminator in the XI cassette may be a *K. marxianus, C. sonorensis* or *S. cerevisiae* terminator, and may be specifically a ScCYC1 or ScGAL10 terminator. The marker expression cassette may be a hygromycin, Ura3 or G418 resistance expression cassette with promoters and terminators as needed. A Ura3 cassette may be a hisG-Ura3-hisG cassette. A G418 cassette may include the ScPDC1 promoter and ScGAl10 terminator. The XI cassette may also include an XK cassette (such as described in 9 below), either upstream or downstream of the XI cassette, and either upstream of downstream of the marker expression cassette.

9. An XK cassette being preceded or followed by a marker expression cassette. The XK cassette may include a *K. marxianus* promoter, a *C. sonorensis* promoter or a *S. cerevisiae* promoter. The XK cassette promoter may be specifically a *K. marxianus*, or *C. sonorensis* PDC or PGK or an *S. cerevisiae* PDC, PGC or TEF1 promoter. The terminator in the XK cassette may be a *K. marxianus, C. sonorensis* or *S. cerevisiae* terminator, and may be specifically a ScCYC1 or ScGAL10 terminator. The marker expression cassette may be a hygromycin, Ura3 or G418 resistance expression cassette with promoters and terminators as needed. A Ura3 cassette may be a hisG-Ura3-hisG cassette. A G418 cassette may include the ScPDC1 promoter and ScGAl10 terminator.

10. An XI cassette, XK cassette, or both, being preceded by an upstream (5'-) region of a host cell XR gene; and followed by a downstream (3'-) region of a host XR gene. This vector may include other components between the upstream and down stream regions of the XR gene.

11. An XI cassette, XK cassette, or both, being preceded by an upstream (5'-) region of a host cell XDH gene; and followed by a downstream (3'-) region of a host XDH gene. This vector may include other components between the upstream and down stream regions of the XDH gene.

12. Any of the foregoing plasmids further including a self-replication site that is active in the host cell.

Specific XI cassettes useful in the foregoing vectors include the *K. marxianus* PDC1 (KmPDC1) promoter, XI gene (any described above), and ScCYC1, ScGAL10 or KmPDC1 terminator; the *C. sonorensis* PDC1 (CsPDC1) promoter, XI gene and ScCYC1, ScGAL10 or CsPDC1 terminator; and the *C. sonorensis* PGK (CsPGK) promoter, XI gene and ScCYC1, ScGAL10 or CsPDC1 terminator.

Specific XK cassettes useful in the foregoing vectors include the *K. marxianus* PDC1 (KmPDC1) promoter, XK gene (any described above, but especially the ScXKS1 gene), and ScCYC1, ScGAL10 or KmPDC1 terminator; the *C. sonorensis* PDC1 (CsPDC1) promoter, XK gene and ScCYC1, ScGAL10 or CsPDC1 terminator; the *C. sonorensis* PGK (CsPGK) promoter, XK gene and ScCYC1, ScGAL10 or CsPDC1 terminator; and *S. cerevisiae* TEF-1 (ScTEF1) promoter, XK gene and ScCYC1, ScGAL10 or CsPDC1 terminator.

In addition to the specific selection marker genes described above, typical selection marker genes encode proteins that (a) confer resistance to antibiotics or other toxins, e.g., zeocin (*Streptoalloteichus hindustanus* ble bleomycin resistance gene), G418 (kanamycin-resistance gene of Tn903), hygromycin (aminoglycoside antibiotic resistance gene from *E. coli*), ampicillin, tetracycline, or kanamycin for host cells; (b) complement auxotrophic deficiencies of the cell, such as amino acid leucine deficiency (*K. marxianus* Leu2 gene) or uracil deficiency (e.g., *K. marxianus* or *S. cerevisiae* Ura3 gene); (c) supply critical nutrients not available from simple media, or (d) confers ability for the cell to grow on a particular carbon source. A xylose isomerase gene can act in this manner, allowing selection to occur on the basis of the ability to grow on xylose.

Successful transformants can be selected for in known manner, by taking advantage of the attributes contributed by the marker gene, or by other characteristics (such as ability to grow on xylose) contributed by the inserted genes. Screening can be performed by PCR or Southern analysis to confirm that the desired insertions and deletions have taken place, to confirm copy number and to identify the point of integration of genes into the host cell's genome. Activity of the enzyme encoded by the inserted gene and/or lack of activity of enzyme encoded by the deleted gene can be confirmed using known assay methods.

The genetically modified yeast cell of the invention containing the exogenous XI gene is useful to ferment pentose sugars to desirable fermentation products such as ethanol and lactic acid. Certain additional genetic modifications may be necessary to enable the yeast cell to produce certain products in acceptable yields, titers and/or productivity For example, integration of an exogenous LDH gene and deletion of native PDC genes may be necessary to obtain high lactic acid yields, as discussed before.

In the fermentation process of the invention, the cell of the invention is cultivated in a fermentation medium that includes a pentose sugar. The pentose sugar is preferably xylose, xylan or other oligomer of xylose. Such sugars are suitably hydrolysates of a hemicellulose-containing biomass. The fermentation medium may contain other sugars as well, notably hexose sugars such as dextrose (glucose) fructose, oligomers of glucose such as maltose, maltotriose and isomaltotriose, and panose. In case of oligomeric sugars, it may be necessary to add enzymes to the fermentation broth in order to digest these to the corresponding monomeric sugar.

The medium will typically contain nutrients as required by the particular cell, including a source of nitrogen (such as amino acids proteins, inorganic nitrogen sources such as ammonia or ammonium salts, and the like), and various vitamins, minerals and the like.

Other fermentation conditions, such as temperature, cell density, selection of substrate(s), selection of nutrients, and the like are not considered to be critical to the invention and are generally selected to provide an economical process. Temperatures during each of the growth phase and the production phase may range from above the freezing temperature of the medium to about 50° C., although the optimal temperature will depend somewhat on the particular microorganism. A preferred temperature, particularly during the production phase, is from about 30-45° C. When the cell is an engineered *K. marxianus*, it can tolerate relatively high temperatures (such as above 40° C. and up to 50° C., especially up to 45° C.). Another preferred species of cell, *C. sonorensis*, can tolerate temperatures up to about 40° C. This temperature range provides for the possibility of conducting the fermentation at such higher temperatures (thereby reducing cooling costs) without a significant loss of productivity. Another advantage provided by the good high temperature tolerance is that if the fermentation becomes contaminated with an undesired microorganism, in many cases the undesired microorganism can be selectively killed off by heating the fermentation medium to 40° C. or more, especially 45° C. or more, without significantly harming the desired cells of the invention.

During the production phase, the concentration of cells in the fermentation medium is typically in the range of about 1-150, preferably about 3-10, even more preferably about 3-6 g dry cells/liter of fermentation medium.

The fermentation may be conducted aerobically, microaerobically or anaerobically. If desired, specific oxygen uptake rate can be used as a process control, as described in WO 03/102200. An advantage of the invention is that the genetically modified cell typically can ferment xylose anaerobically due to the expression of the XI gene and other modifications.

When the fermentation product is an acid, the medium may be buffered during the production phase of the fermentation so that the pH is maintained in a range of about 5.0 to about 9.0, preferably about 5.5 to about 7.0. Suitable buffering agents are basic materials that neutralize lactic acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here. It is within the scope of the invention, however, to allow the pH of the fermentation medium drop from a starting pH that is typically 6 or higher, to below the pKa of the acid fermentation product, such as in the range of about 2 to about 5 or in the range of from about 2.8 to about 4.5.

In a buffered fermentation, acidic fermentation products such as lactic acid are neutralized as they are formed to the corresponding lactate salt. Recovery of the acid therefore involves regenerating the free acid. This is typically done by removing the cells and acidulating the fermentation broth with a strong acid such as sulfuric acid. A salt by-product is formed (gypsum in the case where a calcium salt is the neutralizing agent and sulfuric acid is the acidulating agent), which is separated from the acid. The acid is then recovered through techniques such as liquid-liquid extraction, distillation, absorption, etc., such as are described in T. B. Vickroy, Vol. 3, Chapter 38 of Comprehensive Biotechnology, (ed. M. Moo-Young), Pergamon, Oxford, 1985; R. Datta, et al., FEMS Microbiol. Rev., 1995; 16:221-231; U.S. Pat. Nos. 4,275,234, 4,771,001, 5,132,456, 5,420,304, 5,510,526, 5,641,406, and 5,831,122, and WO 93/00440.

The process of the invention can be conducted continuously, batch-wise, or some combination thereof.

The following examples are provided to illustrate the invention, but are not intended to limit the scope thereof. All parts and percentages are by weight unless otherwise indicated.

EXAMPLE 1A

Construction of Plasmid Containing *S. Cerevisiae* PGK1 Promoter and *S. cerevisiae* Gal10 Terminator (pNC2, FIG. 1); Construction of Plasmid Containing *S. cerevisiae* PDC1 Promoter and *S. cerevisiae* Gal10 Terminator (pNC4, FIG. 2)

The nucleotide sequence of the *S. cerevisiae* PGK1 promoter (ScPGK1) is identified as SEQ. ID. NO. 1. This sequence was obtained as a restriction fragment from a proprietary plasmid designated pBFY004. Alternatively, it can be obtained by PCR amplification using *S. cerevisiae* chromosomal DNA as template and primers designed based on SEQ. ID. NO. 1.

The *S. cerevisiae* GAL10 terminator (ScGAL10) used has the nucleotide sequence identified as SEQ. ID. NO. 2. This sequence was obtained as a restriction fragment from a proprietary plasmid designated pBFY004. Alternatively, it can be obtained by PCR amplification using *S. cerevisiae* chromosomal DNA as template and primers designed based on SEQ. ID NO. 2.

The *S. cerevisiae* PDC1 promoter (ScPDC1) was PCR amplified using the primers identified as SEQ ID. NO. 3 and SEQ. ID. NO. 4, using chromosomal DNA from *S. cerevisiae* strain GY5098 (ATCC 4005098) as the template. Thermocycling was performed by 30 cycles of 1 minute at 94° C., 1 minute at 56° C. and 1 minute at 72° C., followed by a final incubation of 7 minutes at 72° C., using PfuTurbo DNA polymerase (Stratagene, Madison, Wis.). The nucleotide sequence of the ScPDC1 promoter is identified as SEQ. ID. NO. 5.

Plasmid pNC2 (FIG. 1) was generated by combining the ScPGK1 and the ScGal10 terminator on the pGEM5Z(+) (Promega, Wisconsin) backbone vector. The ScPGK1 and the ScGAL10 were separated in the resulting vector by a poly-linker region with the restriction sites XbaI, EcoRI and BamHI for inserting particular genes to be expressed between the yeast promoter and terminator. A ~1.2 kbp NotI restriction fragment comprised of the ScPGK1 promoter and ScGAL10 terminator with multi-cloning sites is identified as SEQ. ID. NO. 6.

The expression vector pNC4 containing expression cassette was constructed in the same general way, except the ScPDC1 gene was used instead of the ScPGK1 gene. The resulting vector (pNC4) is shown in FIG. 2. A ~1.3 kbp NotI fragment comprised of the ScPDC1 promoter and ScGAL10 terminator with multi-cloning sites is identified as SEQ. ID. NO. 7.

EXAMPLE 1B

Insertion of a G418 Resistance Marker Gene into pNC2 (Ex. 1A, FIG. 1) to Create a Plasmid in which the G418 Gene is Operably Linked to the *S. cerevisiae* PGK1 Promoter and ScGAL10 Terminator (pVR22, FIG. 3)

G418 resistance gene was amplified by PCR using Pfu Polymerase (Stratagene, Madison, Wis.) with primers identified as SEQ. ID. NO. 8 and SEQ. ID. NO. 9, using the plasmid pPIC9K (Invitrogen, CA) as the template. Thermocycling was performed by initially incubating the reaction mixture for 5 minutes at 95° C., followed by 35 cycles of 30 seconds at 95° C., 30 seconds at 49° C. and 2 minutes at 72° C., followed by a final incubation for 10 minutes at 72° C. The PCR product was digested with BamHI and XbaI and an 821 bp fragment was isolated and ligated to a ~4303 bp BamHI-XbaI fragment of pNC2 (Ex. 1A, FIG. 1). The resulting plasmid (pVR22, FIG. 3) has the ScPGK1 promoter and ScGAL10 terminator operably linked to the G418 resistance gene.

EXAMPLE 1C

Insertion of a G418 Resistance Marker Gene into pNC4 (Ex. 1A, FIG. 2) to Create a Plasmid in which the G418 Gene is Operably Linked to the *S. cerevisiae* PDC1 Promoter and ScGAL10 Terminator (pVR29, FIG. 4)

G418 resistance gene was amplified by PCR using Pfu Polymerase (Stratagene, Madison, Wis.) with primers identified as SEQ. ID. NO. 8 and SEQ. ID. NO. 9, using plasmid pVR22 (Ex. 1B, FIG. 3) as the template. Thermocycling was performed by initially incubating the reaction mixture for 5 minutes at 95° C., followed by 35 cycles of 30 seconds at 95° C., 30 seconds at 49° C., and 2 minutes at 72° C., followed by a final incubation for 10 minutes at 72° C. The PCR product was digested with BamHI and XbaI and an 821 bp fragment was isolated and ligated to a ~4303 bp BamHI-XbaI fragment of pNC4. (Ex. 1A, FIG. 2). The resulting plasmid, pVR29 (FIG. 4), contained the ScPDC1 promoter and ScGAL10 terminator operably linked to the G418 resistance gene.

EXAMPLE 1D

Construction of a Vector (pBH5b, FIG. 6) Containing the 5'- and 3'-Flanking Sequences of the *K. marxianus* PDC1 Gene, and the G418 Gene Under Control of the ScPDC1 Promoter and ScGAL10 Terminator A 1254 bp fragment of DNA immediately upstream of the *K. marxianus* PDC1 (KmPDC1) gene was PCR amplified with primers identified as SEQ. ID. NO. 10 and SEQ. ID. NO. 11, using the plasmid pSO21 (described in U. S. Published Patent Application 2004/029256A1) as the template. Thermocycling was performed by initially incubating the reaction mixture for 2 minutes at 94° C., then by 35 cycles of 30 seconds at 94° C., 30 seconds at 55° C. and 1.5 minutes at 72° C., followed by a final incubation of 7 minutes at 72° C. The PCR product was separated on a 0.8% agarose gel and a ~1254 bp product isolated. The PCR product and the pVR29 plasmid (Ex. 1C, FIG. 4) were both digested with KpnI and SbfI and ligated to produce a ~6315 bp vector designated as pBH5a (FIG. 5). The pBH5a plasmid contained the G418 resistance gene operatively linked to the ScPDC1 promoter and ScGAL10 terminator and a ~1240 bp fragment of DNA homologous to DNA immediately upstream of the KmPDC1 gene.

A 535 bp fragment of DNA immediately downstream of the KmPDC1 gene was PCR amplified with primers identified by SEQ. ID. NO. 12 and SEQ. ID. NO. 13, using plasmid pSO21 as the template. Thermocycling was performed by initially incubating the reaction mixture for 2 minutes at 94° C., then by 35 cycles of 30 seconds at 94° C., 30 seconds at 55° C. and 45 seconds at 72° C., followed by a final incubation of 4 minutes at 72° C. The PCR product was separated on a 0.8% agarose gel and a 535 bp product isolated. The PCR product was digested with SbfI and MluI and the resulting 529 bp fragment was ligated with the SbfI-MluI fragment of pBH5a to produce plasmid pBH5b (FIG. 6). The pBH5b plasmid contains sequences corresponding to those flanking the KmPDC1 gene, i.e., a ~1.2 kbp upstream flanking sequence and a ~0.5 kbp of DNA downstream flanking sequence, with a single SbfI site located between them. The pBH5b plasmid also contains the G418 resistance marker operatively linked to the ScPDC1 promoter and ScGAL10 terminator.

EXAMPLE 1E

Construction of Vector Containing Poly-his Tag and *S. cerevisiae* CYC1 Terminator (pVR73, FIG. 8); Removal of G418 Resistance Marker Gene from pBH5b (Ex. 1D, FIG. 6) to Form Vector pVR77 (FIG. 7)

Primers identified as SEQ. ID. NO. 14 and SEQ. ID. NO. 15 were designed based on the pYES6CT vector (Invitrogen, CA) for the amplification of bases containing a multiple cloning site, poly-his tag, and *S. cerevisiae* CYC1 terminator (ScCYC1). The primers introduced SbfI and BsmBI sites to the product. PCR conditions were 30 cycles of 1 minute at 94° C., 1 minute at 55° C. and 1 minute at 68° C., followed by a final incubation at 68° C. for 10 minutes using Platinum Pfx DNA polymerase (Invitrogen, CA). The PCR product was column purified, followed by addition of adenine nucleotides to the 5' ends of TA cloning using Taq DNA polymerase incubated at 72° C. for 10 minutes. The 507 bp product was then TA cloned into a TOPOII TA cloning vector (Invitrogen, CA) and designated pVR73 (FIG. 8). The inclusion of the poly-his tag in this vector will cause genes cloned into the unique SbfI site to have the his tag fused to the protein expressed from that gene. This tagging of the protein with the poly-his tag allows for relatively quick western blot detection of the protein using Ni-NTA (HRP) conjugate (Quiagen, USA) and for rapid purification of the expressed gene using Ni-chelating resin and columns (Invitrogen, CA).

Plasmid pBH5b (Ex. 1D, FIG. 6) was digested with Sph1 and a ~4.7 kbp fragment that retains the KmPDC1 promoter and terminator was re-ligated to itself to make plasmid pVR77 (FIG. 7). The G418 antibiotic selection marker from pBH5b was thus eliminated.

EXAMPLE 1F

Construction of a Vector pVR78 (FIG. 9) Containing the KmPDC1 Upstream Flanking Region, Multi-Cloning Site, Poly-his Tag and ScCYC1 Terminator Plasmid pVR73 (Ex. 1E, FIG. 8) was digested with enzymes SbfI and BsmBI to release a 504 bp fragment containing the multi-cloning site, poly-his tag and ScCYC1 terminator. Vector pVR77 was digested using the same enzymes to produce a ~4249 bp fragment containing the KmPDC1 upstream and downstream flanks and vector backbone. The two fragments were ligated to form a ~4752 bp plasmid (pVR78, FIG. 9) that contained the unique SbfI restriction site 184 bp from the poly-his tag. This process removed most of the KmPDC1 downstream flanking region from plasmid pVR78.

EXAMPLE 1G

Modification of Plasmid pVR78 (Ex. 1F, FIG. 9) to Form Plasmid pCM3 (FIG. 10) with a Reduced Distance from the SbfI Restriction Site to the Poly-his Tag for Better Gene Expression Primers identified as SEQ. ID. NO. 16 and SEQ. ID. NO. 17 were designed to amplify the entire region of plasmid pVR78 from the poly-his tag to the ScCYC1 terminator. The primers also had a 5' SbfI site immediately upstream of the poly-his tag and 3' SapI site. PCR reaction was performed using standard methods. PCR conditions consisted of an initial incubation at 94° C. for 2 minutes, followed by 10 cycles of 30 seconds at 94° C., 30 seconds at 63° C. and 1 minute at 68° C. This was followed by an additional 20 cycles of 30 seconds at 94° C., 1 minute at 68° C. The final step was an 8-minute incubation at 68° C. Amplification was performed using Platinum Pfx DNA polymerase (Invitrogen, CA). The PCR product was digested with SbfI and SapI restriction enzymes. A ~3.9 kb fragment obtained by digestion of plasmid pVR78 with the enzymes 5'SbfI and 3'SapI was ligated to the PCR product. This resulting plasmid was designated pCM3 (FIG. 10).

EXAMPLE 1H

Construction of a Plasmid (pPS1, FIG. 11) Containing *E. coli* Hygromycin Resistance Gene Under Transcriptional Control of ScPDC1 Promoter and ScGAL10 Terminator The *E. coli* hph gene that confers resistance to hygromycin B was PCR amplified using the primers identified by SEQ. ID. NO. 18 and SEQ. ID. No. 19, using the plasmid pRLMex30 (Mach et al. 1994, *Curr. Genet.* 25, 567-570) as the template. The hph gene can also be obtained using the same primers with *E. coli* chromosomal DNA serving as the template. Thermocycling was performed at 30 cycles of 1 minute at 94° C., 1 minute at 56° C., and 3 minutes at 72° C., followed by a final incubation of 7 minutes at 72° C. using PfuTurbo DNA polymerase (Stratagene, Madison, Wis.). The PCR product was electrophoretically separated on a 0.8% agarose gel and a 1026 bp fragment isolated. The 1026 bp fragment was then digested with XbaI and BamHI and ligated into the XbaI-BamH1 fragment of pNC4 (Ex. 1A, FIG. 2) containing the ScPDC1 promoter and the ScGAL10 terminator to give the plasmid pPS1 (FIG. 11).

EXAMPLE 1I

Construction of a Vector (pCM9, FIG. 12) Containing the KmPDC1 Upstream Flanking Region, Multi-Cloning Site, Poly-his Tag, ScCYC1 Terminator (all from pCM3, Ex. 1G, FIG. 10) and the *E. coli* Hygromycin Resistance Gene Under Transcriptional Control of ScPDC1 Promoter and ScGAL10 Terminator (from pPS1, Ex. 1H, FIG. 11)

Plasmid pPS1 was digested with SphI and a ~2.2 kbp fragment containing the hph gene under the control of the ScPDC1 promoter and the ScGAL10 terminator was ligated to SphI-digested pCM3. The resultant plasmid (pCM9, FIG. 12) contains the KmPDC1 promoter region followed by a single SbfI site and the ScCYC1 terminator for future xylose isomerase gene expression. Additionally this cassette for gene expression is positioned right next to a ~2.2 kbp fragment containing the hph gene under the control of the ScPDC1 promoter and the ScGAL10 terminator for selection of the transformants in yeast.

EXAMPLE 2A

Reconstruction of *Piromyces* sp. E2 Xylose Isomerase (PXYLA) Gene Based on the Sequence Available in Genbank The method used to reconstruct the *Piromyces* sp. E2 xylose isomerase (PXYLA) gene is adapted from "A method for synthesizing genes and cDNA's by polymerase chain reaction", by Alberto Di Donato et al., Analytical Biochemistry 212, 291-293 (1993). PAGE purified primers are ordered starting from the center of the gene to reconstruct going out. 14-16 bp overlaps are maintained for the primer sets. The primers are each 60-70 bp long. The gene was reconstructed in 17 steps.

The PCR protocol that was followed during this method used Platinum Pfx (Invitrogen, CA) as the DNA polymerase, and its buffer and MgSO$_4$ as directed by the manufacturer. Step 1 is performed using primers identified as SEQ. ID. NO. 20 and SEQ. ID. NO. 21. These primers represent the center of the gene sequence. No template is required in Step 1, as the annealing of the primers and its extension will form the core template on which subsequent PCR reactions will be built. Cycling for Step 1 is 20 cycles of 94° C. for 1 minute, 54° C. for 1 minute and 68° C. for 2 minutes (with 5 additional seconds being added to each successive cycle), followed by storing at 4° C.

In reaction steps 2-17, Platinum Pfx (Invitrogen, CA) was used as the DNA polymerase, and its buffer and MgSO$_4$ were used as directed by the manufacturer. 2.5 µl of the mix from each step was used as template for each subsequent step (50 µl reaction). The primer sets for each reaction are described in Table 1. The template in each case was 5 µl of DNA from the preceding reaction step. The cycling for steps 2-17 was 20 cycles of 94° C. for 1 minute, 46° C. for 1 minute and 68° C. for 2 minutes (with 5 additional seconds being added to each successive cycle), followed by storing at 4° C.

TABLE 1

| Reaction Step No. | SEQ. ID. NOs. |
|---|---|
| 1 | 20, 21 |
| 2 | 22, 23 |
| 3 | 24, 25 |
| 4 | 26, 27 |
| 5 | 28, 29 |
| 6 | 30, 31 |
| 7 | 32, 33 |
| 8 | 34, 35 |
| 9 | 36, 37 |
| 10 | 38, 39 |
| 11 | 40, 41 |
| 12 | 42, 43 |
| 13 | 44, 45 |
| 14 | 46, 47 |
| 15 | 48, 49 |
| 16 | 50, 51 |
| 17 | 52, 53 |

EXAMPLE 2B

Construction of Vector pCM17 (FIG. 13) Containing the Reconstructed PXYLA Gene; Site-Directed Mutagenesis to Alter Bases on the Reconstructed Gene to Coincide with the Sequence in Genbank Database A plasmid containing the reconstructed PXYLA gene (Ex. 2A) was constructed by ligating a ~1.314 kbp fragment produced in the final round of construction to a TOPOII vector (Invitrogen, CA). The reconstructed PXYLA gene differed from the Genbank sequence with respect to five bases. Each of these differences was corrected using a multi-site-directed mutagenesis kit (Stratagene, CA), using this plasmid as the template. Three PAGE or HPLC purified, 5' phosphorylated mutagenic primers identified as SEQ. ID. NO. 54, SEQ. ID. NO. 55 and SEQ. ID. NO. 56 were used to correct four of the errors. Thermal cycling parameters included a one-minute denaturation step and a one-minute annealing step, followed by an eight-minute extension. The parental strand formed during the PCR step was then digested by adding 1 μl DpnI enzyme to the mixture at the end of the thermocycling. The mixture was incubated for 1 hour at 37° C. and then used to transform XL10-Gold Ultracompetent *E. coli* cells supplied with the kit. The mixture was plated on Luria-Bertani+ampicillin (LBA) plates and incubated at 37° C. overnight. The multi-site directed mutagenesis protocol was then repeated to fix the fifth error. Two PAGE or HPLC purified, 5'-phosphorylated mutagenic primers identified as SEQ. ID. NO. 57 and SEQ. ID. NO. 55 were used. Two transformants were sequenced and showed 100% homology to the Genbank sequence of the PXYLA gene. One of the constructs was named pCM17 (FIG. 13). The nucleotide and amino acid sequences of the reconstructed PXYLA gene are identified as SEQ. ID. NO. 58 and SEQ. ID NO. 59.

EXAMPLE 3A

Construction of Vector pCM14 (FIG. 14) Containing the PXYLA Gene Under the Control of KmPDC1 Promoter and ScCYC1 Terminator, and the *E. coli* Hph Hygromycin Resistance Gene Under the Control of ScPDC1 Promoter and ScGAL10 Terminator The PXYLA gene was PCR amplified using the primers identified as SEQ. ID. NO. 60 and SEQ. ID. NO. 61, using pCM17 (Ex. 2B, FIG. 13) as a template. Thermocycling was performed by 35 cycles of 30 seconds at 94° C., 30 seconds at 55° C., 1.5 minutes at 72° C., followed by a final incubation for 8 minutes at 72° C. using Pfx DNA polymerase (Invitrogen, CA). The PCR product was digested with SbfI and electrophoretically separated on a 1.0% agarose gel. A 1319 bp product was isolated and ligated to a ~6829 bp fragment obtained by digesting pCM9 with SbfI, to construct a ~8148 bp plasmid. A mutagenic primer identified as SEQ. ID. NO. 62 was used to pull out a stop codon which was accidentally added immediately upstream of the SbfI site, following the same protocol as described in Example Ex. 2B, to create a ~8148 bp plasmid (pCM14, FIG. 14).

Plasmid pCM14 contains the PXYLA gene under the control of the KmPDC1 promoter and the ScCYC1 terminator, with a poly-his tail at the 3' end of the gene. The plasmid also contains the *E. coli* hph gene under control of ScPDC1 promoter and ScGAL10 terminator.

EXAMPLE 3B

Incorporation of a Ura3 Selection Marker into the pCM14 Plasmid (Ex. 3A, FIG. 14), with Deletion of the Hph Expression Cassette Alani et al., in "A method for gene disruption that allows repeated use of Ura3 selection in the construction of multiply disrupted yeast strains," (Genetics, 1987, 116, 541-545) has described a method of gene integration or gene disruption. This method makes use of a uracil auxotrophic yeast strain and a HisG-ScUra3-HisG repeater cassette. This cassette can be used as a selection marker to introduce genes or to disrupt genes with the advantage that the HisG cassette recombines with itself in subsequent generations. Thus the yeast cell loses the ScUra3 gene during the recombination event and this loss of ScUra3 gene restores back the yeast strain's uracil auxotrophy for subsequent transformation with the same cassette.

A HisG-ScUra3-HisG cassette was obtained from Nancy DaSilva incorporated in a plasmid designated pNADF11 (Nancy DaSilva, UC Irvine, Calif.). The HisG-ScUra3-HisG cassette was isolated from pNADF11 by digesting the plasmid with BamHI and EcoRI enzymes and ligating a ~3.8 kbp fragment to a BamHI and EcoRI-digested plasmid pPUC19 (New England Biolabs, USA). The resulting plasmid is designated pVR65 (FIG. 26).

Plasmid pCM14 (Ex. 3A, FIG. 14) was digested with AatII/SphI and electrophoretically separated on a 1% gel. A ~5907 bp fragment containing the PXYLA cassette was isolated. Plasmid pVR65 was digested with AatII/SphI and electrophoretically separated on a 1% gel. A ~4293 bp HisG-ScUra3-HisG fragment was isolated and ligated to a ~5907 bp fragment from plasmid pCM14, with the inserts isolated. The resulting vector was identified as pCM28 (FIG. 15). It contains the PXYLA gene (with poly-his tag) under the control of the KmPDC1 promoter and ScCYC1 terminator, and the HisG-Ura3-HisG cassette. The *E. coli* hph gene and flanking portions that were present in plasmid pCM14 are eliminated from pCM28.

EXAMPLE 4A

Cloning of the *Kluyveromyces marxianus* Xylose Reductase (KmXYL1) Gene and Upstream and Downstream Flanks A 410 bp fragment of a putative *K. marxianus* xylose reductase (KmXYL1) coding region and approximately 500 bp of the promoter has been determined by a partial genome sequencing of a similar *K. marxianus* within the Génolevures project (Genomic Exploration of the Hemiascomycetous Yeasts: 12. *Kluyveromyces marxianus* var. *marxianus* Bertrand Llorente, Alain Malpertuy, Gaëlle Blandin, François Artiguenave, Patrick Wincker and Bernard Dujon *FEBS Letters* 487(1) pp. 71-75). Based upon this sequence and some of the known sequences from other yeast xylose reductase consensus, primers were designed to isolate the full KmXYL1 gene sequence and promoter. A genome walking approach was used to obtain sequences upstream and downstream of a KmXYL1 gene sequence from a wild type strain of *K. marxianus*. A genome walker kit (BD Biosciences, Paolo Alto, Calif.) was used for obtaining the sequence of the upstream and downstream flanks. Genomic DNA from *K. marxianus* was digested with restriction enzymes from the genome walker kit (Invitrogen, CA). A genomic library made with the fragments was used as template for PCR reactions.

PCR primers identified as SEQ. ID. NO. 63 and SEQ. ID. NO. 64 were designed to walk both the 5' end and 3' end to get the xylose reductase and upstream/downstream flanking sequence. These primers were used to walk along with primers AP1 and AP2 from the genome walker kit (BD Biosciences, CA). This set of primers amplified a ~2.5 kbp fragment upstream of the gene. The fragment was sequenced to reveal the sequence of DNA from the extreme ends of the upstream region towards the KmXYL1 gene. Similarly, primers identified as SEQ. ID. NO. 65 and SEQ. ID. NO. 66 were used to walk along with primers AP1 and AP2 from the genome walker kit. This amplified a ~1.8 kbp fragment downstream of the KmXYL1 gene. The fragment was sequenced to reveal the sequence of DNA from the extreme ends of the downstream region away from xylose reductase.

The sequence information obtained from the genome walking allowed the design of primers identified as SEQ. ID. NO. 67 and SEQ. ID. NO. 68. These primers were used for thermocycling reactions with 500 ng of genomic DNA from *K. marxianus*. Thermocycling was performed by 30 cycles of 1 minute at 94° C., 1 minute at 56° C., 3 minutes at 72° C., followed by a final incubation of 7 minutes at 72° C. using Pfx DNA polymerase (Invitrogen, CA). The PCR product was electrophoretically separated on a 0.8% agarose gel. A ~3.5 kbp product was isolated and ligated into the pCRII topo-cloning vector to give plasmid pVR95 (FIG. 16).

EXAMPLE 4B

Construction of Plasmid pCM19 (FIG. 18) Containing the KmXYL1 Upstream and Downstream Flanks, and the G418 Resistance Marker Gene Under the Control of ScPDC1 Promoter and ScGAL10 Terminator Primers identified as SEQ. ID. NO. 69 and SEQ. ID. NO. 70 were designed to amplify a ~1.3 kbp fragment from plasmid pVR95 (Ex. 4A, FIG. 16). This fragment includes the promoter region of the KmXYL1 gene as well as ~300 bp of the coding region of the gene. These primers were used for thermocycling reactions with 50 ng of plasmid DNA from pVR95 (Ex. 4A, FIG. 16). Thermocycling was performed by 30 cycles of 1 minute at 94° C., 1 minute at 53° C., 1 minute at 68° C., and a final incubation of 8 minutes at 68° C. using Pfx DNA polymerase (Invitrogen, CA). The PCR product was electrophoretically separated, digested with PstI and ligated to pVR29 (Ex. 1C, FIG. 4) that was also digested with PstI. The plasmid obtained by this method was verified for correct orientation of the KmXYL1 gene and promoter region into the pVR29 vector. The plasmid is designated pCM18 (FIG. 17).

Primers identified as SEQ. ID. NO. 71 and SEQ. ID. NO. 72 were designed to amplify a ~1.1 kbp fragment from pVR95. This fragment includes a region downstream of the KmXYL1 gene beyond its terminator. These primers were used for thermocycling reactions with 50 ng of plasmid DNA from pVR95. Thermocycling was performed by 30 cycles of 1 minute at 94° C., 1 minute at 59° C., 1 minute at 68° C., a final incubation of 8 minutes at 68° C. using Pfx DNA polymerase (Invitrogen, CA). Primers identified as SEQ. ID. NO. 73 and SEQ ID. NO. 74 were used for thermocycling reactions with 50 ng of the first PCR product described above to amplify it. Thermocycling was performed by 30 cycles of 1 minute at 94° C., 1 minute at 45° C., 1 minute at 68° C., a final incubation of 8 minutes at 68° C. using Pfx DNA polymerase (Invitrogen, CA). The PCR product obtained after the second thermocycling was electrophoretically separated, digested with ApaI and ligated to plasmid pCM18 that was also digested with ApaI, to form vector pCM19 (FIG. 18). Plasmid pCM19 contained the downstream flank of KmXYL1 gene and the upstream flank of KmXYL1 gene (together with ~300 bp of the coding region of the gene), separated by a cassette containing the G418 gene under the control of the ScPDC1 promoter and ScGAL10 terminator. Correct orientation of the KmXYL1 downstream region with regard to the G418 resistance gene was verified.

EXAMPLE 4C

Construction of a *K. marxianus* Uracil Auxotroph (CD 683) by Replacing a Functional Ura3 Gene with a Non-Functional Gene The *K. marxianus* Ura3 (KmUra3) gene was isolated using the genomic DNA as template and primers designed based on Genbank sequence (accession no. AF528508). An 804 bp fragment was cloned into pBluescript vector (Stratagene, Wisconsin) and labelled pBSKura3Myra (FIG. 19).

This plasmid was digested with EcoRV and a ~4 kbp fragment that has the KmUra3 gene with a missing EcoRV fragment was isolated and re-ligated to form plasmid pBSDeltaUra3Km (FIG. 20). This plasmid had a non-functional gene (DeltaUra3). The plasmid was digested using KpnI and NotI and used to transform a wild type strain of *K. marxianus*. The transformants were selected on 5-FOA plates. Colonies that grew on these plates were screened using primers designed in the missing region of the DeltaUra3 gene. Primers were also designed to isolate the entire gene and those fragments were sequenced to indicate that this new shorter non-functional DeltaUra3 gene had replaced the actual native KmUra3 gene in the transformants. The successfully transformed strains were designated CD683. Strain CD683 strain did not grow Sc-Ura plates, indicating that it was a uracil auxotroph.

EXAMPLE 4D

Generation of a *K. marxianus* Mutant (CD804) with Deleted Xylose Reductase (KmXYL1) Gene by Transforming Strain CD683 (Ex. 4C) with Plasmid pCM19 (Ex. 4B, FIG. 18)

A ~5.2 kbp fragment containing the upstream and downstream regions of the KmXYL1 gene with a G418 resistance expression cassette in between was obtained by digesting pCM19 with PvuII. This fragment was used to transform *K. marxianus* strain CD683 using standard electroporation methods. The transformed cells were recovered and plated on 10 g/L yeast extract, 20 g/L yeast peptone, 50 g/L glucose (YPD)+50 μg/ml G418 plates and incubated at 37° C. for 48-96 hrs. 96 transformants that grew on YPD+50 μg/ml G418 plates were replica plated on YPX (10 g/L yeast extract, 20 g/L yeast peptone+xylose 50 g/L)+50 μg/ml G418 plates. 73 out of the 96 transformants failed to grow on YPX+50 μg/ml G418 plates, confirming their inability to use xylose as a carbon source. This inability indicates that the functional KmXYL1 gene had been deleted and replaced with the G418 cassette in a homologous recombination. Those transformants that were unable to use xylose as a carbon source were designated CD804.

The absence of a functional KmXYL1 gene was verified using PCR primers identified as SEQ. ID. NO. 75 and SEQ. ID. NO. 76, which were designed to PCR amplify the center of the KmXYL1 gene. The presence of the G418 gene was verified by PCR using primers identified as SEQ. ID. NO. 77 and SEQ. ID. NO. 78. The results indicated that the G418 resistance gene fragment was integrated at the locus of the KmXYL1 gene. A further PCR using a set of primers identified as SEQ. ID. NO. 79 and SEQ. ID. NO. 80 further confirms that the G418 resistance gene fragment replaced the native KmXYL1 gene. Southern analysis further confirms that the xylose reductase gene was eliminated from strain CD804.

EXAMPLE 4E

Xylose Reductase Enzyme Activity Assay for Strains CD683 (Ex 4C) and CD804 (Ex. 4D)

Separate baffled shake flasks (250 ml capacity) were inoculated with strains CD683 (Ex. 4C) and CD804 (Ex. 4D). Flasks were incubated at 35° C. with shaking at 250 rpm and grown overnight. The media consisted of 20 g/L yeast extract, 10 g/L peptone, and 100 g/L dextrose. After 18 hours, the cells were spun down at 4000G for 5 minutes, washed with 100 mM sodium phosphate buffer and re-suspended in 0.5 ml breaking buffer. The breaking buffer consisted of 100 mM sodium phosphate buffer (pH7.0), 1 mM dithiothreitol (DTT), 40 mg phenylmethyl sulfonyl fluoride (PMSF) (dissolved in 500 μl DMSO), and 4 Protease inhibitor cocktail tablets (Roche, CA) in a 200 ml volume. The cells were lysed mechanically using glass beads (Invitrogen, CA) and centrifuged at 14,000G for 15 minutes. The supernatant was removed and run through a PD-10 desalting column according to the kit protocol (Amersham Bioscience). XR enzyme assay test solution consisted of 100 mM sodium phosphate buffer (pH 7.0), 0.2 mM NADPH, 0.5 mM D-xylose in a total volume of 1 ml, to which varying amounts of enzyme solution was added and the absorbance was followed at 340 nm. NADPH usage indicates reductase enzyme activity. A blank solution without xylose was used to determine background NADPH usage.

Total protein was determined using Advanced Protein Assay Reagent (Cysoskeleton #ADV01) with BSA as a standard. The xylose reductase enzyme activity of strain CD683, as indicated by NADPH consumption, was 13.7 mU/mg protein. NAPDH consumption by strain CD804 was consistent with a xylose reductase activity of 4.4 mU/mg protein, rather than the expected activity of zero. This NADPH usage by CD804 is attributed to a non-specific aldose reductase enzyme that is carrying out some conversion of xylose to xylulose. Strains CD683 and CD804 are plated alongside each other on YPX plates. Strain CD804 did not show any growth on those plates at the end of 4 days while strain CD683 grew well on those plates.

EXAMPLE 5A

Construction of Plasmid pVR67 (FIG. 22) Containing a Cloned *Saccharomyces cerevisiae* Xylulokinase (ScXKS1) Gene

*S. cerevisiae* cells were obtained from the American Type Culture Collection (ATCC Accession #38626) and grown under standard conditions. Genomic DNA from *S. cerevisiae* was extracted using conventional methodologies. PCR amplification reactions were performed using Pfx polymerase (Invitrogen, CA). Each reaction contained *S. cerevisiae* genomic DNA at a concentration of 500 ng, each of 4dNTPs (i.e., each of dATP, dGTP, dCTP and dTTP) at a concentration of 0.2 mM, and each of the amplification primers identified as SEQ. ID. NO. 81 and SEQ. ID. NO. 82 at 1 μM. The cycling was performed by an initial incubation for 10 minutes at 94° C., followed by 35 cycles consisting of 15 seconds at 94° C., 15 seconds at 55° C., and 90 seconds at 68° C. A ~1.8 kbp fragment was gel purified using conventional procedures and cloned into TA cloning vector (Invitrogen, CA). The resultant plasmid (pVR67, FIG. 22) was sequenced to verify the ScXKS1 gene sequence. The gene exhibits excellent homology to the known sequence in Genbank (Accession # X61377). The nucleotide sequence of the ScXKS1 gene is identified as SEQ. ID. NO. 83. The amino acid sequence of the enzyme coded by this gene is identified as SEQ. ID. NO. 84.

EXAMPLE 5B

Construction of Plasmid pVR52 (FIG. 21) Containing the *S. cerevisiae* TEF1 (ScTEF1) Promoter and ScGAL10 Terminator The *S. cerevisiae* TEF1 (ScTEF1) promoter was cloned out of pTEFZeo (Invitrogen, CA) vector. Primers identified as SEQ. ID. NO. 85 and SEQ. ID. NO. 86 were used to amplify the ScTEF1 promoter and insert XbaI and SstI restriction sites. The PCR product and plasmid pNC2 (Ex. 1A, FIG. 1) were digested with XbaI and SstI enzymes and ligated to obtain plasmid pVR52 (FIG. 21).

EXAMPLE 5C

Construction of Plasmid pVR103 (FIG. 25) Containing the ScXKS1 Gene Under the Control of the ScTEF1 Promoter and ScGal10 Terminator Plasmid pVR67 (Ex. 5A, FIG. 22) was digested with XbaI and BamHI. A ~1.8 kbp fragment containing the ScXKS1 gene was gel purified. Plasmid pVR52 (Ex. 5B, FIG. 21) was also digested with XbaI and BamHI and the fragment so obtained was ligated to the ~1.8 kbp fragment from pVR67 to form plasmid vector pVR96 (FIG. 23). This plasmid contains the ScXKS1 gene under the control of the ScTEF1 promoter and ScGal10 terminator. In this vector, the ATG start site of the ScXKS1 gene is about 130 bp away from the end of the ScTEF1 promoter. To reduce this distance to about 70-73 bp, primers identified as SEQ. ID. NO. 87 and SEQ. ID. NO. 88 were designed that would amplify the ScTEF1 promoter from pTEFzeo vector with the correct distance and restriction sites. pTEFzeo (Invitrogen, CA) was used as the template. Thermocycling was performed by 30 cycles of 30 seconds at 94° C., 30 seconds at 57° C., and 30 seconds at 72° C., followed by a final incubation of 4 minutes at 72° C. using the Failsafe PCR System (Epicentre, Madison, Wis.). The PCR product was separated on a 0.8% agarose gel and a 460 bp fragment was isolated. A second PCR was performed to amplify this fragment using the primers identified as SEQ. ID. NO. 89 and SEQ. ID. NO. 90. The PCR product was digested with EcoRI and ligated to EcoRI-digested plasmid pVR96 (FIG. 23). The resultant plasmid (pVR102, FIG. 24) had two ScTEF1 promoters—the second one being the promoter driving the ScXKS1 gene. The distance between the end of the promoter and the ATG of the gene was exactly 73 bp. Plasmid pVR102 was digested with SphI and ligated to SphI-digested pPUC19 (New England Biolabs, USA). The resultant plasmid (pVR103, FIG. 25) was sequenced to verify the ScXKS1 gene under the control of a ScTEF1 promoter and ScGAL10 terminator.

EXAMPLE 5D

Construction of Plasmid pVR104 (FIG. 27) Containing the ScXKS1 Expression Cassette (from pVR103, Ex. 5C) Alongside a HisG-ScUra3-HisG Cassette (from pVR65, Ex. 3B)

Plasmid pVR65 (Ex. 3B, FIG. 26) was digested with SphI, and the 5'-phosphate ends of the linearized vector were dephosphorylated using shrimp alkaline phosphatase (Roche Diagnostics, USA) following the manufacturer's protocol.

Plasmid pVR103 (Ex. 5C, FIG. 25) was also digested with SphI and a 3.5 kbp fragment that has the ScXKS1 gene under the control of the ScTEF1 promoter and ScGAL10 terminator was ligated to the linearized pVR65 fragment to obtain plasmid pVR104 (FIG. 27).

EXAMPLE 5E

Generation of a K. marxianus Mutant (CD805) that has an Over-Expressed ScXKS1 Gene Activity and Deleted Xylose Reductase Gene by Transforming Strain CD804 (Ex. 4D)

A ~6.8 kbp PvuII fragment from plasmid pVR104 (Ex. 5D, FIG. 27) was used to transform strain CD804 (Ex. 4D), using standard electroporation methods. The transformed cells were recovered in YPD medium, plated after 4 hours on SC-Ura plates (Qbiogene, CA) and incubated at 37° C. for 48-72 hours. Transformants that grew on SC-Ura plates at the end of 72 hours were re-streaked on fresh SC-Ura plates. Re-streaked transformants were screened using colony PCR.

A single positive colony of the transformed strain was inoculated into 50 ml of YPD medium and incubated overnight at 37° C. with 200 rpm shaking. 10 µl of this was plated on 5-FOA plates and incubated overnight at 37° C. Colonies that grew were resistant to 5-FOA and were expected to have lost the ScUra3 gene due to the recombination of the HisG regions. PCR was performed using primers identified as SEQ. ID. NO. 91 and SEQ. ID. NO. 92 to amplify a 700 bp region to indicate an intact ScXKS1 gene and ~1 kb of the HisG gene. A second primer set identified as SEQ. ID. NO. 93 and SEQ. ID. NO. 94 were designed to amplify a ~1 kbp product between the ScXKS1 and end of the gene. These two primer sets confirmed that the ScXKS1 gene had integrated into the chromosome of the transformants and the ScUra3 gene had been removed by spontaneous recombination of the HisG region. This strain was labelled CD805 and was tested further for increased xylulokinase protein activity.

Primers identified as SEQ. ID. NO. 91 and SEQ. ID. NO. 93 were designed to amplify a ~2.6 kbp product between the SeTEF1 promoter and the end of the ScXKS1 gene. Primers identified as SEQ. ID. NO. 92 and SEQ. ID. NO. 95 were designed to amplify a ~1.7 kbp product between the ScXKS1 gene and the start of the fragment. These two primer sets confirmed that the ScXKS1 gene had integrated into the chromosome of strain CD805.

Xylulokinase Activity Assay:

Separate baffled shake flasks (250 ml capacity) were inoculated with strains CD804 (Ex. 4D) and CD805 (Ex. 5E). Flasks were placed at 35° C., shaken at 250 rpm, and grown overnight. The media consisted of 20 g/L yeast extract, 10 g/L peptone and 100 g/L dextrose. After 16 hours the cells were spun down at 4000G for 5 minutes, washed with 100 mM sodium phosphate buffer and re-suspended in 0.5 ml breaking buffer. The breaking buffer consisted of 100 mM sodium phosphate buffer (pH7.0), 1 mM DTT, 40 mg PMSF (dissolved in 500 al DMSO), and 4 Protease inhibitor cocktail tablets (Roche) in a 200 ml volume. The cells were lysed mechanically using glass beads (Invitrogen, CA) and centrifuged at 14,000G for 15 minutes. The supernatant was removed and run through a PD-10 desalting column according to the kit protocol (Amersham Bioscience). 10 µl of extract was added to a 30° C. equilibrated 80 l XuK mixture (containing 61 mg $Na_2ATP.3H_2O$, 10.0 ml 0.1M HEPES/ KOH (pH 7.5), 1.2 ml 0.1M $MgCl_2$ (diluted to 16.0 ml), and 10 µl of 20 mM xylulose for a total volume of 100 ml. Water substituted xylulose as a blank. Reactions were terminated by boiling for two minutes and transferred to ice. 900 µl of Hek2 (40 mM HEPES/KOH (pH 7.5), 10 mM $MgCl_2$, 2.5 mM PEP and 0.2 mM NADH) was added and centrifuged at 14,000G for 10 minutes. The supernatant was transferred to a spectrophotometer curvette, and the initial 340 nm baseline absorbance was established. 10 µl of a 1:1:1 mixture of myokinase, pyruvate kinase, and lactate dehydrogenase was added and final absorbance was measured. Total protein was determined using Advanced Protein Assay Reagent (Cysoskeleton #ADV01) with BSA as a standard. The xylulokinase activity measurement for strain CD804 was 69.7+/−8.0 mU/mg, while that for strain CD805 was 400.8+/−102.7 mU/mg, indicating that CD805 had over-expressed ScXKS1 activity.

EXAMPLE 6A

Construction of Plasmid pCM23 (FIG. 29) Containing Upstream and Downstream Flanks of a K. marxianus Xylitol Dehydrogenase (KmXYL2) Gene, and a E. coli Hph Gene Under the Control of a ScPDC1 Promoter and ScGAL10 Terminator A 988 bp fragment containing the promoter region of K. marxianus xylitol dehydrogenase (KmXYL2) gene was PCR amplified out of the genome with primers indicated as SEQ. ID. NO. 96 and SEQ. ID. NO. 97. Thermocycling was performed by 35 cycles of 30 seconds at 94° C., 30 seconds at 52° C., 1 min at 68° C., followed by a final incubation for 8 minutes at 68° C. using Pfx DNA polymerase (Invitrogen, CA). The product was cloned into a TOPOII vector (Invitrogen, CA). Plasmid pUC19 (New England Biolabs, USA) was digested with EcoRI and separated on a 1.0% gel. A 2.686 kbp band was isolated from the pUC19 plasmid and ligated to a fragment liberated from the TOPOII plasmid by digestion with EcoRI, creating a ~3.674 kbp plasmid referred to as pCM20.

A fragment containing the terminator sequence and downstream region of KmXYL2 was PCR amplified out of the genome using three sets of primers. The first set of primers is identified as SEQ. ID. NO. 98 and SEQ. ID. NO. 99, which amplified the downstream region of interest. Thermocycling was performed by 35 cycles of 30 seconds at 94° C., 30 seconds at 55° C. and 1 minute at 68° C., followed by a final incubation for 8 minutes at 68° C. using Pfx DNA polymerase (Invitrogen, CA). The second set of primers is identified as SEQ. ID. NO. 100 and SEQ. ID. NO. 101. These were used to introduce SphI sites on both ends using 2.5 µl of the first PCR product as a DNA template. Thermocycling was performed by 35 cycles of 30 seconds at 94° C., 30 seconds at 60° C., and 1 minute at 68° C., followed by a final incubation for 8 minutes at 68° C. using Pfx DNA polymerase. The third set of primers is identified as SEQ. ID. NO. 102 and SEQ. ID. NO. 103. These amplified the previous product using 2.5 µl of the second PCR. Thermocycling was performed by 35 cycles of 30 seconds at 94° C., 30 seconds at 47° C. and 1 minute at 68° C., followed by a final incubation for 8 minutes at 68° C. using Pfx DNA polymerase. The final product was cloned into a TOPOII vector (Invitrogen, CA) and digested with SphI and separated on a 1.0% gel. A ~1.008 kbp fragment was isolated and ligated into SphI-digested plasmid pCM20 (from above) to form a ~4.682 kbp plasmid designated pCM21 (FIG. 28).

Plasmid pCM21 was digested with SacI/XbaI and separated on a 1.0% gel. A ~4.665 kbp band was isolated and ligated to a ~2.366 kbp band isolated by digesting plasmid pPS1 (Ex. 1H, FIG. 11) with SacI/SpeI. The resulting ~7.031 kbp plasmid was named pCM23 (FIG. 29). It contains upstream and downstream flanks of the KmXYL2 gene, separated by an E. coli hph gene under the transcriptional control of the ScPDC1 promoter and ScGAL10 terminator.

EXAMPLE 6B

Generation of a K. marxianus Mutant (CD806) from Strain CD805 (Ex. 5E) Using a Fragment from Plasmid pCM23 (Ex. 6A, FIG. 29) to Delete the Xylitol Dehydrogenase Gene A single colony of strain CD805 was transformed with a fragment from plasmid pCM23 using standard electroporation methods. The transformed cells were recovered in YPD medium and plated after 4 hours on YPD+150 µg/ml hygromycin plates and incubated at 37° C. for 48 hours. 86 transformants that grew on YPD+150 µg/ml hygromycin plates after 48 hours were re-streaked on fresh YPD+150 µg/ml hygromycin plates. The transformants were screened by PCR for the presence of the native xylitol dehydrogenase with primers identified by SEQ. ID. NO. 104 and SEQ. ID. NO. 105. Thermocycling was performed by an initial cycle of 10 minutes at 94° C., 35 cycles of 30 seconds at 94° C., 30 seconds at 50° C., 1 minute at 72° C., followed by a final incubation for 8 minutes at 72° C. using Failsafe enzyme (Epicentre, Wisconsin). A PCR product of 1064 bp indicated an intact xylitol dehydrogenase gene. 15 transformants did not produce the expected product, indicating that that xylitol dehydrogenase gene had been successfully deleted from those 15 transformants.

Those 15 transformants were PCR screened using primers identified as SEQ. ID. NO. 106 and SEQ. ID. NO. 107. This primer set was designed to PCR amplify the 5' ends. A positive result (~1.5 kbp fragment) indicates that the hygromycin resistance gene fragment replaced the KmXYL2 gene in the transformant's chromosome in a 5' crossover. A third primer set identified as SEQ. ID. NO. 108 and 109 was designed to PCR amplify the 3' ends. A ~1 kbp product indicates that the hygromycin resistance gene fragment replaced the KmXYL2 gene in the transformant's chromosome in a 3' crossover. Of the 15 transformants, two showed bands corresponding to both PCR products. One of these was labelled strain CD806. Strain CD806 has an overexpressed ScXKS1 gene activity and deleted xylose dehydrogenase (KmXYL2) and xylose reductase (KmXYL1) genes.

Xylitol Dehydrogenase Activity Assay:

Separate baffled shake flasks (250 ml capacity) were inoculated with strains CD805 (Ex. 5E) and CD806 (Ex. 6B). Flasks were placed at 33° C., shaken at 250 rpm, and grown overnight. The media consisted of 20 g/L yeast extract, 10 g/L peptone and 100 g/L dextrose. After 16 hours, the cells were spun down at 4000G for 5 minutes, washed with 100 mM sodium phosphate buffer and re-suspended in 0.5 ml breaking buffer. The breaking buffer consisted of 100 mM sodium phosphate buffer (pH 7.0), 1 mM DTT, 40 mg PMSF (dissolved in 500 µl DMSO) and 4 Protease inhibitor cocktail tablets (Roche) in a 200 ml volume. The cells were lysed mechanically using glass beads (Invitrogen), and centrifuged at 14,000G for 15 minutes. The supernatant was removed and run through a PD-10 desalting column according to the kit protocol (Amersham Bioscience). Sample was added to a test solution consisting of 100 mM sodium phosphate buffer (pH 7.0), 0.2 mM NADH, and 20 mM xylulose. Absorbance was followed at 340 nm Total protein was determined using Advanced Protein Assay Reagent (Cysoskeleton #ADV01) with BSA as a standard. Enzyme analysis of strain CD805 (Ex. 5E) yielded an enzyme activity of 14.5+/−1.6 mU/mg, while the activity strain CD806 was 0.0+/−0.1 mU/mg. These results indicate that xylitol dehydrogenase enzyme activity had been deleted in strain CD806.

EXAMPLE 7A

Generation of K. marxianus Mutant (CD882) Having Exogenous PXYLA Gene, Overexpressed ScXKS1 Gene Activity, and Deletions of the KmXYL1 and KmXYL2 Genes by Transforming Strain CD806 (Ex. 6B) with Plasmid pCM28 (Ex. 3B, FIG. 15)

A single colony of strain CD806 was transformed with NaeI-digested plasmid pCM28 using standard electroporation methods. The transformants were grown at 37° C. overnight, and streaked onto five identical Sc-Ura plates for screening. The presence of the PXYLA gene was verified by PCR using primers identified as SEQ. ID. NO. 110 and SEQ. ID. NO. 111. The resulting transformant (designated CD882) contained the reconstructed PXYLA gene, overexpressed ScXKS1 gene activity, and deletions of the KmXYL1 and KmXYL2 genes.

EXAMPLE 7B

Enzymatic and Western Analysis of Strain CD882 (Ex. 7A)

Protein from CD882 was column purified using Probond $Ni^{2+}$ chelating resin (Invitrogen, Carlsbad, Calif., USA) binding the 6× poly-his tail. A Ni-NTA-HRP conjugated probe (Qiagen, Valencia, Calif., USA) was used for direct detection of tagged proteins. Western analysis of fractions collected during purification further confirms the presence of the XI protein in strain CD882. Enzyme activity measurements were done according to the method described in "The Streptomyces rubiginosus xylose isomerase is misfolded when expressed in Saccharomyces cerevisiae", Gardonyl et al., 2003. The evaluation confirms xylose isomerase activity in the same fraction where the 6× poly-his tail PXYLA gene had been detected by western analysis in strain CD882.

EXAMPLE 8A

Construction of Plasmid (pCM29, FIG. 30) Containing Reconstructed PXYLA Gene with Stop Codon that Prevents Encoding of the Poly-his Tail The reconstructed PXYLA gene (Ex. 2A) was PCR amplified using the primers identified as SEQ. ID. NO. 112 and SEQ. ID. NO. 113 using pCM17 (Ex. 2B, FIG. 13) as a template. Thermocycling was performed by 35 cycles of 30 seconds at 94° C., 30 seconds at 55° C., 1.5 minutes at 72° C., followed by a final incubation for 8 minutes at 72° C. using Pfx DNA polymerase. The PCR product was digested with SbfI and electrophoretically separated on a 1.0% agarose gel. A 1319 bp product was isolated and ligated to a 6829 bp fragment obtained by digesting plasmid pCM9 (Ex. 1I, FIG. 12) with SbfI to construct a ~8148 bp plasmid (pCM29, FIG. 30). The plasmid contained the PXYLA gene with inoperable poly-his tail, under the control of KmPCD1 promoter and ScCYC1 terminator, and the *E. coli* hph expression cassette.

EXAMPLE 8B

Generation of a *K. marxianus* Mutant Strain (CD861) Containing Non-his-Tagged PXYLA Gene, Overexpressed ScXKS1 Gene Activity and Deleted Xylose Dehydrogenase and Xylose Reductase Genes, by Transforming Strain CD806 (Ex. 6B) with Plasmid pCM29 (Ex. 8A, FIG. 30)

A 3.192 Kb PvuII/SphI fragment obtained by digesting pCM29 is used to transform strain CD806, using standard electroporation methods. The transformed cells were recovered in YPD medium and plated after 6 hours on YPX+300 µg/ml G418+150 µg/ml hygromycin (pH 7.0). After 5 days at 30° C., several hundred small colonies and one larger colony had grown. The large colony was designated CD861.

Genome walking was performed on strain CD861 to ascertain how the PXYLA gene had integrated. The PXYLA gene was found to have integrated with more than one copy immediately upstream of the promoter region of the native PDC gene. One copy was under the control of a ~1236 bp KmPCD1 promoter region, present in plasmid pCM29, which includes about 142 bp of an upstream gene, and the ScCYC1 terminator. Another copy was immediately downstream of this ScCYC1 terminator, and included a 1026 bp promoter that matches the native KmPDC1 promoter length. This promoter is missing the 142 bp region of the upstream gene and an additional ~68 bp at the 5' end, compared to the promoter in pCM29 and the first copy. The second copy was also under the control of a ScCYC1 terminator. Immediately downstream of this second ScCYC1 terminator was the native, 1026 bp KmPDC1 promoter, followed by the native KmPDC1 gene.

EXAMPLE 8C

Xylose Isomerase, Xylose Reductase, Xylitol Dehydrogenase and Xylulokinase Enzyme Analysis of CD861 (Ex. 8B)

Separate baffled shake flasks (250 ml capacity) were inoculated with CD806 (Ex. 6B) and CD861 (Ex. 8B). Flasks were incubated at 30° C. and grown overnight with shaking at 250 rpm. The media consisted of 20 g/L yeast extract, 10 g/L peptone and 100 g/L dextrose supplemented with 300 µg/ml G418 and 150 µg/ml hygromycin. Cells were lysed using Y-PER solution (Pierce-Rockford, Ill.) followed by de-salting using PD-10 columns (Amersham Biosciences, Piscataway, N.J.). A test solution consisting of 100 mM TES-NaOH, 250 mM xylose, 10 mM $MgCl_2$, 0.6 mM NADH, 1 U SDH (sigma) (pH 7.0) was brought up to 1.0 mL with the addition of 100 µL of cell extract. Xylose isomerase activity was determined using a blank with the same test solution, only without xylose. Xylose isomerase activity for strain CD806 was zero, while that of strain CD861 was 1.07+/−0.21 U/mg of crude extract. This verifies that strain CD861 contained a functioning xylose isomerase gene.

Xylose reductase, xylitol dehydrogenase and xylulokinase assays were also conducted to verify activity/loss of activity in the final strain. Strain CD861 (Ex. 8B) and strain CD683 (Ex. 4C) were separately grown overnight in media consisting of 20 g/L yeast extract, 10 g/L peptone, and 100 g/L dextrose (supplemented with 300 µg/ml G418 and 150 µg/ml hygromycin for strain CD861). Cells were lysed using the Y-PER solution. Total protein was determined using Advanced Protein Assay Reagent (Cysoskeleton #ADV01) with BSA as a standard. Xylose reductase enzyme activity in strain CD861 was 260+/−41.8 mU/mL vs. 516.5+/−10.6 mU/mL for strain CD683. The ~50% reduction in activity indicates the deletion of the xylose reductase gene, with the measured activity being attributed to a non-specific aldose reductase enzyme that is carrying out some conversion of xylose to xylulose. Xylitol dehydrogenase enzyme activity was 12.4+/−4.4 mU/mL for strain CD861 vs. 110.4+/−7.2 mU/mL for strain CD683. Xylulokinase enzyme activity was 370.5+/−147.6 mU/mL for strain CD861 vs. 44.8+/−8.2 mU/mL for strain CD683.

EXAMPLE 8D

Kinetic Analysis of PXYLA Gene in Strain CD861 (Ex. 8B)

A single colony of strain CD861 was inoculated for overnight growth in media consisting of 10 g/L yeast extract, 20 g/L peptone, and 100 g/L dextrose. Cells were harvested by centrifugation, washed once with 10 ml 100 mM sodium phosphate, 1 mM PMSF (pH 7.0) and centrifuged again. To this, 2 ml of Y-PER solution was added and gently resuspended and the cell solution was incubated at room temperature for 30 minutes with intermittent agitation. Cells were spun down and the supernatant was desalted using PD-10 columns (Amersham Biosciences). Enzyme assays were conducted as described in Example 8C, with the only difference being the substrate was varied from 0.05-10 mM xylose. $K_m$ and $V_{max}$ were derived from Michaelis-Menten plots, which gave a corresponding $V_{max}$ of ~1.8 with a corresponding $K_m$ of 2.2 mM xylose. A Linweaver-Burk plot gave a corresponding $V_{max}$ of ~1.0 with a corresponding $K_m$ of 1.2 mM xylose.

EXAMPLE 8E

Inhibition Studies of PXYLA Activity in Strain CD861 (Ex. 8B) Using Xylitol

Strain CD861 was grown in xylose media containing varying concentrations of xylitol, a known xylose isomerase inhibitor. The $K_m$ for the xylose isomerase enzyme doubled when xylitol levels are increased from 0 to 0.25 mM, and doubled again when xylitol levels are increased to 0.50 mM.

EXAMPLE 8F pH Tolerance of PXYLA Gene in Strain CD861 (Ex. 8B)

A single colony of CD861 was inoculated for overnight growth in media consisting of 10 g/L yeast extract, 20 g/L peptone and 100 g/L dextrose. Cells were harvested by centrifugation, washed once with 10 ml 100 mM sodium phosphate, 1 mM PMSF (pH 7.0) and centrifuged again. To this, 2 ml of Y-PER solution was added and gently resuspended and the cell solution was incubated at room temperature for 30 minutes with intermittent agitation. Duplicate test solutions consisted of 100 mM TES-NaOH, 10 mM $MgCl_2$, 0.6 mM NADH, 250 mM Xylose and 1 U SDH, respectively adjusted to pH 7.0, 6.6, 5.9, 4.6 and 3.8 using 5M Lactic Acid (Sigma, USA) in 900 µL volume. To this 100 µL of enzyme or a dilution thereof was added to bring the final volume to 1 mL Enzyme activity was measured as in Example 8C. The optimum activity was obtained at pH 6.5. At pH 5.9 the protein retained 45% of the maximum activity.

EXAMPLE 9A

Microaerobic Shake Flask Characterisation of Strains CD806 (Ex. 6B), CD861 (Ex. 8B), and CD882 (Ex 7A)

Single colonies of strains CD806, CD861 and CD882 were separately inoculated for overnight growth in 100 ml media consisting of 20 g/L yeast extract, 10 g/L peptone, and 100 g/L dextrose supplemented with 300 µg/ml G418 and 300 µg/ml hygromycin. Cell dry weights were determined and the appropriate volume of media for 2 grams cell dry weight (gcdw) was centrifuged and re-suspended in 50 ml media consisting of 20 g/L yeast peptone, 10 g/L yeast extract, 50 g/L Xylose and 10 mM $MgCl_2$, at pH 7.0. Cells were placed in a 250 ml baffled shake flask and placed at 30° C. with 70 rpm shaking. Strain CD806 produced 0.7 g/L xylitol as its only product. Strain CD882 produced 3.8 g/L xylitol as well as 0.4 g/L acetate as its only measurable products. Strain CD861 produced 13.5 g/L ethanol, 0.4 g/L xylitol and small amounts of glycerol, acetate, and succinic (<2 g/L total).

EXAMPLE 9B

Tube Shake Flask Characterisation of CD806 (Example 6B), CD861 (Example 8B), and CD882 (Example 7A)

Single colonies of strains CD806, CD861 and CD882 were separately inoculated for overnight growth in 100 ml media consisting of 20 g/L yeast extract, 10 g/L peptone, and 100 g/L dextrose supplemented with 300 g/ml G418 and 300 µg/ml hygromycin. 50 ml of overnight growth from each strain was centrifuged, then re-suspended in 25 ml of production media consisting of 20 g/L yeast peptone, 10 g/L yeast extract, 50 g/L xylose and 10 mM $MgCl_2$, at pH 7. A 1 ml aliquot of the cell re-suspension was added to 45 ml of production media in a 50 ml Falcon tube, and initial OD was taken (see appendix for OD values). This was repeated several times to ensure that enough samples could be taken throughout the experiment. The tubes were then placed in production conditions, 33° C. and 200 rpm. Strain CD861 produced 21 g/L ethanol and exhibited a volume productivity of 0.3 g/L-hr. under these conditions. Strain CD806 failed to consume any xylose. Strains CD861 and CD882 were both capable of anaerobic grow.

EXAMPLE 10A

Construction of Plasmid pVR113 (FIG. 31) Containing *L. helveticus* L-Lactate Dehydrogenase Gene (LhLDH) Under Control of ScPGK Promoter and ScGAL10 Terminator and ScUra3 Gene without Flanking his Repeats PCR was performed using plasmid pCM28 (Ex. 3B, FIG. 15) as a template and primers identified as SEQ. ID. NO. 114 and SEQ. ID. NO. 115, to introduce SphI sites while removing the flanking HisG repeats. Thermocycling was performed by an initial cycle of 10 minutes at 94° C., followed by 35 cycles of 30 seconds at 94° C., 30 seconds at 45° C., 1.4 minutes at 72° C., followed by a final incubation for 8 minutes at 72° C. using Taq DNA polymerase enzyme (Qiagen, USA). The resulting plasmid was digested with SphI to obtain a ~1.45 kbp fragment containing the ScUra3 gene without flanking HisG repeats.

A plasmid (identified as pVR39 in FIG. 6 and Example 1E of WO 03/102152A1) containing an *L. helveticus* lactate dehydrogenase (LhLDH) gene under the control of the ScPGK promoter and the ScGAL10 terminator, and the G418 resistance marker gene under control of the ScPGK promoter and ScGAL10 terminator, was digested with SphI to create a ~5.16 kbp fragment. This ~5.16 kbp fragment was ligated to the ~1.45 kbp fragment from above to form a ~6.61 kbp plasmid (pVR113, FIG. 31).

EXAMPLE 10B

Generation of *K. marxianus* Mutant Strain (CD896) Containing Exogenous Lactate Dehydrogenase Gene, Non-his-Tagged PXYLA Gene, Overexpressed ScXKS1 Gene Activity and Deleted Xylose Dehydrogenase and Xylose Reductase Genes, by Transforming Strain CD861 (Ex. 8B) with Plasmid pVR113 (Ex. 10A, FIG. 31)

A single colony of strain CD861 was transformed with plasmid pVR113 using standard electroporation methods. The transformed cells were recovered in YPD for 4 hours followed by plating on Sc-Ura plates. One positive transformant (strain CD896) was selected by PCR screening for the LhLDH/ScUra3 cassette. The transformant showed positive PCR results with xylose isomerase and xylulokinase primers, and negative for xylose reductase and xylitol dehydrogenase primers as well.

EXAMPLE 10C

Shake Flask Characterization of Strain CD896 (Ex. 10B)

A single colony of strain CD896 (Ex. 10B) was inoculated into 50 mL of YPD (10 g/L yeast extract, 20 g/L peptone and 100 g/L glucose in a 250 mL baffled shake flask) and grown for 16 hours at 250 rpm and 37° C. From this culture, 3 gcdw was inoculated into YP (10 g/L yeast extract, 20 g/L peptone) with 50 g/L xylose and 23 g/L $CaCO_3$ in shake flasks (microaerobic) and 250 mL glass bottles (anaerobic). The flasks were incubated at 42° C. and samples withdrawn for HPLC at random intervals. Fermentation of strain CD896 under microaerobic conditions gave an L-lactic acid titer of 39 g/L and yields of 77%-79% on xylose consumed. The volumetric productivity of L-lactic acid produced was 1 g/L/hr while the initial xylose consumption rate was between 1.0 and 1.4 g/L/hr. Fermentation of strain CD896 on YP+50 g/L xylose+23 g/L calcium carbonate under anaerobic production conditions produced 10 g/L L-lactic acid in the first 24 hrs after which xylose consumption stalled.

EXAMPLE 11A

Construction of Duplicate Plasmids Containing the Reconstructed PXYLA Gene with (pCM31, FIG. 32) and without (pVR118, FIG. 33) Encoded Poly-his Tail, Together with the ScUra3 Gene without Flanking His Repeats This experiment was designed to elucidate the effect of the poly-his tag on the activity of the reconstructed PYXLA gene. 5 μg of pCM14 (Ex. 3A, FIG. 14) was digested with SphI and electrophoretically separated on a 1.0% agarose gel. A ~5889 bp product was isolated and ligated to a 1450 bp fragment obtained by digesting plasmid pVR113 (Ex. 10A, FIG. 31) with SphI, to form a ~7339 bp plasmid (pCM31, FIG. 32). Plasmid pCM31 contains the PXYLA gene with poly-his tail and under control of the KmPDC1 promoter and ScCYC1 terminator, and the ScUra3 expression cassette. Separately, 5 μg of plasmid pCM29 (Ex. 8A, FIG. 30) was digested with SphI, and electrophoretically separated on a 1.0% agarose gel. A ~5892 bp product was isolated, and ligated to a 1450 bp fragment obtained by digesting plasmid pVR113 with SphI to form a ~7342 bp plasmid (pVR118, FIG. 33). Plasmid pVR118 is similar to plasmid pCM31, but contains a stop codon that prevents encoding of the poly-his tail.

EXAMPLE 11B

Generation of *K. marxianus* Mutant Strains Containing Reconstructed PXYLA Gene with (CD929) and without (CD931) Encoded Poly-his Tag, Together with ScUra3 Gene without Flanking his Repeats, by Transforming Strain CD806 (Ex. 6B) with Plasmids pCM31 (Ex. 11A, FIG. 32) and pVR118 (Ex. 11A, FIG. 33)

A single colony of *K. marxianus* strain CD806 (Ex. 6B) was transformed with plasmid pCM31 using standard electroporation methods. The transformed cells were recovered in YPD medium and plated after 4 hours on Sc-Ura plates. Two transformants were verified by PCR to contain the reconstructed PXYLA gene (with encoded poly-his tag) and overexpressed ScXKS1 gene, and also to confirm the deletions of the KmXYL1 and KmXYL2 genes. One of these transformants was designated strain CD929.

*K. marxianus* strain CD806 was transformed with plasmid pVR118 using standard electroporation methods. A transformant that was verified by PCR to contain the reconstructed PXYLA gene (without encoded poly-his tag) and overexpressed ScXKS1 gene, and to have deletions of the KmXYL1 and KmXYL2 genes, was designated strain CD931.

Genome walking of strain CD931 shows that the PXYLA gene had integrated twice, in the same manner as described for strain CD861 (Ex. 8B).

EXAMPLE 11C

Shake Flask Characterizations of Strains CD929 and CD931 (Ex. 11B)

Single colonies of CD929 and CD931 (Ex. 11B) were separately inoculated into 100 mL of 10 g/L yeast extract, 20 g/L peptone, 70 g/L glucose, 300 μg/ml G418+150 g/ml hygromycin in a 250 mL baffled shake flask. The cultures were incubated overnight at 35° C. with 250 rpm. The cells were inoculated into 50 mL falcon tubes containing 45 mL production media (10 g/L yeast extract, 20 g/L peptone, 50 g/L xylose, 100 mM Tes-NaOH, 10 mM $MgCl_2$, pH 7.0), to an OD of 0.2. The tubes were placed at 37° C. and 250 rpm, sampled at random intervals and analysed by HPLC. Strain CD929 produced 1.7 g/L EtOH and accumulated 1.1 g/L xylulose. Strain CD931 produced 15.2 g/L EtOH while accumulating 4.5 g/L of xylulose. The relative performance of these strains indicates that ethanol formation is about nine times greater when the xylose isomerase gene does not contain the poly-his tag. Similarly, xylulose formation is increased four-fold when the poly-his tail is absent.

EXAMPLE 12A

Reinsertion of KmXYL2 Gene into Strain CD861 (Ex. 8B) by Transformation with Plasmid pCM52 (FIG. 34); Shake Flask Evaluations of the Resulting Transformants The KmXYL2 gene along with 982 bp of the 5' flank and 200 bp of the 3' flank was amplified from genomic DNA of a wild type *K. marxianus* strain, using primers identified as SEQ. ID. NO. 116 and SEQ. ID. NO. 117. These primers introduce SacII restriction sites. The resulting PCR product was digested with SacII and ligated to a similarly digested, shrimp alkaline phosphate-treated plasmid pVR113 (Ex. 10A, FIG. 31). The resulting plasmid was designated pCM52 (FIG. 34). Primers identified as SEQ. ID. NO. 118 and SEQ. ID. NO. 119 were used to screen pCM52. The amplified KmXYL2 gene was sequenced and found to contain two errors, one of which was silent and one causing an amino acid change 85V→I.

Plasmid pCM52 was digested with PvuII and transformed into strain CD861 (Ex. 8B) using standard electroporation methods. Transformants were plated onto Sc-Ura plates and incubated at 37° C. Primers identified as SEQ. ID. NO. 104 and SEQ. ID. NO. 105 were used to amplify the coding region of the KmXYL2 gene and primers identified as SEQ. ID. NO. 120 and SEQ. ID. NO. 121 were used to amplify the region containing the ScUra3 gene through the 5' flank of and into the coding region of the KmXYL2 gene. Five transformants positive for both bands and showing KmXDH activity (XDH+ transformants) were taken forward for shake flask analysis. The KmXDH activity of the XDH+ transformants shows that the errors introduced into the gene did not destroy its activity.

Isolates from each of the five XDH+ transformants were obtained by passaging them through YPX plates twice. The isolates were then inoculated into YPX medium (pH 6.5) and incubated overnight at 35° C. 2 gcdw of each was harvested by centrifugation and re-suspended in 50 ml 10 g/L yeast extract, 20 g/L peptone, 50 g/L xylose, 10 mM $MgCl_2$ and 7.5 g/L $CaCO_3$. The flasks are put into production at 35° C. and 70 rpm shaking. Strain CD861 (Ex. 8B) is similarly cultivated, to compare the effect of the KmXYL2 re-insertion.

Strain CD861 has a volumetric productivity of 0.46 g/L-hr and a xylose consumption rate of 1.47 g/L-hr. The five XDH+ transformants averaged 70% lower productivity and 65% lower xylose consumption. After ~48 hours, strain CD861 produced ~14 g/L ethanol and ~4.7 g/L xylitol, whereas the five XDH+ transformants produced ~2.8-6.3 g/L ethanol and 1.2-2.2 g/L xylitol. All but one of the XDH+ transformants stopped producing ethanol after about 40 hours, although they all continued to consume xylose linearly past 40 hours.

Cells taken at the start of production and after 67 hours of production are lysed and protein quantification was performed using the advanced protein assay reagent (Cytoskeleton-USA). A 10× solution was prepared by adding 2.355 ml 1M sodium phosphate buffer (pH 7.0) to 5 mg-NADH (Sigma), ending in a final NADH concentration of 1.5 mM. Water is added to a volume of 950 μL (less sample volume). Cell free extract is then added and absorbance followed at 340 nm for several minutes to determine background. 50 μL of 0.4 M xylulose was then added and absorbance at 340 nm was followed to determine XDH activity. XDH activity for the five XDH+ transformants taken at the start of production ranged from 287-374 mU/mg. After 67 hours production, XDH activities ranged from 62-86 mU/mg. XDH activity for strain CD861 was 16 mU/mg at the start of production and 3 mU/mg after 67 hours of production.

EXAMPLE 12B

Deletion of ScXKS1 Gene from Strain CD861 (Ex. 8B) by Transformation with Plasmid pCM28 (Ex. 3B, FIG. 15); Shake Flask Evaluations of the Resulting Transformants Plasmid pCM28 was separately linearized with NaeI and PvuII and transformed into strain CD861 using standard electroporation methods. Cells were recovered in YPD for 3 hours followed by plating onto Sc-Ura dropout media. 32 colonies were re-streaked onto duplicate plates. These were PCR screened using primers identified as SEQ. ID. NO. 122 and SEQ. ID. NO. 123 to amplify the coding region of the ScXKS1 gene. Six colonies that failed to produce the band (so indicating the absence of the ScXKS1 gene) were inoculated overnight in YPD to allow loopout of the ScUra3 gene, and plated onto FOA plate to select for those in which the loopout event occurred. Colonies that arose were re-streaked onto YPD to select for single colony isolates. One isolate from each transformation was screened using the above primers, and also for the presence of PXYLA, KmXYL1 and KmXYL2 genes. An additional PCR screening was performed to screen for a double crossover event, in which the ScXKS1 cassette was replaced with the PXYLA cassette from plasmid pCM28. All six isolates tested positive for PXYLA and negative for KmXYL1, KmXYL2 and ScXKS1 genes. One of these was designated CD1065 and sent forward for shake flask evaluation.

Strains CD1065 and CD861 were separately inoculated into 250-ml shake flasks containing 50 ml YPD, and incubated overnight at 37° C. and 250 rpm. Cells were harvested and 4 gcdw were inoculated into 50 ml YPX. The flask was incubated at 35° C. and shaken at 70 rpm. Samples were withdrawn periodically to monitor fermentation activity. Strain CD1065 exhibits a 10-20 hour time lag during which it consumes xylose very slowly. This is attributed to glucose repression of native xylulokinase genes. After this induction period, the xylose consumption rate increases, and strain CD1065 produces about 13 g/L ethanol after 65 hours. Strain CD861 produces ethanol much more rapidly, producing about 18 g/L ethanol after about 20 hours. Strain CD1065 produces about 3.7 g/L xylulose after about 20 hours, but xylulose concentration decreases gradually thereafter. Xylulokinase activity is about 0 for strain CD1065 and about 417 mU/mg for strain CD861. Xylose consumption rates for strain CD861 are approximately double those of strain CD1065. Xylose isomerase activity is about 0.96 U/mg for strain CD1064 and about 1.79 U/mg for strain CD861. These results indicate that the overexpression of xylulokinase significantly improves xylose utilization and ethanol production rates under these conditions.

Cells from strains CD861 and CD1065 were removed following the production phase, streaked onto YPX plates and placed in an anaerobe jar. Both grew comparably.

EXAMPLE 12C

Reinsertion of KmXYL1 Gene into Strain CD861 (Ex. 8B) by Transformation with Plasmid pCM55 (FIG. 35); Shake Flask Evaluations of the Resulting Transformants The KmXYL1 gene along with 890 bp of the 5' flank and 414 bp of the 3' flank was amplified from genomic DNA of a wild type *K. marxianus* strain, using primers identified as SEQ. ID. NO. 124 and SEQ. ID. NO. 125. These primers introduce SacII restriction sites. The resulting PCR product was digested with SacII and ligated to a similarly digested, shrimp alkaline phosphate-treated plasmid pVR113 (Ex. 10A, FIG. 31). The resulting plasmid was designated pCM55 (FIG. 35). Primers identified as SEQ. ID. NO. 118 and SEQ. ID. NO. 126 were used to screen plasmid pCM55, and restriction mapping with BstBI and SbfI was used to confirm the orientation. The amplified KmXYL1 gene was sequenced and found to contain three errors, one of which was silent and the others causing amino acid changes 71V→A, 112Y→H and 302I→V.

Plasmid pCM55 was digested with PvuII and transformed into strain CD861 (Ex. 8B) using standard electroporation methods. Transformants were plated onto Sc-Ura plates and incubated at 37° C. Primers identified as SEQ. ID. NO. 127 and SEQ. ID. NO. 128 were used to amplify the coding region of the KmXYL1 gene and primers identified as SEQ. ID. NO. 121 and SEQ. ID. NO. 129 were used to amplify the region containing the ScUra3 gene through the 3' flank of and into the coding region of the KmXYL1 gene. Six transformants positive for both bands (XR+ transformants) were taken forward for shake flask analysis.

Isolates from each of the five XR+ transformants were obtained by restreaking from minimal media onto YPD. The isolates were then re-streaked onto YPX+300 µg/mL G418+ 300 µg/mL hygromycin prior to inoculation in YPX media. These transformants were then inoculated into a medium containing 10 g/L yeast extract, 20 g/L peptone, 50 g/L xylose (pH 6.5) and incubated at 35° C. for 48 hours. 1 gcdw of each was harvested by centrifugation and re-suspended in 50 ml 10 g/L yeast extract, 20 g/L peptone, 50 g/L xylose, 10 mM $MgCl_2$ and 7.5 g/L $CaCO_3$. The flasks are put into production at 35° C. and 70 rpm shaking. Strain CD861 (Ex. 8B) is similarly cultivated, using 2 gcdw, to compare the effect of the KmXYL1 re-insertion.

Strain CD861 has a volumetric productivity of 0.79 g/L-hr and a xylose consumption rate of 2.02 g/L-hr (based on 2 gcdw). Five of the XR+ transformants exhibited a lag of about 20-50 hours, and thereafter exhibited volume productivities ranged from 0.05-0.13 g/L-hr and xylose consumption rates of 0.45-0.67 g/L-hr. Ethanol yields for these five XR+ transformants were 18-33%, compared to 51% for strain CD861.

Cells taken at the start of production and after 67 hours of production are lysed and protein quantification was performed using the advanced protein assay reagent (Cytoskeleton-USA). A 100 µL dilution of cell extract was added to a 900 µL aliquot of a solution of 100 mM sodium phosphate, 0.5 M D-xylose and 0.2 mM NADPH equilibrated to 37° C. Absorbance was followed to determine KmXYL1 activity. Five of the XR+ strains have XR activities in the range of ~34-86 mU/mg. The KmXYL1 activity of these five XR+ transformants shows that the errors introduced into the gene did not destroy its activity. The KmXYL1 activity of strain CD861 is approximately 4 mU/mg.

The sixth XR+ transformant shows a KmXYL1 activity of 19.5 mU/mg, much lower than the others. As such, it resembles strain CD861 much more than the others do. This sixth XR+ strain performs similarly to CD861 on the shake flask cultivation (after an initial lag period) and produces about 13.8 g/L of ethanol after about 51.5 hours.

These results show that native XR activity has an adverse affect on the ability of these strains to ferment xylose to ethanol under these conditions.

EXAMPLE 12D

Reinsertion of KmXYX1 and KmXYL2 Genes into Strain CD861 (Ex. 8B) by Transformation with Plasmid pCM58 (FIG. 36); Shake Flask Evaluations of the Resulting Transformants A plasmid is constructed in the same manner as described for plasmid pCM52 (Ex. 12A, FIG. 34), except that the KmXYL2 gene flanks are oriented in the opposite direction than in plasmid pCM52. This plasmid is designated pCM53. The KmXYL2 gene in plasmid pCM53 is sequenced and found to contain four errors, three of which are silent and the other amounts to a mutation of amino acid 260I V.

The KmXYL1 gene along with region of the 5' flank and a region of the 3' flank of the gene was amplified from genomic DNA of a wild type *K. marxianus* strain, using primers identified as SEQ. ID. NO. 130 and SEQ. ID. NO. 131. These primers introduce SacI and NotI restriction sites. The resulting PCR product was digested with SacI and NotI and ligated to a similarly digested plasmid pCM53. The resulting plasmid was designated pCM58 (FIG. 36). Primers identified as SEQ. ID. NO. 66 and SEQ. ID. NO. 119 were used to screen plasmid pCM58, and restriction mapping with ScaI and XmnI was used to confirm the orientation. The amplified KmXYL1 gene was sequenced and found to contain two errors, one of which was silent and the other causing an amino acid change 71V A.

Plasmid pCM58 was digested with PvuII and transformed into strain CD861 (Ex. 8B) using standard electroporation methods. Transformants were plated onto Sc-Ura plates and incubated at 37° C. Primers identified as SEQ. ID. NO. 132 and SEQ. ID. NO. 133 were used to amplify the coding region of the KmXYL1 gene and primers identified as SEQ. ID. NO. 134 and SEQ. ID. NO. 105 were used to amplify the region containing the KmXYL2 gene and flanks. Five transformants positive for both bands were taken forward for further analysis.

The five selected transformants were inoculated into a liquid medium containing 10 g/L yeast extract, 20 g/L peptone, 50 g/L xylose (pH 6.5) and incubated at 35° C. for 48 hours. 4 gcdw of each was harvested by centrifugation and re-suspended in 50 ml 10 g/L yeast extract, 20 g/L peptone, 50 g/L xylose, 10 mM $MgCl_2$ and 7.5 g/L $CaCO_3$. The flasks are put into production at 35° C. and 70 rpm shaking. Strain CD861 (Ex. 8B) is similarly cultivated to compare the effect of the KmXYL1 and KmXYL2 re-insertions.

Strain CD861 consumes essentially all the xylose in 30 hours, producing 16.1 g/L ethanol in that time. Ethanol yield for strain CD861 was 67%. The five XR+, XDH+ transformants all consumed xylose much more slowly, and produced average ethanol yields of about 16%. Strain CD861 produced a xylitol yield of 10%, but the five transformants averaged a xylitol yield of 56%. Xylose reductase activity for strain CD861 was about 2 mU/mg, whereas it ranged from 126-425 mU/mg in the transformants, after 73.5 hours cultivation. Xylitol dehydrogenase activity in strain CD861 was zero, but ranged from 21 to 98 mU/mg in the transformants after 73.5 hours cultivation. The increase in activities of these enzymes indicates that the reinserted KmXYL1 and KmXYL2 genes were functional in the five transformants. Xylose isomerase activity was higher in strain CD861 (~131 mU/mg) than in the five transformants (~26-45 mU/mg). However, xylitol that was present may have inhibited xylose isomerase activity in the five XR+, XDH+ transformants, resulting in an artificially low value.

This data further indicates that the deletion or disruption of the aldose reductase/xylitol dehydrogenase pathway is beneficial in the strains having an exogenous xylose isomerase gene, under these fermentation conditions.

EXAMPLE 13A

Construction of XDH-Targeting Plasmid pMI410 (FIG. 38) for *Candida sonorensis* Transformation Genomic DNA of *C. sonorensis* (ATCC Accession No. 32109) was obtained as described in WO 03/049525.

A portion of the *C. sonorensis* lambda library described in WO 03/049525 was screened by using the *Pichia stipitis* XYL2 gene (Kötter et al. 1990 Curr. Genet, 18: 493-500) as a probe. The XYL2 gene was labeled with 32P-dCTP using the Random Primed Labeling Kit (Boehringer Mannheim). Hybridization was performed by incubation overnight at 55° C. in a solution containing 6×SSC 5×Denhardt's 0.5% SDS 100 g/ml denatured herring sperm DNA. The filters were washed after hybridization at room temperature in a solution of 2×SSC for 5 min and repeated, followed a wash at 55 C in 2×SSC-0.1 SDS for 30 minutes. This resulted in isolation of hybridizing clones that contained the *C. sonorensis* xylitol dehydrogenase gene (CsXDH).

The 5' region of the CsXDH gene was PCR amplified using primers identified as SEQ. ID. NO. 135 and SEQ. ID. NO. 136 and the CsXDH gene was used as a template. The PCR product was cut with SacI and SalI to produce a 642 bp fragment that was gel isolated.

Plasmid pMI281 was prepared by cutting plasmid pMI278 (described in FIG. 14 of WO 03/049525) with XbaI, and circularizing a 4976 bp fragment so obtained. The 642 bp fragment form above was ligated to a 4965 bp fragment obtained by digesting plasmid pMI281 with SacI and SalI. The resulting plasmid was named pMI409 (FIG. 37).

The 3' region of the CsXDH gene was PCR amplified using the primers identified as SEQ. ID. NO. 137 and SEQ. ID. NO. 138 and the same lambda library clone as a template. The PCR product was cut with NotI and ApaI. A 457 bp fragment was gel isolated and ligated to a 5551 bp fragment obtained by digesting plasmid pMI409 with NotI and ApaI. The resulting plasmid was named pMI410 (FIG. 38).

EXAMPLE 13B

Construction of XR-Targeting Plasmid pMI412 (FIG. 40) for *C. sonorensis* Transformation A xylose reductase sequence homologue was amplified by PCR using oligonucleotides identified as SEQ. ID. NO. 139 and SEQ. ID. NO. 140 and genomic DNA of *C. sonorensis* as a template. The oligonucleotides were designed based on conserved sequences found in known fungal xylose reductase and aldose reductase sequences. The 700 bp PCR product was labeled and used as a probe for the isolation of the genomic CsXR lambda clones from the genomic library similarly as described in WO 03/049525.

The 5' region of the *C. sonorensis* xylose reductase (CsXR) gene was PCR amplified using primers identified as SEQ. ID. NO. 141 and SEQ. ID. NO. 142. A portion of the *C. sonorensis* lambda library clone described in WO 03/049525 that contains the CsXR gene was used as a template. The PCR product was cut with SacI and SalI. A 526 bp fragment was gel isolated and ligated to a 4965 bp fragment obtained by digesting plasmid pMI281 with SacI and SalI. The resulting plasmid was named pMI411 (FIG. 39).

The 3' region of the CsXR gene was PCR amplified using the primers identified as SEQ. ID. NO. 143 and SEQ. ID. NO. 144 and the same lambda library clone as a template. The PCR product was cut with NotI and ApaI. A ~591 bp fragment was gel isolated and ligated to a 5435 bp fragment obtained by digesting plasmid pMI411 with NotI and ApaI. The resulting plasmid was named pMI412 (FIG. 40).

EXAMPLE 13C

Construction of PXYLA Expression Plasmid pMI417 (FIG. 42) for Simultaneous Insertion of PXYLA and Deletion of CsXR in *C. sonorensis*

The PXYLA gene from ATG to the single AgeI site was PCR amplified using primers identified as SEQ. ID. NO. 145 and SEQ. ID. NO. 146 and pCM29 (Ex. 8A, FIG. 30) as the template. The PCR product was cut with AgeI and KpnI and a 453 bp fragment was gel isolated. Plasmid pCM29 was cut with AgeI. An 8151 bp fragment was gel isolated and partially digested with KpnI. The resulting 6501 bp fragment was gel isolated and ligated to the 453 bp PCR fragment. The plasmid was named pMI400.

Plasmid pMI278 was cut with BamHI, filled in with the Klenow enzyme and partially digested with XbaI. The resulting 6675 bp fragment was gel isolated. Plasmid pMI400 was cut with SbfI, made blunt ended with T4 polymerase, and cut with XbaI. The resulting 1358 bp fragment was gel isolated and ligated to the 6675 bp fragment of pMI278 to form plasmid pMI403 (FIG. 41).

Plasmid pMI412 (Ex. 13B, FIG. 40) was cut with SalI and NotI. A 4037 bp fragment was isolated and ligated to a 5042 bp fragment obtained by digesting pM1403 with SalI and NotI. The resulting plasmid was named pMI417 (FIG. 42). Plasmid pMI417 contains the PXYLA gene and a G418 marker gene with associated promoter and terminator regions between upstream and downstream regions of the CsXR gene. The PXYLA gene is under the control of the *C. sonorensis* PGK promoter and the ScGAL10 terminator.

EXAMPLE 13D

Construction of ScXKS1 Expression Plasmid pMI425 (FIG. 43) for Simultaneous Insertion of ScXKS1 and Deletion of CsXDH in *C. sonorensis* Transformation The ScXKS1 5' region from ATG to the single BglII site was PCR amplified using primers identified as SEQ. ID. NO. 147 and SEQ. ID. NO. 148 and pVR103 (Ex. 5C, FIG. 25) as the template. The PCR product was cut with NotI and BglII and a 267 bp fragment was gel isolated. Plasmid pVR103 (Ex. 5C, FIG. 25) was cut with NotI and BglII. A 4633 bp fragment was obtained and ligated to the 267 bp PCR fragment. The plasmid was named pMI406.

Plasmid pMI403 (Ex. 13C, FIG. 41) is cut with EcoNI, filled in using the Klenow enzyme and cut with SalI. A 6505 bp fragment is gel isolated. Plasmid pMI271 (described in FIG. 7 of WO 03/049525) is cut with BamHI, filled in using the Klenow enzyme and cut with SalI. The resulting 1666 bp fragment is gel isolated and ligated to the 6505 bp fragment. The resulting plasmid is named pMI423.

Plasmid pMI410 (Ex. 13A, FIG. 38) and plasmid pMI406 were each digested with XbaI, dephosphorylated using calf intestinal alkaline phosphatase, and cut with BamHI. 5032 bp and 1814 bp fragments were gel isolated. Plasmid pMI423 was digested with XbaI and the resulting 2817 bp fragment gel isolated. The three fragments were ligated and the resulting plasmid named pMI425 (FIG. 43). Plasmid pMI425 contains a portion of the promoter region for the CsXDH gene, an hph gene with associated promoter and terminator regions, the ScXKS1 gene under the control of a *C. sonorensis* PGK promoter and a ScGAL10 terminator, followed by a portion of the terminator region for the CsXDH gene.

EXAMPLE 13E

Generation of *C. sonorensis* Mutant Strains (Cs/T-1, Cs/T-25, SC/T-34 and Cs/T-51) Containing the Reconstructed PXYLA Gene and ScXKS1 Gene Plasmids pMI417 (Ex. 13C, FIG. 42) and pMI425 (Ex. 13D, FIG. 43) are used to transform a *C. sonorensis* colony using chemical methods similar to those described in WO 03/049525. The transformed cells were plated onto YPD+200 µg/ml G418 or onto YPD+200 µg/ml hygromycin and 200 µg/ml G418. PCR analysis with PXYLA and ScXKS1 probes confirms the presence of strains as follows:

Strain Cs/T-1: 1 copy of PXYLA and 1 copy of ScXKS1

Strain CS/T-25: 1 copy of PXYLA and 2 copies of ScXKS1

Strain Cs/T-51: 2 copies of PXYLA and 1 copy of ScXKS1

Strain CS/T-34: 2 copies of PXYLA and 2 copies of ScXKS1

EXAMPLE 13F

Generation of *C. sonorensis* Mutant Strains (Cs/417-201, -206, -208 and -214) Containing the Reconstructed PXYLA Gene with and without a Deletion of the CsXR Gene by Transformation with Plasmid pMI417 (Ex. 13C, FIG. 42)

Plasmid pMI417 is digested with SacI and ApaI and used to transform a *C. sonorensis* colony using chemical methods similar to those described in WO 03/049525. The transformed cells were plated onto YPD+200 μg/ml G418. PCR analysis identifies colonies having the PXYLA gene and the CsXR deletion. Southern analysis confirms that the strain designated Cs/417-206 contains one copy of the PXYLA gene whereas the strain designated Cs/417-214 contains two copies of the PXYLA gene, in addition to the CsXR deletion. Strain Cs/417-201 contains two copies of the PXYLA gene but no CsXR deletion. Cs/417-208 contains a single copy of the PXYLA gene and no CsXR deletion.

EXAMPLE 13G

Generation of a C. sonorensis Mutant Strains (Cs/417-214/425A and Cs/417-214/425B) Containing the Reconstructed PXYLA Gene, the ScXKS1 Gene, a Deletion of the CsXR and with (A) and without (B) Deletion of the CsXDH Gene, by Transforming Cs/417-214 (Ex. 13F) with Plasmid pMI425 (Ex. 13D, FIG. 43)

Plasmid pMI425 is digested with PmeI and PspOMI and used to transform strain Cs/417-214 using chemical methods similar to those described in WO 03/049525. The transformed cells were plated onto YPD+200 μg/ml hygromycin or onto YPD+200 μg/ml hygromycin+200 g/ml G418. PCR and Southern analysis is used to identify colonies that contain the ScXKS1 gene and to determine whether a deletion of the CsXDH gene has occurred. A strain having two copies of the reconstructed PXYLA gene, a copy of the ScXKS1 gene, a deletion of the CsXR gene and a deletion of the CsXDH gene is designated Cs/417-214/425A. A strain having two copies of the reconstructed PXYLA gene, a copy of the ScXKS1 gene, a deletion of the CsXR gene but no deletion of the CsXDH gene is designated Cs/417-214/425B.

EXAMPLE 13H

Generation of *C. sonorensis* Mutant Strain (C29/403-7) Containing the Reconstructed PXYLA Gene and a Functional Lactate Dehydrogenase (LDH) Gene by Transformation with Plasmid pMI403 (Ex. 13C, FIG. 41)

Plasmid pMI403 is used to transform a mutant *C. sonorensis* strain corresponding to that identified as strain 246-27 in WO 03/049525, using chemical methods similar to those described there. Strain 246-27 contains a functional, exogenous lactate dehydrogenase (LDH) gene. The transformed cells were plated onto YPD+200 μg/ml G418. A strain exhibiting 70 mU/mg XI activity is designated C29/403-7. It apparently contains multiple copies of the PXYLA gene, under the control of the CsPGK promoter and ScGAL10 terminator. In addition, strain C29/403-7 contains the functional lactate dehydrogenase gene.

EXAMPLE 13I

Generation of *C. sonorensis* Mutant Strain (C29/403-7/425) Containing the Reconstructed PXYLA Gene, the ScXKS1 Gene and a Functional LDH Gene, by Transforming Strain C29/403-7 (Ex. 13H) with Plasmid pMI425 (Ex. 13D, FIG. 43)

Plasmid pMI425 is digested with SalI and NotI and used to transform strain C29/403-7 (Example 13H), using chemical methods similar to those described in WO 03/049525. The transformed cells were plated onto YPD+200 μg/ml hygromycin and onto YPD+200 ug/ml hygromycin and 200 μg/ml G418. PCR and Southern analysis are used to identify transformants containing the PXYLA and ScSKS1 genes, which are collectively designated C29/403-7/425. Strain C29/403-7/425 contains the functional lactate dehydrogenase gene.

EXAMPLE 13J

Generation of *C. sonorensis* Mutant Strains (C29/417-4 and C29/417-9) Containing the Reconstructed PXYLA Gene and a Deletion of the CsXR Gene Plasmid pMI417 (FIG. 13C, FIG. 42) is digested with SacI and ApaI and used to transform a mutant *C. sonorensis* strain corresponding to that identified as strain 246-27 in WO 03/049525, using chemical methods similar to those described there. The transformed cells were plated onto YPD+200 μg/ml G418. PCR analysis identifies colonies having the PXYLA gene and the CsXR deletion. Southern analysis confirms that a mutant strain designated C29/417-4 contains one copy of the PXYLA gene, and a mutant strain designated C29/417-9 contains two copies of the PXYLA gene, in addition to the CsXR deletion.

EXAMPLE 13K

Generation of *C. sonorensis* Mutant Strains Containing the Reconstructed PXYLA Gene, the ScXKS1 Gene, an LDH Gene, a Deletion of the CsXR Gene and with (C29/417-9/425-11) and without (C29/417-9/425-9) Deletion the CsXDH Gene, by Transforming Strain C29/417-9 (Ex. 13J) with Plasmid pMI425 (Ex. 13D, FIG. 43)

Plasmid pMI425 is digested with PmeI and ApaI and used to transform strain C29/417-9 (Ex. 13J), using chemical methods similar to those described in WO 03/049525. The transformed cells were plated onto YPD+200 g/ml hygromycin. PCR analysis identifies colonies having the ScXKS1 gene and those also containing the CsXDH deletion. Transformants with and without the CsXDH deletion are designated C29/417-9/425-11 and C29/417-9/425-9, respectively.

EXAMPLE 14

Shake Flask Characterisation of *C. sonorensis* Strains from Examples 13E-13K

The following table summarizes strains selected for shake flask characterizations, and reports xylose isomerase and xylulokinase activities.

Ethanol-Producing Strains

| Strain Designation | Ex. # | XI[1] | XK[2] | XR[3] | XDH[4] | XI activity (mU/mg) | XK activity (mU/mg) |
|---|---|---|---|---|---|---|---|
| Cs/T-1 | 13E | 1 | 1 | + | + | 170 | 840 |
| Cs/T-25 | 13E | 1 | 2 | + | + | 40 | 1060 |
| Cs/T-34 | 13E | 2 | 2 | + | + | 50 | 1600 |
| Cs/T-51 | 13E | 2 | 1 | + | + | 80 | 730 |
| Cs/417-214 | 13F | 2 | 0 | − | + | 70 | 70 |
| Cs/417-206 | 13F | 1 | 0 | − | + | 30 | 140 |
| Cs/417-201 | 13F | 2 | 0 | + | + | 60 | 100 |
| Cs/417-208 | 13F | 1 | 0 | + | + | 60 | 120 |
| Cs/417-214/425A | 13G | 2 | 1 | − | − | 50 | 1440 |
| Cs/417-214/425B | 13G | 2 | 1 | − | + | 50 | 860 |

| Lactic Acid-Producing Strains (all containing exogenous LDH) | | | | | | |
|---|---|---|---|---|---|---|
| Strain Designation | Ex. # | XI[1] | XK[2] | XR[3] | XDH[4] | XI activity (mU/mg) | XK activity (mU/mg) |
| C29/403-7 | 13H | 2 | 0 | + | + | 90 | N.D.[5] |
| C29/403-7/425 | 13I | 2 | 1 | + | + | 90 | N.D. |
| C29/417-4 | 13J | 1 | 0 | − | + | 20 | 250 |
| C29/417-9 | 13J | 2 | 0 | − | + | 30 | 150 |
| C29/417-9/425-11 | 13K | 2 | 1 | − | − | 50 | 960 |
| C29/417-9/425-9 | 13K | 2 | 1 | − | + | 30 | 920 |

Xylulokinase and xylose isomerase activities for these samples were determined as follows:

The samples (5-10 ml) were centrifuged and washed once with 100 mM sodium phosphate buffer, pH 7.0. After washing, the samples were resuspended into Y-PER yeast protein extraction reagent (Pierce, Rockford, Ill.) containing protease inhibitors (Complete Mini, EDTA free, Roche). After 20 minutes incubation at room temperature, the cells were centrifuged 13,000 rpm for 10 minutes at +4° C. Supernatant samples were collected for activity measurements.

Xylulokinase activity was determined by a two-step protocol. In step 1, the reaction contained 50 mM HEPES/KOH pH 7.5, 5 mM ATP, 6 mM $MgCl_2$ and 20 mM xylulose. The background reaction was determined by adding water instead of xylose. After adding the enzyme sample, the reactions were incubated at 30° C. for 0 and 240 seconds. After the incubation the reactions were stopped by incubating them at 95° C. for 5 min. After reaction was stopped 40 mM HEPES/KOH pH 7.5, 10 mM $MgCl_2$, 2.5 mM PEP and 0.2 mM NADH was added to the reaction and absorbance at 340 nm was measured. After measuring the initial absorbance, a mixture of myokinase, pyruvate kinase and lactate dehydrogenase was added. This reaction was incubated further for 1 hour and absorbance at 340 nm was measured. The xylulokinase activity was calculated from the ADP production during the assays.

Xylose isomerase activity was determined by monitoring the oxidation of NADH at 340 nm at 30° C. The reaction contains (in addition to the sample) 100 mM TES-NaOH, pH 7.0, 250 mM xylose, 10 mM $MgCl_2$, 0.6 mM NADH and 2.5 U sorbitol dehydrogenase. The background was detected by measuring the activity without xylose. The xylose isomerase assay was performed in a Cobas Mira automated analyzer (Roche).

Protein concentrations were determined with the Lowry method (Lowry, O. H., Rosebrough, N.J., Farr, A. L. and Randall, R. J. (1951), Protein measurement with the Folin phenol reagent, J. Biol. Chem. 193:265-275). Bovine serum albumin (Sigma) was used as a protein standard.

EXAMPLE 14A

Microaerobic Shake Flask Characterizations of Wild-Type *C. sonorensis* and Strains Cs/T-1, -25, -34, -51 (Ex. 13E), Cs/417-201, -206, -208, -214 (Ex. 13F) and Cs/417-214/425A and -B (Ex. 13G)

50 ml of YP (10 g/L yeast extract and 20 g/L peptone)+5% glucose+10 mM $MgCl_2$ in 250 ml flasks was inoculated with cells grown on YPD plates and incubated overnight with 250 rpm shaking at 30° C. A ~5 ml aliquot was removed for XI, XK and protein assays. $OD_{600}$ was measured and an amount of cells equivalent of $OD_{600}$=12 (corresponding to 4 g/L cell dry weight) ($OD_{600}$=40 for strains Cs/417-214/425A and -B) in 50 ml was collected by centrifugation and resuspended in 50 ml of YP+5% xylose+10 mM $MgCl_2$. The resuspended cells were transferred into a 250 ml flask containing 1.2 g $CaCO_3$. The cultures were incubated at 30° C. with 100 rpm shaking. Samples for HPLC (for measuring xylose consumption and ethanol, xylitol, acetate and xylulose production) and $OD_{600}$ measurements were collected daily. The fermentation was carried out for approximately 11 days.

Strains Cs/T-1, -25, -34-51 and Cs/417-214/425A and -B produced 2-5 g/L ethanol, with xylitol being the main product for these strains. The wild-type *C. sonorensis* strain and strains Cs/417-201, -206, -208 and -214 did not produce ethanol under the microaerobic conditions. This indicates that both xylose isomerase and xylulokinase are needed for ethanol production under microaerobic conditions. All XR+ strains also produced acetate.

Strains Cs/417-201, -206, -208, -214 and Cs/417-214/425B consumed xylose slowly and no ethanol, xylitol or acetate was produced under these microaerobic conditions. Strain Cs/417-201/425A also consumed xylose slowly and produced some xylitol. At 11 days, strains Cs/417-206 and Cs/417-214 produced 0.7 and 1.2 g/L of xylulose, respectively. This suggests that under these microaerobic conditions, xylulose accumulated in XI+ strains that did not have overexpressed XK, and that the amount of xylulose accumulation depends on XI activity level.

EXAMPLE 14B

Anaerobic Shake Flask Characterizations of Wild-Type *C. sonorensis* and Strains Cs/T-25, -34 (Ex. 13E), Cs/417-201, -214 (Ex. 13F), Cs/417-214/425A and B (Ex. 13G)

50 ml of YP+5% glucose+10 mM $MgCl_2$ in 250 ml flasks was inoculated with cells grown on YPD plates and incubated overnight with 250 rpm shaking at 30° C. A 5 ml aliquot was removed for XI, XK and protein assays. $OD_{600}$ was measured and an amount of cells equivalent of $OD_{600}$=12 (corresponding to 4 g/L cell dry weight) ($OD_{600}$=40 for strains Cs/417-214/425A and -B) in 50 ml was collected by centrifugation and resuspended in 50 ml of YP+5% xylose+10 mM $MgCl_2$+24 g/L $CaCO_3$. The cultures were incubated at 30° C. with 100 rpm shaking in 100 ml shake flasks sealed with water locks. The cultivation was sampled. Samples for HPLC (for measuring xylose consumption and ethanol, xylitol, acetate and xylulose production) and $OD_{600}$ measurements were collected periodically. The cultivation was continued for 15 days.

Strains Cs/T-25 and -34 produced 2 g/L ethanol during the first 8 days of incubation whereas the wild-type *C. sonorensis* strain did not produce detectable ethanol. Strains Cs/417-201 and -214 also failed to produce ethanol under these conditions, indicating that both xylose isomerase and xylulokinase genes are needed to obtain anaerobic fermentation ability on xylose in these strains.

Strain Cs/417-214/425A produced ~13 g/L ethanol after 4 days and ~25 g/L ethanol after 11 days. Yield on xylose to ethanol was approximately 55% after 4 days and 53% after 11 days. Xylose consumption was 22-23 g/L after 4 days and 48-49 g/L after 11 days. Strain Cs/417-214/425B consumed ~16 g/L of xylose in 4 days and produced 7 g/L ethanol. This indicates that in these strains, disruption of the native XR/XDH pathway combined with exogenous XI gene expression and XK overexpression is important to achieve good ethanol production. Disruption of both the CsXR and CsXDH genes is seen to provide the best ethanol production under anaerobic conditions.

EXAMPLE 14C

Microaerobic Shake Flask Characterizations of LDH-Producing C. sonorensis Mutant Strain 246-27 and Strains C29/403-7 (Ex. 13H) and C29/403-7/425 (Ex. 13I)

Microaerobic shake flask cultivations were performed for each of these three strains, using the general conditions described in Example 14A, except that lactate production was also monitored.

Under these microaerobic conditions, strain 246-27 and strain C29/403-7 consumed xylose at about 0.5 g/L/hr and all produced lactic acid at about 0.4 g/L/hr. Strain C29/403-7/425 produced about 10-15% more lactic acid and about 10-15% less xylitol than strain C29/403-7 under these conditions. Strain C29/403-7 produced more xylulose than the others, suggesting that xylulose accumulates in this strain because of xylose isomerase activity.

At the end of the cultivations, cells from each flask are streaked onto YP+xylose and onto YP+glucose plates and incubated in anaerobe jars for 9 days. None grew anaerobically, but all grew aerobically in xylose and glucose media.

EXAMPLE 14D

Anaerobic Shake Flask Characterizations of LDH-Producing C. sonorensis Mutant Strain 246-27 and Strains C29/403-7 (Ex. 13H), 029/403-7/425 (Ex. 13I) and C29/417-9 (Ex. 13J)

Anaerobic shake flask cultivations were performed for each of these three strains, using the general conditions described in Example 14B, except that lactate production was also monitored.

All consumed xylose at a rate of about 0.1 g/L/hr. Strains 246-27, C29/403-7, C29/403-7/425 and C29/417-9 produced 4.1, 4.8, 6.4 and 3.0 g/L of lactic acid, 0.3, 0.45, 0.3 and 0.3 g/L xylitol and 0.3, 1.45, 0.9 and 0.85 g/L xylulose, respectively, after 141 hours. Under these conditions, the overexpression of the xylulokinase enzyme leads to improved lactic acid production. Strains with overexpressed xylose isomerase but without overexpressed xylulokinase accumulate xylulose, indicating that the xylose isomerase gene is active.

EXAMPLE 14E

Microaerobic Shake Flask Characterizations of LDH-Producing C. sonorensis Mutant Strain 246-27 and Strains C29/417-4 and -9 (Ex. 13J), C29/417-9/425-9 and -11 (Ex. 13K)

Microaerobic shake flask cultivations were performed for each of these three strains, using the general conditions described in Example 14C. Cultivations were continued for 7 days.

Under these microaerobic conditions, strain 246-27 consumed xylose faster than the other strains. Strain C29/417-4, -9, C20/417-425-9 and -11 produced about 2-5 g/L lactic acid after 7 days, after which time 25-35 g/L residual xylose remained. The ability of strain C29/417-9/425-11 to produce lactic acid confirms that the xylose isomerase and xylulokinase pathway is operative in these strains. Strain 0291417-9/425-11 consumed xylose slightly faster than the C29/417-9/425-9 strain, but also accumulated 1-2 g/L xylitol.

EXAMPLE 14F

Anaerobic Shake Flask Characterizations of LDH-Producing C. sonorensis Mutant Strains C29/417-9 (Ex. 13J), C29/417-9/425-9 and -11 (Ex. 13K)

Anaerobic shake flask cultivations were performed for each of these three strains, using the general conditions described in Example 14D.

Strains C29/417-9, C29/417-9/425-9 and C29/417-9/425-11 produced 4.4, 6.2 and 24.4 g/L lactic acid after 146 hours. Yield of lactic acid on xylose was 0.40, 0.70 and 0.95 g/g, respectively for these strains. No xylitol was produced by either strain C29/417-9/425-9 or -11, whereas strain C29/417-9 produced 2.7 g/L xylitol. Under these conditions, the overexpression of the xylulokinase enzyme leads to improved lactic acid production. This indicates that in these strains, disruption of the native xylose reductase/xylitol dehydrogenase pathway combined with exogenous xylose isomerase and xylulokinase overexpression provides good lactic acid production. Disruption of both the CsXR and CsXDH genes is seen to provide the best production under anaerobic conditions.

EXAMPLE 15A

Generation of K. marxianus Mutant Strains (CD1103 and CD1106) Containing the Cyllamyces aberensis Xylose Isomerase (CaXYLA) Gene Cyllamyces aberensis DNA (isolate few 1 from cow, U.K.) was obtained from Gareth Wyn Griffith, Institute of Biological Sciences, University of Wales, Aberystwyth, Ceredigion SY23 3DA, Great Britain. PCR reactions were conducted using this DNA as the template, using 0.5 µM of the sense primer identified as SEQ. ID. NO. 149 and 0.5 µM of the antisense primer identified as SEQ. ID. NO. 150 Phusion HF buffer and 0.2 mM of each dNTP. In this construct, the first methionine encoded as detected at the 5' end sequence of the gene served as the initiation methionine, and an in-frame stop codon was included in addition to SbfI restriction sites. Before 3 minutes denaturation, 2 U of Phusion polymerase (Finnzymes Oy, Espoo, Finland) was added. The reaction was cycles 35 times as follows: 10 seconds at 98° C., 30 seconds at 45° C. and 1 minute at 72° C. with a final extension of 8 minutes at 72° C. A 1346 bp PCR fragment was obtained and ligated to TOPO plasmid with the TOPO TA Cloning Kit (Invitrogen, Carlsbad, Calif.) and sequenced. The C. aberensis xylose isomerase (CaXYLA) gene has the nucleotide sequence identified as SEQ. ID. NO. 151. The deduced amino acid sequence for the protein encoded by this gene is given as SEQ. ID. NO. 152.

K. marxianus genomic DNA was obtained from a wild-type K. marxianus strain similar to that described before. The K. marxianus Ura3 gene (KmURA3) gene plus about 750 bp of the Ura3 promoter region and about 250 bp to the Ura3 terminator region was isolated in a standard protocol using Failsafe Polymerase (Epicenter), with the genomic DNA as template and primers identified as SEQ. ID. NO. 153 and SEQ. ID. NO. 154. PCR conditions were 5 minutes at 95° C., 15 cycles of 30 seconds at 95° C., 30 seconds at 55° C. and 2 minutes at 68° C., followed by 25 cycles of 30 seconds at 95° C. and 2.5 minutes at 68° C., ending in a blunt end generation cycle of 68° C. for 8 minutes. The resulting ~1.8 kb PCR product was cloned into pCR-XL-TOPO vector (Invitrogen) and sequenced for verification. The resulting plasmid was designated pSO90. The nucleotide sequence of the cloned KmURA3 gene appears as SEQ. ID. NO. 155. Plasmid pSO90 is digested with SphI and the ~1.8 kbp KmURA3 region is gel isolated and ligated into a similarly digested and shrimp alkaline phosphatase treated ~4570 bp fragment of plasmid pCM9 (Ex. 1I, FIG. 12). The resulting plasmid (pSO91, FIG. 44) contains the KmURA3 selection gene, the KmPDC1 promoter, a SbfI site and the SeCYC1 terminator.

The CaXYLA-containing plasmid from above was digested and a ~1.4 kbp fragment containing the CaXYLA gene is gel isolated. Plasmid pSO91 is similarly digested and shrimp alkaline phosphate treated to obtain a 6376 bp fragment. These fragments are ligated with HC T4 Ligase (Invitrogen) to form a plasmid (pSO99, FIG. 45) that contains a KmUra3 selection gene and the CaXYLA gene under control of the KmPDC1 promoter and SeCYC1 terminator.

A K. marxianus colony corresponding to CD 806 (Ex. 6B) is cultured. 20 ml of cells are spun down and transformed with plasmid pSO99 using standard electroporation methods, after digestion of the plasmid with AatII and BsmBI (without clean-up). 100 µL of cells were plated on SC-Ura plates and allowed to grow at 37° C. until colonies formed. The colonies were streaked onto secondary Sc-Ura plates, where all exhibited secondary growth. The transformants were screened by PCR for the presence of the intact KmURA3 gene (inserted with plasmid pSO99) with primers identified as SEQ. ID. NO. 156 and SEQ. ID. NO. 157 and also for an internal region of the CaXYLA gene using primers identified as SEQ. ID. NO. 158 and SEQ. ID. NO. 159. CD1103 contains the CaXYLA gene, an intact KmURA3 gene, and a disrupted KmURA3 gene. CD1106 contains the CaXYLA gene and the disrupted KmURA3.

EXAMPLE 15B

Anaerobic Fermentation with Strains CD1103 and CD1106 (Ex. 15A)

Baffled shake flasks containing 100 ml of media (20 g/L yeast extract, 10 g/L peptone, 100 g/L glucose) were separately inoculated with strains CD1103 and 1106 were incubated overnight at 35° C. and shaking at 250 rpm. Cells were harvested after ~14 hours, and 4 g/L cell dry weight of each strain were added to separate 50 ml Falcon screw top tubes containing 45 ml yeast peptone, 50 g/L D-xylose, 7.5 g/L $CaCO_3$ and 10 mM $MgCl_2$. Tubes were cultivated anaerobically for 65 hours at 30° C. with shaking at 70 rpm. Strain 1103 produced over 9 g/L of ethanol, and strain 1106 produced over 7 g/L ethanol in that time. XI activity was determined by lysing cells taken from the growth phase. XI activity was measured and found to be approximately 83 mU/mg for each of strains 1103 and 1106.

EXAMPLE 16A

Cloning B. thetaiotaomicron Xylose Isomerase (BtXYLA) Gene (pSO89, FIG. 46)

*Bacteroides thetaiotaomicron* genomic DNA was obtained from Washington University (St. Louis, Mo.) Department of Molecular Biology and Pharmacology. The BtXLYA gene was isolated in a standard protocol using Pfx Polymerase (Stratagene), with the genomic DNA as template and primers identified as SEQ. ID. NO. 160 and SEQ. ID. NO. 161. PCR conditions were 95° C. for 3 minutes; 15 cycles of 30 seconds at 95° C., 30 seconds at 60° C. and 2 minutes at 68° C., followed by 20 cycles of 30 seconds at 95° C. and 2.5 minutes at 68° C., ending in a blunt end generation cycle of 68° C. for 8 minutes. The resulting ~1.4 kb PCR product was cloned into pCR-XL-TOPO vector (Invitrogen) and sequenced for verification. The resulting plasmid was designated pSO89 (FIG. 46). The nucleotide and deduced amino acid sequences of the cloned BtXYLA gene appear as SEQ. ID. NO. 162 and SEQ. ID. NO. 163, respectively.

EXAMPLE 16B

Creation of Plasmid Containing BtXYLA and KmURA3 Selection Gene Plasmid (pSO96, FIG. 47)

The ~1.4 kb BtXYLA gene was gel extracted from plasmid pSO89 after an SbfI digest and ligated to a similarly digested 6376 bp fragment of plasmid pSO91 (Ex. 16A, FIG. 44). The resulting plasmid (pSO96, FIG. 47) contains the KmURA3 selection gene, the BtXYLA gene under the control of the KmPDC1 promoter, and SeCYC1 terminator.

EXAMPLE 16C

Creation of K. marxianus Mutants (CD1089-1096) by Transforming a Strain Corresponding to CD806 (Ex. 6B) with Plasmid pSO96 (Ex. 16B, FIG. 47)

A K. marxianus colony corresponding to CD 806 (Ex. 6B) is cultured. 20 ml of cells are spun down and transformed with plasmid pSO96 using standard electroporation methods. Plasmid pSO96 is digested with AatII and BsmBI prior to integration. 100 µL of cells were plated on Sc-Ura plates and allowed to grow at 37° C. until colonies formed. The colonies were streaked onto secondary plates of SC-Ura. The transformants were screened by PCR for the presence of the intact KmURA3 gene with primers identified as SEQ. ID. NO. 156 and SEQ. ID. NO. 157. A PCR screening for a ~450 bp region upstream of the BtXYLA stop codon and just inside of the SeCYC1 terminator is performed with primers identified as SEQ. ID. NO. 164 and SEQ. ID. NO. 165. Of the transformants testing positive for both the native KmURA3 and BtXYLA gene, eight are selected and designated CD1089-1096, respectively.

For determination of xylose isomerase activity, strains were grown at 30° C., 250 rpm for ~14 hours in YPD (10 g/L yeast extract, 20 g/L peptone, 100 g/L dextrose). Cells were lysed according to protocol for Y-PER (Pierce #78990). Total protein was determined using Advanced Protein Assay Reagent (Cysoskeleton #ADV01) with BSA as a standard. Xylose isomerase activities for strains CD 806 and CD1089-1096 are as follows:

| Strain | XI activity (mU/mg) |
| --- | --- |
| CD806 (Ex. 6B) | 0 |
| CD1089 | 143 ± 13 |
| CD1090 | 48 ± 1 |

-continued

| Strain | XI activity (mU/mg) |
|---|---|
| CD1091 | 41 ± 6 |
| CD1092 | 108 ± 21 |
| CD1093 | 45 |
| CD1094 | 74 ± 29 |
| CD1095 | 10 ± 13 |
| CD1096 | 87 ± 34 |

The higher activities of CD1089 and CD1092 may be due to the integration of multiple copies of the BtXYLA gene or a preferred site of integration.

EXAMPLE 16D

Shake Flask Characterisation of Strains CD1089-1096 (Ex. 16C)

Single colonies of strains CD806, and CD1089-1096 were separately inoculated for growth in 100 ml media consisting of 10 g/L yeast extract, 20 g/L peptone, and 100 g/L dextrose. The cells were grown for 14 hours at 30° C., after which the cells were collected and cell dry weight determined. 1.4 g/L cell dry weight of each culture is added to separate 50 mL Falcon tubes containing 10 g/L yeast extract, 20 g/L peptone, 50 g/L D-xylose, 7.5 g/L CaCO$_3$, and 10 mM MgCl$_2$. These cultures were incubated at 30° C. with shaking at 70 rpm. Broth samples were taken for HPLC analysis approximately every 24 hours. After 72 hours, results of this anaerobic fermentation were as shown in the following table.

| Strain | Xylose Consumed (g) | Ethanol Produced (g) | Xylitol Produced (g) |
|---|---|---|---|
| CD806 (Ex. 6B) | ~2.5 | ~0.4 | ~0 |
| CD1089 | ~19.6 | ~7.3 | ~1.45 |
| CD1090 | ~10.7 | ~4.0 | ~0.9 |
| CD1091 | ~11.0 | ~4.15 | ~0.9 |
| CD1092 | ~16.55 | ~6.2 | ~1.1 |
| CD1093 | ~7.5 | ~4.1 | ~0.9 |
| CD1094 | ~9.6 | ~3.7 | ~0.9 |
| CD1095 | ~1.7 | 0 | 0 |
| CD1096 | ~9.45 | ~3.95 | ~0.9 |

In microaerobic shake flask fermentation studies, strains CD1089 and CD1092 produced up to about 1 gram of ethanol after about 7 hours fermenting at 30° C. and 70 rpm.

Strains CD1089-1096 were plated at the end of a low oxygen xylose cultivation onto YPX plates and placed in an anaerobic chamber for two days. All except CD1095 exhibited anaerobic growth under these conditions, with strains CD1089 and CD1092 showing the greatest anaerobic growth.

EXAMPLE 17

Shake-Flask Fermentation of Strains CD804 (Ex. 4D), CD805 (Ex. 5E) and CD806 (Ex. 6B) in Media with Xylose and Externally Added Commercial Enzyme Glucose Isomerase Strains CD804, CD805 and CD806 were separately inoculated to an OD$_{600}$ of 0.1 from YPD agar plates and were grown for 16 hours at 33° C. with 250 rpm, in 250 mL baffled shake flasks containing 50 mL YPD supplemented with 50 µg/ml G418. After determining that residual glucose remained in each flask and that the cells were consequently in exponential growth phase, 0.5 g/L cell dry weight equivalents of each strain were harvested by centrifugation and separately resuspended in 250 mL baffled shake flasks containing 47.5 mL YP supplemented with 50 g/L D-xylose. 2.5 ml glucose isomerase (Gensweet SGI; Genencor Inc., CA) (also known as xylose isomerase) was added to the shake-flasks and the cultures were grown at 33° C. with 70 rpm. For controls, 0.5 g/L cell dry weight equivalents of strains each of strains CD804, 805 and 806 were separately resuspended in 250 mL baffled shake flasks containing 50 mL YP supplemented with 50 g/L D-xylose where the glucose isomerase was omitted. These shake-flasks were also incubated at 33° C. with 70 rpm. Samples were withdrawn at various time intervals and the cells were removed by filtration. Culture supernatant was analyzed for xylose, xylitol and ethanol by HPLC methods.

After 25 hours, strain CD804 (Ex. 4D) had consumed 15 g/L D-xylose and produced about 4.7 g/L of xylitol and 1 g/L of ethanol from the flask containing the glucose isomerase. In contrast, strains CD805 (Ex. 5C) and CD806 (Ex. 6B) had each consumed 25 g/L D-xylose in the presence of glucose isomerase. Strain CD805 produced in this time about 1.9 g/L of xylitol and 7.1 g/L of ethanol. Strain CD806 produced in this time about 1.8 g/L of xylitol and 6.8 g/L of ethanol. Xylulose seems to be consumed by the strains at very high rates, something which is not observed in S. cerevisiae. The non-oxidative pentose phosphate pathway controls the fermentation rate of xylulose but not of xylose in S. cerevisiae TMB3001. FEM Yeast Res. 2002 August; 2(3):277-82. Johansson B, Hahn-Hagerdal B). Without added glucose isomerase, each of strains CD804, CD805 and CD806 consumed xylose very slowly.

EXAMPLE 18

Transformation of Strain Corresponding to CD806 (Ex. 6B) with Self-Replicating Plasmid pCM48 (FIG. 49) to Introduce PXYLA Gene; Cultivation of the Resulting Strains A cassette containing the KmPDC1 promoter, PXYLA gene and ScCYC1 terminator was PCR amplified using primers identified as SEQ. ID. NO. 166 and SEQ. ID. NO. 167, using plasmid pCM29 (Ex. 8A, FIG. 30) as the template. These primers were designed to incorporate PacI and MluI restriction sites. Thermocycling conditions were an initial incubation of 94° C. for 2 minutes, followed by 30 cycles of 94° C. for 30 seconds, 50° C. for 30 seconds, and 70° C. for 3 minutes. This was followed by a final incubation at 70° C. for 8 minutes. The product was digested with the above restriction enzymes and a 2.804 kbp fragment so obtained was ligated into fragment obtained by similarly digesting a plasmid designated pSO57 (FIG. 48) (containing a pKD1 self-replication site), to yield the plasmid pCM48 (FIG. 49). The transformants were restriction mapped using EcoRI and SbfI, and two were taken forward for sequencing. The entire PXYLA coding region was sequenced and verified to be identical for both transformants to the sequence on plasmid pCM29.

2 µg of undigested plasmid pCM48 was transformed into a strain corresponding to CD806 (Ex. 6B) using to standard electroporation methods. Cells were recovered for four hours in YPX, plated on YPX plates containing 300 µg/ml G418 and 150 µg/ml hygromycin and incubated at 37° C. for 2 days. This produced a large number of transformants.

Several transformants were re-streaked onto identical plates and incubated at 37° C. for several days. Four transformants were selected and inoculated into ~100 ml of YPX in a 250 ml-baffled shake flask and incubated at 37° C. with 250 rpm shaking. Strain CD861 was included and biomass prepared in the same manner. After 17 hours, 2 gcdw of each was inoculated into separate 250 mL-baffled shake flasks containing 50 mL media (10 g/L yeast extract, 20 g/L yeast peptone, 50 g/L xylose, 7.5 g/L CaCO$_3$, 10 mM MgCl$_2$, and pH 7.0). The four transformants produced about 9-12.3 g/L ethanol after about 40 hours. The parent strain produced no ethanol.

10 mL of the overnight culture was harvested by centrifugation and taken forward to enzyme assays. Xylose isomerase activities for the four transformants ranged from 456 to 531 mU/mg.

We claim:

1. A fermentation process in which a genetically modified yeast cell having a genome and a functional, exogenous xylose isomerase gene which encodes a xylose isomerase enzyme that is at least 90% homologous to SEQ. ID. NO. 59, wherein the exogenous xylose isomerase gene is operatively linked to promoter and terminator sequences that are functional in the yeast cell, and the modified yeast cell further has a deletion or disruption of a native gene that produces an enzyme that catalyzes the conversion of xylose to xylitol is cultured under fermentation conditions in a fermentation broth that includes a pentose sugar, wherein the fermentation process includes a growth phase and a production phase, and during the production phase the concentration of cells in the fermentation broth is in the range of 3 to 10 g dry cells/liter of fermentation broth.

2. A fermentation process of claim 1 wherein ethanol is produced as a major fermentation product.

3. A fermentation process of claim 1 wherein lactate is produced as a major fermentation product.

4. The fermentation process of any of claim 1 in which the pentose sugar includes xylose.

5. The fermentation process of claim 1 in which the fermentation broth further includes a hexose sugar.

6. The fermentation process of claim 1 which is an anaerobic fermentation.

7. The fermentation process of claim 1 wherein the final concentration of the fermentation product is at least 14 g/L.

* * * * *